(12) United States Patent
Jiang et al.

(10) Patent No.: US 12,344,631 B2
(45) Date of Patent: Jul. 1, 2025

(54) C17 POLAR-SUBSTITUTED HETEROAROMATIC SYNTHETIC TRITERPENOIDS AND METHODS OF USE THEREOF

(71) Applicant: REATA PHARMACEUTICALS, INC., Irving, TX (US)

(72) Inventors: Xin Jiang, Coppell, TX (US); Christopher F. Bender, Garland, TX (US); Ha Do, Irving, TX (US); Haizhou Sun, Irving, TX (US); Melean Visnick, Irving, TX (US)

(73) Assignee: REATA PHARMACEUTICALS, INC., Irving, TX (US)

( * ) Notice: Subject to any disclaimer, the term of this patent is extended or adjusted under 35 U.S.C. 154(b) by 733 days.

(21) Appl. No.: 16/933,635

(22) Filed: Jul. 20, 2020

(65) Prior Publication Data

US 2021/0040142 A1    Feb. 11, 2021

Related U.S. Application Data

(60) Provisional application No. 62/952,048, filed on Dec. 20, 2019, provisional application No. 62/876,467, filed on Jul. 19, 2019.

(51) Int. Cl.
| | | |
|---|---|---|
| A61K 9/14 | (2006.01) | |
| A61K 9/19 | (2006.01) | |
| C07J 53/00 | (2006.01) | |
| A61K 9/00 | (2006.01) | |

(52) U.S. Cl.
CPC ........... C07J 53/002 (2013.01); *A61K 9/0014* (2013.01); *A61K 9/0019* (2013.01); *A61K 9/0053* (2013.01)

(58) Field of Classification Search
CPC .................................................. C07J 53/002
See application file for complete search history.

(56) References Cited

U.S. PATENT DOCUMENTS

| | | | |
|---|---|---|---|
| 4,395,423 A | 7/1983 | Neumann | |
| 5,064,823 A | 11/1991 | Lee et al. | |
| 6,326,507 B1 | 12/2001 | Gribble et al. | |
| 6,369,101 B1 | 4/2002 | Carlson | |
| 6,503,913 B1 | 1/2003 | Goldmann et al. | |
| 6,552,075 B2 | 4/2003 | Gribble et al. | |
| 6,642,217 B2 | 11/2003 | Krasutsky et al. | |
| 6,649,654 B1 | 11/2003 | Karin et al. | |
| 6,951,847 B2 | 10/2005 | Gibson et al. | |
| 6,974,801 B2 | 12/2005 | Honda et al. | |
| 7,053,119 B2 | 5/2006 | Karin et al. | |
| 7,144,875 B2 | 12/2006 | Gibson et al. | |
| 7,176,237 B2 | 2/2007 | Honda et al. | |
| 7,288,568 B2 | 10/2007 | Gribble et al. | |
| 7,399,606 B2 | 7/2008 | Karin et al. | |
| 7,410,958 B2 | 8/2008 | Krasutsky et al. | |
| 7,435,755 B2 | 10/2008 | Konopleva et al. | |
| 7,678,830 B2 | 3/2010 | Honda et al. | |
| 7,714,012 B2 | 5/2010 | Honda et al. | |
| 7,795,305 B2 | 9/2010 | Konopleva et al. | |
| 7,863,327 B2 | 1/2011 | Gribble et al. | |
| 7,915,402 B2 | 3/2011 | Anderson et al. | |
| 7,943,778 B2 | 5/2011 | Jiang et al. | |
| 8,034,955 B2 | 10/2011 | Gribble et al. | |
| 8,067,394 B2 | 11/2011 | Honda et al. | |
| 8,067,465 B2 | 11/2011 | Honda et al. | |
| 8,071,632 B2 | 12/2011 | Jiang et al. | |

(Continued)

FOREIGN PATENT DOCUMENTS

| | | |
|---|---|---|
| CN | 103665087 | 3/2014 |
| WO | WO 1999/065478 | 12/1999 |

(Continued)

OTHER PUBLICATIONS

"RTA 402, Therapeutic Properties I", slides/handouts presented by Reata Pharmaceuticals, Inc. at private partnering meetings at BioSquare 2006 conference, Mar. 8-10, 2006, Geneva, Switzerland.

(Continued)

*Primary Examiner* — Jared Barsky
(74) *Attorney, Agent, or Firm* — Parker Highlander PLLC

(57) ABSTRACT

Disclosed herein are compounds of the formula:

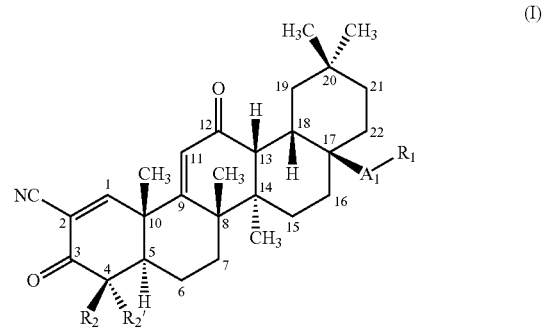

(I)

wherein the variables are defined herein. Also provided are pharmaceutical compositions thereof. In some aspects, the compounds and compositions provided herein may be used as antioxidant inflammation modulators. In some aspects, the present disclosure provides methods wherein the compounds and composition described herein are used for the treatment of diseases and disorders, including those associated with inflammation and cancer.

9 Claims, 1 Drawing Sheet

(56) References Cited

U.S. PATENT DOCUMENTS

| | | |
|---|---|---|
| 8,088,824 B2 | 1/2012 | Walling et al. |
| 8,124,656 B2 | 2/2012 | Anderson et al. |
| 8,124,799 B2 | 2/2012 | Anderson et al. |
| 8,129,429 B2 | 3/2012 | Sporn et al. |
| 8,258,329 B2 | 9/2012 | Anderson et al. |
| 8,299,046 B2 | 10/2012 | Sporn et al. |
| 8,338,618 B2 | 12/2012 | Jiang et al. |
| 8,394,967 B2 | 3/2013 | Jiang et al. |
| 8,440,820 B2 | 5/2013 | Anderson et al. |
| 8,440,854 B2 | 5/2013 | Anderson et al. |
| 8,455,544 B2 | 6/2013 | Sporn et al. |
| 8,586,775 B2 | 11/2013 | Gribble et al. |
| RE45,288 E | 12/2014 | Anderson et al. |
| 8,921,419 B2 | 12/2014 | Gribble et al. |
| RE45,325 E | 1/2015 | Anderson et al. |
| 8,993,640 B2 | 3/2015 | Anderson et al. |
| 9,090,574 B2 | 7/2015 | Anderson et al. |
| 9,102,681 B2 | 8/2015 | Anderson et al. |
| 9,233,998 B2 | 1/2016 | Anderson et al. |
| 9,249,089 B2 | 2/2016 | Jiang et al. |
| 9,278,912 B2 | 3/2016 | Jiang et al. |
| 9,278,913 B2 | 3/2016 | Gribble et al. |
| 9,290,536 B2 | 3/2016 | Anderson et al. |
| 9,512,094 B2 | 12/2016 | Jiang et al. |
| 9,556,222 B2 | 1/2017 | Anderson et al. |
| 9,593,074 B2 | 3/2017 | Bender et al. |
| 9,670,147 B2 | 6/2017 | Anderson et al. |
| 9,701,709 B2 | 7/2017 | Anderson et al. |
| 9,757,359 B2 | 9/2017 | Sporn et al. |
| 9,796,668 B2 | 10/2017 | Anderson et al. |
| 9,856,286 B2 | 1/2018 | Sheikh et al. |
| 9,889,143 B2 | 2/2018 | Jiang et al. |
| 10,093,614 B2 | 10/2018 | Anderson et al. |
| 10,105,372 B2 | 10/2018 | Meyer et al. |
| 10,398,711 B2 | 9/2019 | Jiang et al. |
| 10,501,489 B2 | 12/2019 | Bender et al. |
| 10,556,858 B2 | 2/2020 | Anderson et al. |
| 2002/0042535 A1 | 4/2002 | Gribble et al. |
| 2003/0119732 A1 | 6/2003 | Konopleva et al. |
| 2003/0232786 A1 | 12/2003 | Honda et al. |
| 2003/0236303 A1 | 12/2003 | Gribble et al. |
| 2004/0002463 A1 | 1/2004 | Honda et al. |
| 2004/0097436 A1 | 5/2004 | Krasutsky et al. |
| 2005/0208151 A1 | 9/2005 | Hurez et al. |
| 2005/0288363 A1 | 12/2005 | Gribble et al. |
| 2006/0258752 A1 | 11/2006 | Vander Jagt et al. |
| 2007/0155742 A1 | 7/2007 | Honda et al. |
| 2007/0232577 A1 | 10/2007 | Xu et al. |
| 2007/0244081 A1 | 10/2007 | Krasutsky et al. |
| 2007/0249561 A1 | 10/2007 | Taylor |
| 2007/0259839 A1 | 11/2007 | Krasutsky et al. |
| 2007/0259842 A1 | 11/2007 | Krasutsky et al. |
| 2008/0220057 A1 | 9/2008 | Gribble et al. |
| 2008/0233195 A1 | 9/2008 | Sporn et al. |
| 2008/0261985 A1 | 10/2008 | Honda et al. |
| 2009/0048204 A1 | 2/2009 | Walling et al. |
| 2009/0048205 A1 | 2/2009 | Meyer et al. |
| 2009/0060873 A1 | 3/2009 | Sporn et al. |
| 2009/0093447 A1 | 4/2009 | Konopleva et al. |
| 2009/0326063 A1 | 12/2009 | Sporn et al. |
| 2010/0041904 A1 | 2/2010 | Jiang et al. |
| 2010/0048887 A1 | 2/2010 | Anderson et al. |
| 2010/0048892 A1 | 2/2010 | Anderson et al. |
| 2010/0048911 A1 | 2/2010 | Jiang et al. |
| 2010/0056777 A1 | 3/2010 | Anderson et al. |
| 2010/0261930 A1 | 10/2010 | Honda et al. |
| 2011/0009363 A1 | 1/2011 | Honda et al. |
| 2011/0196007 A1 | 8/2011 | Honda et al. |
| 2011/0245206 A1 | 10/2011 | Jiang et al. |
| 2011/0245233 A1 | 10/2011 | Anderson et al. |
| 2011/0281955 A1 | 11/2011 | Meyer et al. |
| 2012/0022156 A1 | 1/2012 | Zhang et al. |
| 2012/0071684 A1 | 3/2012 | Walling et al. |
| 2012/0214814 A1 | 8/2012 | Anderson et al. |
| 2012/0220652 A1 | 8/2012 | Sporn et al. |
| 2012/0238767 A1 | 9/2012 | Jiang et al. |
| 2012/0245374 A1 | 9/2012 | Anderson et al. |
| 2012/0252776 A1 | 10/2012 | Anderson et al. |
| 2012/0283450 A1 | 11/2012 | Anderson et al. |
| 2012/0330050 A1 | 12/2012 | Walling et al. |
| 2013/0237721 A1 | 9/2013 | Gribble et al. |
| 2013/0303607 A1 | 11/2013 | Gribble et al. |
| 2013/0317007 A1 | 11/2013 | Anderson et al. |
| 2013/0324599 A1 | 12/2013 | Anderson et al. |
| 2013/0345276 A1 | 12/2013 | Sporn et al. |
| 2014/0066408 A1 | 3/2014 | Jiang et al. |
| 2014/0073700 A1 | 3/2014 | Wagner et al. |
| 2014/0088163 A1 | 3/2014 | Jiang et al. |
| 2014/0088188 A1 | 3/2014 | Jiang et al. |
| 2014/0100227 A1 | 4/2014 | Bender et al. |
| 2014/0179928 A1 | 6/2014 | Anderson et al. |
| 2014/0275618 A1 | 9/2014 | Gribble et al. |
| 2014/0323579 A1 | 10/2014 | Sheikh et al. |
| 2015/0080465 A1 | 3/2015 | Chin et al. |
| 2015/0148384 A1 | 5/2015 | Anderson et al. |
| 2015/0152071 A1 | 6/2015 | Jiang et al. |
| 2015/0259377 A1 | 9/2015 | Anderson et al. |
| 2015/0376121 A1 | 12/2015 | Anderson et al. |
| 2016/0145200 A1 | 5/2016 | Anderson et al. |
| 2017/0165278 A1 | 6/2017 | Jiang et al. |
| 2017/0260227 A1 | 9/2017 | Bender et al. |
| 2018/0002277 A1 | 1/2018 | Anderson et al. |
| 2018/0009839 A1 | 1/2018 | Anderson et al. |
| 2018/0161311 A1 | 6/2018 | Sporn et al. |
| 2018/0235981 A1 | 8/2018 | Jiang et al. |
| 2018/0237383 A1 | 8/2018 | Anderson et al. |
| 2019/0153022 A1 | 5/2019 | Visnick et al. |
| 2019/0350941 A1 | 11/2019 | Meyer |

FOREIGN PATENT DOCUMENTS

| | | |
|---|---|---|
| WO | WO 2000/073253 | 12/2000 |
| WO | WO 2002/003996 | 1/2002 |
| WO | WO 2002/026761 | 4/2002 |
| WO | WO 2002/026762 | 4/2002 |
| WO | WO 2002/047611 | 6/2002 |
| WO | WO 2003/059339 | 7/2003 |
| WO | WO 2003/062260 | 7/2003 |
| WO | WO 2004/064723 | 8/2004 |
| WO | WO 2005/042002 | 5/2005 |
| WO | WO 2005/046732 | 5/2005 |
| WO | WO 2006/029221 | 3/2006 |
| WO | WO 2007/005879 | 1/2007 |
| WO | WO 2007/112043 | 10/2007 |
| WO | WO 2007/127791 | 11/2007 |
| WO | WO 2008/000068 | 1/2008 |
| WO | WO 2008/000070 | 1/2008 |
| WO | WO 2008/016095 | 2/2008 |
| WO | WO 2008/064132 | 5/2008 |
| WO | WO 2008/064133 | 5/2008 |
| WO | WO 2008/097596 | 8/2008 |
| WO | WO 2008/111497 | 9/2008 |
| WO | WO 2008/136838 | 11/2008 |
| WO | WO 2009/023232 | 2/2009 |
| WO | WO 2009/023845 | 2/2009 |
| WO | WO 2009/058849 | 5/2009 |
| WO | WO 2009/089545 | 7/2009 |
| WO | WO 2009/129546 | 10/2009 |
| WO | WO 2009/129548 | 10/2009 |
| WO | WO 2009/129545 | 11/2009 |
| WO | WO 2009/146216 | 12/2009 |
| WO | WO 2009/146218 | 12/2009 |
| WO | WO 2010/011782 | 1/2010 |
| WO | WO 2010/053817 | 5/2010 |
| WO | WO 2010/093944 | 8/2010 |
| WO | WO 2011/130302 | 10/2011 |
| WO | WO 2012/096718 | 7/2012 |
| WO | WO 2012/106190 | 8/2012 |
| WO | WO 2012/125488 | 9/2012 |
| WO | WO 2013/163344 | 10/2013 |
| WO | WO 2013/169740 | 11/2013 |
| WO | WO 2013/188818 | 12/2013 |
| WO | WO 2014/040052 | 3/2014 |
| WO | WO 2014/040056 | 3/2014 |

(56) References Cited

FOREIGN PATENT DOCUMENTS

| | | |
|---|---|---|
| WO | WO 2014/040060 | 3/2014 |
| WO | WO 2014/040073 | 3/2014 |
| WO | WO-2014040056 A1 * 3/2014 ............. A61K 31/58 |
| WO | WO 2014/176415 | 10/2014 |
| WO | WO 2015/027206 | 2/2015 |
| WO | WO 2016/033132 | 3/2016 |
| WO | WO 2017/053868 | 3/2017 |
| WO | WO 2018/089539 | 5/2018 |
| WO | WO 2021/016191 | 1/2021 |

OTHER PUBLICATIONS

"RTA 402, Therapeutic Properties II", slides/handouts presented by Reata Pharmaceuticals, Inc. at private partnering meetings at BIO 2006 conference, Apr. 9-12, 2006, Chicago, Illinois.
"RTA 402, Therapeutic Properties III", slides presented by Reata Pharmaceuticals, Inc. as a podium presentation at BIO 2006 conference, Apr. 9-12, 2006, Chicago, Illinois.
"RTA 402, Therapeutic Properties IV", slides/handouts presented by Reata Pharmaceuticals, Inc. at private partnering meetings at BioPartnering Europe 2006 conference, Oct. 8-10, 2006, London, England.
"RTA 402, Therapeutic Properties IX", slides/handouts presented by Reata Pharmaceuticals, Inc. at a private partnering meeting at BIO Europe 2007 conference, Nov. 12-14, 2007, Hamburg, Germany.
"RTA 402, Therapeutic Properties V", slides/handouts presented by Reata Pharmaceuticals, Inc. at private partnering meetings at BIO 2007 conference, May 6-9, 2007, Boston Massachusetts.
"RTA 402, Therapeutic Properties VI", slides/bandouts presented by Reata Pharmaceuticals, Inc. at private partnering meetings at BIO 2007 conference, May 6-9, 2007, Boston, Massachusetts.
"RTA 402, Therapeutic Properties VII", slides presented by Reata Pharmaceuticals, Inc. as a podium presentation at BIO 2007 conference, May 6-9, 2007, Boston, Massachusetts.
"RTA 402, Therapeutic Properties VIII", slides/handouts presented by Reata Pharmaceuticals, Inc. at private partnering meetings at BIO Europe 2007 conference, Nov. 12-14, 2007, Hamburg, Germany.
Ahmad et al., "Triterpenoid CDDO-Me blocks the NF-κB pathway by direct inhibition of IKKbeta on Cys-179," *J. Biol. Chem.*, 281:35764-35769, 2006.
Ahmad et al., "Triterpenoid CDDO-methyl ester inhibits the Janus-activated kinase-1 (JAK1) signal transducer and activator of transcription-3 (STAT3) pathway by direct inhibition of JAK1 and STAT3," *Cancer Res.*, 68 (8): 2920-2926, 2008.
Akiyama et al., "Cell mediators of inflammation in the Alzheimer disease brain," *Alzheimer Dis. Assoc. Disord.*, 14 (1): S47-S53, 2000.
Albini and Sporn, "Opinion: the tumour microenvironment as a target for chemoprevention," *Nature Reviews Cancer*, 7: 139-147, 2007.
Andreef et al., "PPARγ nuclear receptor as a novel molecular target in leukemias," 2002 Keystone Symposia, Abstract 501:149, 2002.
Ballesta-Acosta et al., "A new 24-nor-oleanane triterpenoid from Salvia carduacea," *J. Nat. Prod.*, 65(10): 1513-1515, 2002.
Bore et al., "The anti-inflammatory triterpenoid methyl 2-cyano-3,12-dioxoolean 1,9(11)-dien-28-oate methanol solvate hydrate," *Acta Crystallorg C.*, 58(Pt 3):o199-o200, 2002.
Bowden et al, "Constituents of the fruit of pseudopanax arboretum (*Araliaceae*)," *Australian Journal of Chemistry*, 28(1): 91-107, 1975.
Brookes et al., "The triterpenoid 2-cyano-3,12-dioxoolcana-1,9-dien-28-oic acid and its derivatives elicit human lymphoid cell apoptosis through a novel pathway involving the unregulated mitochondrial permeability transition pore," *Cancer Res.*, 67:1793-1802, 2007.
Buchanan et al., "The conversion of turracanthin and turracanthin A into simple melaiacins by a route involving an oxidative rearrangement of probable biogenetic importance," *J Chem. Soc C*, 17:2280-2284, 1970.

Chauhan et al., "The bortezomib/proteasome inhibitor PS-341 and triterpenoid CDDO-Im induce synergistic anti-multiple myeloma (MM) activity and overcome bortezomib resistance," *Blood*, 103:3158-3166, 2004.
Chen et al., "FOXP3 and RORγt: Transcriptional regulation of Treg and Th17," *Int. Immunopharmacol.*, 11:536-542, 2011.
Cheong et al., "Structures of triterpenes from dryobalanops aromatic," *Phytochemistry*, 11:1771-17780, 1972.
Chintbarlapalli et al., "2-Cyano-3,12-dioxoolean-1,9-dien-28-oic acid and related compounds inhibit growth of colon cancer cells through peroxisome proliferator-activated receptor γ-dependent and -independent pathways," *Mol. Pharmacol.*, 68:119-128, 2005.
Chintharlapalli et al., "2-Cyano-lup-1-en-3-oxo-20-oic acid, a cyano derivative of betulinic acid, activates peroxisome proliferator-activated receptor γ in colon and pancreatic cancer cells.," *Carcinogenesis*, 28 (11): 2337-2346, 2007.
Chintharlapalli et al., "Structure-dependent activity of glycyrrhetinic acid derivatives as peroxisome proliferator-activated receptor γ agonists in colon cancer cells," Molecular *Cancer Therapeutics*, 6 (5): 1588-1598, 2007.
Clinicaltrial.gov Study NCT00508807, "RTA 402 in Advanced Solid Tumors or Lymphoid Malignancies," and associated updates, first published Jul. 30, 2007.
Clinicaltrial.gov Study NCT00529113, "Study With Gemcitabine and RTA 402 for Patients With Unresectable Pancreatic Cancer," and associated updates, first published Sep. 14, 2007.
Clinicaltrial.gov Study NCT00529438, "RTA 402 in Patients With Advanced Solid Tumors or Lymphoid Malignancies," and associated updates, first published Sep. 14, 2007.
Clinicaltrial.gov Study NCT00535314, "Study of Two Dose Levels of RTA 402 in Patients With Advanced Malignant Melanoma," and associated updates, first published Sep. 26, 2007.
Clinicaltrial.gov Study NCT00550849, "Study to Assess the Safety, Tolerability, and Pharmacodynamics of RTA 402 in Patients With Hepatic Dysfunction," and associated updates, first published Oct. 30, 2007.
Clinicaltrial.gov Study NCT00664027, "Phase IIa Trial to Determine the Effects of Bardoxolone Methyl on Renal Function in Patients With Diabetic Nephropathy," and associated updates, first published Apr. 22, 2008.
Clinicaltrial.gov Study NCT00811889, "Trial to Determine the Effects of Bardoxolone Methyl on eGFR in Patients With Type 2 Diabetes and Chronic Kidney Disease," and associated updates, first published Dec. 19, 2008.
Clinicaltrial.gov Study NCT01053936, "Phase II Pharmacodynamic Trial to Determine the Effects of Bardoxolone Methyl on eGFR in Patients With Type 2 Diabetes and Chronic Kidney Disease," and associated updates, first published Jan. 22, 2010.
Clinicaltrial.gov Study NCT01351675, "Bardoxolone Methyl Evaluation in Patients With Chronic Kidney Disease and Type 2 Diabetes," and associated updates, first published May 11, 2011.
Clinicaltrial.gov Study NCT01461161, "A Single-Dose, Open-Label, Randomized, Food Effect and Blinded, Randomized, Dose Proportionality Study in Healthy Volunteers With Bardoxolone Methyl," and associated updates, first published Oct. 27, 2011.
Clinicaltrial.gov Study NCT01500798, "A Pharmacodynamic Study of Measured Glomerular Filtration Rate in Patients With Chronic Kidney Disease and Type 2 Diabetes," and associated updates, first published Dec. 28, 2011.
Clinicaltrial.gov Study NCT01503866, "A Phase I Study to Investigate the Absorption, Metabolism and Excretion in Healthy Male Subjects," and associated updates, first published Jan. 4, 2012.
Clinicaltrial.gov Study NCT01549769, "Pharmacokinetic and Pharmacodynamic Study of Bardoxolone Methyl in Patients With Chronic Kidney Disease and Type 2 Diabetes," and associated updates, first published Mar. 9, 2012.
Clinicaltrial.gov Study NCT01551446, "Pilot Assessment of the Effects of Bardoxolone Methyl on Renal Perfusion, Systemic Haemodynamics and Cardiac Function in Patients With Chronic Kidney Disease and Type 2 Diabetes," and associated updates, first published Mar. 12, 2012.
Clinicaltrial.gov Study NCT01563562, "Single-Dose, Open-Label Pharmacokinetic Study of Bardoxolone Methyl in Subjects With

(56) References Cited

OTHER PUBLICATIONS

Mild, Moderate, and Severe Hepatic Impairment and Normal Hepatic Function," and associated updates, first published Mar. 27, 2012.
Clinicaltrial.gov Study NCT01576887, "A Double-Blind, Randomized, Placebo-Controlled Safety Study Evaluating the Effects of Residual Renal Function (RFF) in Patients With End-Stage Renal Disease and Type 2 Diabetes Mellitus on Peritoneal Dialysis," and associated updates, first published Apr. 13, 2012.
Clinicaltrial.gov Study NCT01598363, "An Open-Label Study of the Effect of Bardoxolone Methyl on the Single Dose Pharmacokinetics of Digoxin and Rosuvastatin in Healthy Volunteers," and associated updates, first published May 15, 2012.
Clinicaltrial.gov Study NCT01655186, "A Double-Blind, Randomized, Placebo-Controlled Study Evaluating the Effects of Bardoxolone Methyl on Body Composition in Patients With Stage 4 Chronic Kidney Disease and Type 2 Diabetes Mellitus," and associated updates, first published Aug. 1, 2012.
Clinicaltrial.gov Study NCT01689116, "Multiple-Dose Study of Effect of Bardoxolone Methyl on QT/QTC Interval Volunteers," and associated updates, first published Sep. 21, 2012.
Clinicaltrial.gov Study NCT02029716, "RTA 408 Lotion in Healthy Volunteers," and associated updates, first published Jan. 8, 2014.
Clinicaltrial.gov Study NCT02029729, "RTA 408 in the Treatment of Advanced Solid Tumors (NSCLC & Melanoma)—Discover," and associated updates, first published Jan. 8, 2014.
Clinicaltrial.gov Study NCT02036970, "Bardoxolone Methyl Evaluation in Patients With Pulmonary Hypertension (PH)—Lariat," and associated updates, first published Jan. 15, 2014.
Clinicaltrial.gov Study NCT02065375, "RTA 408 Ophthalmic Suspension for the Treatment of Ocular Inflammation and Pain Following Ocular Surgery," and associated updates, first published Feb. 19, 2014.
Clinicaltrial.gov Study NCT02128113, "RTA 408 Ophthalmic Suspension for the Prevention of Corneal Endothelial Cell Loss Following Cataract Surgery—Guard," and associated updates, first published May 1, 2014.
Clinicaltrial.gov Study NCT02142959, "RTA 408 Lotion in Patients at Risk for Radiation Dermatitis—Primrose," and associated updates, first published May 20, 2014.
Clinicaltrial.gov Study NCT02255422, "RTA 408 Capsules in Patients With Mitochondrial Myopathy—Motor," and associated updates, first published Oct. 2, 2014.
Clinicaltrial.gov Study NCT02255435, "RTA 408 Capsules in Patients With Friedreich's Ataxia—MOXIe," and associated updates, first published Oct. 2, 2014.
Clinicaltrial.gov Study NCT02259231, "RTA 408 Capsules in Patients With Melanoma—Reveal," and associated updates, first published Oct. 8, 2014.
Clinicaltrial.gov Study NCT02657356, "Bardoxolone Methyl in Patients With Connective Tissue Disease-associated Pulmonary Arterial Hypertension—Catalyst," and associated updates, first published Jan. 15, 2016.
Clinicaltrial.gov Study NCT03019185, "A Phase 2/3 Trial of the Efficacy and Safety of Bardoxolone Methyl in Patients With Alport Syndrome—Cardinal," and associated updates, first published Jan. 12, 2017.
Clinicaltrial.gov Study NCT03068130, "Extended Access Program to Assess Long-term Safety of Bardoxolone Methyl in Patients With Pulmonary Hypertension Ranger," and associated updates, first published Mar. 1, 2017.
Clinicaltrial.gov Study NCT03264079, "Effect of Itraconazole on the Pharmacokinetics of Bardoxolone Methyl in Healthy Adults," and associated updates, first published Aug. 28, 2017.
Clinicaltrial.gov Study NCT03366337, "A Phase 2 Trial of the Safety and Efficacy of Bardoxolone Methyl in Patients With Rare Chronic Kidney Diseases—Phoenix," and associated updates, first published Dec. 8, 2017.
Clinicaltrial.gov Study NCT03593499, "Expanded Access to Omaveloxolone for Melanoma for Patients Previously Enrolled in 408-C-1401," and associated updates, first published Jul. 20, 2018.

Clinicaltrial.goy Study NCT03664453, "A Pharmacokinetic Study of Omaveloxolone in Healthy Volunteers," and associated updates, first published Sep. 10, 2018.
Clinicaltrial.gov Study NCT03749447, "An Extended Access Program for Bardoxolone Methyl in Patients With CKD (EAGLE)," and associated updates, first published Nov. 21, 2018.
Clinicaltrial.gov Study NCT03902002, "A Pharmacokinetic Study of Omaveloxolone in Subjects With Hepatic Impairment and Normal Hepatic Function," and associated updates, first published Apr. 3, 2019.
Clinicaltrial.gov Study NCT03918447, "A Trial of Bardoxolone Methyl in Patients With ADPKD—Falcon," and associated updates, first published Apr. 17, 2019.
Clinicaltrial.gov Study NCT03931590, "A Human AME Study for Omaveloxolone," and associated updates, first published Apr. 30, 2019.
Clinicaltrial.gov Study NCT04008186, "A Clinical Drug-Drug Interaction (DDI) Study With Omaveloxolone," and associated updates, first published Jul. 4, 2019.
Cohen et al., "A general method for removal of a 4-methyl group from triterpenoids. Synthesis of 4β-demethylglycyrrhetinic acid," *J. Chem. Soc, Perkin Trans* 1, (19): 2076-2082, 1973.
Connolly et al., "Grandiofolione: a novel tetranortriterpenoid," *Chemical Communications*, 23:867-568, 1966.
Couch et al., "2-cyano-3,12-dioxooleana-1,9(11)-diene-28-oic acid disrupts microtubule polymerization: a possible mechanism contributing to apoptosis," *Molecular Pharmacology*, 69 (4): 1158-1165, 2006.
Couch et al., "Studies on the reactivity of CDDO, a promising new chemopreventive and chemotherapeutic agent: implications for a molecular mechanism of action," *Bioorganic and Medicinal Chemistry Letters*, 15 (9): 2215-2219, 2005.
Damsté et al., "A sedimentary tetrahydrophenanthrene derivative of tetrahymanol," *Tetrahedron Letters*, 40(20: 3949-3952, 1999.
De Mico et al., "A Versatile and Highly Selective Hypervalent Todine (III)/2,2,6,6-Tetramethyl-1-piperidinyloxyl-Mediated Oxidation of Alcohols to Carbonyl Compounds," *J. Org. Chem.*, 62: 6974, 1997.
Dean et al., "Halogenolysis of metbyl glycyrrhetate with lithium iodidedimethylformamide," *J. Chem. Soc.*, 6655-6659, 1965.
Deng and Snyder, "Preparation of a 24-Nor-1,4-dien-3-one triterpene derivative from betulin: a new route to 24-nortriterpene analogues," *J. of Organic Chemistry*, 67 (9): 2864-2873, 2002.
Dezube et al., "Interim results of a phase I trial with a novel orally administered synthetic triterpenoid RTA 402 (CDDO-Me) in patients with solid tumors and lymphoid malignancies," *J. Clin. Oncol.*, 2007 ASCO Annual Meeting Proceedings, 25(18S):14101, 2007.
Dinkova-Kostova et al., "Direct evidence that sulfhydryl groups of Keap1 are the sensors regulating induction of phase 2 enzymes that protect against carcinogens and oxidants," *Proc. Natl. Acad. Sci.*, 99(18): 11908-11913, 2002.
Dinkova-Kostova et al., "Extremely potent triterpenoid inducers of the phase 2 response: correlations of protection against oxidant and inflammatory stress," *Proc. Natl. Acad. Sci.*, 102(12): 4584-4589, 2005.
Dirsch et al., "The triterpenoid quinonemethide pristimerin inhibits induction of inducible nitric oxide synthase in murine macrophages," *Eur J Pharmacol.*, 336(2-3): 211-217, 1997.
Dracinsky et al., "Preparation and Conformational Study of 19β,28-Epoxy-18α-olean-5-ene Derivatives," *Collection of Czechoslovak Chemical Communications*, 71(3): 387-410, 2006.
Dragnev et al., "Specific chemopreventive agents trigger proteasomal degradation of G1 cyclins: implications for combination therapy," *Clin. Cancer Research*, 10 (7): 2570-2577, 2004.
Duan et al., "Di- and triterpenoids from Triptergium hypoglaucum," *Phytochemistry*, 46(3): 535-543, 1997.
Duan et al., "Immunosuppressive terpenoids from extracts of tripterygium wilfordii," *Tetrahedron*, 57 (40): 8413-8424, 2001.
Dulubova et al., "RTA 1701 is an orally-bioavailable, potent, and selective RORγt inhibitor that suppresses Th17 differentiation in vitro and is efficacious in mouse models of autoimmune disease," *J. Immunol.*, 200 (1 Suppl.):121.14, 2018. (Abstract only).

(56) References Cited

OTHER PUBLICATIONS

Elliot et al., "The triterpenoid CDDO inhibits expression of matrix metalloproteinase-1, matrix metalloproteinase-13 and Bcl-3 in primary human chondrocytes," *Arthritis Res. Ther.*, 5:R285-R291, 2003.
Elsawa et al., "Preferential Inhibition of Malignant Cell Growth by CDDO in Waldenstrom Macroglobulinemia," *Blood*, 108(11):2528, 2006.
Favaloro et al., "Design and synthesis of tricyclic compounds with enone functionalities in rings A and C: a novel class of highly active inhibitors of nitric oxide production in mouse macrophages," *J. Med. Chem.*, 45:4801-4805, 2002.
Finlay et al., "Novel A-ring cleaved analogs of oleanolic and arsolic acids which affect growth regulation in NRP.152 prostate cells," *Biorg. Med. Chem. Lett.*, 7(13): 1769-1772, 1997.
Finlay et al., "The Effect of A and C Ring Modification of Oleanolic and Ursolic Acid on the Inhibition of Nitric Oxide Formation in Mouse Macrophages," 213th American Chemical Society National Meeting, Abstract: 084, 1997.
Gaffen et al., "IL-23-IL-17 immune axis: discovery, mechanistic understanding, and clinical testing", *Nat. Rev. Immunol.*, 14(9):585-600, 2014.
Gao et al., "Synthetic triterpenoids inhibit growth and induce apoptosis in human glioblastoma and neuroblastoma cells through inhibition of prosurvival Akt, NF-κB and Notch1 signaling," *J. of Neuro-oncology*, 84 (2): 147-157, 2007.
Grant et al., "Boron trifluoride catalyzed rearrangements of novel epoxide derivatives of manool and manoyl oxide," *Australian Journal of Chemistry*, 46 (8): 1125-1145, 1993.
Grieco and Speake, "Synthetic Studies on Quassinoids: Total Synthesis and Biological Evaluation of (+)-Des-D-chaparrinone," *J. Org. Chem.*, 63:5929-5936, 1998.
Guix et al., "The physiology and pathophysiology of nitric oxide in the brain", *Prog. Neurobiol.*, 76:126-152, 2005.
Hail et al., "Evidence supporting a role for calcium in apoptosis induction by the synthetic triterpenoid 2-cyano-3,12-dioxooleana-1,9-dien-28-oic acid (CDDO)," *J. Biol. Chem.*, 279:11179-11187, 2004.
Han et al., "CDDO-Imidazolide inhibits growth and survival of c-Myc-induced mouse B cell and plasma cell neoplasms," *Molecular Cancer*, 5:22, 2006.
Hayes and McMahon, "NRF2 and KEAP1 mutations: permanent activation of an adaptive response in cancer", *Trends Biochem. Sci.*, 34(4):176-88, 2009.
Hill et al., "Synthetical approaches to the pristimerin chromophore," *J. of the Chemical Society*, 361-375, 1965.
Hirota et al., "Suppression of tumor promoter-induced inflammation of mouse ear by ursolic acid and 4,4-dimethycholestane derivatives," *Agric. Biol. Chem.*, 54:1073-1075, 1990.
Hirota et al., "Total synthesis of (±)-amarolide, a quassinoid bitter principle," *J. Org. Chem.*, 56:1119-1127, 1991.
Honda et al., "A novel dicyanotriterpenoid, 2-cyano-3,12-dioxooleana-1,9(11)-dien-28-onitrile, active at picomolar concentrations for inhibition of nitric oxide production," *Bioorg. Med. Chem. Lett.*, 12:1027-1030, 2002.
Honda et al., "An efficient synthesis of tricyclic compounds (+)-(4aβ, 8aβ, 10α)-1,2,3,4,4a,6,7,8,8a,9,1-,10a-Dodecahydro-1,1,4a-Trimethyl-2-Oxophenanthrene-8a-Carboxolic acid, its methyl ester, and (+)-(4aβ,8aβ, 10aα)-3,4,4a,6,7,8,8a,9,10,10a-Decahydro-8a, hydroxymethyl-1,1,4a-trimethylphenanthren-2(1H)-one," *Org. Prep. Proced. Int.*, 37(6): 546-550. 2005.
Honda et al., "Design and synthesis of 23, 24-dinoroleanolic acid derivatives, novel triterpenoid-steroid hybrid molecules," *J. Org. Chem.*, 63:4846-4849, 1998.
Honda et al., "Design and synthesis of 2-cyano-3,12-dioxoolean-1,9-dien-28-oic acid, a novel and highly active inhibitor of nitric oxide production in mouse macrophages," *Bioorg Med Chem Lett.*, 8(19):2711-2714, 1998.
Honda et al., "Design, synthesis, and biological evaluation of biotin conjugates of 2-cyano-3,12-dioxooleana-1,9(11)-dien-28-oic acid for the isolation of the protein targets," *J. Med. Chem.*, 47 (20): 4923-4932, 2004.
Honda et al., "Efficient synthesis of (−)- and (+)-tricyclic compounds with enome functionalities in rings A and C. A novel class of orally active anti-inflammatory and cancer chemopreventive agents," *Org Biomol Chem.*, 1:4384-4391, 2003.
Honda et al., "New enone derivatives of oleanolic acid and ursolic acid as inhibitors of nitric oxide production in mouse macrophages," *Bioorg. Med. Chem. Lett.*, 7:1623-1628, 1997.
Honda et al., "New synthetic oleanane and arsane triterpenoids as inhibitors of nitric oxide production in mouse macrophages," The Fifth Chemical Congress of North America, Cancun, Mexico, Abstract 552 and slides for oral presentation, Nov. 1997.
Honda et al., "Novel synthetic oleanane and ursane triterpenoids with various enone functionalities in ring A as inhibitors of nitric oxide production in mouse macrophages," *J. Med. Chem.*, 43:1866-1877, 2000.
Honda et al., "Novel synthetic oleanane triterpenoids: a series of highly active inhibitors of nitric oxide production in mouse macrophages," *Bioorg Med Chem Lett*, 9(24):3429-3434, 1999.
Honda et al., "Novel tricyclic compounds having acetylene groups at C-8a and cyano enones in rings A and C: highly potent anti-inflammatory and cytoprotective agents," *J. Med. Chem.*, 50:1731-1734, 2007.
Honda et al., "Revision and confirmation of the regiochemistry of isoxazoles derived from methyl oleanonate and lanost-8-en-3-one. Synthesis of a new lanostane triterpenoid with a cyano-enone functionality in ring A," *J. Org. Chem.*, 68:4991-4993, 2003.
Honda et al., "Synthesis of (±)-3,3-ethylenedioxy-14a-hydroxy-S-picrasene-11,16-dione, a 14aH-picrasane derivative," *Chem. Lett.*, 299-302, 1981.
Honda et al., "Synthesis of a novel dicyano abietane analogue: a potential antiinflammatory agent," *J. Org. Chem.*, 71:3314-3316, 2006.
Honda et al., "Synthetic oleanane and ursane triterpenoids with modified rings A and C: A series of highly active inhibitors of nitric oxide production in mouse macrophages," J. Med. Chem., 43:4233-4246, 2000.
Hong et al., "Phase I trial of a novel oral NF-κB/pSTAT3 inhibitor RTA-402 in patients with solid tumors and lymphoid malignancies," 44th Annual Meeting of the American Society of Clinical Oncology, 2008.
Hu et al., "The IL-17 pathway as a major therapeutic target in autoimmune diseases", *Ann. N.Y. Acad. Sci.*, 1217:60-76, 2011.
Huerta et al., "Characterization of novel small-molecule NRF2 activators: Structural and biochemical validation of stereospecific KEAP1 binding," *Biochim. Biophys. Acta*, 1860:2537-2552, 2016.
Hyer et al., "Synthetic triterpenoids cooperate with tumor necrosis factor-related apoptosis-inducing ligand to induce apoptosis of breast cancer cells," *Cancer Res.* 65:4799-4808, 2005.
Ikeda et al., "Induction of redox imbalance and apoptosis in multiple myeloma cells by the novel triterpenoid 2-cyano-3,12-dioxoolean-1,9-dien-28-oic acid," *Mol. Cancer Ther.*, 3:39-45, 2004.
Ikeda et al., "The novel triterpenoid CDDO and its derivatives induce apoptosis by disruption of intracellular redox balance," *Cancer Res.*, 63:5551-5558, 2003.
Ikeda et al., "Triterpenoid CDDO-Im downregulates PML/RAR αexpression in acute promyelocytic leukemia cell," *Cell Death and Differentiation*, 12 (5): 523-531, 2005.
Inoue et al., "CDDO induces apoptosis via the intrinsic pathway in lymphoid cells," *Leukemia*, 18 (5): 948-952, 2004.
International Search Report and Written Opinion issued in corresponding PCT Application No. PCT/US2020/042788, mailed on Oct. 23, 2020.
Ito et al., "Involvement of caspase-8 in the induction of osteosarcoma cell apoptosis by the novel triterpenoid CDDO," 47th Annual Meeting, Orthopaedic Research Society, Feb. 25-28, 2001, San Francisco, California, p. 0863, Poster Session, 2001.
Ito et al., "The novel triterpenoid 2-cyano-3, 12-dioxoolean-1,9-dien-28-oic acid induces apoptosis of human myeloid leukemia

(56) References Cited

OTHER PUBLICATIONS cells by a caspase-8-dependent mechanism," *Cell Growth & Differentiation*, 11(5):261-267, 2000.

Ito et al., "The novel triterpenoid CDDO induces apoptosis and differentiation of human osteosarcoma cells by a caspase-8 dependent mechanism," *Mol. Pharmacol.*, 59:1094-1099, 2001.

Ivanov et al., "The orphan nuclear receptor RORγt directs the differentiation program of proinflammatory IL-17+ T helper cells", *Cell*, 126:1121-1133, 2006.

Iwakura and Ishigame, "The IL-23/IL-17 axis in inflammation", 116(5):1218-1222, 2006.

Jang et al., "24-nor-ursane type triterpenoids from the stems of Rumex japonicus," *Chem. Pharm Bull (Tokyo)*, 53(12): 1594-1596, 2005.

Ji et al., "The synthetic triterpenoid CDDO-imidazolide induces monocytic differentiation by activating the Smad and ERK signaling pathways in HL60 leukemia cells," *Molecular Cancer Therapeutics*, 5 (6): 1452-1458, 2006.

Johansen et al., "Pharmacology and preclinical pharmacokinetics of the triterpenoid CDDO methyl ester," *Proc. Amer. Assoc. Cancer Res.*, 44:1728, 2003.

Johns et al., "Triterpenes of *lantanta tillaefolia*, 24-hydroxy-3-oxours-12-en-28-oic acid, a new triterpene," 36:2537-2547, 1983.

Kahne and Collum, "Kinetic cyanations of ketone enolates," *Tetrahedron Lett.*, 22:5011-5014, 1981.

Kamal et al., "23-oxoisopristimerin III: an new natural phenolic (9→8)-24-nor-D:A-friedo-oleanane triterpene," *Tetrahedron Letters*, 24(27):2799-2800, 1983.

Kamal et al., "Structures of two new phenolic 24-nor-D:A-friedoleananes related to zeylasterone: a partial synthesis of trimethylzeylasterone," *Tetrahetron Letters*, 24(19): 2025-2028, 1983.

Kamal et al., "The structure of zeylasterone, the first of a new series of phenolic 24-nor-D: A friedo-oleanane triterpenes," *Tetrahedron Letters*, 21(49): 4749-4752, 1980.

Kansanen et al., "Regulation of Nrf2-dependent gene expression by 15-deoxy-Δ12,14-prostaglandin J2," *Free Radic. Biol. Med.*, 47(9):1310-7, 2009.

Khalid et al., "Isolation and characterization of pristimerin as the antiplasmodial and antileishmanial agent of maytenus senegalensis (Lam.) Exell," *ARKIVOC*, 129-134, 2007.

Kim et al., "An inducible pathway for degradation of FLIP protein sensitizes tumor cells to TRAIL-induced apoptosis," *J. of Biological Chemistry*, 277 (25): 22320-22329, 2002.

Kim et al., "Caspase-3 activation is involved in apoptosis induced by a synthetic triterpenoid in Non-small cell lung cancer (NSCLC) cells," *Proc. Amer. Assoc. Cancer Res.*, 41:770, Abstract #4894, 2000.

Kim et al., "Identification of a novel synthetic triterpenoid, methyl-2-cyano-3,12-dioxooleana-1,9-dien-28-oate, that potently induces caspase-mediated apoptosis in human lung cancer cells," *Molecular Cancer Therapeutics*, 1:177-184, 2002.

Kincl et al., "Pituitary gonadotropin inhibitory action of neutral steroids," *Acta. Endocrinologica*, 46: 300-306, 1964.

Kircher, "Triterpenes, in organ pipe cactus," *Phytochemistry*, 19:2707-2712, 1980; Database CAPLUS on STN AN:1981:550946.

Klyne et al., "The molecular rotations of polyclyclic compounds. III. Polyelyclic alcohols and their derivatives," *J Chem Soc.*, 1979-1988, 1954.

Kobayashi et al., "The antioxidant defense system Keap1-Nrf2 comprises a multiple sensing mechanism for responding to a wide range of chemical compounds," *Mol. Cell Biol.*, 29(2):493-502, 2009.

Kolak et al., "Antioxidant and anticholinesterase constituents of Salvia poculata," *Turkish Journal of Chemistry*, 33(6): 813-823, 2009.

Konopleva et al., "Activation of nuclear transcription factor PPARγ by the novel triterpenoid CDDO as targeted therapy in breast cancer," 2002 Keystone Symposium, Abstract No. 539, 2002.

Konopleva et al., "Mechanisms and Activity of PPARγ-Active Triterpenoids CDDO and CDDO-Me in Leukemias," *Blood*, 106:2460, 2005.

Konopleva et al., "Novel synthetic triterpenoid CDDO-Me: potent antiproliferative, proapoptotic and differentiating agent in AML," *Blood*, 96(11), Part 1: 121A, abstract # 522, 2000.

Konopleva et al., "Novel synthetic triterpenoid, CDDO, and its methyl ester: Potent antiproliferative, proapoptotic and differentiating agents in AML," *Blood*, 94(Suppl 1):479a, Abstract #2140, 1999.

Konopleva et al., "Novel triterpenoid CDDO-Me is a potent inducer of apoptosis and differentiation in acute myelogenous leukemia," *Blood*, 99(1):326-335, 2002.

Konopleva et al., "Peroxisome proliferator-activated receptor γ and retinoid X receptor ligands are potent inducers of differentiation and apoptosis in leukemias," *Mol. Cancer Ther.*, 3:1249-1262, 2004.

Konopleva et al., "PPARγ Ligand CDDO Induces Apoptosis in Leukemias Via Multiple Apoptosis Pathways," Abstracts of the 44th Annual Meeting of the American Society of Hematology, Abstract No. 2209, 2002.

Konopleva et al., "PPARγ Ligands Are Potent Inducers of Apoptosis in Leukemias and Lymphomas," American Society of Hematology 43rd Annual Meeting and Exposition, Abstract No. 501, 2001.

Konopleva et al., "PPARγ Nuclear Receptor as a Novel Molecular Target in Leukemia Therapy," *Proc. Amer. Assoc. Cancer Res.*, 43:4730, 2002.

Konopleva et al., "PPARγ nuclear receptor as a novel therapeutic target in AML," Blood, 96(11):460a, Abstract #1982, 2000.

Konopleva et al., "PPARγ nuclear receptor as a novel therapeutic target in AML," Proc. of the AACR, 42, Abstract #4458, 2001.

Konopleva et al., "Suppression of ERK Activation is Required for Triterpenoid Methyl-CDDO-Induced Apoptosis in AML," *Blood*, 102(11):1404, 2003.

Konopleva et al., "Synthetic triterpenoid 2-cyano-3,12-dioxooleana-1,9-dien-28-oic acid induces growth arrest in HER2-overexpressing breast cancer cells," *Mol. Cancer Ther.*, 5:317-328, 2006.

Konopleva et al., "Synthetic triterpenoid CDDO as a novel therapy for resistant breast cancer," *Proc. Amer. Assoc. Cancer Res.*, 44:2726, 2003.

Konopleva et al., "The novel triterpenoid CDDO-Me suppresses MAPK pathways and promotes p38 activation in acute myeloid leukemia cells," *Leukemia*, 19:1350-1354, 2005.

Konopleva et al., "The synthetic triterpenoid 2-cyano-3,12-dioxooleana-1,9-dien-28-oic acid induces caspase-dependent and -independent apoptosis in acute myelogenous leukemia," *Cancer Res.*, 64:7927-7935, 2004.

Korovin and Tkachev, "Synthesis of quinoxalines fused with triterpenes, ursolic acid and betulin derivatives," *Russian Chemical Bulletin*, (*Translation of Izvestiya Akademii Nauk, Seriva Khimicheskaya*), 20 (2): 304-310, 2001.

Koschmieder et al. "CDDO induces granulocytic differentiation of myeloid leukemic blasts through translational up-regulation of p42 CCAAT enhancer-binding protein alpha," *Blood*, 110 (10): 3695-3705, 2007.

Kress et al., "Triterpenoids display single agent activity in a mouse model of CLL/SBL," *Blood*, 108(11):2530, 2006.

Kress et al., "Triterpenoids display single agent anti-tumor activity in a transgenic mouse model of chronic lymphocytic leukemia and small B cell lymphoma," *PLOS One*, 6(e559):1-11, 2007.

Kurinna et al., "The novel triterpenoid CDDO-Me promotes apoptosis in Gleevec-resistant chronic myeloid leukemia cells by caspase-independent mechanisms," *Proc. Amer. Assoc. Cancer Res.*, 46:2240, 2005.

Kutschabsky et al., "Molecular and crystal structure of a new 24-nor triperpenoid carboxylic acid from Acanthopanax trifoliatus," *Croatica Chemica Acta*, 58(4): 427-434, 1986.

Lapillonne et al., "Activation of peroxisome proliferator-activated receptor γ by a novel synthetic triterpenoid 2-cyano-3,12-dioxooleana-1,9-dien-28-oic acid induces growth arrest and apoptosis in breast cancer cells," *Cancer Res.*, 63:5926-5939, 2003.

Larock et al., "Carbocycle synthesis via carbopalladation of nitriles," *J. of the American Chemical Society*, 121 (13): 3238-3239, 1999.

(56) References Cited

OTHER PUBLICATIONS

Lavie et al., "Studies on epoxides. IV. Rearrangements in triterpenoids," *Tetrahedron Letters*, 17: 2097-2100, 1968.
Lavie et al., "Tetranortriterpenoids from Melia azadirachta," *Chemical Communications*, 6:278-280, 1967.
Lei et al., "Regulatory T cell-mediated anti-inflammatory effects promote successful tissue repair in both indirect and direct manners," *Front, Pharmacol.*, 6(184):1-10, 2015.
Li and Förstermann, "Nitric oxide in the pathogenesis of vascular disease", *J. Pathol.*, 190:244-254, 2000.
Li et al., "Terpenoids from tripterygium wilfordii," *Phytochemistry*, 45(4): 791-796, 1997.
Liby et al., "Novel semisynthetic analogues of betulinic acid with diverse cytoprotective, antiproliferative, and proapoptotic activities," *Mol. Cancer. Ther.*, 6(7): 2113-2119, 2007.
Liby et al., "The rexinoid LG100268 and the synthetic triterpenoid CDDO-methyl amide are more potent than erlotinib for prevention of mouse lung carcinogenesis," *Mol. Cancer Ther.*, 7:1251-1257, 2008.
Liby et al., "The synthetic triterpenoid CDDO-Imidazolide suppresses STAT phosphory lation and induces apoptosis in myeloma and lung cancer cells," *Clinical Cancer Research*, 12 (14 Part 1): 4288-4293, 2006.
Liby et al., "The synthetic triterpenoids CDDO-Methyl ester and CDDO-ethyl amide prevent lung cancer induced by vinyl carbamate in A/J mice," *Cancer Research*, 67 (6): 1-7, 2007.
Liby et al., "The synthetic triterpenoids, CDDO and CDDO-imidazolide, are potent inducers of here oxygenase-1 and Nrf2/ARE signaling," *Cancer Res.*, 65:4789-4798, 2005.
Liby et al., "Triterpenoids and rexinoids as multifunctional agents for the prevention and treatment of cancer," *Nat. Rev. Cancer*, 7 (5): 357-369, 2007.
Ling et al., "The novel triterpenoid C-28 methyl ester of 2-cyano-3, 12-dioxoolen-1, 9-dien-28-oic acid inhibits metastatic murine breast tumor growth through inactivation of STAT3 signaling," *Cancer Res.*, 67:4210-4218, 2007.
Ling et al., "The novel triterpenoid CDDO-Me inhibits metastatic murine breast tumor through inhibition of Stat3 signaling," 2007 AACR Annual Meeting, Abstract No. 301, 2007.
Liu et al,. "New lupane-type triterpenoid saponins from leaves of Oplopanax horridus (Devil's Club)," *Nat Prod Comm.*, 5(7): 1019-1022, 2010.
Liu et al., "Chemical constituents from root of rubus irenaeus," *Zhongcaoyao*, 34 (5): 394-396, 2003.
Marples and Spilling, "Ene reactions of unsaturated acyloins," *Tetrahedron Letters*, 26 (52): 6515-6518, 1985.
Marples and Spilling, "Facile intramolecular ene reactions of steroidal unsaturated acyloins," *Tetrahedron*, 48 (19): 4017-4026, 1992.
Martinez et al., "Regulation and Function of Proinflammatory TH17 Cells," *Ann. N.Y. Acad Sci.*, 1143:188-211, 2008.
Melichar et al., "Growth-inhibitory effect of a novel synthetic triterpenoid, 2-cyano-3,12-dioxoolean-1,9-dien-28-oic acid, on ovarian carcinoma cell lines not dependent on peroxisome proliferator-activated receptor-γ expression," *Gynecologie Oncology*, 93:149-154, 2004.
Mencherini et al., "Triterpenoid constituents from the roots of the Paeonia rockii ssp. rockii," *J Nat Prod.*, 74(10): 2116-2121, 2011.
Minns et al., "A novel triterpenoid induces transforming growth factor β production by intraepithelial lymphocytes to prevent ileitis," *Gastroenterology*, 127:119-126, 2004.
Mix et al., "A synthetic triterpenoid selectively inhibits the induction of matrix metalloproteinases 1 and 13 by inflammatory cytokines," *Arthritis Rheum.*, 44:1096-1104, 2001.
Mix et al., "Peroxisome proliferator-activated receptor-γ-independent repression of collagenase gene expression by 2-cyano-3,12-dioxooleana-1,9-dien-28-oic acid and prostaglandin 15-deoxy-delta(12,14) J2: a role for Smad signaling," *Mol. Pharmacol.*, 65(2): 309-318, 2004.

Murphy et al., "Immunomodulatory Effects of the Triterpenoid CDDO after Allogeneic Bone Marrow Transplantation in Mice: Reduction of Acute Graft-Versus-Host Disease Lethality," *Blood*, 106:1316, 2005.
Murray and Zweifel, "Preparation of Phenyl Cyanate and Its Utilization for the Synthesis of α, β-Unsaturated Nitriles," *Synthesis*, 150-151, 1980.
Muzart, "Synthesis of unsaturated carbonyl compounds via a chromium-mediated allylic oxidation by 70% tert.butylhydroperoxide," *Tetrahedron Lett.*, 28:4665-4668, 1987.
Na and Surh et al., "Transcriptional regulation via cysteine thiol modification: a novel molecular strategy for chemoprevention and cytoprotection," *Mol. Carcinog.*,45 (6): 368-380, 2006.
Nair et al., "Triterpenes. XLVII. Oxidation rates of triterpenoid secondary alcohols with chromic acid," *Collection of Czechoslovak Chemical Communications*, 41(3): 770-779, 1976.
Nanduri et al., "Biological investigation and structure-activity relationship studies on azadirone from azadirachta indica A. juss," *Bioorganic and Medicinal Chemistry*, 13 (22): 4111-4115, 2003.
Nelson et al., "Oxidative demethylation at C-4 of a steroid via nitroxide photolysis," *J. of the American Chemical Society*, 97 (3): 648-649, 1975.
Niikura et al., "The effects of synthetic triterpenoids on superficial zone protein synthesis in articular chondrocytes," Abstract, *Orthopedic Research Society*, San Diego, 2007.
Niikura et al., "The effects of synthetic triterpenoids on szp synthesis in articular chondrocytes," Abstract P197, *Osteoarthritis and Cartilage*, 14(Suppl B):S112-S113, 2006.
Nishimura et al., "Activity-guided isolation of triterpenoid acyl CoA cholesteryl acyl transferase (ACAT) inhibitors from Ilex kudincha," *J Nat Prod.*, 62(7): 1061-1064, 1999.
Nishino et al., "Inhibition of the tumor-promoting action of 12-O tetradecanoylphorbol-13-acetate by some oleanane-type triterpenoid compounds," *Cancer Res.*, 48:5210-5215, 1988.
Osburn et al., "Genetic of pharmacologic amplification of Nrf2 signaling inhibits acute inflammatory liver injury in mice," *Toxicological Sciences*, 104:218-227, 2008.
Ovemell and Whitehurts, "Reactions of steroid A-ring lactones with Grignard reagents," *J. of the Chemical Society [Section] C: Organic*, 2: 378-384, 1971.
Pappas et al., "Photoisomerization of phenalen-1-one oxide. New course of light-induced alpha beta-epoxy ketone rearrangement," *J. of the American Chemical Society*, 92 (19): 5797-5798, 1970.
Peakman et al., "Characterization of 24-nor-triterpenoids occurring in sediments and crude oils by comparison with synthesized standards," *Tetrahedron*, 47(23): 3779-3786, 1991.
Pedersen et al., "The triterpenoid CDDO induces apoptosis in refractory CLL B cells," *Blood*, 100:2965-2972, 2002.
Place et al., "The novel synthetic triterpenoid, CDDO-imidazolide, inhibits inflammatory response and tumor growth in vivo," *Clin. Cancer Res.*, 9:2798-2806, 2003.
Rasmusson et al., "Azasteroids: structure-activity relationships for inhibition of 5 α-reductase and of androgen receptor binding," *J. Med. Chem.*, 29 (11): 2298-2315, 1986.
Ray et al., "The novel triterpenoid 2-cyano-3,12-dioxooleana-1,9-dien-28-oic acid (CDDO) induces apoptosis of human diffuse large B-cell lymphoma cells through a peroxisome proliferator-activated receptor γ-independent pathway," *Exp. Hematology*, 34:1201-1210, 2006.
Reisman et., "RTA 1701 is an oral RORγt inhibitor that suppresses the IL-17A response in non-human primates," *J. Immunol.*, 200(1 Suppl.):175.22, 2018, (Abstract only).
Ribo et al., "Synthesis of methyl 1, 11-dioxooleanan-2, 12-dien-30-oate and its 24-nor derivative," *Afinidad*, 38(373): 197-200, 1981.
Ricciardolo et al., "Nitric oxide in health and disease of the respiratory system", *Physiol Rev.*, 84:731-765, 2004.
Rossi et al., "Anti-inflammatory cyclopentenone prostaglandins are direct inhibitors of IκB kinase," *Nature*, 403:103-108, 2000.
Rouquette et al., "A ring-D functionalized nor-triterpenoid of the lupane series as a key intermediate in the formation of widespread hydrocarbon derivatives of higher plant origin in petroleum," *Organic Geochemistry*, 36(9): 1227-1233, 2005.

(56) References Cited

OTHER PUBLICATIONS

Ruvolo et al., "The novel triterpenoid methyl-CDDO inhibits Bcl2 phosphorylation and potently kills U937 cells," Blood, 94(10), Suppl. 1, Part 1: 280A, abstract #1251, 1999.
Ruzicka et al., Triterpenes LXXXIX. Decomposition of hederagenin to the C26-stage, Helvetica Chimica Acta, 27:1185-1196, 1944. (Translation appended).
Samudio et al., "2, cyano-3,12 dioxoolean-1,9 diene-28-imidazolide induces apoptosis in pancreatic cancer via redox-dependent cytoplasmic stress," Proc. Amer. Assoc. Cancer Res., 46: Abstract No. 5899, 2005.
Samudio et al., "2-Cyano-3,12-dioxooleana-1,9-dien-28-imidazolide (CDDO-Im) directly targets mitochondrial glutathione to induce apoptosis in pancreatic cancer," J. Biol. Chem., 280:36273-36282, 2005.
Samudio et al., "A novel mechanism of action of methyl-2-cyano-3,12 dioxoolean-1,9 diene-28-oate (CDDO-Me): Direct permeabilization of the inner mitochondrial membrane to inhibit electron transport and induce apoptosis," Proc. Am. Assoc. Cancer Res., 47, Abstract 4693, 2006.
Samudio et al., "A novel mechanism of action of methyl-2-cyano-3, 12 dioxoolean-1,9 diene-28-oate: direct permeabilization of the inner mitochondrial membrane to inhibit electron transport and induce apoptosis," Mol. Pharmacol., 69:1182-1193, 2006.
Samudio et al., "The novel triterpenoid CDDOme potently synergizes with inhibition of bcl-2 function to induce apoptosis in AML via disruption of intracellular redox homeostasis," Proc. Amer. Assoc. Cancer Res., 46: Abstract No. 4955, 2005.
Satoh et al., "Activation of the Keap1/Nrf2 pathway for neuroprotection by electrophilic phase II inducers," PNAS, 103 (3): 768-773, 2006.
Scholz et al., "Sensitive and specific methods for the determination of CDDO methyl ester in mouse, rat, dog, monkey, and human plasma by LC-tandem mass spectrometry," Proc. Amer. Assoc. Cancer Res., 4: Abstract No. 6321, 2003.
Sharpless et al., "Electrophilic and nucleophilic organoselenium reagents. New routes to $\alpha,\beta$-unsaturated carbonyl compounds," J. Am. Chem. Soc., 95:6137, 1973.
Shin et al., "Inhibitory roles of NRF2 and an oleanolic triterpenoid on adipocyte differentiation and obesity," dissertation submitted to John Hopkins University in conformity with the requirements for the degree of Doctor of Philosophy, Mar. 2009.
Shin et al., "NRF2 modulates aryl hydrocarbon receptor signaling: influence on adipogenesis," Molecular and Cellular Biology, 27 (20): 7188-7197, 2007.
Shin et al., "Role of Nrf2 in prevention of high-fat diet-induced obesity by synthetic triterpenoid CDDO-imidazolide" Eur. J. Pharmacol., 620(1-3):138-144, 2009.
Shishodia et al., "A synthetic triterpenoid, CDDO-Me, inhibits IκBα kinase and enhances apoptosis induced by TNF and chemotherapeutic agents through down-regulation of expression of nuclear factor κB-regulated gene products in human leukemic cells," Clin Cancer Research, 12(6):1828-1838, 2006.
Siddiqui et al., "Kanerin and 12, 13-dihydroursolic acid, two new pentacyclic triterpenes from the leaves of Nerium oleander," J Nat Prod., 52(1): 57-62, 1989.
Simonsen et al., "Tetracyclic hydroxy acids," In the Terpenes, Cambridge University, Cambridge, 5:221-285, 1957.
Singh et al., "Anti-inflammatory activity of oleanolic acid in rats and mice," J. Pharm.Pharmacol., 44:456-458, 1992.
Spor and Liby, "NRF2 and cancer: the good, the bad and the importance of context", Nat. Rev. Cancer, 12(8):564-71, 2012.
Sporn and Roberts, "Peptide growth factors and inflammation, tissue repair, and cancer," J. Clin. Invest., 78:329-332, 1986.
Sporn et al., "Prospects for prevention and treatment of cancer with selective PPARγ modulators (SPARMs)," Trends in Molecular Medicine, 7(9):395-400, 2001.
Stadbeim et al., "The novel triterpenoid 2-cyano-3,12-dioxooleana-1,9-dien-28-oic acid (CDDO) potently enhances apoptosis induced by tumor necrosis factor in human leukemia cells," J. Biol. Chem., 277:16448-16455, 2002.
Subba Rao et al., "Chemical modifications of natural triterpenes—glycyrrhetinic and boswellic acids: evaluation of their biological activity," Tetrahedron, 64(51):11541-11548, 2008.
Suh et al., "A novel synthetic oleanane triterpenoid, 2-cyano-3,12-dioxoolean-1,9-dien-28-oic acid (CDDO), induces cell differentiation in human myeloid leukemias," Proceedings of the American Association for Cancer Research Annual Meeting, 40:300, abstract 1988.
Suh et al., "A novel synthetic oleanane triterpenoid, 2-cyano-3,12-dioxoolean-1,9-dien-28-oic acid, with potent differentiating, antiproliferative, and anti-inflammatory activity," Cancer Res., 59(2):336-341, 1999.
Suh et al., "New triterpenoids as cancer preventive and anti-inflammatory agents," Proceedings of the American Association for Cancer Research, Abstract No. 1457, 38:216, 1997.
Suh et al., "Novel triterpenoids suppress inducible nitric oxide synthase (iNOS) and inducible cyclooxygenase (COX-2) in mouse macrophages," Cancer Res., 58:717-723, 1998.
Suh et al., "Novel triterpenoids suppress inducible nitric oxide synthase (iNOS) and inducible cyclooxygenase (COX-2)," Proceedings of the American Association for Cancer Research Annual Meeting, 39: Abstract No. 1821, 1998.
Suh et al., "Synthetic triterpenoids activate a pathway for apoptosis in AML cells involving downregulation of FLIP and sensitization to Trail," Leukemia, 17:2122-2129, 2003.
Suh et al., "Synthetic triterpenoids enhance transforming growth factor β/Smad signaling," Cancer Res., 63:1371-1376, 2003.
Suh et al., "Triterpenoids CDDO and CDDO-Me Down-Regulate FLIP Expression and Sensitize AML Cells to Trail-Induced Apoptosis," American Society of Hematology 43rd Annual Meeting and Exposition, Abstract No. 498, 2001.
Sultana et al., "Phytochemical studies on Alstonia scholaris," Zeitschrift für Naturforschung. B, A Journal of Chemical Sciences, 65(2): 203-210, 2010.
San et al., "Structure-activity relationships of oleanan- and arsane-type triterpenoids," Botanical Studies, 47:339-368, 2006.
Sun et al., "The Synthetic Triterpenoid, CDDO, Suppresses Alloreactive T Cell Responses and Reduces Murine Early Acute Graft-versus-Host Disease Mortality," Biology of Blood and Marrow Transplantation, 13 (5): 521-529, 2007.
Tabe et al., "Chromatin-Mediated Transcriptional Activation with Novel Peroxisome Proliferator—Activated Receptor gamma(PPARγ) Ligand 2-cyano-1,9-dien-28-oic Acid (CDDO) in Acute Promyelocytic Leukemia Cells," Abstracts of the 44th Annual Meeting of the American Society of Hematology, Abstract 2191, 2002.
Thimmulappa et al., "Nrf2 is a critical regulator of the innate immune response and survival during experimental sepsis," J. Clinical Investigation, 116 (4): 984-995, 2006.
Thimmolappa et al., "Nrf2-dependent protection from LPS induced inflammatory response and mortality by CDDO-imidazolide," Biochem. Biophys. Res. Commun., 351:883-889, 2006.
Thimmulappa et al., "Preclinical evaluation of targeting the Nrf2 pathway by triterpenoids (CDDO-Im and CDDO-Me) for protection from LPS-induced inflammatory response and reactive oxygen species in human peripheral blood mononuclear cells and neutrophils," Antioxidants and Redox Signalling, 9:1-8, 2007.
Tran et al., "The synthetic triterpenoid CDDO-methyl ester modulates microglial activities, inhibits TNF production, and provides dopaminergic neuroprotection," Journal of Neuroinflammation, 5:1-14, 2008.
Tsao et al., "DRIP205 co-activator overexpression enhances PPARγ-mediated differentiation of leukemia cells by CDDO," Proc. Amer. Assoc. Cancer Res., 46: Abstract No. 1855, 2005.
Tsao et al., "Targeted Induction of Apoptosis in Leukemias by PPARγ Ligation," American Society of Hematology 43rd Annual Meeting and Exposition, Abstract No. 2381, 2001.
Urban et al., "Influence of esterification and modification of A-ring in a group of lupane acids on their cytotoxicity," Bioorganic and Medicinal Chemistry, 13 (19): 5527-5535, 2005.

(56) References Cited

OTHER PUBLICATIONS

Urban et al., "Synthesis of A-seco derivatives of betulinic acid with cytotoxic activity," *J. of Natural Products*, 67 (7): 1100-1105, 2004.
Uskoković et al., "D-Homosteroids. I. 3β-Hydroxy-17a,17a-dimethyl-D-homoandrostane-17-one and related compounds," *J. of the American Chemical Society*, 81: 4561-4566, 1959.
Vannini et al., "The synthetic oleanane triterpenoid, CDDO-methyl ester, is a potent antiangiogenic agent," *Molecular Cancer Therapeutics*, 6 (12 Part 1), 3139-3146, 2007.
Vilayur and Harris, "Emerging therapies for chronic kidney disease: what is their role?" *Nature Reviews*, 5:375-383, 2009.
Vincenti et al., "The synthetic triterpenoid TP-222 inhibits RANKL induction of differentiation and MMP-9 gene expression in osteoclasts," Abstract 1385, American College of Rheumatology Annual Scientific Meeting, 2006.
Wada and Tanaka, "Synthetic lanostane-type triterpenoids as inhibitors of DNA topoisomerase II," *Bioorganic and Medicinal Chemistry Letters*, 15(12):2966-2969, 2005.
Wang et al., "A novel synthetic triterpenoid, 2-cyano-3,12-dioxoolean-1,9-dien-28-oic acid (CDDO) induces adipocyte differentiation in 3T3-L1 cells," *Proceedings of the American Association for Cancer Research Annual Meeting*, 40:300, abstract # 1989, 1999.
Wang et al., "A synthetic triterpenoid, 2-cyano-3,12-dioxooleana-1,9-dien-28-oic acid (CDDO), is a ligand for the peroxisome proliferator-activated receptor γ," *Mol. Endocrin.*, 14(10):1550-1556, 2000.
Wang et al., "Synthetic triterpenoid CDDO and its derivatives increase ceramides and are cytotoxic to pediatric acute lymphoblastic leukemia cell lines," *Proc. Am. Assoc. Cancer Res.*, 47: 4643, 2006.
Wen et al., "Pentacyclic triterpenes. Part 2: Synthesis and biological evaluation of maslinic acid derivatives as glycogen phosphorylase inhibitors," *Bioorganic and Medicinal Chemistry Letters*, 16 (3): 722-726, 2006.
Wolff et al., "Novel monoaromatic triterpenoid hydrocarbons occurring in sediments," *Tetrahedron*, 45(21): 6721-6728, 1989.
Yan et al., "CNS-specific therapy for ongoing EAE by silencing IL-17 pathway in astrocytes", *Mol. Ther.*, 20(7):1338-1348, 2012.
Yates et al., "Pharmacodynamic characterization of chemopreventive triterpenoids as exceptionally potent indocers of Nrf2-regulated genes," *Mol. Cancer Ther.*, 6:154-162, 2007.
Yates et al., "Potent protection against aflatoxin-induced tumorigenesis through induction of Nrf2-regulated pathways by the triterpenoid 1-[2-cyano-3-,12-dioxooleana-1,9(11)-dien-28-oyl]imidazole," *Cancer Res.*, 66 (4): 2488-2494, 2007.
Yore et al., "The synthetic triterpenoid 1-[2-cyano-3,12-dioxooleana-1,9(11)-dien-28-oyl]imidazole blocks nuclear factor-κB activation through direct inhibition of IkappaB kinase β," *Mol. Cancer Ther.*, 5 (12): 3232-3239, 2006.
You et al., "Synthesis and cytotoxic activity of a-ring modified betulinic acid derivatives," *Bioorganic and Medicinal Chemistry Letters*, 13 (19): 3137-3140, 2003.
Yue et al., "Depletion of intracellular glutathione contributes to JNK-mediated death receptor 5 upregulation and apoptosis induction by the novel synthetic triterpenoid methyl-2-cyano-3, 12-dioxooleana-1, 9-dien-28-oate (CDDO-Me)," *Cancer & Biology Ther.*, 5(5):492-497, 2006.
Zapata et al., "CDDO and CDDO-Im Reduce Tumor Burden in a Transgenic Mouse Model of CLL," *Blood*, 104:3477, 2004.
Zapata et al., "Triterpenoids show activity against leukemic cells in a transgenic mouse model of CLL," *Proc. Amer. Assoc. Cancer Res.*, 46: Abstract No. 5179, 2005.
Zhang et al., "Synthetic triterpenoid CDDO as effective therapy for HER2-expressing resistant breast cancer," *Proc. Amer. Assoc. Cancer Res.*, Abstract No. 3799, 2004.
Zhang et al., "The novel synthetic oleanane triterpenoid CDDO (2-cyano-3, 12-dioxoolean-1, 9-dien-28-oic acid) induces apoptosis in Mycosis fungoides/Sézary syndrome cells," *J. Invest. Dermatol.*, 123:380-387, 2004.
Zhou et al., "A new triterpenoid from the roots of Tripterygium wildfordii," *Chinese Chemical Letters*, 21(5): 600-602, 2010.
Ziegler et al., "Isolation and Structure of Eucosterol and 16 β-Hydroxyeucosterol, Two Novel Spirocyclic Nortriterpenes, and of a New 24-Nor-5α-chola-8,16-diene-23-oic Acid from Bulbs of Several Encomis Species," *Helv Chim Acta*, 59(6):1997-2011, 1976.
Zou et al., "c-Jun NH2-terminal kinase-mediated up-regulation of death receptor 5 contributes to induction of apoptosis by the novel synthetic triterpenoid methyl-2-cyano-3,12-dioxooleana-1, 9-dien-28-oate in human lung cancer cells," *Cancer Res.*, 64:7570-7578, 2004.

\* cited by examiner

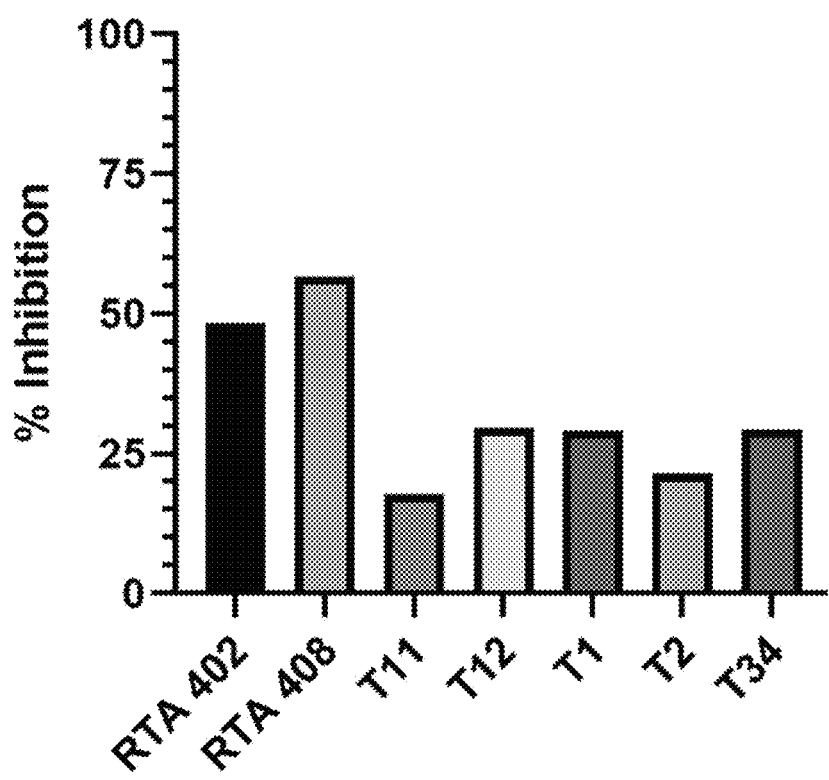

C17 POLAR-SUBSTITUTED HETEROAROMATIC SYNTHETIC TRITERPENOIDS AND METHODS OF USE THEREOF

This application claims the benefit of priority to U.S. Provisional Application No. 62/876,467, filed on Jul. 19, 2019, and 62/952,048, filed on Dec. 20, 2019, the entire contents of both of which are hereby incorporated by reference.

BACKGROUND OF THE INVENTION

I. Field of the Invention

The present invention relates generally to the fields of biology, chemistry, and medicine. More particularly, it concerns compounds, compositions and methods for the treatment and prevention of diseases and disorders such as those associated with oxidative stress and inflammation.

II. Description of Related Art

The anti-inflammatory and anti-proliferative activity of the naturally occurring triterpenoid, oleanolic acid, has been improved by chemical modifications. For example, 2-cyano-3,12-diooxooleana-1,9(11)-dien-28-oic acid (CDDO) and related compounds have been developed (Honda et al., 1997; Honda et al., 1998; Honda et al., 1999; Honda et al., 2000a; Honda et al., 2000b; Honda, et al., 2002; Suh et al. 1998; Suh et al., 1999; Place et al., 2003; Liby et al., 2005; and U.S. Pat. No. 6,326,507, 6,974,801, 7,435,755, 7,795,305, 7,863,327, 7,915,402, 7,943,778, 8,034,955, 8,071,632, 8,124,656, 8,124,799, 8,129,429, 8,338,618, 8,394,967, 8,440,820, 8,440,854, 8,455,544, 8,586,775, 8,993,640, 9,090,574, 9,102,681, 9,249,089, 9,278,912, 9,278,913, 9,290,536, 9,593,074, 9,701,709, 9,512,094, 9,556,222, 9,670,147, 9,757,359, 9,856,286, 9,889,143, 10,093,614, 10,105,372, 10,398,711, 10,501,489, or 10,556,858). Bardoxolone methyl (CDDO-Me; RTA 402) and omaveloxolone (RTA 408), have been evaluated clinically, including, for example, for the treatment of cancer, chronic kidney disease, pulmonary arterial hypertension, and Friedreich's Ataxia (Pergola et al., 2011; Hong et al., 2012; U.S. Pat. No. 8,993,640).

Synthetic triterpenoid analogs of oleanolic acid (OA) have also been shown to be inhibitors of cellular inflammatory processes, such as the induction by IFN-γ of inducible nitric oxide synthase (iNOS) and of COX-2 in mouse macrophages. See Honda et al. (2000a); Honda et al. (2000b), and Honda et al. (2002). Synthetic derivatives of another triterpenoid, betulinic acid, have also been shown to inhibit cellular inflammatory processes, although these compounds have been less extensively characterized (Honda et al., 2006). The pharmacology of these synthetic triterpenoid molecules is complex. Compounds derived from oleanolic acid have been shown to affect the function of multiple protein targets and thereby modulate the activity of several important cellular signaling pathways related to oxidative stress, cell cycle control, and inflammation (e.g., Dinkova-Kostova et al., 2005; Ahmad et al., 2006; Ahmad et al., 2008; Liby et al., 2007a). Derivatives of betulinic acid, though they have shown comparable anti-inflammatory properties, also appear to have significant differences in their pharmacology compared to OA-derived compounds (Liby et al., 2007b). Given that the biological activity profiles of known triterpenoid derivatives vary, and in view of the wide variety of diseases that may be treated or prevented with compounds having potent antioxidant and anti-inflammatory effects, and the high degree of unmet medical need represented within this variety of diseases, it is desirable to synthesize new compounds with diverse structures that may have improved biological activity profiles for the treatment of one or more indications.

SUMMARY OF THE INVENTION

The present disclosure provides novel synthetic triterpenoid derivatives with anti-inflammatory and/or antioxidant properties, pharmaceutical compositions, and methods for their manufacture, and methods for their use.

In one aspect, there are provided compounds of the formula:

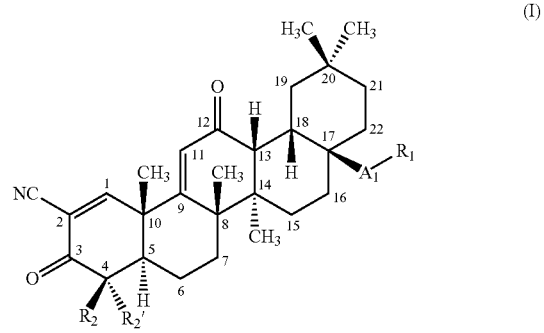

(I)

wherein:

$A_1$ is -heteroarenediyl$_{(C \leq 3)}$-;

$R_1$ is a polar-substituted alkyl$_{(C \leq 3)}$; and $R_2$ and $R_2'$ are each independently hydrogen or methyl;

or a pharmaceutically acceptable salt thereof.

In some embodiments, the compounds are further defined:

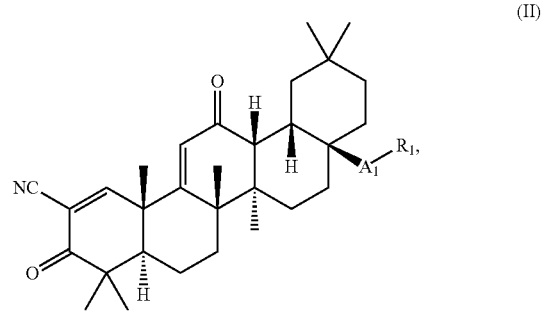

(II)

wherein:

$A_1$ is -heteroarenediyl$_{(C \leq 3)}$-; and $R_1$ is a polar-substituted alkyl$_{(C \leq 3)}$;

or a pharmaceutically acceptable salt thereof.

In some embodiments, the compounds are further defined:

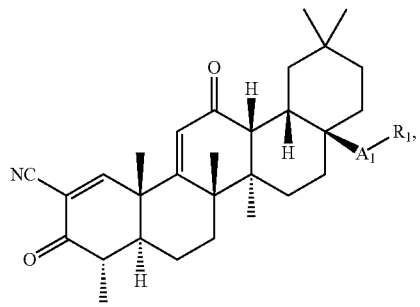

(III)

wherein:
$A_1$ is -heteroarenediyl$_{(C \leq 3)}$-;
$R_1$ is a polar-substituted alkyl$_{(C \leq 3)}$; and
or a pharmaceutically acceptable salt thereof.
In some embodiments, -$A_1$-$R_1$ is:

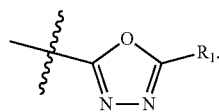

In other embodiments, -$A_1$-$R_1$ is:

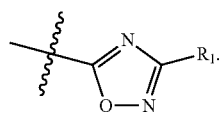

In still other embodiments, -$A_1$-$R_1$ is:

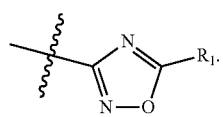

In yet other embodiments, -$A_1$-$R_1$ is:

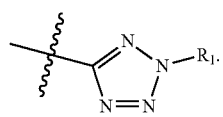

In some embodiments, $R_1$ is polar-substituted ethyl. In other embodiments, $R_1$ is polar-substituted methyl. In some embodiments, $R_1$ is monopolar-substituted alkyl$_{(C \leq 3)}$. In further embodiments, $R_1$ is monopolar-substituted ethyl. In other embodiments, $R_1$ is monopolar-substituted methyl. In some embodiments, $R_1$ is monoaminoalkyl$_{(C \leq 3)}$, monofluoroalkyl$_{(C \leq 3)}$, or monohydroxyalkyl$_{(C \leq 3)}$. In some embodiments, $R_1$ is monoaminoalkyl$_{(C \leq 3)}$, such as 2-aminoethyl, or aminomethyl. In other embodiments, $R_1$ is monofluoroalkyl$_{(C \leq 3)}$, such as 2-fluoroethyl or fluoromethyl. In still other embodiments, $R_1$ is monohydroxyalkyl$_{(C \leq 3)}$, such as 2-hydroxyethyl or hydroxymethyl. In yet other embodiments, $R_1$ is —CH$_2$CH$_2$NHC(O)OCH$_3$, CH$_2$CH$_2$NHC(O)NHCH$_2$CH$_3$, or —CH$_2$CH$_2$NHC(O)CH$_3$.

In some embodiments, is -$A_1$-$R_1$ is

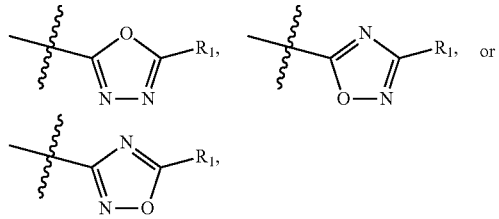

$R_1$ is aminomethyl, fluoromethyl, or hydroxymethyl, $R_2$ is hydrogen or methyl, and $R_2'$ is methyl. In some of these embodiments, -$A_1$-$R_1$ is

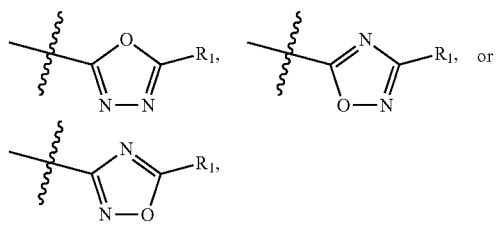

$R_1$ is fluoromethyl, $R_2$ is hydrogen or methyl, and $R_2'$ is methyl.

It is to be understood that the present invention specifically relates to each and every combination of features and embodiments described herein, including any combination of general and/or specific features/embodiments. In particular, the invention specifically relates to each combination of meanings (including general and/or specific meanings) for the various groups and variables comprised in formula (I).

In some embodiments, the compound is further defined as:

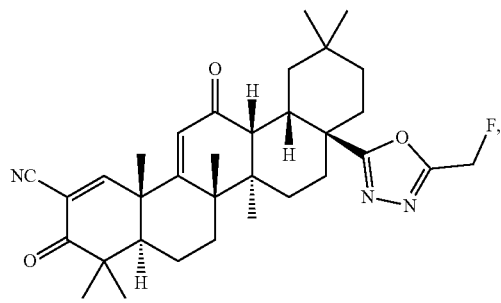

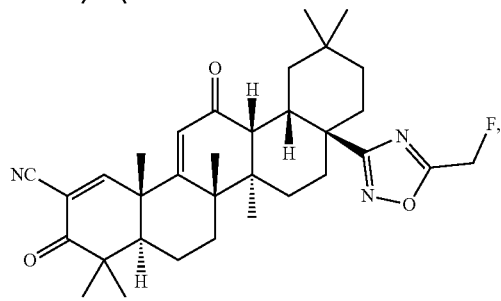

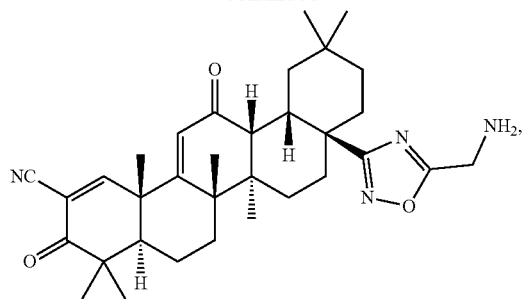
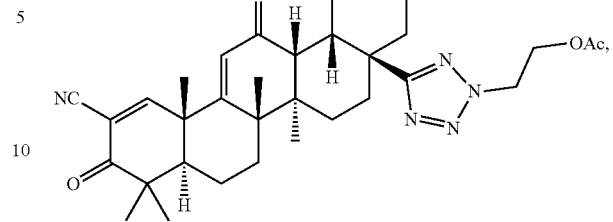
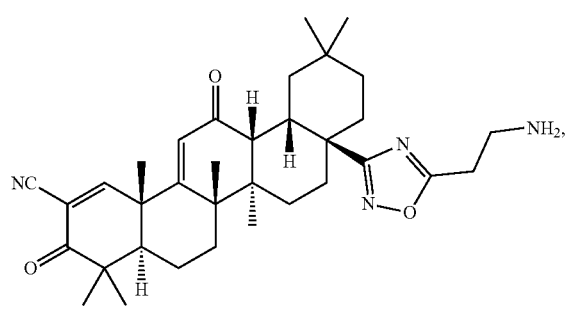
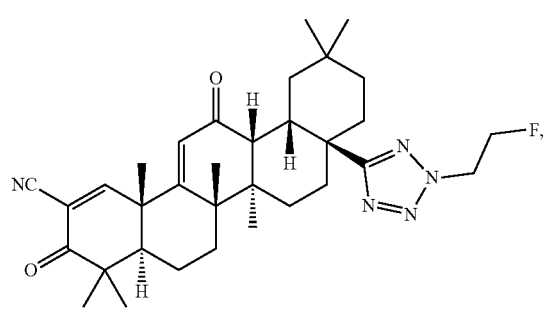
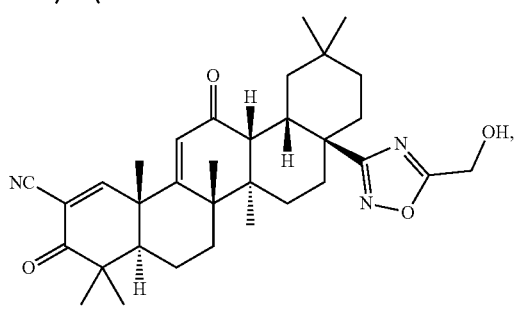
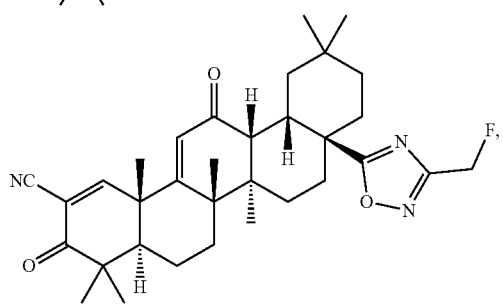
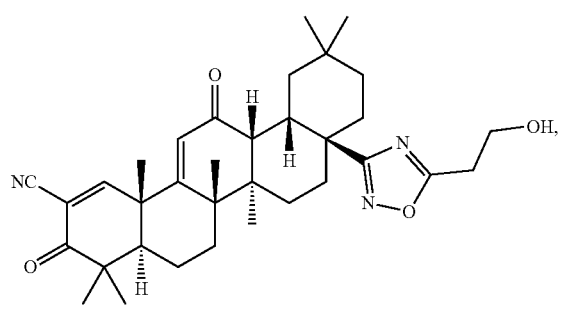
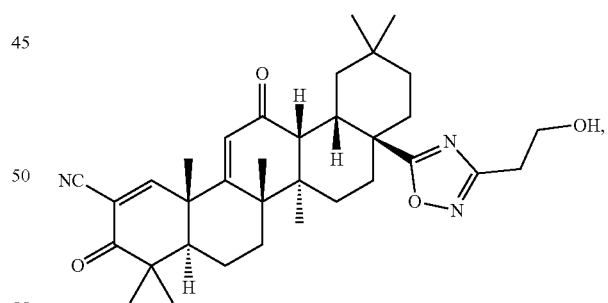
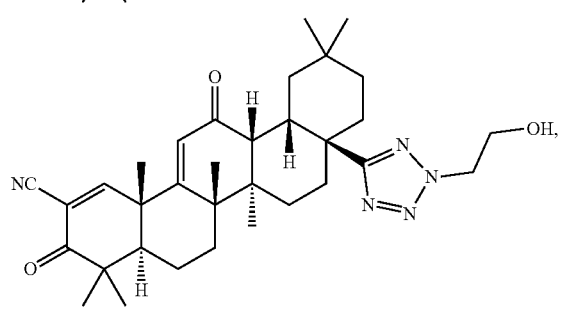
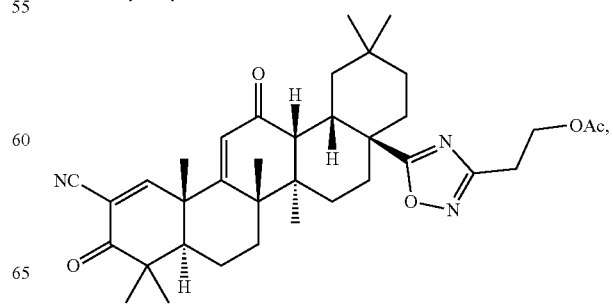

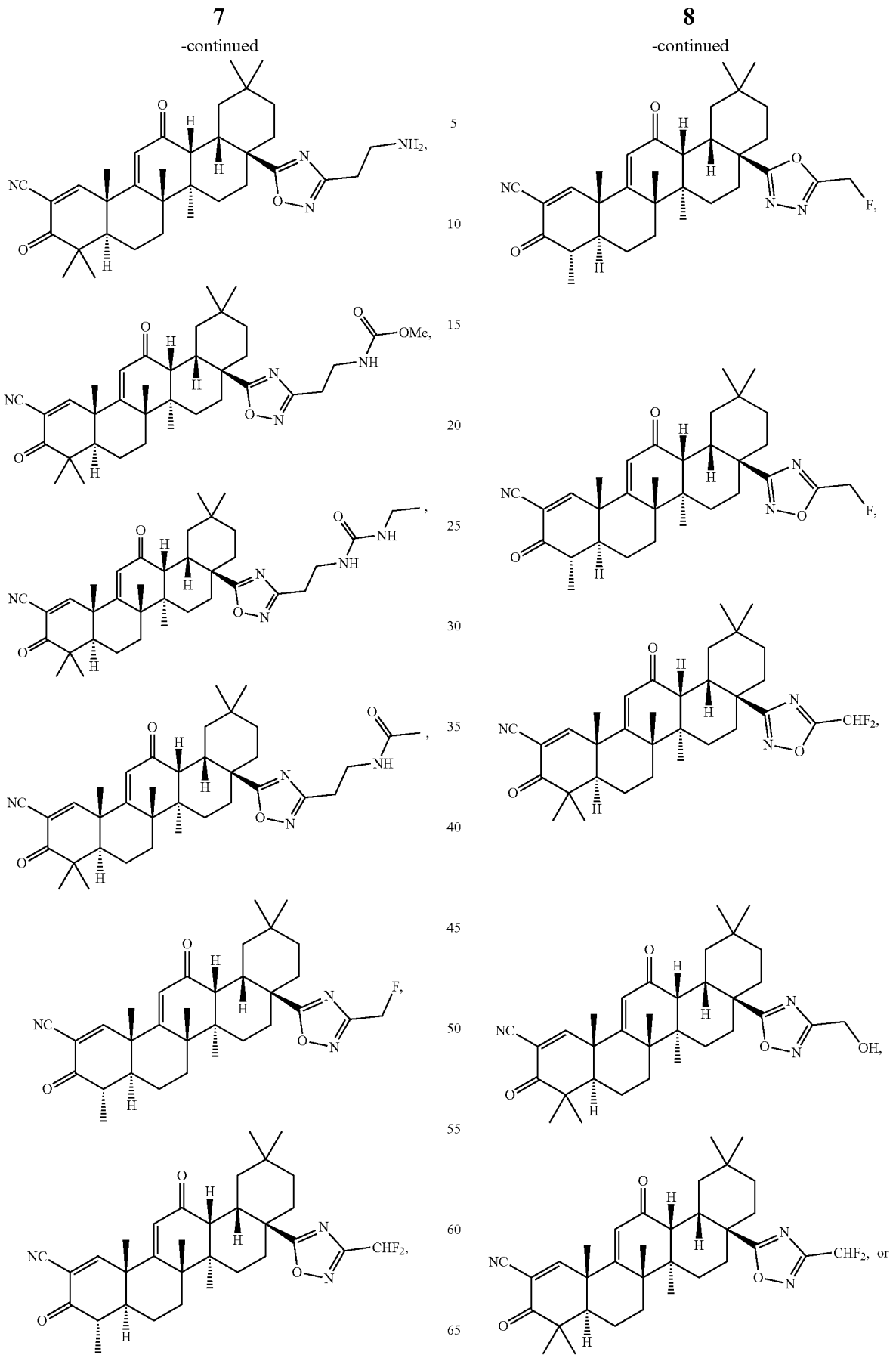

-continued
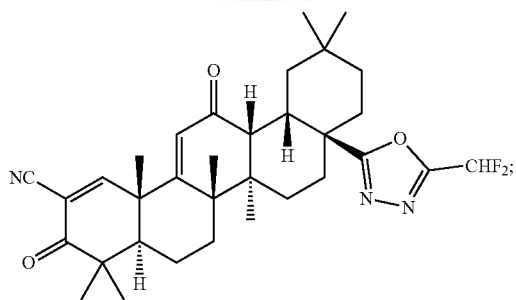
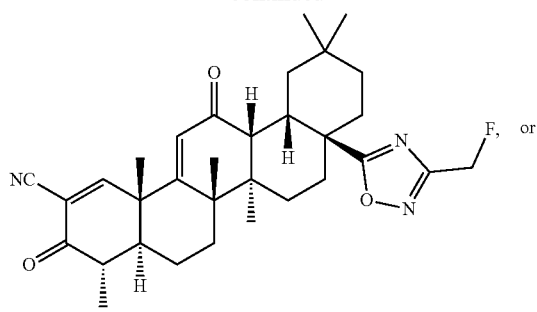
or a pharmaceutically acceptable salt of any of these formulas.
In further embodiments, the compound is further defined as:
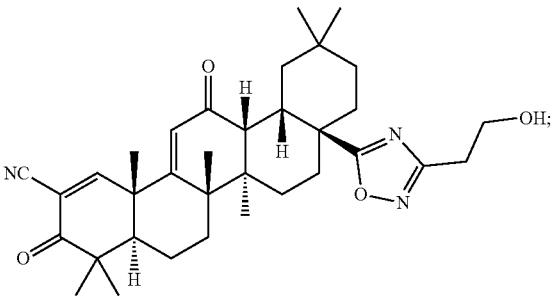
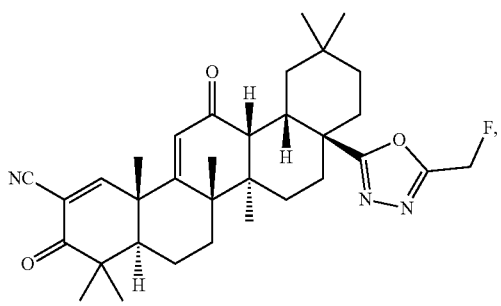
or a pharmaceutically acceptable salt of any of these formulas.
In still further embodiments, the compound is further defined as:
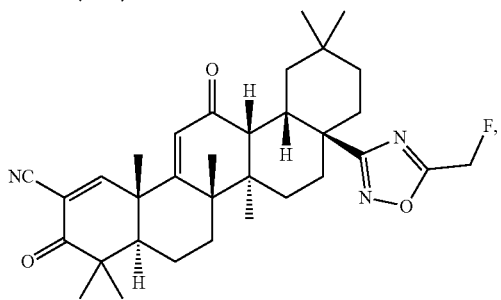
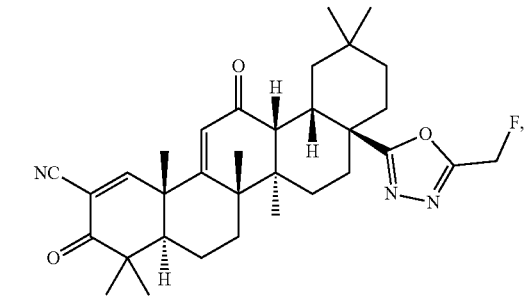
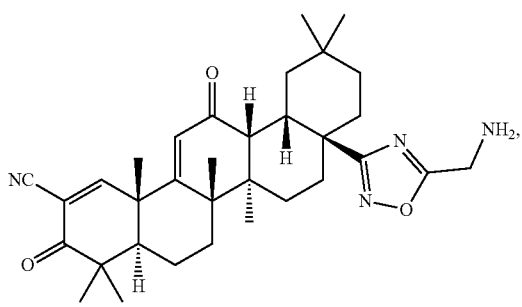
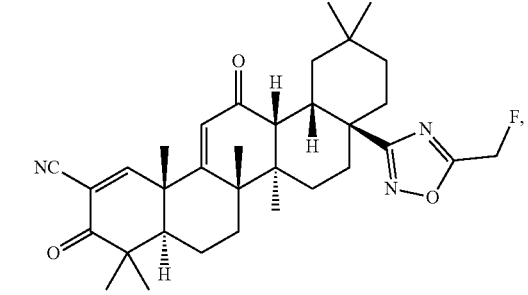
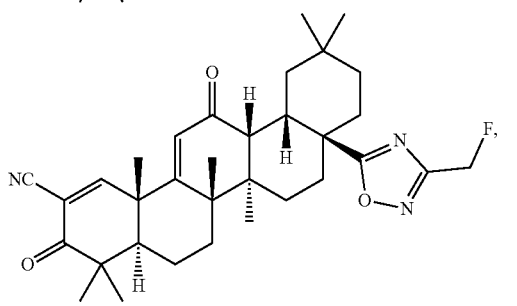
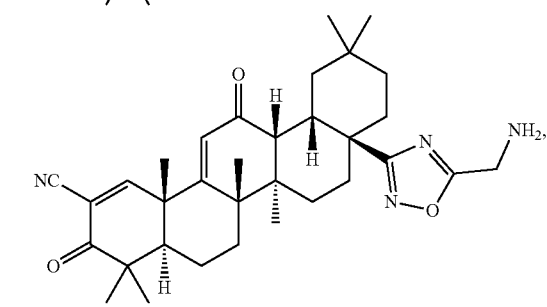

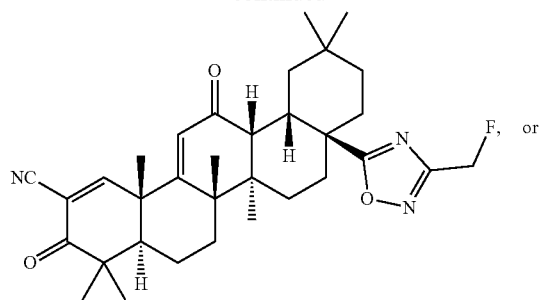

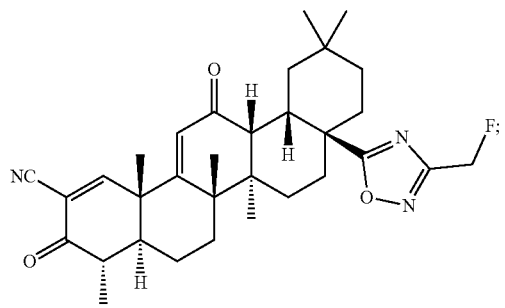

or a pharmaceutically acceptable salt of any of these formulas.

In yet further embodiments, the compound is further defined as:

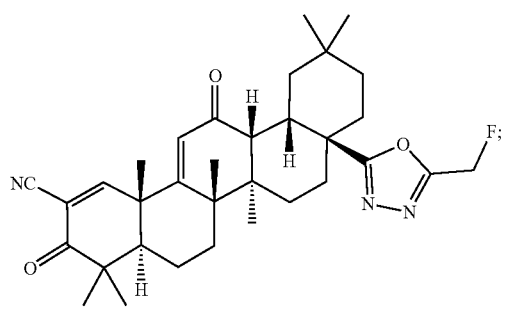

or a pharmaceutically acceptable salt thereof.

In other embodiments, the compound is further defined as:

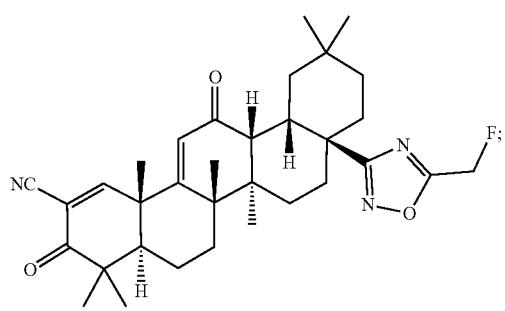

or a pharmaceutically acceptable salt thereof.

In still other embodiments, the compound is further defined as:

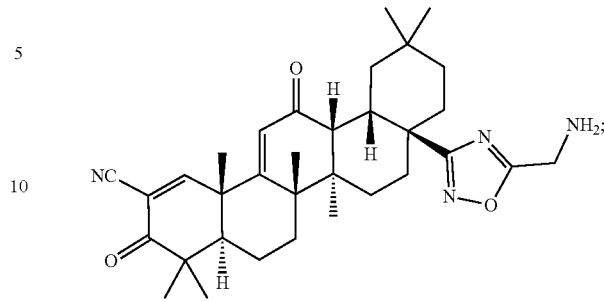

or a pharmaceutically acceptable salt thereof.

In yet other embodiments, the compound is further defined as:

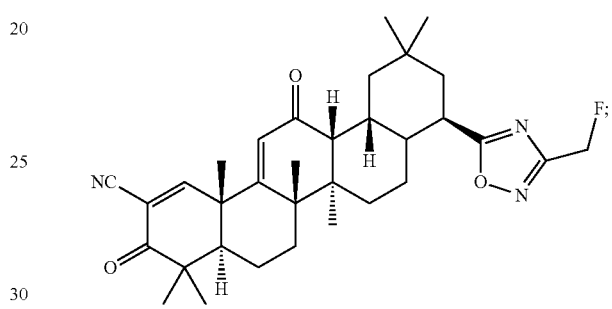

or a pharmaceutically acceptable salt thereof.

In other embodiments, the compound is further defined as:

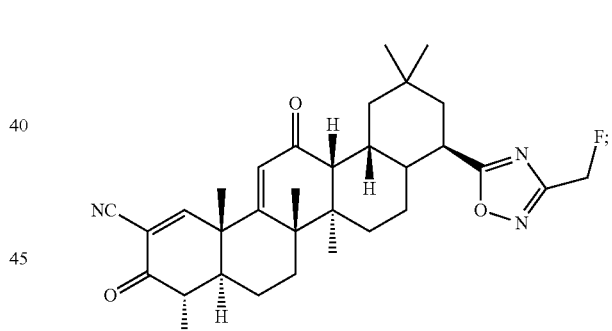

or a pharmaceutically acceptable salt thereof.

In still other embodiments, the compound is further defined as:

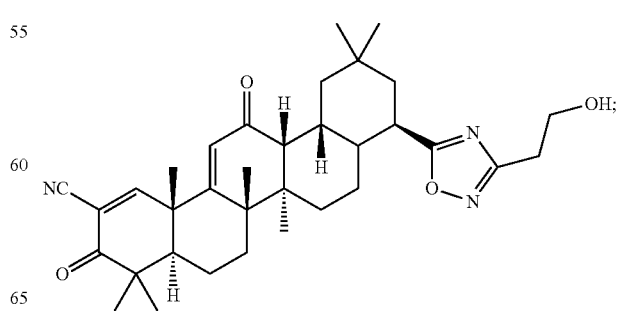

or a pharmaceutically acceptable salt thereof.

In some embodiments, the compound is further defined as:

(4aR,6aS,6bR,8aS,12aS,12bR,14bS)-8a-(5-(fluoromethyl)-1,3,4-oxadiazol-2-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

(4aR,6aS,6bR,8aS,12aS,12bR,14bS)-8a-(5-(fluoromethyl)-1,2,4-oxadiazol-3-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

(4aR,6aS,6bR,8aS,12aS,12bR,14bS)-8a-(5-(aminomethyl)-1,2,4-oxadiazol-3-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

(4aR,6aS,6bR,8aS,12aS,12bR,14bS)-8a-(5-(2-aminoethyl)-1,2,4-oxadiazol-3-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

(4aR,6aS,6bR,8aS,12aS,12bR,14bS)-8a-(5-(hydroxymethyl)-1,2,4-oxadiazol-3-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

(4aR,6aS,6bR,8aS,12aS,12bR,14bS)-8a-(5-(2-hydroxyethyl)-1,2,4-oxadiazol-3-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

(4aR,6aS,6bR,8aS,12aS,12bR,14bS)-8a-(2-(2-hydroxyethyl)-2H-tetrazol-5-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

2-(5-((4aS,6aR,6bS,8aR,12aS,14aR,14bS)-11-cyano-2,2,6a,6b,9,9,12a-heptamethyl-10,14-dioxo-1,3,4,5,6,6a,6b,7,8,8a,9,10,12a,14,14a,14b-hexadecahydropicen-4a(2H)-yl)-2H-tetrazol-2-yl)ethyl acetate;

(4aR,6aS,6bR,8aS,12aS,12bR,14bS)-8a-(2-(2-fluoroethyl)-2H-tetrazol-5-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

(4aR,6aS,6bR,8aS,12aS,12bR,14bS)-8a-(3-(fluoromethyl)-1,2,4-oxadiazol-5-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

(4aR,6aS,6bR,8aS,12aS,12bR,14bS)-8a-(3-(2-hydroxyethyl)-1,2,4-oxadiazol-5-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

2-(5-((4aS,6aR,6bS,8aR,12aS,14aR,14bS)-11-cyano-2,2,6a,6b,9,9,12a-heptamethyl-10,14-dioxo-1,3,4,5,6,6a,6b,7,8,8a,9,10,12a,14,14a,14b-hexadecahydropicen-4a(2H)-yl)-1,2,4-oxadiazol-3-yl)ethyl acetate;

(4aR,6aS,6bR,8aS,12aS,12bR,14bS)-8a-(3-(2-aminoethyl)-1,2,4-oxadiazol-5-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

methyl (2-(5-((4aS,6aR,6bS,8aR,12aS,14aR,14bS)-11-cyano-2,2,6a,6b,9,9,12a-heptamethyl-10,14-dioxo-1,3,4,5,6,6a,6b,7,8,8a,9,10,12a,14,14a,14b-hexadecahydropicen-4a(2H)-yl)-1,2,4-oxadiazol-3-yl)ethyl)carbamate;

1-(2-(5-((4aS,6aR,6bS,8aR,12aS,14aR,14bS)-11-cyano-2,2,6a,6b,9,9,12a-heptamethyl-10,14-dioxo-1,3,4,5,6,6a,6b,7,8,8a,9,10,12a,14,14a,14b-hexadecahydropicen-4a(2H)-yl)-1,2,4-oxadiazol-3-yl)ethyl)-3-ethylurea;

N-(2-(5-((4aS,6aR,6bS,8aR,12aS,14aR,14bS)-11-cyano-2,2,6a,6b,9,9,12a-heptamethyl-10,14-dioxo-1,3,4,5,6,6a,6b,7,8,8a,9,10,12a,14,14a,14b-hexadecahydropicen-4a(2H)-yl)-1,2,4-oxadiazol-3-yl)ethyl)acetamide;

(4S,4aS,6aS,6bR,8aS,12aS,12bR,14bR)-8a-(3-(fluoromethyl)-1,2,4-oxadiazol-5-yl)-4,6a,6b,11,11,14b-hexamethyl-3,13-dioxo-3,4,4a,5,6,6a,6b,7,8,8a,9,10,11,12,12a,12b,13,14b-octadecahydropicene-2-carbonitrile;

(4S,4aS,6aS,6bR,8aS,12aS,12bR,14bR)-8a-(3-(difluoromethyl)-1,2,4-oxadiazol-5-yl)-4,6a,6b,11,11,14b-hexamethyl-3,13-dioxo-3,4,4a,5,6,6a,6b,7,8,8a,9,10,11,12,12a,12b,13,14b-octadecahydropicene-2-carbonitrile;

(4S,4aS,6aS,6bR,8aS,12aS,12bR,14bR)-8a-(5-(fluoromethyl)-1,3,4-oxadiazol-2-yl)-4,6a,6b,11,11,14b-hexamethyl-3,13-dioxo-3,4,4a,5,6,6a,6b,7,8,8a,9,10,11,12,12a,12b,13,14b-octadecahydropicene-2-carbonitrile;

(4S,4aS,6aS,6bR,8aS,12aS,12bR,14bR)-8a-(5-(fluoromethyl)-1,2,4-oxadiazol-3-yl)-4,6a,6b,11,11,14b-hexamethyl-3,13-dioxo-3,4,4a,5,6,6a,6b,7,8,8a,9,10,11,12,12a,12b,13,14b-octadecahydropicene-2-carbonitrile;

(4aR,6aS,6bR,8aS,12aS,12bR,14bS)-8a-(5-(difluoromethyl)-1,2,4-oxadiazol-3-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

(4aR,6aS,6bR,8aS,12aS,12bR,14bS)-8a-(3-(hydroxymethyl)-1,2,4-oxadiazol-5-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

(4aR,6aS,6bR,8aS,12aS,12bR,14bS)-8a-(3-(difluoromethyl)-1,2,4-oxadiazol-5-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile; or (4aR,6aS,6bR,8aS,12aS,12bR,14bS)-8a-(5-(difluoromethyl)-1,3,4-oxadiazol-2-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile.

In further embodiments, the compound is further defined as:

(4aR,6aS,6bR,8aS,12aS,12bR,14bS)-8a-(5-(fluoromethyl)-1,3,4-oxadiazol-2-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

(4aR,6aS,6bR,8aS,12aS,12bR,14bS)-8a-(5-(fluoromethyl)-1,2,4-oxadiazol-3-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

(4aR,6aS,6bR,8aS,12aS,12bR,14bS)-8a-(5-(aminomethyl)-1,2,4-oxadiazol-3-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

(4aR,6aS,6bR,8aS,12aS,12bR,14bS)-8a-(3-(fluoromethyl)-1,2,4-oxadiazol-5-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

(4S,4aS,6aS,6bR,8aS,12aS,12bR,14bR)-8a-(3-(fluoromethyl)-1,2,4-oxadiazol-5-yl)-4,6a,6b,11,11,14b-hexamethyl-3,13-dioxo-3,4,4a,5,6,6a,6b,7,8,8a,9,10,11,12,12a,12b,13,14b-octadecahydropicene-2-carbonitrile; or (4aR,6aS,6bR,8aS,12aS,12bR,14bS)-8a-(3-(2-hydroxyethyl)-1,2,4-oxadiazol-5-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile.

In still further embodiments, the compound is further defined as:

(4aR,6aS,6bR,8aS,12aS,12bR,14bS)-8a-(5-(fluoromethyl)-1,3,4-oxadiazol-2-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

(4aR,6aS,6bR,8aS,12aS,12bR,14bS)-8a-(5-(fluoromethyl)-1,2,4-oxadiazol-3-yl)-4,4,6a,6b,11,11,14b-heptamethyl- 3,13-dioxo-3,4,4a,5,6,6a,6b,7,8,8a,9,10,11,12,12a,12b, 13,14b-octadecahydropicene-2-carbonitrile;
(4aR,6aS,6bR,8aS,12aS,12bR,14bS)-8a-(5-(aminomethyl)-1,2,4-oxadiazol-3-yl)-4,4,6a,6b,11,11,14b-heptamethyl-3,13-dioxo-3,4,4a,5,6,6a,6b,7,8,8a,9,10,11,12,12a,12b, 13,14b-octadecahydropicene-2-carbonitrile;
(4aR,6aS,6bR,8aS,12aS,12bR,14bS)-8a-(3-(fluoromethyl)-1,2,4-oxadiazol-5-yl)-4,4,6a,6b,11,11,14b-heptamethyl-3,13-dioxo-3,4,4a,5,6,6a,6b,7,8,8a,9,10,11,12,12a,12b, 13,14b-octadecahydropicene-2-carbonitrile; or
(4S,4aS,6aS,6bR,8aS,12aS,12bR,14bR)-8a-(3-(fluoromethyl)-1,2,4-oxadiazol-5-yl)-4,6a,6b,11,11,14b-hexamethyl-3,13-dioxo-3,4,4a,5,6,6a,6b,7,8,8a,9,10,11,12,12a, 12b,13,14b-octadecahydropicene-2-carbonitrile.

In some embodiments, the compound is further defined as:
(4aR,6aS,6bR,8aS,12aS,12bR,14bS)-8a-(5-(fluoromethyl)-1,3,4-oxadiazol-2-yl)-4,4,6a,6b,11,11,14b-heptamethyl-3,13-dioxo-3,4,4a,5,6,6a,6b,7,8,8a,9,10,11,12,12a,12b, 13,14b-octadecahydropicene-2-carbonitrile.

In other embodiments, the compound is further defined as:
(4aR,6aS,6bR,8aS,12aS,12bR,14bS)-8a-(5-(fluoromethyl)-1,2,4-oxadiazol-3-yl)-4,4,6a,6b,11,11,14b-heptamethyl-3,13-dioxo-3,4,4a,5,6,6a,6b,7,8,8a,9,10,11,12,12a,12b, 13,14b-octadecahydropicene-2-carbonitrile.

In still other embodiments, the compound is further defined as:
(4aR,6aS,6bR,8aS,12aS,12bR,14bS)-8a-(5-(aminomethyl)-1,2,4-oxadiazol-3-yl)-4,4,6a,6b,11,11,14b-heptamethyl-3,13-dioxo-3,4,4a,5,6,6a,6b,7,8,8a,9,10,11,12,12a,12b, 13,14b-octadecahydropicene-2-carbonitrile.

In yet other embodiments, the compound is further defined as:
(4aR,6aS,6bR,8aS,12aS,12bR,14bS)-8a-(3-(fluoromethyl)-1,2,4-oxadiazol-5-yl)-4,4,6a,6b,11,11,14b-heptamethyl-3,13-dioxo-3,4,4a,5,6,6a,6b,7,8,8a,9,10,11,12,12a,12b, 13,14b-octadecahydropicene-2-carbonitrile.

In other embodiments, the compound is further defined as:
(4S,4aS,6aS,6bR,8aS,12aS,12bR,14bR)-8a-(3-(fluoromethyl)-1,2,4-oxadiazol-5-yl)-4,6a,6b,11,11,14b-hexamethyl-3,13-dioxo-3,4,4a,5,6,6a,6b,7,8,8a,9,10,11,12,12a, 12b,13,14b-octadecahydropicene-2-carbonitrile.

In other embodiments, the compound is further defined as:
(4aR,6aS,6bR,8aS,12aS,12bR,14bS)-8a-(3-(2-hydroxyethyl)-1,2,4-oxadiazol-5-yl)-4,4,6a,6b,11,11,14b-heptamethyl-3,13-dioxo-3,4,4a,5,6,6a,6b,7,8,8a,9,10,11,12,12a, 12b,13,14b-octadecahydropicene-2-carbonitrile.

In another aspect, the present disclosure provides compounds of the formula:

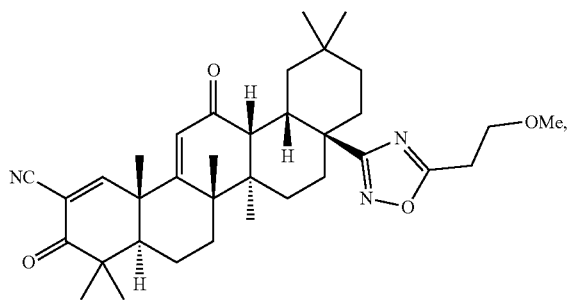

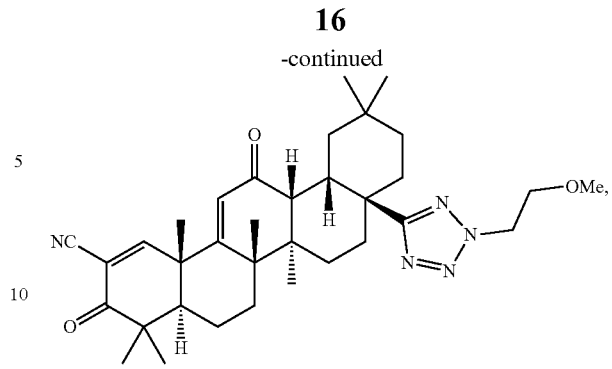

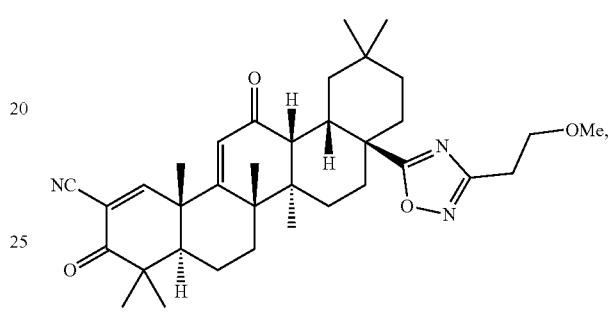

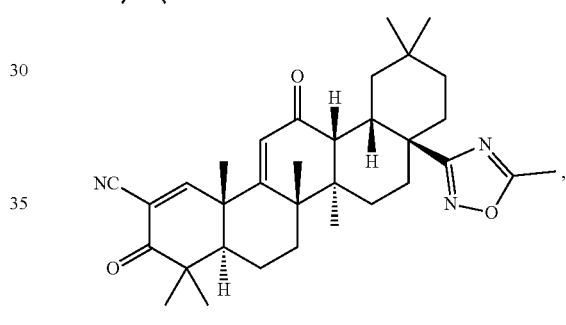

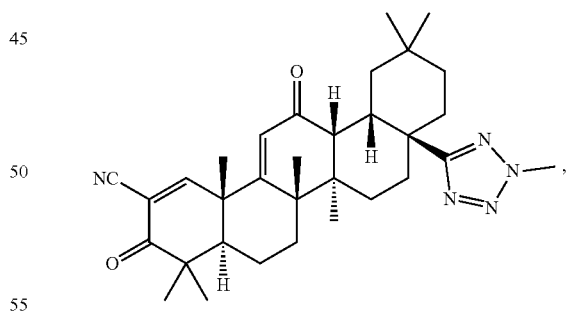

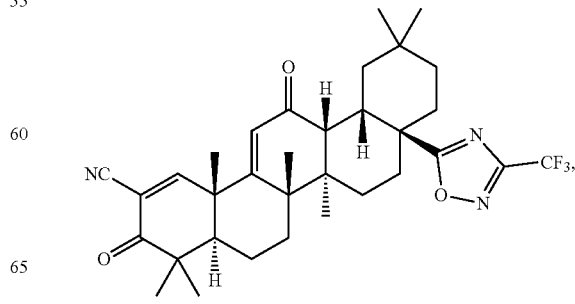

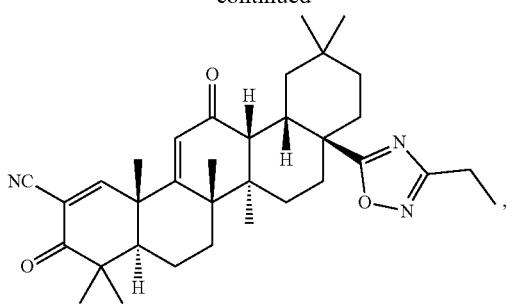
,
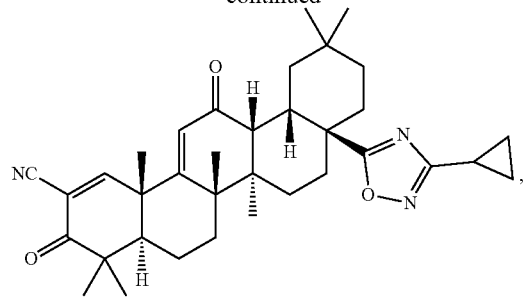
,
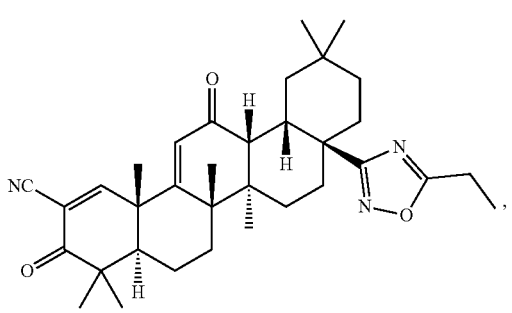
,
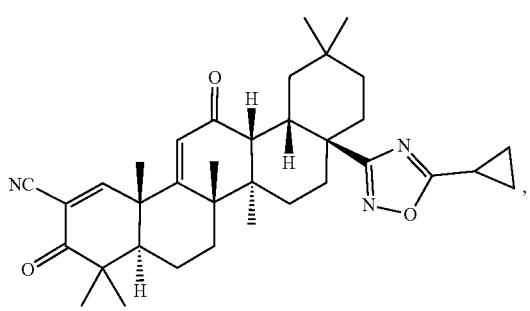
,
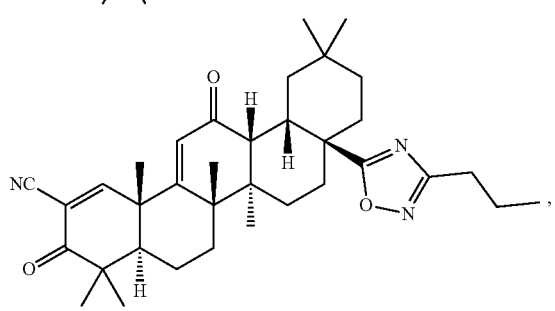
,
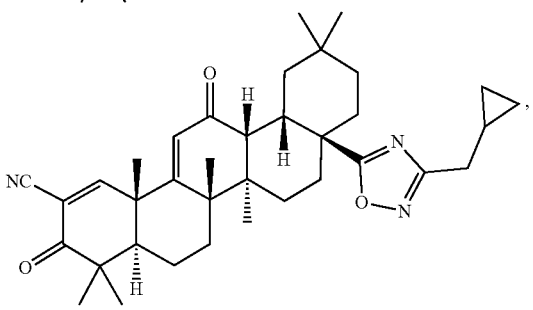
,
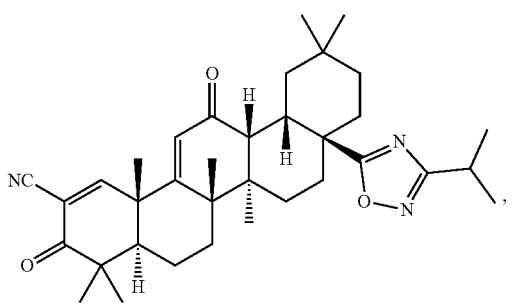
,
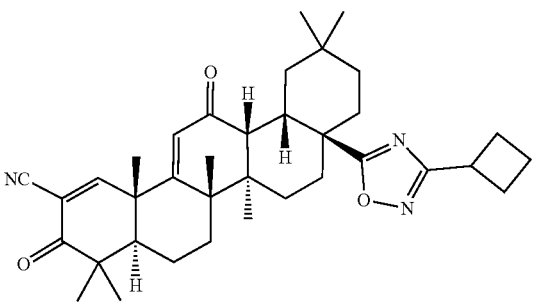
,
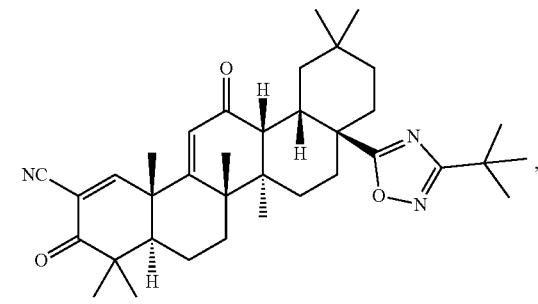
,
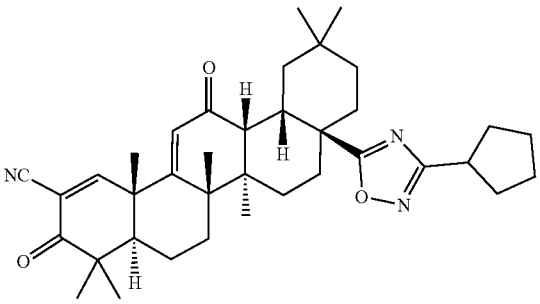
,

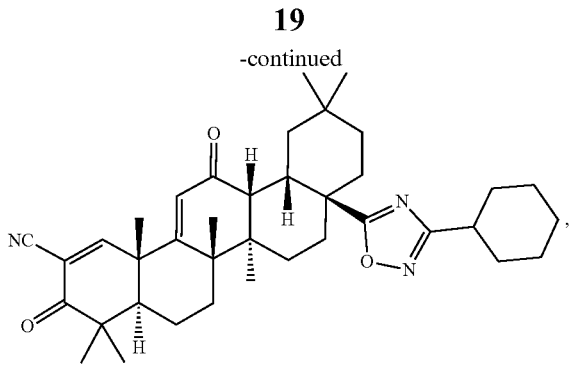

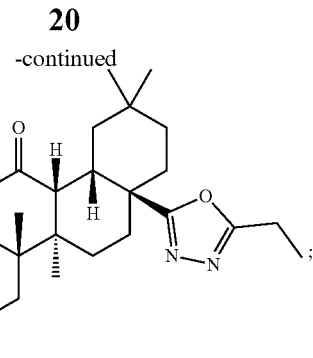

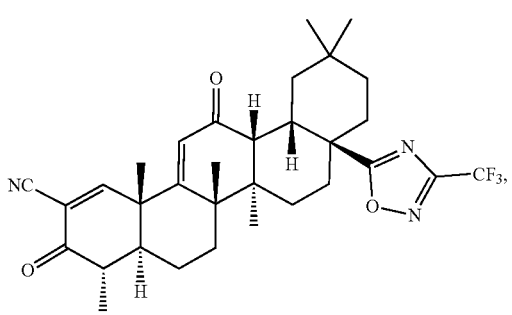

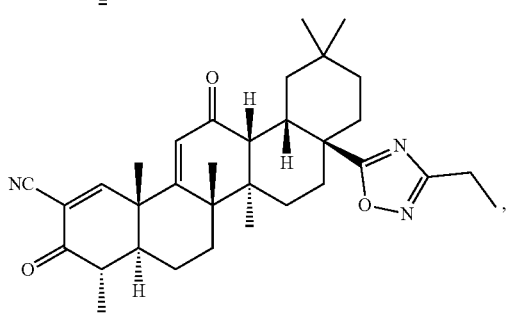

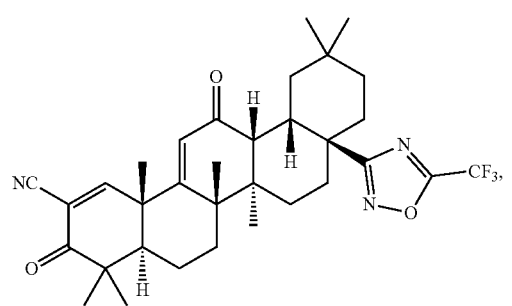

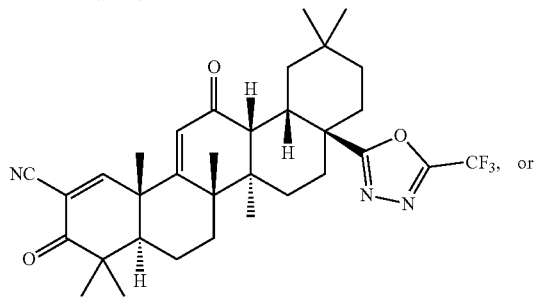

or a pharmaceutically acceptable salt of any of these formulas.

In yet another aspect, the present disclosure provides:
(4aR,6aS,6bR,8aS,12aS,12bR,14bS)-8a-(5-(2-methoxyethyl)-1,2,4-oxadiazol-3-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;
(4aR,6aS,6bR,8aS,12aS,12bR,14bS)-8a-(2-(2-methoxyethyl)-2H-tetrazol-5-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;
(4aR,6aS,6bR,8aS,12aS,12bR,14bS)-8a-(3-(2-methoxyethyl)-1,2,4-oxadiazol-5-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;
(4aR,6aS,6bR,8aS,12aS,12bR,14bS)-4,4,6a,6b,11,11,14b-heptamethyl-8a-(5-methyl-1,2,4-oxadiazol-3-yl)-3,13-dioxo-3,4,4a,5,6,6a,6b,7,8,8a,9,10,11,12,12a,12b,13,14b-octadecahydropicene-2-carbonitrile;
(4aR,6aS,6bR,8aS,12aS,12bR,14bS)-4,4,6a,6b,11,11,14b-heptamethyl-8a-(2-methyl-2H-tetrazol-5-yl)-3,13-dioxo-3,4,4a,5,6,6a,6b,7,8,8a,9,10,11,12,12a,12b,13,14b-octadecahydropicene-2-carbonitrile;
(4aR,6aS,6bR,8aS,12aS,12bR,14bS)-4,4,6a,6b,11,11,14b-heptamethyl-3,13-dioxo-8a-(3-(trifluoromethyl)-1,2,4-oxadiazol-5-yl)-3,4,4a,5,6,6a,6b,7,8,8a,9,10,11,12,12a,12b,13,14b-octadecahydropicene-2-carbonitrile;
(4aR,6aS,6bR,8aS,12aS,12bR,14bS)-8a-(3-ethyl-1,2,4-oxadiazol-5-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;
(4aR,6aS,6bR,8aS,12aS,12bR,14bS)-8a-(5-ethyl-1,2,4-oxadiazol-3-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;
(4aR,6aS,6bR,8aS,12aS,12bR,14bS)-4,4,6a,6b,11,11,14b-heptamethyl-3,13-dioxo-8a-(3-propyl-1,2,4-oxadiazol-5-yl)-3,4,4a,5,6,6a,6b,7,8,8a,9,10,11,12,12a,12b,13,14b-octadecahydropicene-2-carbonitrile;
(4aR,6aS,6bR,8aS,12aS,12bR,14bS)-8a-(3-isopropyl-1,2,4-oxadiazol-5-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;
(4aR,6aS,6bR,8aS,12aS,12bR,14bS)-8a-(3-(tert-butyl)-1,2,4-oxadiazol-5-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;
(4aR,6aS,6bR,8aS,12aS,12bR,14bS)-8a-(3-cyclopropyl-1,2,4-oxadiazol-5-yl)-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;
(4aR,6aS,6bR,8aS,12aS,12bR,14bS)-8a-(5-cyclopropyl-1,2,4-oxadiazol-3-yl)-4,4,6a,6b,11,11,14b-heptamethyl-3, 13-dioxo-3,4,4a,5,6,6a,6b,7,8,8a,9,10,11,12,12a,12b,13,
14b-octadecahydropicene-2-carbonitrile;
(4aR,6aS,6bR,8aS,12aS,12bR,14bS)-8a-(3-(cyclopropylm-
ethyl)-1,2,4-oxadiazol-5-yl)-4,4,6a,6b,11,11,14b-heptam-
ethyl-3,13-dioxo-3,4,4a,5,6,6a,6b,7,8,8a,9,10,11,12,12a,
12b,13,14b-octadecahydropicene-2-carbonitrile;
(4aR,6aS,6bR,8aS,12aS,12bR,14bS)-8a-(3-cyclobutyl-1,2,
4-oxadiazol-5-yl)-4,4,6a,6b,11,11,14b-heptamethyl-3,13-
dioxo-3,4,4a,5,6,6a,6b,7,8,8a,9,10,11,12,12a,12b,13,14b-
octadecahydropicene-2-carbonitrile;
(4aR,6aS,6bR,8aS,12aS,12bR,14bS)-8a-(3-cyclopentyl-1,2,
4-oxadiazol-5-yl)-4,4,6a,6b,11,11,14b-heptamethyl-3,13-
dioxo-3,4,4a,5,6,6a,6b,7,8,8a,9,10,11,12,12a,12b,13,14b-
octadecahydropicene-2-carbonitrile;
(4aR,6aS,6bR,8aS,12aS,12bR,14bS)-8a-(3-cyclohexyl-1,2,
4-oxadiazol-5-yl)-4,4,6a,6b,11,11,14b-heptamethyl-3,13-
dioxo-3,4,4a,5,6,6a,6b,7,8,8a,9,10,11,12,12a,12b,13,14b-
octadecahydropicene-2-carbonitrile;
(4S,4aS,6aS,6bR,8aS,12aS,12bR,14bR)-4,6a,6b,11,11,14b-
hexamethyl-3,13-dioxo-8a-(3-(trifluoromethyl)-1,2,4-
oxadiazol-5-yl)-3,4,4a,5,6,6a,6b,7,8,8a,9,10,11,12,12a,
12b,13,14b-octadecahydropicene-2-carbonitrile;
(4S,4aS,6aS,6bR,8aS,12aS,12bR,14bR)-8a-(3-ethyl-1,2,4-
oxadiazol-5-yl)-4,6a,6b,11,11,14b-hexamethyl-3,13-di-
oxo-3,4,4a,5,6,6a,6b,7,8,8a,9,10,11,12,12a,12b,13,14b-
octadecahydropicene-2-carbonitrile;
(4aR,6aS,6bR,8aS,12aS,12bR,14bS)-4,4,6a,6b,11,11,14b-
heptamethyl-3,13-dioxo-8a-(5-(trifluoromethyl)-1,2,4-
oxadiazol-3-yl)-3,4,4a,5,6,6a,6b,7,8,8a,9,10,11,12,12a,
12b,13,14b-octadecahydropicene-2-carbonitrile;
(4aR,6aS,6bR,8aS,12aS,12bR,14bS)-4,4,6a,6b,11,11,14b-
heptamethyl-3,13-dioxo-8a-(5-(trifluoromethyl)-1,3,4-
oxadiazol-2-yl)-3,4,4a,5,6,6a,6b,7,8,8a,9,10,11,12,12a,
12b,13,14b-octadecahydropicene-2-carbonitrile; or
(4aR,6aS,6bR,8aS,12aS,12bR,14bS)-8a-(5-ethyl-1,3,4-oxa-
diazol-2-yl)-4,4,6a,6b,11,11,14b-heptamethyl-3,13-di-
oxo-3,4,4a,5,6,6a,6b,7,8,8a,9,10,11,12,12a,12b,13,14b-
octadecahydropicene-2-carbonitrile.

In still another aspect, the present disclosure provides pharmaceutical compositions comprising a compound of the present disclosure and an excipient. In some embodiments, the pharmaceutical composition is formulated for administration orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, the pharmaceutical composition is formulated for oral administration. In other embodiments, the pharmaceutical composition is formulated for administration via injection. In some embodiments, the pharmaceutical composition is formulated for intraarterial administration, intramuscular administration, intraperitoneal administration, or intravenous administration. In some embodiments, the pharmaceutical composition is formulated for administration topically. In some embodiments, the pharmaceutical composition is formulated for topical administration to the skin or to the eye. In some embodiments, the pharmaceutical composition is formulated as a unit dose.

In another aspect, the present disclosure provides methods of treating or preventing a disease or disorder in a patient in need thereof comprising administering to the patient a pharmaceutically effective amount of a compound or composition of the present disclosure. In some embodiments, the patient is a mammal, such as a human. In some embodiments, the disease or disorder is a condition associated with inflammation and/or oxidative stress. In some embodiments, the disease or disorder is cancer. In some embodiments, the disease or disorder is a cardiovascular disease, such as atherosclerosis. In some embodiments, the disease or disorder is an autoimmune disease, such as Crohn's disease, rheumatoid arthritis, lupus, or psoriasis. In some embodiments, the disease or disorder is a neurodegenerative disease, such as Alzheimer's disease, Parkinson's disease, amyotrophic lateral sclerosis, or Huntington's disease. In some embodiments, the disease or disorder is chronic kidney disease, diabetes, mucositis, inflammatory bowel disease, dermatitis, sepsis, ischemia-reperfusion injury (including complications from sickle cell anemia), influenza, osteoarthritis, osteoporosis, pancreatitis, asthma, chronic obstructive pulmonary disease, cystic fibrosis, idiopathic pulmonary fibrosis, multiple sclerosis, muscular dystrophy, cachexia, or graft-versus-host disease. In some embodiments, the disease or disorder is an eye disease, such as uveitis, glaucoma, macular degeneration, or retinopathy. In some embodiments, the disease or disorder is neuropsychiatric, such as schizophrenia, depression, bipolar disorder, epilepsy, post-traumatic stress disorder, attention deficit disorder, autism, or anorexia nervosa. In some embodiments, the disease or disorder is associated with mitochondrial dysfunction, such as Friedreich's ataxia. In some embodiments, the disease or disorder is chronic pain. In some embodiments, the disease or disorder is neuropathic pain.

In still another aspect, the present disclosure provides methods of inhibiting nitric oxide production comprising administering to a patient in need thereof an amount of a compound or composition of the present disclosure sufficient to cause inhibition of IFN-γ-induced nitric oxide production in one or more cells of the patient.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows CYP3A4 inhibition in human liver microsomes at 1 with each sample, containing 0.1 mg/mL human liver microsomes, 5 μM midazolam as substrate, and 1 μM of test compound, was incubated at 37° C. for 10 min. For additional details, see Example 3.

DESCRIPTION OF ILLUSTRATIVE EMBODIMENTS

Disclosed herein are new compounds and compositions with antioxidant and/or anti-inflammatory properties, methods for their manufacture, and methods for their use, including for the treatment and/or prevention of disease.

I. Compounds of the Present Invention

The compounds of the present invention (also referred to as "synthetic triterpenoid derivatives provided herein," "compounds of the present disclosure" or "compounds disclosed herein") are shown, for example, above, in the summary of the invention section, the Examples below, Table 1, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

TABLE 1

Examples of Synthetic Triterpenoid Derivatives Provided Herein

| Compound ID | Structural Formula |
|---|---|
| T1 | |
| T2 | |
| T3 | |

TABLE 1-continued

Examples of Synthetic Triterpenoid Derivatives Provided Herein

| Compound ID | Structural Formula |
|---|---|
| T4 | |
| T5 | |
| T6 | |
| T7 | |
| T8 | |

TABLE 1-continued
Examples of Synthetic Triterpenoid Derivatives Provided Herein
| Compound ID | Structural Formula |
|---|---|
| T9 | 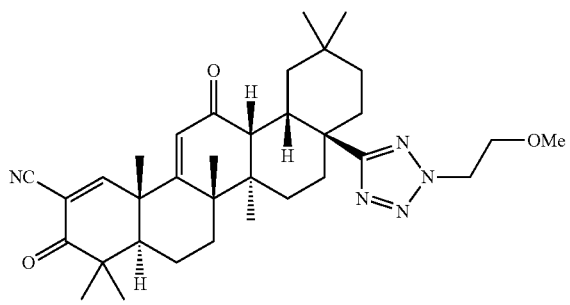 |
| T10 | 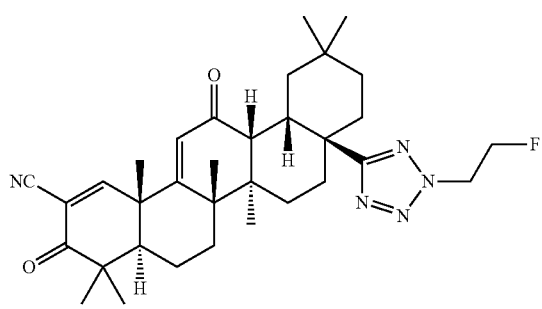 |
| T11 | 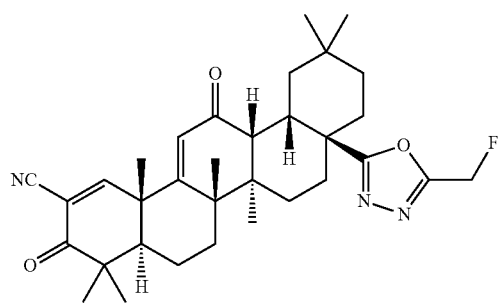 |
| T12 | 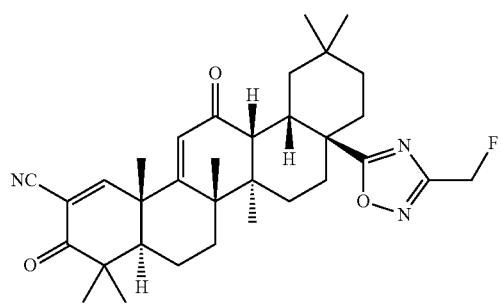 |
| T13 | 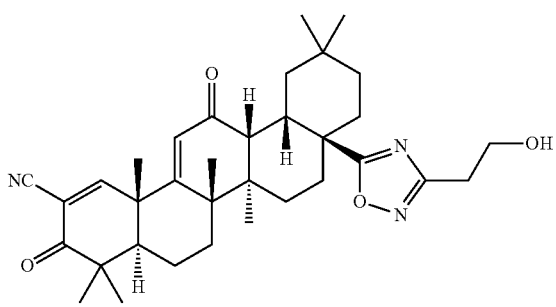 |

TABLE 1-continued
Examples of Synthetic Triterpenoid Derivatives Provided Herein
| Compound ID | Structural Formula |
|---|---|
| T14 | 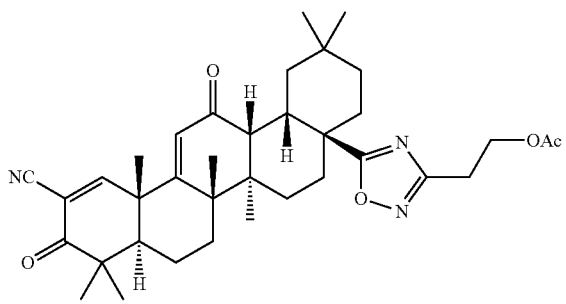 |
| T15 | 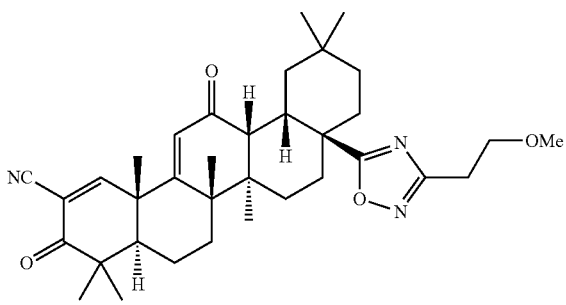 |
| T16 | 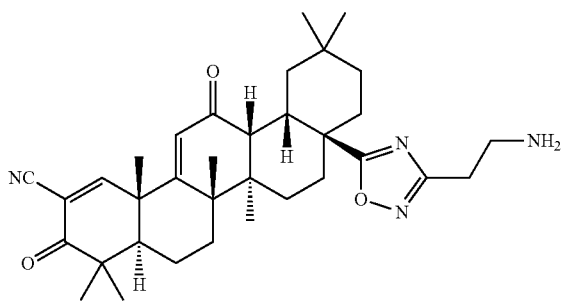 |
| T17 | 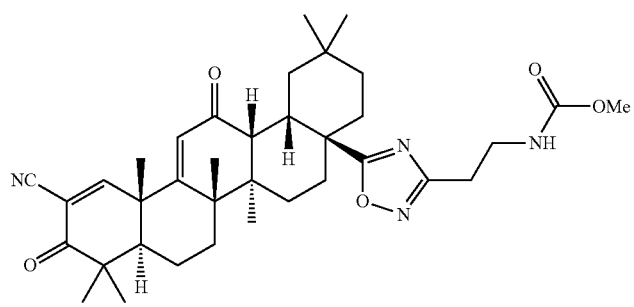 |
| T18 | 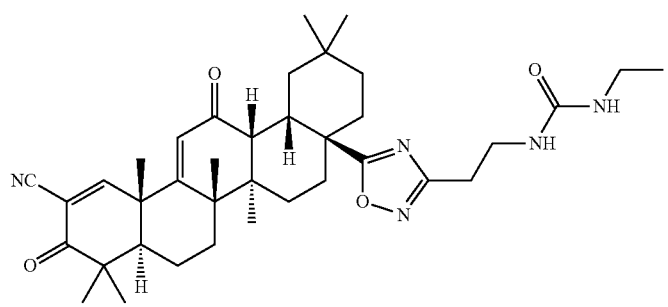 |

TABLE 1-continued
Examples of Synthetic Triterpenoid Derivatives Provided Herein
| Compound ID | Structural Formula |
|---|---|
| T19 | 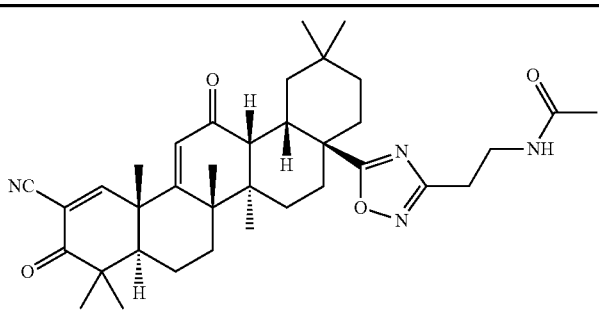 |
| T20 | 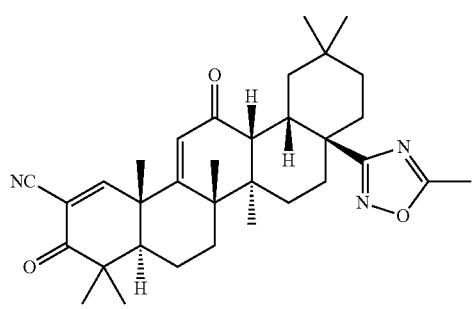 |
| T21 | 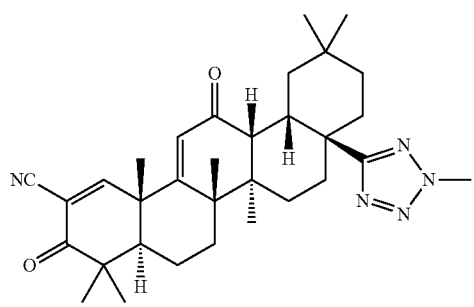 |
| T22 | 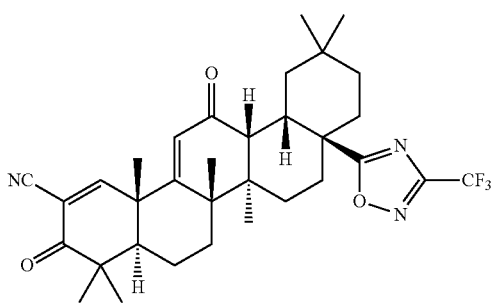 |
| T23 | 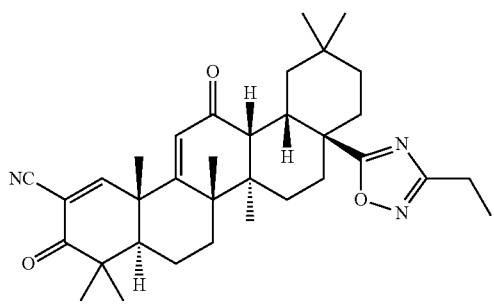 |

TABLE 1-continued
Examples of Synthetic Triterpenoid Derivatives Provided Herein
| Compound ID | Structural Formula |
|---|---|
| T24 | 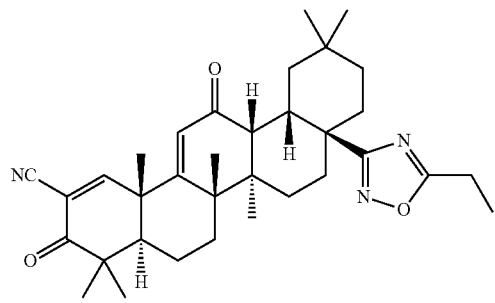 |
| T25 | 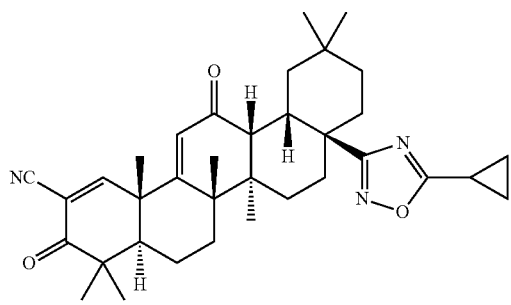 |
| T26 | 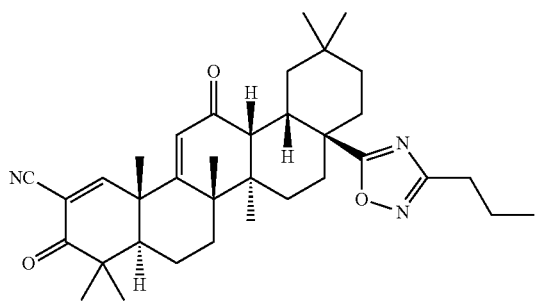 |
| T27 | 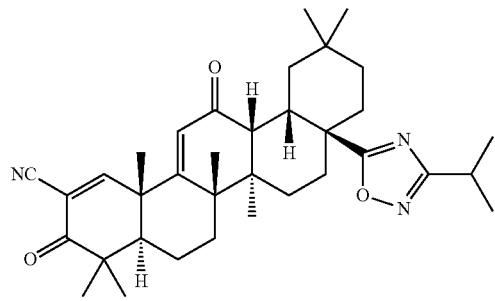 |
| T28 | 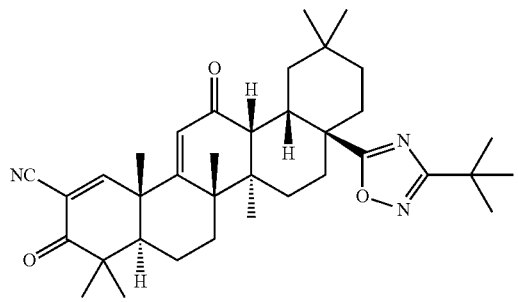 |

TABLE 1-continued
Examples of Synthetic Triterpenoid Derivatives Provided Herein
| Compound ID | Structural Formula |
|---|---|
| T29 | 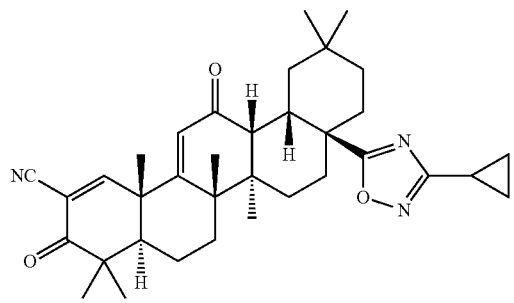 |
| T30 | 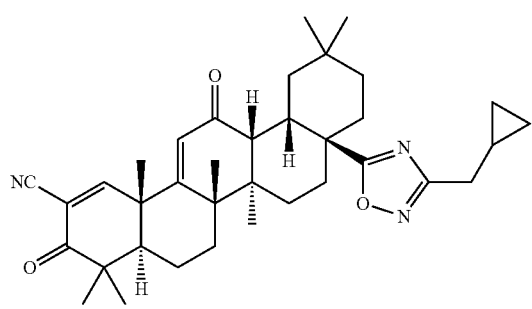 |
| T31 | 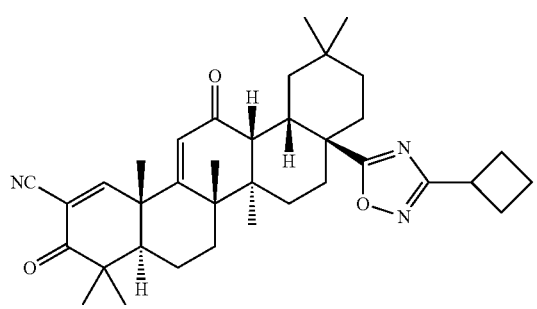 |
| T32 | 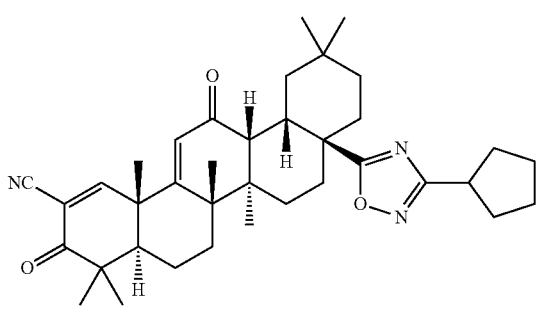 |
| T33 | 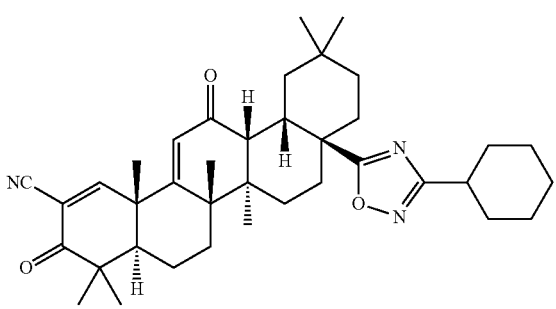 |

TABLE 1-continued
Examples of Synthetic Triterpenoid Derivatives Provided Herein
| Compound ID | Structural Formula |
|---|---|
| T34 | 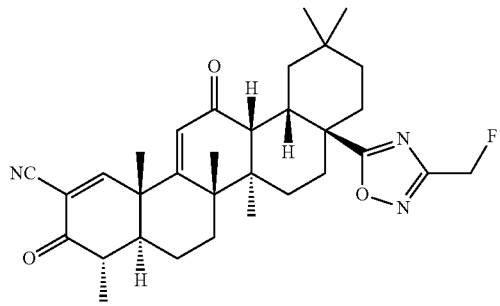 |
| T35 | 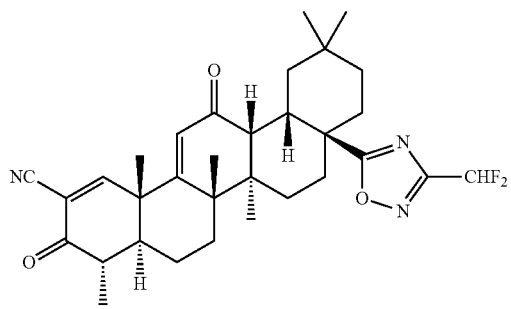 |
| T36 | 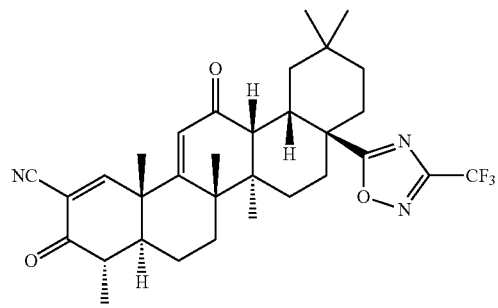 |
| T37 | 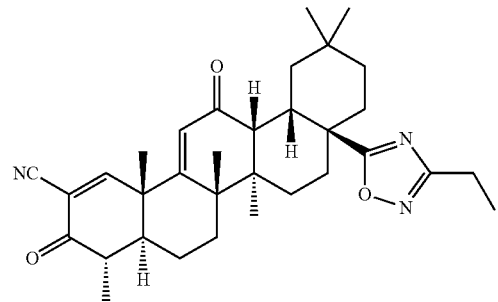 |
| T38 | 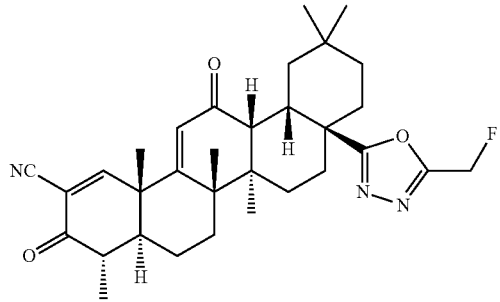 |

TABLE 1-continued

Examples of Synthetic Triterpenoid Derivatives Provided Herein

| Compound ID | Structural Formula |
|---|---|
| T39 | |
| T40 | |
| T41 | |
| T42 | |
| T43 | |

TABLE 1-continued

Examples of Synthetic Triterpenoid Derivatives Provided Herein

| Compound ID | Structural Formula |
|---|---|
| T44 | |
| T45 | |
| T46 | |

All the compounds of the present invention may in some embodiments be used for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all the compounds of the present invention are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the compounds of the present invention have the advantage that they may be more efficacious than, be less toxic than, be longer acting than, be more potent than, produce fewer side effects than, be more easily absorbed than, more metabolically stable than, more lipophilic than, more hydrophilic than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Compounds of the present disclosure may contain one or more asymmetrically-substituted carbon or nitrogen atom and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration. In some embodiments, the present compounds may contain two or more atoms which have a defined stereochemical orientation.

Chemical formulas used to represent compounds of the present invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

In some embodiments, compounds of the present invention function as prodrugs or can be derivatized to function as prodrugs. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively.

In some embodiments, compounds of the present invention exist in salt or non-salt form. With regard to the salt form(s), in some embodiments the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present invention.

II. Biological Activity

Assay results for the suppression of IFNγ-induced NO production are shown for several of the compounds of the present invention in Table 2 and Table 3 in Example 2. Table 2 presents the results compared to those of bardoxolone methyl (RTA 402, CDDO-Me). Table 3 present the results compared to comparison compounds CC1, CC2, and CC3. Details regarding this assay are provided in the Examples section below.

In some embodiments, the synthetic triterpenoid derivatives provided herein that were substituted with polar substituents at the C17 heteroaryl groups exhibited improved nitric oxide inhibition compared with compounds lacking such substituents, such as those disclosed in U.S. Pat. No. 9,512,094, which is incorporated herein by reference. For example, the $IC_{50}$ value for fluoro-substituted T12 is 36% lower (1.27 nM vs. 1.98 nM) than the corresponding unsubstituted compound, CC2 (TX63501; U.S. Pat. No. 9,512,094). In another example, the $IC_{50}$ values for hydroxy-substituted T13 and acetoxy-substituted T14 were 88% and 90% lower (0.56 nM and 0.48 nM, respectively vs. 4.85 nM) than the corresponding unsubstituted compound, T23. In another example, the $IC_{50}$ values for fluoro-substituted T1, amino-substituted T2, and hydroxy-substituted T4 are 67%, 70%, and 52% lower (1.24 nM, 1.15 nM, and 1.82 nM, respectively vs. 3.79 nM) than the corresponding unsubstituted compound, T20. Similarly, amino-substituted T3 and hydroxy-substituted T5 are 72% and 83% lower (2.60 nM and 1.57 nM, respectively vs. 9.21 nM) than the corresponding unsubstituted compound, T24. In another example, the $IC_{50}$ value for fluoro-substituted T11 is 52% lower (0.98 nM vs. 2.05 nM) than the corresponding unsubstituted compound, CC1 (TX63384; U.S. Pat. No. 9,512,094). In yet another example, the $IC_{50}$ value for fluoro-substituted T34 is 31% lower (0.93 nM vs. 1.34 nM) than the corresponding unsubstituted compound, CC3 (TX63787; U.S. Pat. No. 9,290,536). In some embodiments, complete replacement of all the hydrogens with polar substituents results in a decrease in nitric oxide inhibitory activity. Compare the trifluoromethyl derivative T22 (23.95 nM) with the monofluoromethyl derivative T12 (1.27 nM).

In some embodiments, the compounds of the present disclosure exhibit reduced inhibition of cytochrome P450 3A4 (CYP3A4) relative to known compounds. CYP3A4 is an important enzyme in the body, which oxidizes small foreign organic molecules (xenobiotics), such as toxins or drugs, so that they can be removed from the body. Modulation of CYP3A4 may amplify or weaken the action of drugs that are modified by CYP3A4. Inhibition of CYP3A4 may have negative side effects (e.g. reduced drug clearance, amplification of the action of the drug, and/or increase the probability of drug-drug interactions) and may complicate dosing. Therefore, drugs that do not inhibit CYP3A4 are often more desirable.

Assay results for the inhibition of CYP3A4 are shown for several of the compounds of the present disclosure in Tables 4-7 in Example 3. In some embodiments, the synthetic triterpenoid derivatives provided herein that were substituted with polar substituents at the C17 heteroaryl groups exhibited reduced CYP3A4 inhibition compared with compounds lacking such substituents, such as those disclosed in U.S. Pat. Nos. 9,512,094 and 9,290,536, both of which are incorporated herein by reference. For example, the CYP3A4 inhibition values for fluoro-substituted T1, amino-substituted T2, and fluoro-substituted T12 were 36%, 53%, and 35% lower (29.1%, 21.4%, and 29.7% inhibition, respectively, vs. 45.8% inhibition) than the corresponding unsubstituted compound, CC2 (TX63501; U.S. Pat. No. 9,512, 094). In another example, the CYP3A4 inhibition for fluoro-substituted T11 was 15% lower (17.7% inhibition vs. 20.7% inhibition) than the corresponding unsubstituted compound, CC1 (TX63384; U.S. Pat. No. 9,512,094). In another example, the CYP3A4 inhibition for fluoro-substituted T34 was 22% lower (29.4% inhibition vs. 37.7% inhibition) than the corresponding unsubstituted compound, CC3 (TX63787; U.S. Pat. No. 9,290,536). In addition, each of T1, T2, T11, T12, and T34 exhibited reduced CYP3A4 inhibition compared with historical data for RTA 402 and RTA 408 performed under comparable conditions (FIG. 1).

III. Diseases Associated with Inflammation and/or Oxidative Stress

Inflammation is a biological process that provides resistance to infectious or parasitic organisms and the repair of damaged tissue. Inflammation is commonly characterized by localized vasodilation, redness, swelling, and pain, the recruitment of leukocytes to the site of infection or injury, production of inflammatory cytokines such as TNF-α and IL-1, and production of reactive oxygen or nitrogen species such as hydrogen peroxide, superoxide and peroxynitrite. In later stages of inflammation, tissue remodeling, angiogenesis, and scar formation (fibrosis) may occur as part of the wound healing process. Under normal circumstances, the inflammatory response is regulated and temporary and is resolved in an orchestrated fashion once the infection or injury has been dealt with adequately. However, acute inflammation can become excessive and life-threatening if regulatory mechanisms fail. Alternatively, inflammation can become chronic and cause cumulative tissue damage or systemic complications. Based at least on the evidence presented above, the compounds of the present disclosure may be used in the treatment or prevention of inflammation or diseases associated with inflammation.

Many serious and intractable human diseases involve dysregulation of inflammatory processes, including diseases such as cancer, atherosclerosis, and diabetes, which were not traditionally viewed as inflammatory conditions. In the case of cancer, the inflammatory processes are associated with tumor formation, progression, metastasis, and resistance to therapy. Atherosclerosis, long viewed as a disorder of lipid metabolism, is now understood to be primarily an inflammatory condition, with activated macrophages playing an important role in the formation and eventual rupture of atherosclerotic plaques. Activation of inflammatory signaling pathways has also been shown to play a role in the development of insulin resistance, as well as in the peripheral tissue damage associated with diabetic hyperglycemia. Excessive production of reactive oxygen species and reactive nitrogen species such as superoxide, hydrogen peroxide, nitric oxide, and peroxynitrite is a hallmark of inflammatory conditions. Evidence of dysregulated peroxynitrite production has been reported in a wide variety of diseases (Szabo et al., 2007; Schulz et al., 2008; Forstermann, 2006; Pall, 2007). Aging-related diseases such as dementia, muscle wasting, cardiovascular diseases, neurodegenerative diseases, and arthritis frequently involve chronic inflammation and oxidative stress as major contributing factors. In some embodiments, the compounds provided herein may be used to treat and/or prevent aging-related diseases, such as dementia, muscle wasting, cardiovascular diseases, neurodegenerative diseases, or arthritis.

Autoimmune diseases such as rheumatoid arthritis, lupus, psoriasis, and multiple sclerosis involve inappropriate and chronic activation of inflammatory processes in affected tissues, arising from dysfunction of self vs. non-self-recognition and response mechanisms in the immune system. In some embodiments, the compounds provided herein may be used in the treatment and/or prevention of autoimmune diseases, such as rheumatoid arthritis, lupus, psoriasis, or multiple sclerosis. In neurodegenerative diseases such as Alzheimer's and Parkinson's diseases, neural damage is correlated with activation of microglia and elevated levels of pro-inflammatory proteins such as inducible nitric oxide synthase (iNOS). In some embodiments, the compounds provided herein may be used in the treatment and/or prevention of neurodegenerative diseases, such as Alzheimer's disease or Parkinson's disease. Chronic organ failure such as renal failure, heart failure, liver failure, and chronic obstructive pulmonary disease is closely associated with the presence of chronic oxidative stress and inflammation, leading to the development of fibrosis and eventual loss of organ function. In some embodiments, the compounds provided herein may be used in the treatment and/or prevention of chronic organ failure, such as renal failure, heart failure, liver failure, or chronic obstructive pulmonary disease. Oxidative stress in vascular endothelial cells, which line major and minor blood vessels, can lead to endothelial dysfunction and is believed to be an important contributing factor in the development of systemic cardiovascular disease, complications of diabetes, chronic kidney disease and other forms of organ failure, and a number of other aging-related diseases including degenerative diseases of the central nervous system and the retina. In some embodiments, the compounds provided herein may be used in the treatment and/or prevention of systemic cardiovascular disease, complications of diabetes, chronic kidney disease and other forms of organ failure, and a number of other aging-related diseases including degenerative diseases of the central nervous system and the retina.

Many other disorders involve oxidative stress and inflammation in affected tissues, including inflammatory bowel disease; inflammatory skin diseases; mucositis related to radiation therapy and chemotherapy; eye diseases such as uveitis, glaucoma, macular degeneration, and various forms of retinopathy; transplant failure and rejection; ischemia-reperfusion injury; chronic pain; degenerative conditions of the bones and joints including osteoarthritis and osteoporosis; asthma and cystic fibrosis; seizure disorders; and neuropsychiatric conditions including schizophrenia, depression, bipolar disorder, post-traumatic stress disorder, attention deficit disorders, autism-spectrum disorders, and eating disorders such as anorexia nervosa. In some embodiments, the compounds provided herein may be used in the treatment and/or prevention of inflammatory bowel disease; inflammatory skin diseases; mucositis related to radiation therapy and chemotherapy; eye diseases such as uveitis, glaucoma, macular degeneration, and various forms of retinopathy; transplant failure and rejection; ischemia-reperfusion injury (including complications of sickle cell anemia); chronic pain; degenerative conditions of the bones and joints including osteoarthritis and osteoporosis; asthma and cystic fibrosis; seizure disorders; and neuropsychiatric conditions including schizophrenia, depression, bipolar disorder, post-traumatic stress disorder, attention deficit disorders, autism-spectrum disorders, or eating disorders such as anorexia nervosa. Dysregulation of inflammatory signaling pathways is believed to be a major factor in the pathology of muscle wasting diseases including muscular dystrophy and various forms of cachexia. In some embodiments, the compounds provided herein may be used in the treatment and/or prevention of muscle wasting diseases, such as muscular dystrophy and various forms of cachexia.

A variety of life-threatening acute disorders also involve dysregulated inflammatory signaling, including acute organ failure involving the pancreas, kidneys, liver, or lungs, myocardial infarction or acute coronary syndrome, stroke, septic shock, trauma, severe burns, and anaphylaxis.

Many complications of infectious diseases also involve dysregulation of inflammatory responses. Although an inflammatory response can kill invading pathogens, an excessive inflammatory response can also be quite destructive and in some cases can be a primary source of damage in infected tissues. Furthermore, an excessive inflammatory response can also lead to systemic complications due to overproduction of inflammatory cytokines such as TNF-α and IL-1. This is believed to be a significant factor in mortality arising from severe influenza, severe acute respiratory syndrome due to infection with coronaviruses including SARS-CoV-2, which causes COVID-19, and other viruses causing upper respiratory disease, and sepsis. In some embodiments, the compounds provided herein may be used in the treatment and/or prevention of influenza, severe acute respiratory syndrome due to infection with coronaviruses including SARS-Cov-2 or other viruses causing upper respiratory disease, or sepsis.

The aberrant or excessive expression of either iNOS or cyclooxygenase-2 (COX-2) has been implicated in the pathogenesis of many disease processes. For example, it is clear that NO is a potent mutagen (Tamir and Tannebaum, 1996), and that nitric oxide can also activate COX-2 (Salvemini et al., 1994). Furthermore, there is a marked increase in iNOS in rat colon tumors induced by the carcinogen, azoxymethane (Takahashi et al., 1997). A series of synthetic triterpenoid analogs of oleanolic acid have been shown to be powerful inhibitors of cellular inflammatory processes, such as the induction by IFN-γ of inducible nitric oxide synthase (iNOS) and of COX-2 in mouse macrophages. See Honda et al. (2000a); Honda et al. (2000b), and Honda et al. (2002), which are all incorporated herein by reference. Elevated brain tissue levels of iNOS have also been associated with Alzheimer's disease (Sporn et al., 1996). In some embodiments, the compounds provided herein may be used in the treatment and/or prevention of Alzheimer's disease.

In one aspect, compounds disclosed herein are characterized by their ability to inhibit the production of nitric oxide in macrophage-derived RAW 264.7 cells induced by exposure to γ-interferon. They are further characterized by their ability to induce the expression of antioxidant proteins such as NQO1 and reduce the expression of pro-inflammatory proteins such as COX-2 and inducible nitric oxide synthase (iNOS). These properties are relevant to the treatment of a wide array of diseases and disorders involving oxidative stress and dysregulation of inflammatory processes including cancer, complications from localized or total-body exposure to ionizing radiation, mucositis resulting from radiation therapy or chemotherapy, autoimmune diseases, cardiovascular diseases including atherosclerosis, ischemia-reperfusion injury (including complications of sickle cell anemia), acute and chronic organ failure including renal failure and heart failure, respiratory diseases, diabetes and complications of diabetes, severe allergies, transplant rejection, graft-versus-host disease, neurodegenerative diseases, diseases of the eye and retina, acute and chronic pain, degenerative bone diseases including osteoarthritis and osteoporosis, inflammatory bowel diseases, dermatitis and other skin diseases, sepsis, burns, seizure disorders, and neuropsychiatric disorders. In some embodiments, the compounds provided herein may be used in the treatment and/or prevention of cancer, complications from localized or total-body exposure to ionizing radiation, mucositis resulting from radiation therapy or chemotherapy, autoimmune diseases, cardiovascular diseases including atherosclerosis, ischemia-reperfusion injury (including complications of sickle cell anemia), acute and chronic organ failure including renal failure and heart failure, respiratory diseases, diabetes and complications of diabetes, severe allergies, transplant rejection, graft-versus-host disease, neurodegenerative diseases, diseases of the eye and retina, acute and chronic pain, degenerative bone diseases including osteoarthritis and osteoporosis, inflammatory bowel diseases, dermatitis and other skin diseases, sepsis, burns, seizure disorders, or neuropsychiatric disorders.

Without being bound by theory, the activation of the antioxidant/anti-inflammatory Keap1/Nrf2/ARE pathway is believed to be implicated in both the anti-inflammatory and anti-carcinogenic properties of the compounds disclosed herein.

In another aspect, compounds disclosed herein may be used for treating a subject having a condition caused by elevated levels of oxidative stress in one or more tissues. Oxidative stress results from abnormally high or prolonged levels of reactive oxygen species such as superoxide, hydrogen peroxide, nitric oxide, and peroxynitrite (formed by the reaction of nitric oxide and superoxide). The oxidative stress may be accompanied by either acute or chronic inflammation. The oxidative stress may be caused by mitochondrial dysfunction, by activation of immune cells such as macrophages and neutrophils, by acute exposure to an external agent such as ionizing radiation or a cytotoxic chemotherapy agent (e.g., doxorubicin), by trauma or other acute tissue injury, by ischemia/reperfusion, by poor circulation or anemia, by localized or systemic hypoxia or hyperoxia, by elevated levels of inflammatory cytokines and other inflammation-related proteins, and/or by other abnormal physiological states such as hyperglycemia or hypoglycemia. In some embodiments, the compounds provided herein may be used in the treatment and/or prevention of mitochondrial dysfunction and disorders associated therewith.

In animal models of many such conditions, stimulating expression of inducible heme oxygenase (HO-1), a target gene of the Nrf2 pathway, has been shown to have a significant therapeutic effect including models of myocardial infarction, renal failure, transplant failure and rejection, stroke, cardiovascular disease, and autoimmune disease (e.g., Sacerdoti et al., 2005; Abraham & Kappas, 2005; Bach, 2006; Araujo et al., 2003; Liu et al., 2006; Ishikawa et al., 2001; Kruger et al., 2006; Satoh et al., 2006; Zhou et al., 2005; Morse and Choi, 2005; Morse and Choi, 2002). This enzyme breaks free heme down into iron, carbon monoxide (CO), and biliverdin (which is subsequently converted to the potent antioxidant molecule, bilirubin). Carbon monoxide has been shown to have signaling functions, and biliverdin reductase, the enzyme that catalyzes the conversion of biliverdin to bilirubin, has been shown to function as a dual-specificity kinase as well as modulate HO-1 expression (Motterlini & Foresti, 2017; Florczyk et al., 2008).

In another aspect, compounds of the present disclosure may be used in preventing or treating tissue damage or organ failure, acute and chronic, resulting from oxidative stress exacerbated by inflammation. Examples of diseases that fall in this category include: heart failure, liver failure, transplant failure and rejection, renal failure, pancreatitis, fibrotic lung diseases (cystic fibrosis, COPD, and idiopathic pulmonary fibrosis, among others), diabetes (including complications), atherosclerosis, ischemia-reperfusion injury including complications of sickle cell anemia, glaucoma, stroke, autoimmune disease, autism, macular degeneration, and muscular dystrophy. For example, in the case of autism, studies suggest that increased oxidative stress in the central nervous system may contribute to the development of the disorder (Chauhan and Chauhan, 2006).

Evidence also links oxidative stress and inflammation to the development and pathology of many other disorders of the central nervous system, including psychiatric disorders such as psychosis, major depression, post-traumatic stress disorder (PTSD), and bipolar disorder; seizure disorders such as epilepsy; pain and sensory syndromes such as migraine, neuropathic pain or tinnitus; and behavioral syndromes such as the attention deficit disorders. See, e.g., Dickerson et al., 2007; Hanson et al., 2005; Kendall-Tackett, 2007; Lencz et al., 2007; Dudhgaonkar et al., 2006; Lee et al., 2007; Morris et al., 2002; Ruster et al., 2005; McIver et al., 2005; Sarchielli et al., 2006; Kawakami et al., 2006; Ross et al., 2003, which are all incorporated by reference herein. For example, elevated levels of inflammatory cytokines, including TNF, interferon-γ, and IL-6, are associated with major mental illness (Dickerson et al., 2007). Microglial activation has also been linked to major mental illness. Therefore, downregulating inflammatory cytokines and inhibiting excessive activation of microglia could be beneficial in patients with schizophrenia, major depression, bipolar disorder, autism-spectrum disorders, and other neuropsychiatric disorders. In some embodiments, the compounds provided herein may be used in the treatment and/or prevention of disorders of the central nervous system, including psychiatric disorders such as psychosis, major depression, post-traumatic stress disorder (PTSD), and bipolar disorder; seizure disorders such as epilepsy; pain and sensory syndromes such as migraine, neuropathic pain or tinnitus; or behavioral syndromes such as the attention deficit disorders.

Accordingly, in pathologies involving oxidative stress alone or oxidative stress exacerbated by inflammation, treatment may comprise administering to a subject a therapeutically effective amount of a compound of the present disclosure, such as those described above or throughout this specification. Treatment may be administered preventively, in advance of a predictable state of oxidative stress (e.g., organ transplantation or the administration of radiation therapy to a cancer patient), or it may be administered therapeutically in settings involving established oxidative stress and inflammation.

The compounds disclosed herein may be generally applied to the treatment of inflammatory conditions, such as sepsis, dermatitis, autoimmune disease and osteoarthritis. In one aspect, the compounds of the present disclosure may be used to treat inflammatory pain and/or neuropathic pain, for example, by inducing Nrf2 and/or inhibiting NF-κB.

In some embodiments, the compounds disclosed herein may be used in the treatment and prevention of diseases such as cancer, inflammation, Alzheimer's disease, Parkinson's disease, multiple sclerosis, autism, amyotrophic lateral sclerosis, Huntington's disease, autoimmune diseases such as rheumatoid arthritis, lupus, Crohn's disease and psoriasis, inflammatory bowel disease, all other diseases whose pathogenesis is believed to involve excessive production of either nitric oxide or prostaglandins, and pathologies involving oxidative stress alone or oxidative stress exacerbated by inflammation.

Another aspect of inflammation is the production of inflammatory prostaglandins such as prostaglandin E. These molecules promote vasodilation, plasma extravasation, localized pain, elevated temperature, and other symptoms of inflammation. The inducible form of the enzyme COX-2 is associated with their production, and high levels of COX-2 are found in inflamed tissues. Consequently, inhibition of COX-2 may relieve many symptoms of inflammation, and a number of important anti-inflammatory drugs (e.g., ibuprofen and celecoxib) act by inhibiting COX-2 activity. Recent research, however, has demonstrated that a class of cyclopentenone prostaglandins (cyPGs) (e.g., 15-deoxy prostaglandin J2, a.k.a. PGJ2) plays a role in stimulating the orchestrated resolution of inflammation (e.g., Rajakariar et al., 2007). COX-2 is also associated with the production of cyclopentenone prostaglandins. Consequently, inhibition of COX-2 may interfere with the full resolution of inflammation, potentially promoting the persistence of activated immune cells in tissues and leading to chronic, "smoldering" inflammation. This effect may be responsible for the increased incidence of cardiovascular disease in patients using selective COX-2 inhibitors for long periods of time.

In one aspect, the compounds disclosed herein may be used to control the production of pro-inflammatory cytokines within the cell by selectively activating regulatory cysteine residues (RCRs) on proteins that regulate the activity of redox-sensitive transcription factors. Activation of RCRs by cyPGs has been shown to initiate a pro-resolution program in which the activity of the antioxidant and cytoprotective transcription factor Nrf2 is potently induced and the activities of the pro-oxidant and pro-inflammatory transcription factors NF-κB and the STATs are suppressed. In some embodiments, this increases the production of antioxidant and reductive molecules (NQO1, HO-1, SOD1, γ-GCS) and decreases oxidative stress and the production of pro-oxidant and pro-inflammatory molecules (iNOS, COX-2, TNF-α). In some embodiments, the compounds of the present disclosure may cause the cells that host the inflammatory event to revert to a non-inflammatory state by promoting the resolution of inflammation and limiting excessive tissue damage to the host.

IV. Pharmaceutical Formulations and Routes of Administration

In another aspect, for administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of a compound disclosed herein formulated with one or more excipients and/or drug carriers appropriate to the indicated route of administration. In some embodiments, the compounds disclosed herein are formulated in a manner amenable for the treatment of human and/or veterinary patients. In some embodiments, formulation comprises admixing or combining one or more of the compounds disclosed herein with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. In some embodiments, the pharmaceutical formulations may be subjected to pharmaceutical operations, such as sterilization, and/or may contain drug carriers and/or excipients such as preservatives, stabilizers, wetting agents, emulsifiers, encapsulating agents such as lipids, dendrimers, polymers, proteins such as albumin, nucleic acids, and buffers.

Pharmaceutical formulations may be administered by a variety of methods, e.g., orally or by injection (e.g. subcutaneous, intravenous, and intraperitoneal). Depending on the route of administration, the compounds disclosed herein may be coated in a material to protect the compound from the action of acids and other natural conditions which may inactivate the compound. To administer the active compound by other than parenteral administration, it may be necessary to coat the compound with, or co-administer the compound with, a material to prevent its inactivation. In some embodiments, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The compounds disclosed herein may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The compounds disclosed herein can be administered orally, for example, with an inert diluent or an assimilable edible carrier. The compounds and other ingredients may also be enclosed in a hard or soft-shell gelatin capsule, compressed into tablets, or incorporated directly into the patient's diet. For oral therapeutic administration, the compounds disclosed herein may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such pharmaceutical formulations is such that a suitable dosage will be obtained.

The therapeutic compound may also be administered topically to the skin, eye, ear, or mucosal membranes. Administration of the therapeutic compound topically may include formulations of the compounds as a topical solution, lotion, cream, ointment, gel, foam, transdermal patch, or tincture. When the therapeutic compound is formulated for topical administration, the compound may be combined with one or more agents that increase the permeability of the compound through the tissue to which it is administered. In other embodiments, it is contemplated that the topical administration is administered to the eye. Such administration may be applied to the surface of the cornea, conjunctiva, or sclera. Without wishing to be bound by any theory, it is believed that administration to the surface of the eye allows the therapeutic compound to reach the posterior portion of the eye. Ophthalmic topical administration can be formulated as a solution, suspension, ointment, gel, or emulsion. Finally, topical administration may also include administration to the mucosa membranes such as the inside of the mouth. Such administration can be directly to a particular location within the mucosal membrane such as a tooth, a sore, or an ulcer. Alternatively, if local delivery to the lungs is desired the therapeutic compound may be administered by inhalation in a dry-powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical carrier. In some embodiments, the specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals. In some embodiments, the human equivalent dose (HED) in mg/kg can be calculated in accordance with the following formula (see, e.g., Reagan-Shaw et al., *FASEB J.*, 22(3):659-661, 2008, which is incorporated herein by reference):

$$\text{HED (mg/kg)} = \text{Animal dose (mg/kg)} \times (\text{Animal } K_m/\text{Human } K_m)$$

Use of the $K_m$ factors in conversion results in HED values based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are specific to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a patient may be determined by physical and physiological factors such as type of animal treated, age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some embodiments, the amount is less than 10,000 mg per day with a range of 750 mg to 9,000 mg per day.

In some embodiments, the amount of the active compound in the pharmaceutical formulation is from about 2 to about 75 weight percent. In some of these embodiments, the amount is from about 25 to about 60 weight percent.

Single or multiple doses of the agents are contemplated. Desired time intervals for delivery of multiple doses can be determined by one of ordinary skill in the art employing no more than routine experimentation. As an example, patients may be administered two doses daily at approximately 12-hour intervals. In some embodiments, the agent is administered once a day.

The agent(s) may be administered on a routine schedule. As used herein a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the patient has eaten or will eat.

V. Combination Therapy

In addition to being used as a monotherapy, the compounds of the present disclosure may also be used in combination therapies. In some embodiments, compounds of the present disclosure may be combined with one or more agents that promote proper folding or assembly of CFTR (correctors) or that enhance the function of CFTR (potentiators). For example, combinations can include a compound of the invention combined with one or more correctors, one or more potentiators, a corrector and a potentiator. In other examples, the combination includes an amplifier either with just one of the compounds of the present invention or in combination with a compound of the present invention and the above described combinations of correctors and potentiators.

In some embodiments, there are provided combination therapies, wherein a compound disclosed herein is combined with another CF treatment, for example, a compound designed to improve function of CFTR that has reached the cell membrane and is capable of at least partial function. Such compounds are known as CFTR potentiators, and the first disease-specific therapy for CF, ivacaftor, has been clinically demonstrated to improve CFTR function in patients with several of the significant mutations. Compounds that prevent misfolding of CFTR are known as correctors. In some embodiments the compounds of the present invention may be used to function as correctors. The enhanced efficacy for the treatment of CF from combining two correctors, or a corrector with a potentiator, is well understood in the art and such combinations have been approved for marketing or are currently being studied in clinical trials. Combinations of three agents are also being studied in clinical trials. It is recognized that that polytherapies are or may soon become the standard of care. In some embodiments, other classes of CFTR modulators, such as "amplifiers" that increase the steady-state levels of CFTR, may become available and may also be used as part of a polytherapy.

Other potential combinations will be apparent to the skilled practitioner. In some embodiments, effective combination therapy is achieved with a single composition or pharmacological formulation that includes multiple agents, or with two or more distinct compositions or formulations, administered at the same time, wherein one composition includes a compound of the present disclosure, and the other(s) include(s) the additional agent(s), formulated together or separately. Alternatively, in other embodiments, the therapy precedes or follows the other agent treatment by intervals ranging from minutes to months.

VI. Definitions

The definitions below supersede any conflicting definition in any reference that is incorporated by reference herein. The fact that certain terms are defined, however, should not be considered as indicative that any term that is undefined is indefinite. Rather, all terms used are believed to describe the present disclosure in terms such that one of ordinary skill can appreciate the scope and practice the present disclosure.

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanyl" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "thiocarbonyl" means —C(=S)—; "sulfonyl" means —S(O)$_2$—; and "sulfinyl" means —S(O)—.

In the context of chemical formulas, the symbol "—" means a single bond, "=" means a double bond, and "≡" means triple bond. The symbol " ---- " represents an optional bond, which if present is either single or double. The symbol " ==== " represents a single bond or a double bond. Thus, the formula

covers, for example,

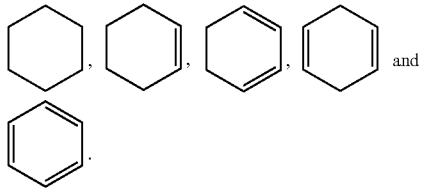

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol " ～～ ", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol " ◀■ " means a single bond where the group attached to the thick end of the wedge is "out of the page." The symbol " ▥▥▥ " means a single bond where the group attached to the thick end of the wedge is "into the page". The symbol " ～～ " means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper. For example, the following two depictions are equivalent:

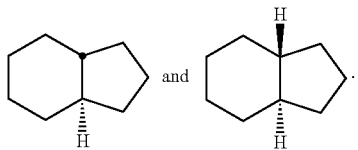

When a variable is depicted as a "floating group" on a ring system, for example, the group "R" in the formula:

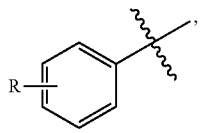

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

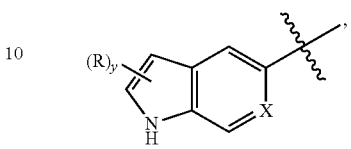

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" or "C=n" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "alkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocycloalkyl$_{(C≤8)}$" is two, the minimum number of carbon atoms in the group "cycloalkyl$_{(C≤8)}$" is three, and the minimum number of carbon atoms in the groups "aryl$_{(C≤8)}$" and "arenediyl$_{(C≤8)}$" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C$_{1-4}$-alkyl", "C1-4-alkyl", "alkyl$_{(C1-4)}$", and "alkyl$_{(C≤4)}$" are all synonymous. Except as noted below, every carbon atom is counted to determine whether the group or compound falls with the specified number of carbon atoms. For example, the group dihexylamino is an example of a dialkylamino$_{(C12)}$ group; however, it is not an example of a dialkylamino$_{(C6)}$ group. Likewise, phenylethyl is an example of an aralkyl$_{(C=8)}$ group. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system. An aromatic compound or chemical group may be depicted as a single resonance structure; however, depiction of one resonance structure is taken to also refer to any other resonance structure. For example:

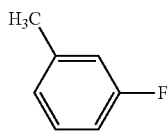

is also taken to refer to

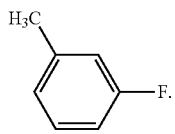

Aromatic compounds may also be depicted using a circle to represent the delocalized nature of the electrons in the fully conjugated cyclic π system, two non-limiting examples of which are shown below:

The term "alkyl" refers to a monovalent saturated aliphatic group with a carbon atom as the point of attachment, a linear or branched acyclic structure, and no atoms other than carbon and hydrogen. The groups —CH₃ (Me), —CH₂CH₃ (Et), —CH₂CH₂CH₃ (n-Pr or propyl), —CH(CH₃)₂ (i-Pr, ⁱPr or isopropyl), —CH₂CH₂CH₂CH₃ (n-Bu), —CH(CH₃)CH₂CH₃ (sec-butyl), —CH₂CH(CH₃)₂ (isobutyl), —C(CH₃)₃ (tert-butyl, t-butyl, t-Bu or ᵗBu), and —CH₂C(CH₃)₃ (neo-pentyl) are non-limiting examples of alkyl groups. The term "alkanediyl" refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH₂— (methylene), —CH₂CH₂—, —CH₂C(CH₃)₂CH₂—, and —CH₂CH₂CH₂— are non-limiting examples of alkanediyl groups. The term "alkylidene" refers to the divalent group =CRR' in which R and R' are independently hydrogen or alkyl. Non-limiting examples of alkylidene groups include: =CH₂, =CH(CH₂CH₃), and =C(CH₃)₂. An "alkane" refers to the class of compounds having the formula H—R, wherein R is alkyl as this term is defined above.

The term "cycloalkyl" refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH₂)₂ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" refers to a divalent saturated aliphatic group with two carbon atoms as points of attachment, no carbon-carbon double or triple bonds, and no atoms other than carbon and hydrogen. The group

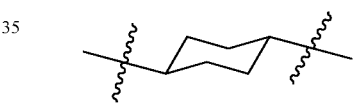

is a non-limiting example of cycloalkanediyl group. A "cycloalkane" refers to the class of compounds having the formula H—R, wherein R is cycloalkyl as this term is defined above.

The term "heterocycloalkyl" refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. The term "heterocycloalkanediyl" refers to a divalent cyclic group, with two carbon atoms, two nitrogen atoms, or one carbon atom and one nitrogen atom as the two points of attachment, said atoms forming part of one or more ring structure(s) wherein at least one of the ring atoms of the non-aromatic ring structure(s) is nitrogen, oxygen or sulfur, and wherein the divalent group consists of no atoms other than carbon, hydrogen, nitrogen, oxygen and sulfur. If more than one ring is present, the rings are fused. As used herein, the term heterocycloalkanediyl does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkanediyl groups include:

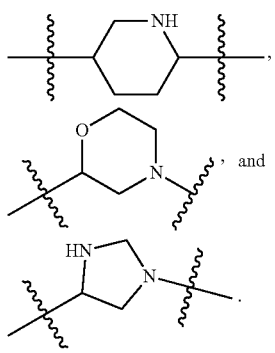

The term "alkenyl" refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" refers to a divalent unsaturated aliphatic group, with two carbon atoms as points of attachment, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule.

The term "alkynyl" refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl.

The term "aryl" refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

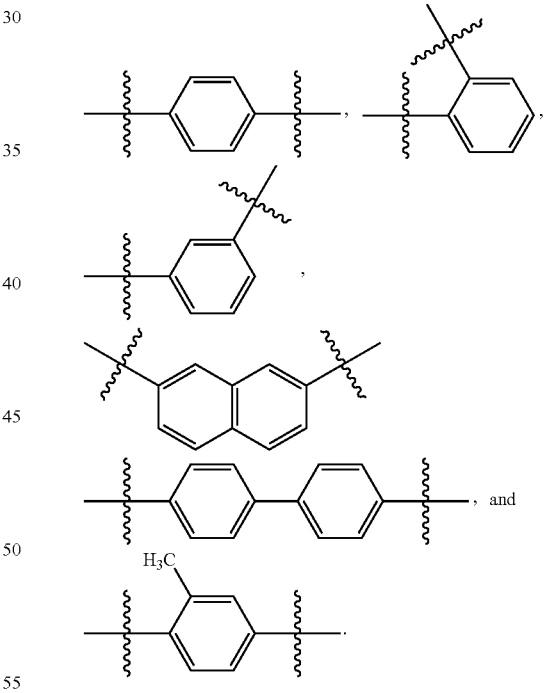

An "arene" refers to the class of compounds having the formula H—R, wherein R is aryl as that term is defined above. Benzene and toluene are non-limiting examples of arenes.

The term "aralkyl" refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl.

The term "heteroaryl" refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include benzoxazolyl, benzimidazolyl, furanyl, imidazolyl (Im), indolyl, indazolyl, isoxazolyl, methylpyridinyl, oxazolyl, oxadiazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. The term "heteroarenediyl" refers to a divalent aromatic group, with two aromatic carbon atoms, two aromatic nitrogen atoms, or one aromatic carbon atom and one aromatic nitrogen atom as the two points of attachment, said atoms forming part of one or more aromatic ring structures, each with three to eight ring atoms, wherein at least one of the ring atoms of the aromatic ring structure(s) is nitrogen, oxygen or sulfur, and wherein the divalent group consists of no atoms other than carbon, hydrogen, aromatic nitrogen, aromatic oxygen and aromatic sulfur. If more than one ring is present, the rings are fused; however, the term heteroarenediyl does not preclude the presence of one or more alkyl or aryl groups (carbon number limitation permitting) attached to one or more ring atoms. Non-limiting examples of heteroarenediyl groups include:

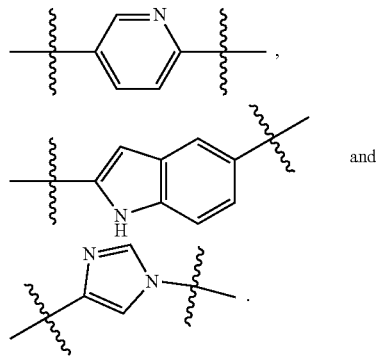

and

The term "acyl" refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH (CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group.

The term "alkoxy" refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), or —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group.

The term "alkylamino" refers to the group —NHR, in which R is an alkyl, as that term is defined above. Non-limiting examples include: —NHCH$_3$ and —NHCH$_2$CH$_3$. The term "dialkylamino" refers to the group —NRR', in which R and R' can be the same or different alkyl groups. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", and "alkoxyamino" when used without the "substituted" modifier, refers to groups, defined as —NHR, in which R is cycloalkyl, alkenyl, alkynyl, aryl, aralkyl, heteroaryl, heterocycloalkyl, and alkoxy, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$.

When a chemical group is used with the "substituted" modifier, one or more hydrogen atom has been replaced, independently at each instance, by —OH, —F, —Cl, —Br, —I, —NH$_2$, —NO$_2$, —CO$_2$H, —CO$_2$CH$_3$, —CO$_2$CH$_2$CH$_3$, —CN, —SH, —OCH$_3$, —OCH$_2$CH$_3$, —C(O)CH$_3$, —NHCH$_3$, —NHCH$_2$CH$_3$, N(CH$_3$)$_2$, —C(O)NH$_2$, —C(O) NHCH$_3$, —C(O)N(CH$_3$)$_2$, —OC(O)CH$_3$, —NHC(O)CH$_3$, —S(O)$_2$OH, or —S(O)$_2$NH$_2$. For example, the following groups are non-limiting examples of substituted alkyl groups: —CH$_2$OH, —CH$_2$Cl, —CF$_3$, —CH$_2$CN, —CH$_2$C (O)OH, —CH$_2$C(O)OCH$_3$, —CH$_2$C(O)NH$_2$, —CH$_2$C(O) CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "hydroxyalkyl" is a subset of substituted alkyl, in which one or more hydrogen atom has been replaced with a hydroxy (i.e. —OH) group, such that no other atoms aside from carbon, hydrogen, and oxygen are present. The groups —CH$_2$OH, —CH$_2$CH$_2$OH, —CH(OH)CHOH, —CH$_2$CH(OH)CH$_3$, and —CH(OH)CH$_2$OH are non-limiting examples of hydroxyalkyl groups. The term "monohydroxyalkyl" is a subset of substituted alkyl, in which one hydrogen atom has been replaced with a hydroxy (i.e. —OH) group, such that no other atoms aside from carbon, hydrogen, and one oxygen are present. The groups —CH$_2$OH, —CH$_2$CH$_2$OH, and —CH$_2$CH(OH)CH$_3$ are non-limiting examples of monohydroxyalkyl groups. The term "fluoroalkyl" is a subset of substituted alkyl, in which one or more hydrogen atom has been replaced with a fluoro, such that no other atoms aside from carbon, hydrogen, and fluorine are present. The groups —CH$_2$F, —CHF$_2$, and —CF$_3$ are non-limiting examples of fluoroalkyl groups. The term "monofluoroalkyl" is a subset of substituted alkyl, in which one hydrogen atom has been replaced with a fluoro, such that no other atoms aside from carbon, hydrogen, and one fluorine are present. The groups —CH$_2$F, —CH$_2$CH$_2$F, and —CH$_2$CH (F)CH$_3$ are non-limiting examples of monofluoroalkyl groups. The term "aminoalkyl" is a subset of substituted alkyl, in which one or more hydrogen atom has been replaced with an amino (i.e. —NH$_2$) group, such that no other atoms aside from carbon, hydrogen, and nitrogen are present. The groups —CH$_2$NH$_2$, —CH(NH$_2$)CH$_3$, —CH$_2$CH$_2$NH$_2$, —CH$_2$CH(NH$_2$)CH$_3$ and —CH(NH$_2$)CH$_2$NH$_2$ are non-limiting examples of aminoalkyl groups. The term "monoaminoalkyl" is a subset of substituted alkyl, in which one hydrogen atom has been replaced with an amino (i.e. —NH$_2$) group, such that no other atoms aside from carbon, hydrogen, and one nitrogen are present. The groups —CH$_2$NH$_2$, —CH$_2$CH$_2$NH$_2$, and —CH$_2$CH(NH$_2$)CH$_3$ are non-limiting examples of monoaminoalkyl groups. Non-limiting examples of substituted aralkyls are: (3-chlorophenyl)-methyl, and 2-chloro-2-phenyl-eth-1-yl. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups. The groups —NHC(O)OCH$_3$ and —NHC(O)NHCH$_3$ are non-limiting examples of substituted amido groups.

When a chemical group is used with the "polar-substituted" modifier, one or more hydrogen atom has been replaced, independently at each instance, by one of the following polar substituents: —OH, —F, —NH$_2$, —CO$_2$H, —CO$_2$CH$_3$, —C(O)NH$_2$, —C(O)NHCH$_3$, —OC(O)CH$_3$, —NHC(O)CH$_3$, —NHC(O)OCH$_3$, —NHC(O)OCH$_2$CH$_3$, —NHC(O)NHCH$_3$, —NHC(O)NHCH$_2$CH$_3$, —S(O)$_2$OH, or —S(O)$_2$NH$_2$, provided that not every hydrogen is so replaced. Non-limiting examples of polar-substituted alkyl groups include —CH$_2$F, —CHF$_2$, —CH$_2$CH$_2$F, —CHFCH$_2$F, —CF$_2$CH$_3$, —CH$_2$OH, —CH$_2$CH$_2$OH, —CH$_2$CH$_2$CH$_2$NH$_2$, —CH$_2$CH$_2$OH, and —CH(NH$_2$)CH$_2$OH.

When a chemical group is used with the "monopolar-substituted" modifier, one and only one hydrogen atom has been replaced by one of the following polar substituents: —OH, —F, —NH$_2$, —CO$_2$H, —CO$_2$CH$_3$, —C(O)NH$_2$, —C(O)NHCH$_3$, —OC(O)CH$_3$, —NHC(O)CH$_3$, —NHC(O)OCH$_3$, —NHC(O)OCH$_2$CH$_3$, —NHC(O)NHCH$_3$, —NHC(O)NHCH$_2$CH$_3$, —S(O)$_2$OH, or —S(O)$_2$NH$_2$. Non-limiting examples of monopolar-substituted alkyl groups include —CH$_2$F, —CH$_2$CH$_2$F, —CHFCH$_3$, —CH$_2$OH, —CH$_2$CH$_2$OH, —CH(OH)CH$_2$OH, —CH$_2$NH$_2$, —CH$_2$CH$_2$NH$_2$, and —CH(NH$_2$)CH$_3$.

Some of the abbreviations used herein are as follows: Ac refers to an acetyl group (—C(O)CH$_3$); Boc refers to tert-butyloxycarbonyl; COPD stands for chronic obstructive pulmonary disease; COX-2 refers to cyclooxygenase-2; CYP3A4 stands for cytochrome P450 3A4; cyPGs refers to cyclopentenone prostaglandins; DBDMH refers to 1,3-Dibromo-5,5-dimethylhydantoin; DIBAL-H is diisobutylaluminium hydride; DMAP refers to 4-dimethylaminopyridine; DMF is dimethylformamide; DMSO is dimethyl sulfoxide; EDC is 1-ethyl-3-(3-dimethylaminopropyl)carbodiimide; Et$_2$O, diethyl ether; HO-1 refers to inducible heme oxygenase; IFNγ or IFN-γ refer to interferon-γ; IL-1 refers to the interleukin-1 family; iNOS stands for inducible nitric oxide synthase; NCS refers to N-Chlorosuccinimide; NMO refers to N-methylmorpholine N-oxide; NO stands for nitric oxide; NQO1 stands for NAD(P)H dehydrogenase (quinone 1); Nrf2 refers to nuclear factor erythroid 2-related factor 2; OA refers to oleanolic acid; Py stands for Pyridine; T3P refers to propylphosphonic anhydride; TFA is trifluoroacetic acid; TFAA stands for trifluoroacetic anhydride; THF is tetrahydrofuran; TNFα or TNF-α, tumor necrosis factor-α; TPAP is tetrapropylammonium perruthenate; Ts stands for tosyl; TsOH or p-TsOH is p-toluenesulfonic acid; 4 Å MS refers to 4 angstrom molecular sieves.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects or patients.

An "active ingredient" (AI) or active pharmaceutical ingredient (API) (also referred to as an active compound, active substance, active agent, pharmaceutical agent, agent, biologically active molecule, or a therapeutic compound) is the ingredient in a pharmaceutical drug that is biologically active.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to the patient or subject, is sufficient to effect such treatment or prevention of the disease as those terms are defined below.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half. The term "relative $IC_{50}$" refers to the fold difference in potency between two compounds. It is determined by dividing the $IC_{50}$ value of a compound of interest by the $IC_{50}$ value of a benchmark compound within each experimental assay using the following equation:

$$\text{Relative } IC50 \text{ (Fold)} = \frac{IC50 \text{ (Compound of Interest)}}{IC50 \text{ (Benchmark)}}$$

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malmalonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of the present disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug, agent, or preparation) is a composition used to diagnose, cure, treat, or prevent disease, which comprises an active pharmaceutical ingredient (API) (defined above) and optionally contains one or more inactive ingredients, which are also referred to as excipients (defined above).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an active pharmaceutical ingredient of the present disclosure. The prodrug itself may or may not have activity in its prodrug form. For example, a compound comprising a hydroxy group may be administered as an ester that is converted by hydrolysis in vivo to the hydroxy compound. Non-limiting examples of suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, and esters of amino acids. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2', where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

The term "unit dose" refers to a formulation of the compound or composition such that the formulation is prepared in a manner sufficient to provide a single therapeutically effective dose of the active ingredient to a patient in a single administration. Such unit dose formulations that may be used include but are not limited to a single tablet, capsule, or other oral formulations, or a single vial with a syringeable liquid or other injectable formulations.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Synthesis and Characterization

A. General Information

Unless otherwise stated, commercially reagents were used as received, and all reactions were run under nitrogen atmosphere. All solvents were of HPLC or ACS grade. Nuclear magnetic resonance (NMR) spectra were recorded on a Varian Inova-400 spectrometer at operating frequencies of 400 MHz CH NMR). Chemical shifts (δ) are given in ppm relative to residual solvent (usually chloroform δ 7.26 ppm for $^1$H NMR) and coupling constants (J) in Hz. Multiplicity is tabulated as s for singlet, d for doublet, t for triplet, q for quadruplet, and m for multiplet. Mass spectra were recorded on Agilent 6120 mass spectrometer. The compounds of the present disclosure may be prepared according to the methods outlined in Example 1 as well as methods known to a skilled artisan, including those disclosed in WO 2012/125488 and WO 2014/040056, both of which are incorporated by reference herein.

B. Synthetic Routes to Compounds of the Present Disclosure

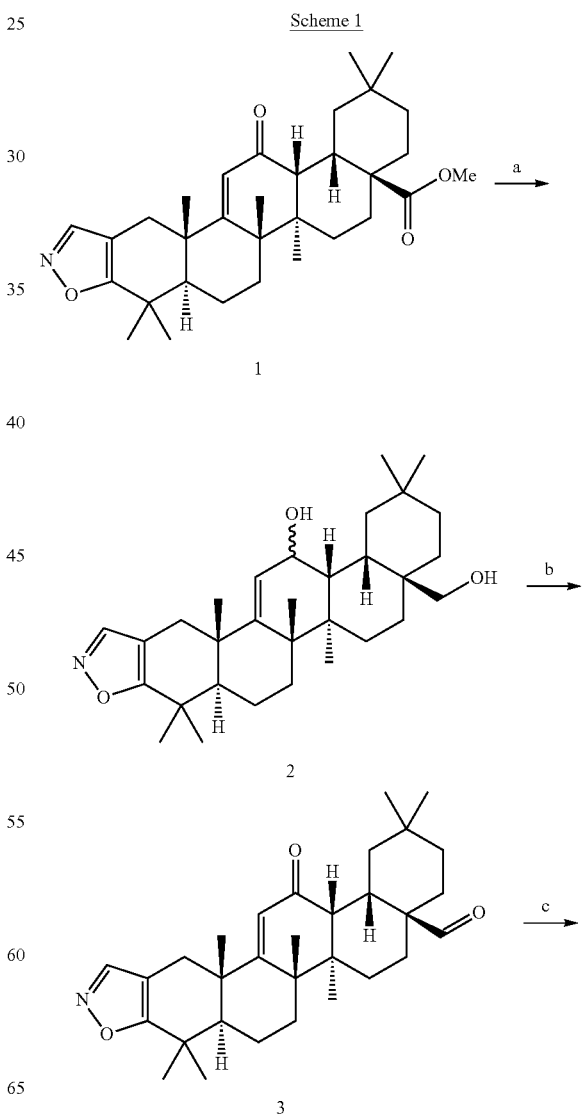

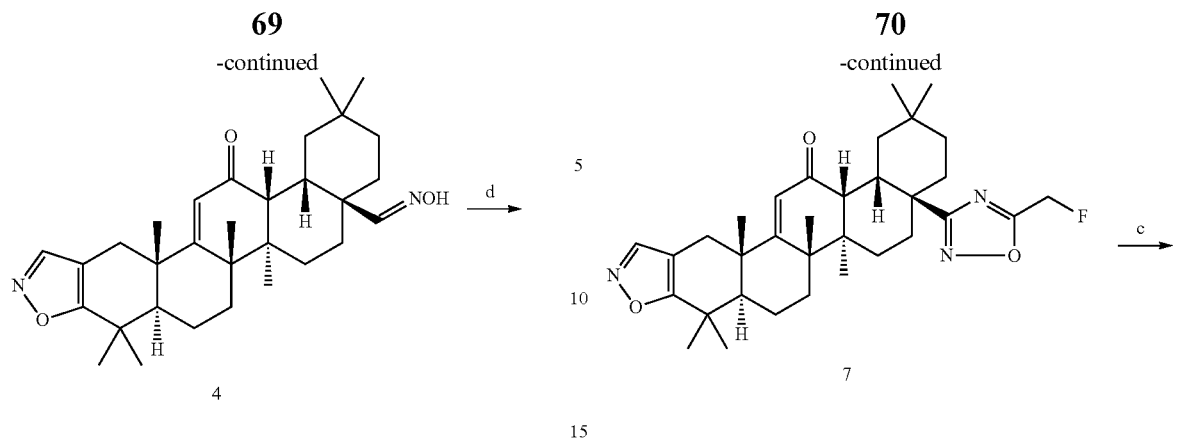
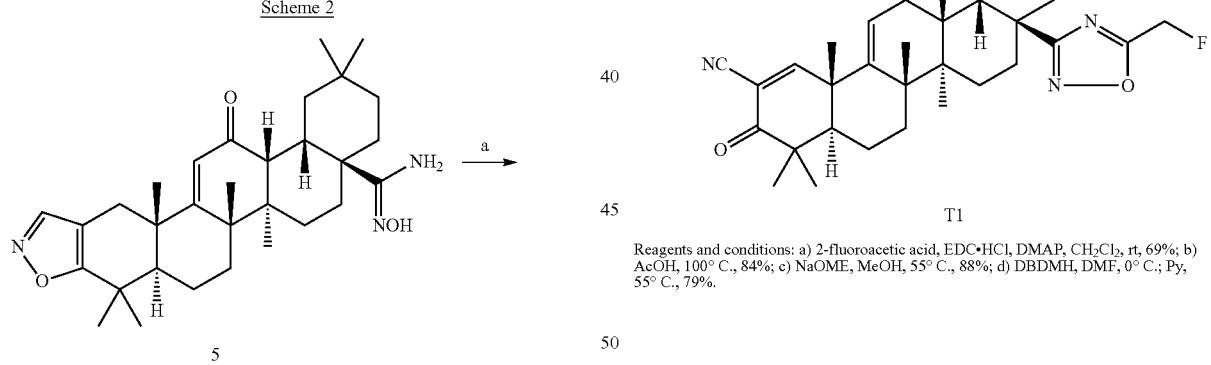
Reagents and conditions: a) DIBAL—H, toluene, THF, 0° C.-rt; b) NMO, TPAP, 4Å MS, CH₂Cl₂, rt, 68% from 1; c) NH₂OH—HCl, NaOAc, EtOH, H₂O, rt, 77%; d) aq. HCl, NCS, MeCN, -10° C., aq. NH₃, rt, 68%.
Reagents and conditions: a) 2-fluoroacetic acid, EDC·HCl, DMAP, CH₂Cl₂, rt, 69%; b) AcOH, 100° C., 84%; c) NaOME, MeOH, 55° C., 88%; d) DBDMH, DMF, 0° C.; Py, 55° C., 79%.
Scheme 3
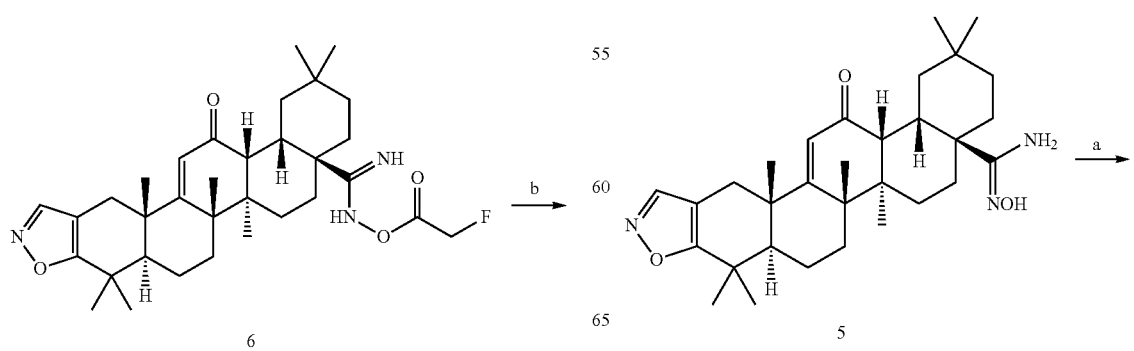

Scheme 4
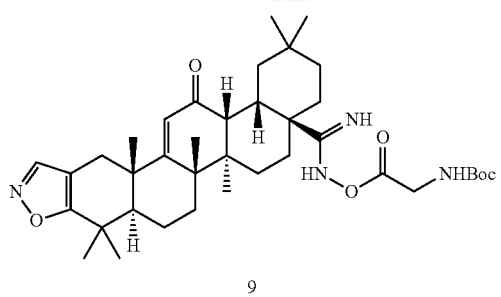
9
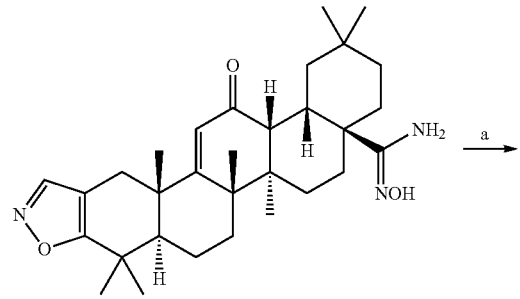
5
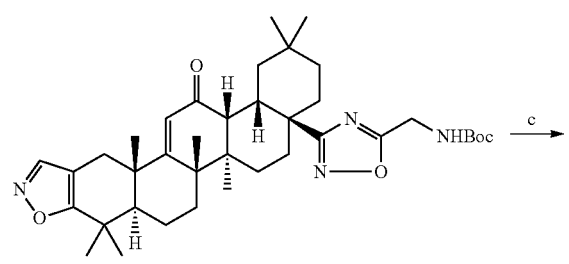
10
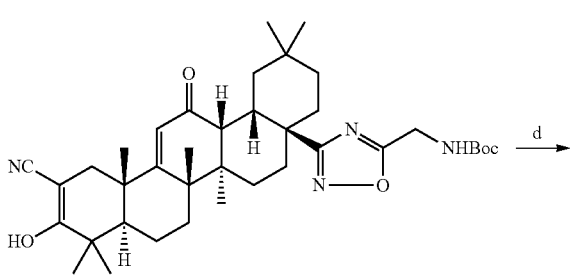
11
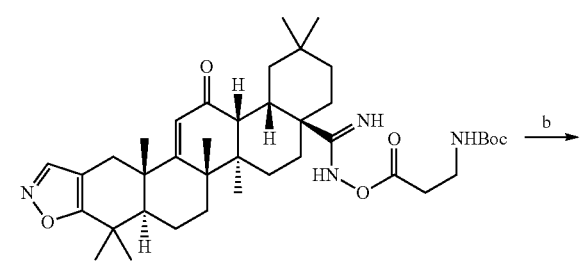
13
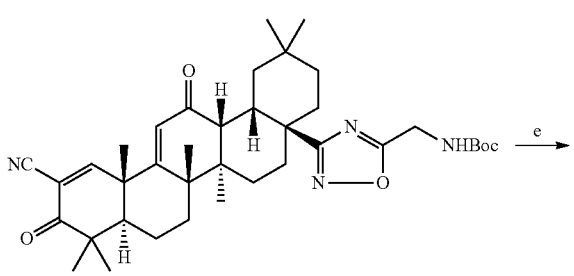
12
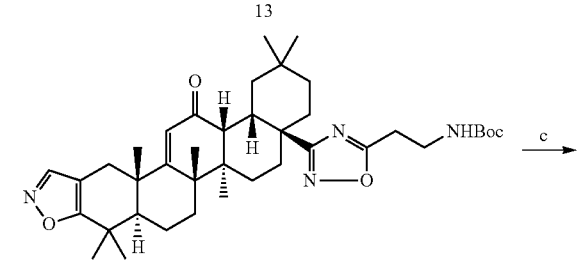
14
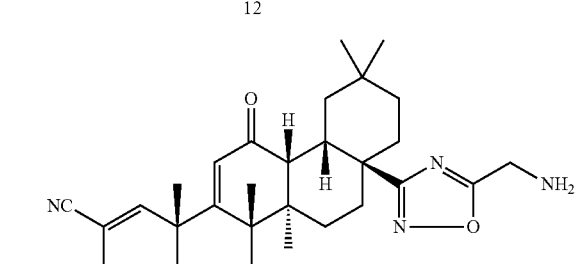
T2
Reagents and conditions:
a) Boc-glycine, EDC·HCl, DMAP, CH$_2$Cl$_2$, rt, 79%;
b) 1,4-dioxane, 160° C., 80%;
c) K$_2$CO$_3$, MeOH, rt, 89%;
d) DBDMH, DMF, 0° C.; Py, 60° C., 90%;
e) TFA, CH$_2$Cl$_2$, rt, 49%.
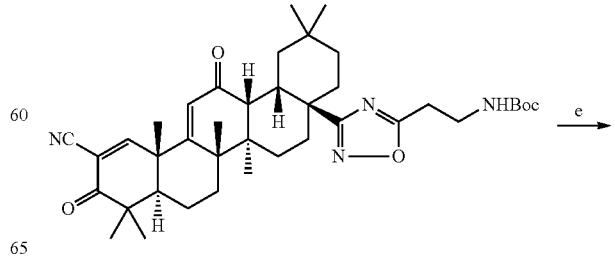
15
16

73
-continued
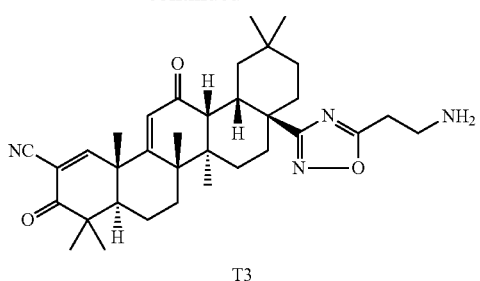
T3
Reagents and conditions:
a) Boc-β-Ala-OH, EDC•HCl, DMAP, CH₂Cl₂, rt, quantitative yield;
b) 1,4-dioxane, 160° C., 70%;
c) K₂CO₃, MeOH, rt, 84%;
d) DBDMH, DMF, 0° C.; Py, 60° C., 82%;
e) TFA, CH₂Cl₂, rt, 78%.
Scheme 5
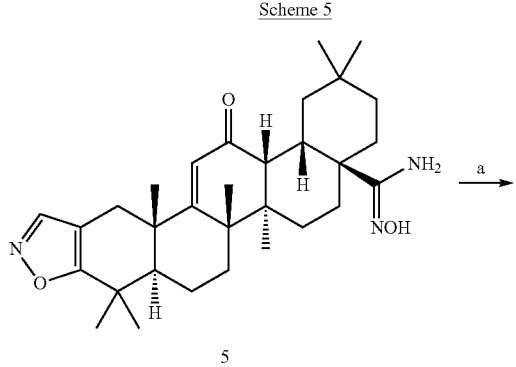
74
-continued
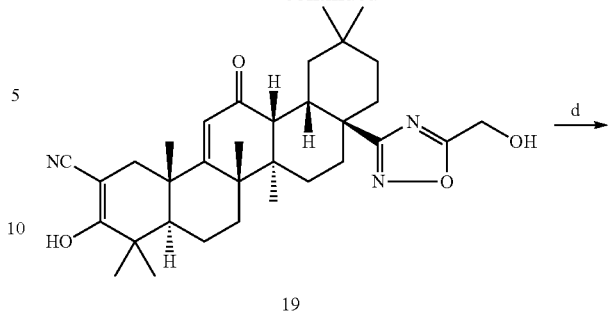
19
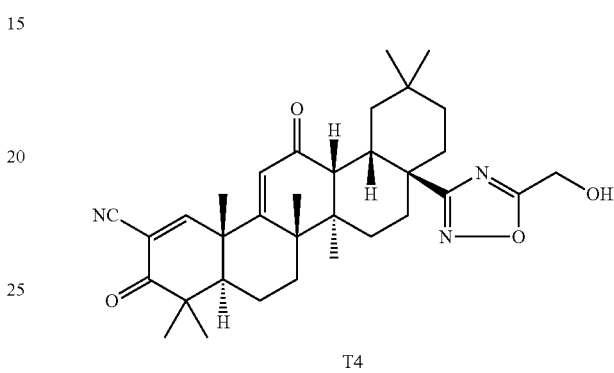
T4
Reagents and conditions:
a) acetoxyacetyl chloride, Et₃N, CH₂Cl₂, 0° C., quantitative yield;
b) AcOH, 100° C., 86%;
c) NaOMe, MeOH, 55° C., 90%;
d) DBDMH, DMF, 0° C.; Py, 60° C., 82%.
Scheme 6
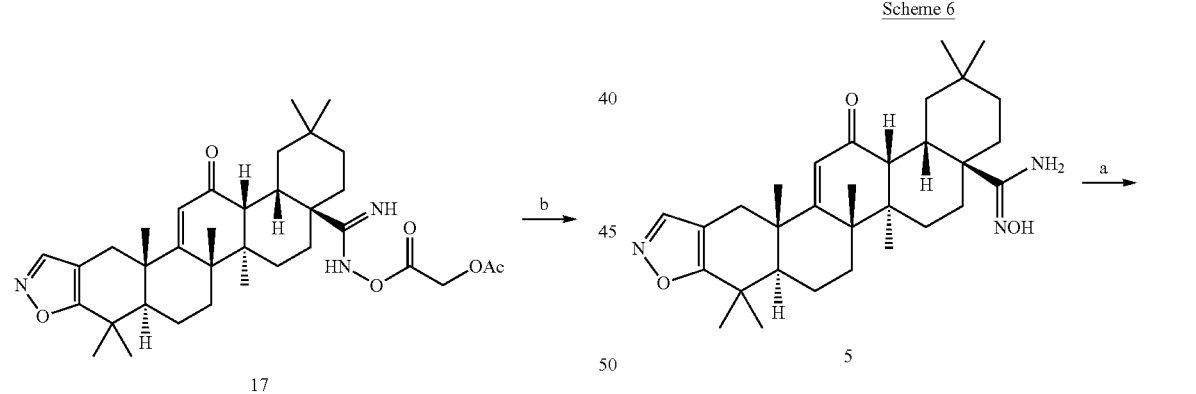
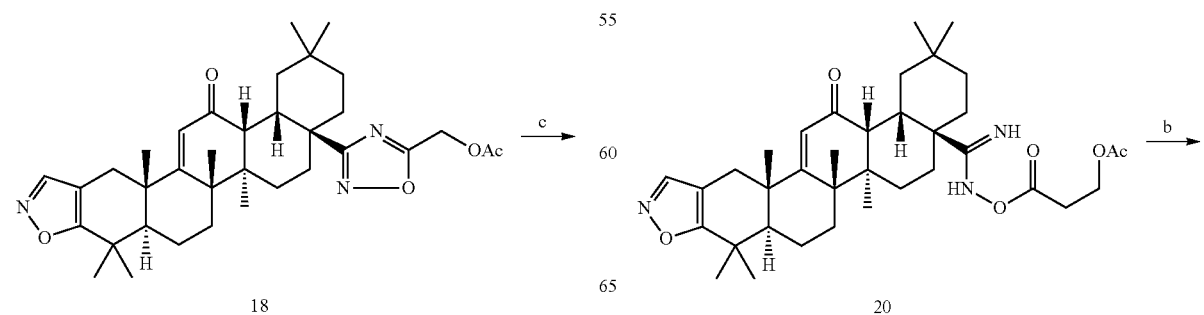

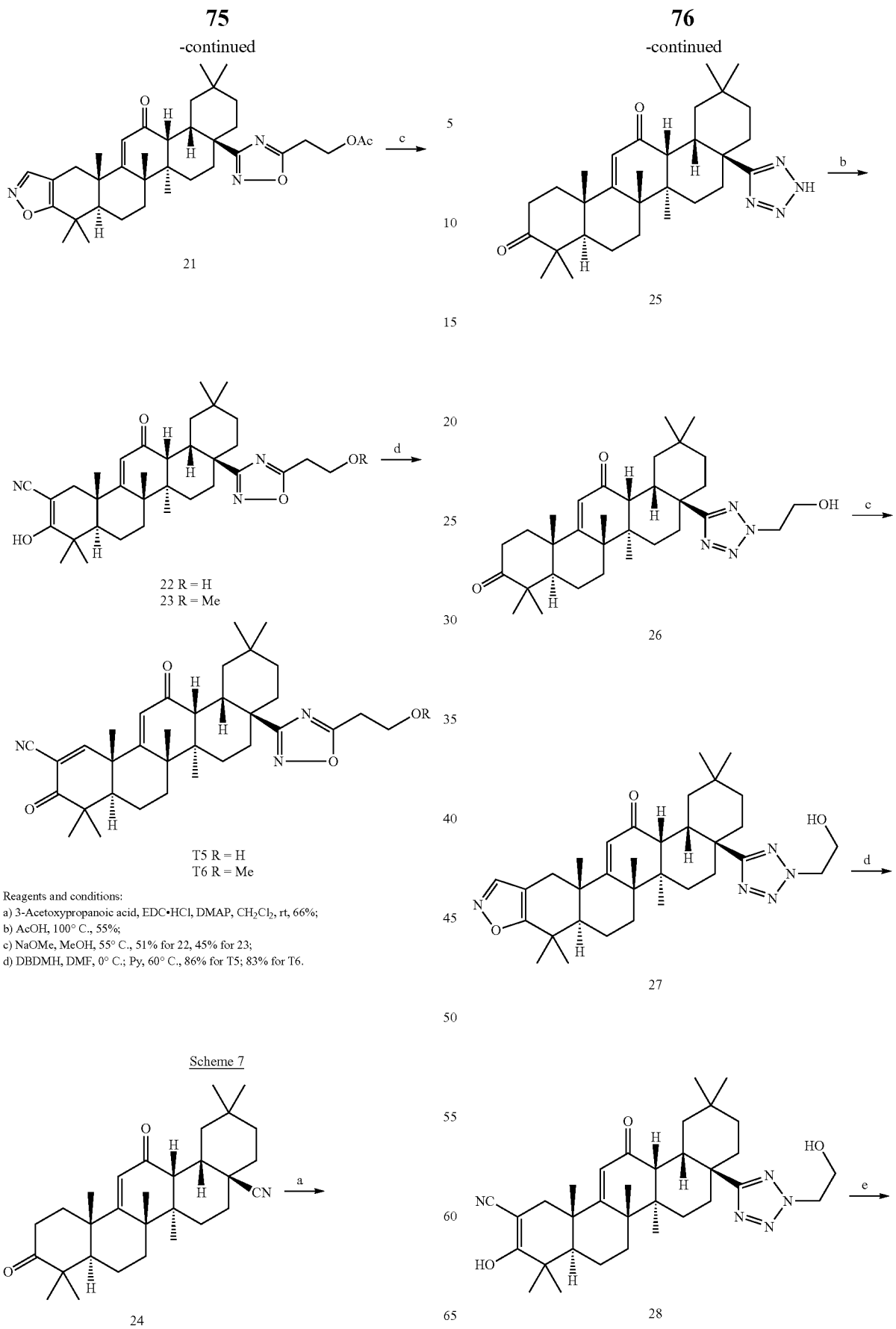

77
-continued
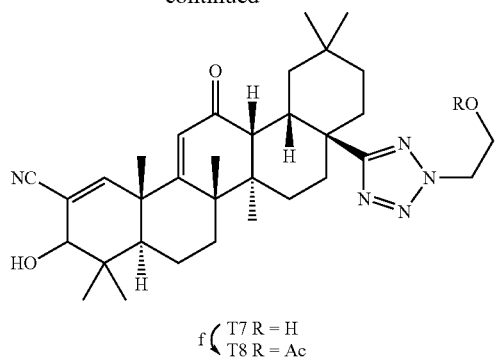
Reagents and conditions:
a) n-Bu₃SnN₃, o-xylene, 150° C., 47%;
b) 2-bromoethanol, Cs₂CO₃, MeCN, 60° C., 82%;
c) HCO₂Et, NaOMe, MeOH, 0° C.-rt; 6N aq. HCl, NH₂OH•HCl, EtOH, 55° C., 72%;
d) NaOMe, MeOH, 55° C., quantitative yield;
e) DBDMH, DMF, 0° C.; pyridine, 55° C., 68%;
f) Ac₂O, pyridine, DMAP, CH₂Cl₂, 0° C., 71%.
Scheme 8
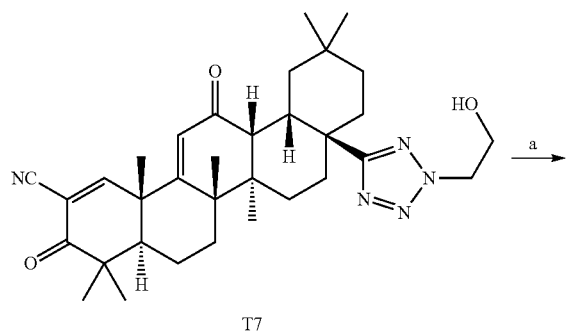
T7
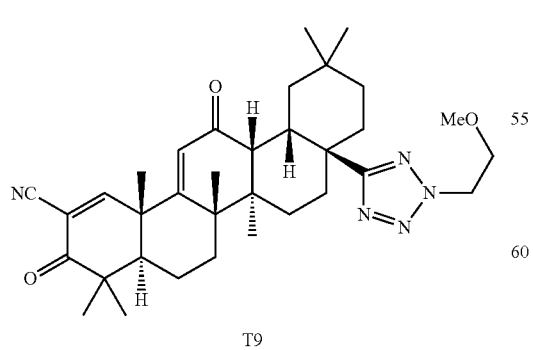
T9
Reagents and conditions:
a) trimethyloxonium tetrafluoroborate, Proton sponge, CH₂Cl₂, rt, 43%.
78
Scheme 9
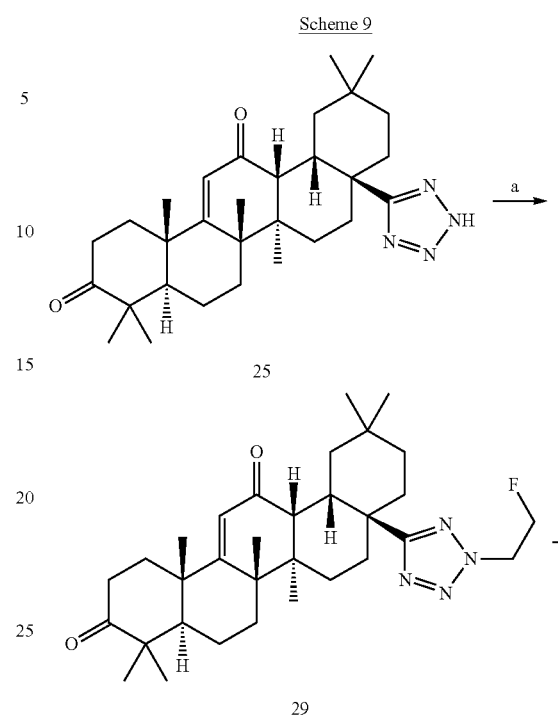
25
29
30
31
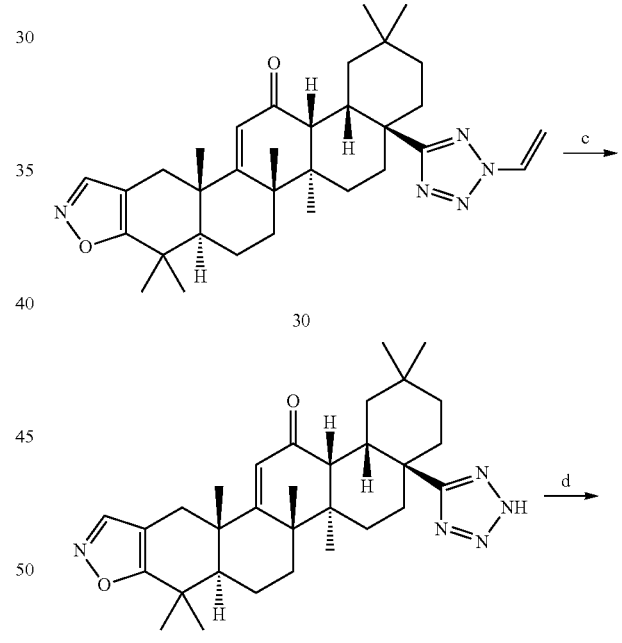
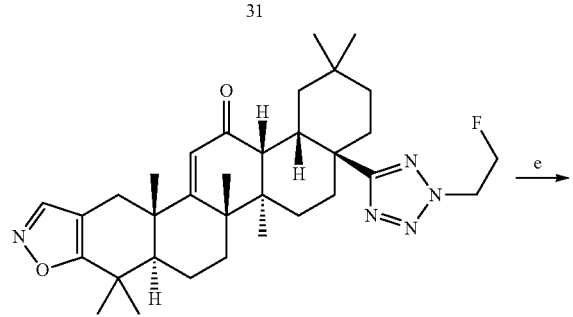
32

79
-continued

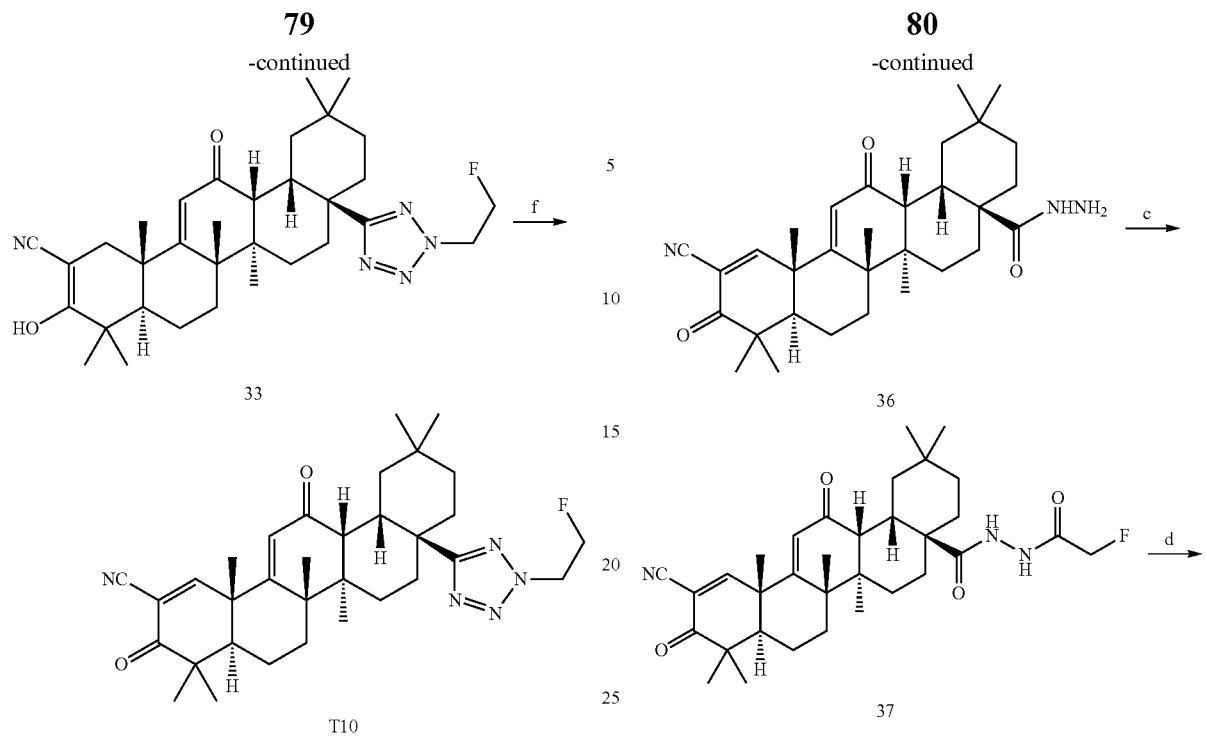

80
-continued

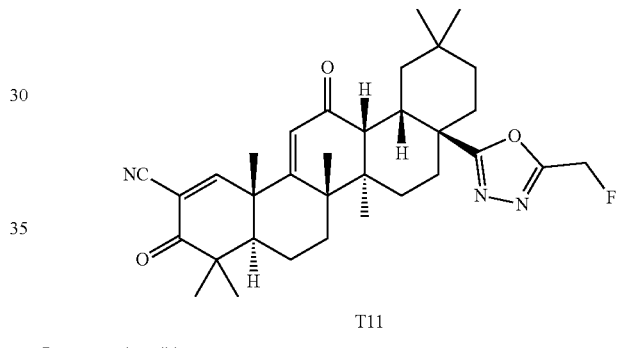

Reagents and conditions:
a) 1-fluoro-2-iodoethane, Cs₂CO₃, MeCN, 60° C., 52%;
b) HCO₂Et, NaOMe, MeOH, 0° C.-rt; 6N aq. HCl, NH₂OH•HCl, EtOH, 55° C., 71%;
c) O₃/O₂, MeOH, CH₂Cl₂, -78° C.; NaBH₄, rt, 99%;
d) 1-fluoro-2-iodoethane, Cs₂CO₃, MeCN, 60° C., 60%;
e) K₂CO₃, MeOH, rt, 79%;
f) DBDMH, DMF, 0° C.; pyridine, 55° C., 71%.

Reagents and conditions:
a) (COCl)₂, DMF, CH₂Cl₂, 0° C.-rt;
b) hydrazine hydrate, CH₂Cl₂, 0° C.-rt, 90%;
c) 2-fluoroacetic acid, EDC•HCl, DMAP, CH₂Cl₂, rt, 60%;
d) TSOH•H₂O, toluene, reflux, 60%.

Scheme 10

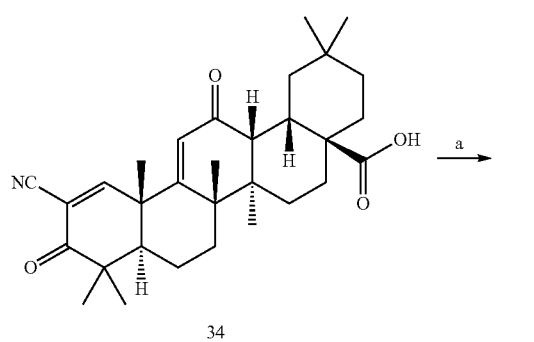

Scheme 11

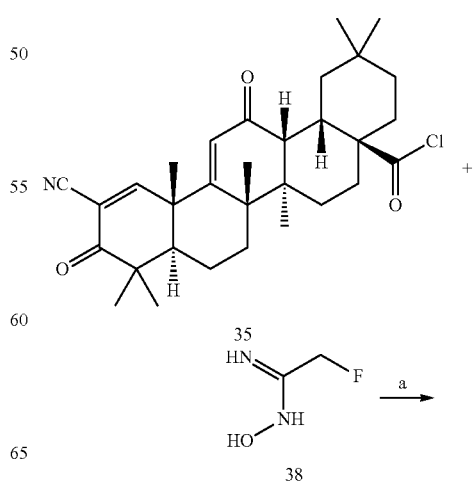

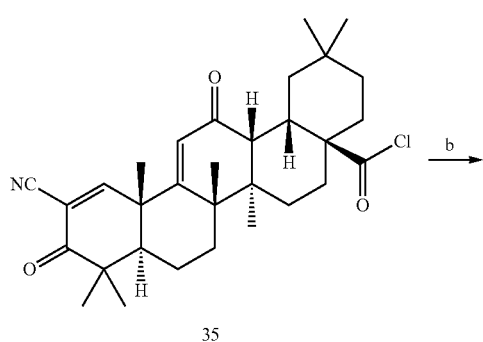

81
-continued
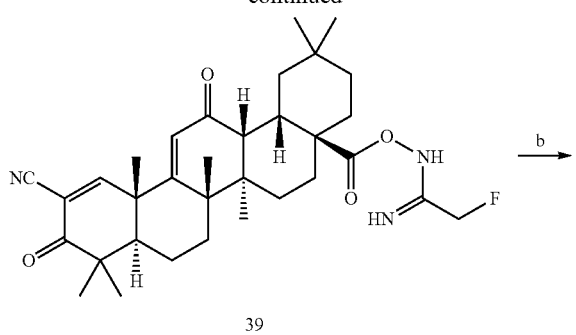
39
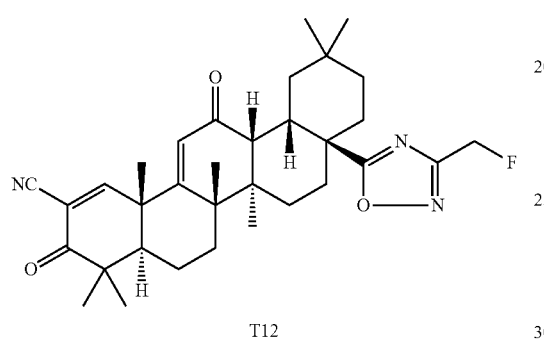
T12
Reagents and conditions:
a) Et₃N, CH₂Cl₂, 0° C.-rt, 84%;
b) T3P, Et₃N, EtOAc, 125° C., microwave, 6%.
Scheme 12
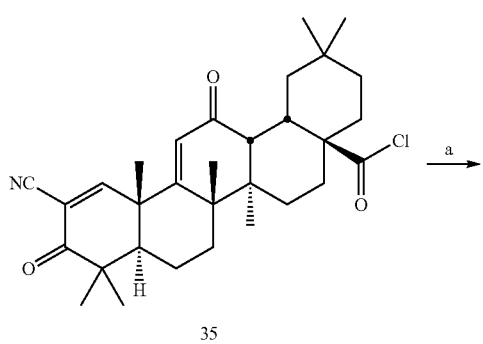
35
82
-continued
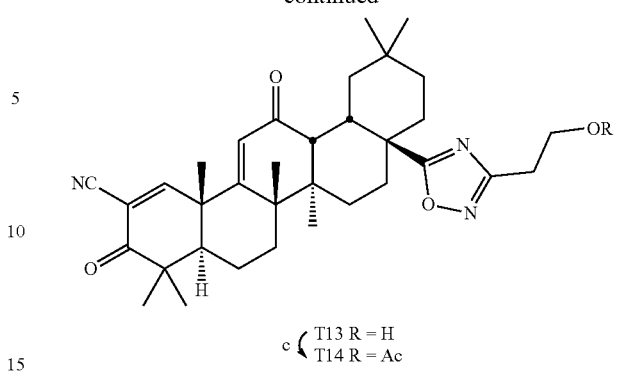
c ⎰ T13 R = H
  ⎱ T14 R = Ac
Reagents and conditions:
a) 3-Hydroxypropionamide oxime, Et₃N, CH₂Cl₂, rt, 46% from 34;
b) Bu₄NOH, water, THF, rt, 45%;
c) 12N aq. HCl, AcOH, 75° C., 44%.
Scheme 13
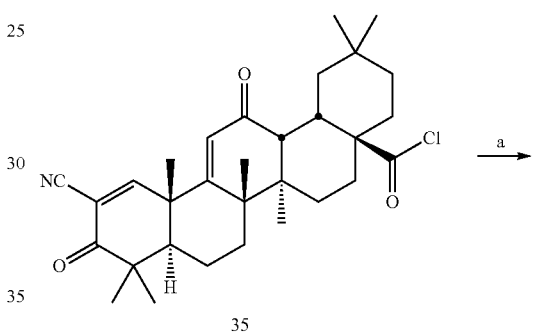
35
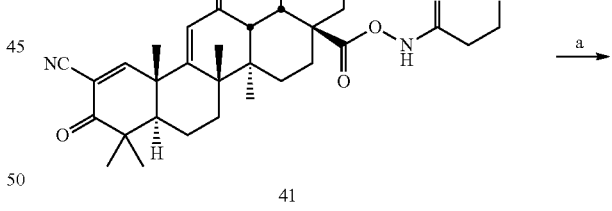
41
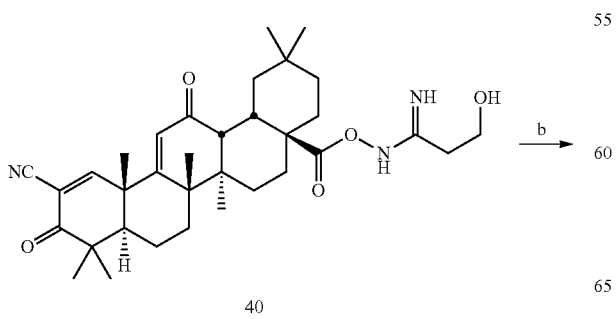
T15
Reagents and conditions: a) 3-Methoxypropionamidoxime hydrochloride, Et₃N, CH₂Cl₂, rt; b) Bu₄NOH, water, THF, rt, 37% from 34.
40

Scheme 14
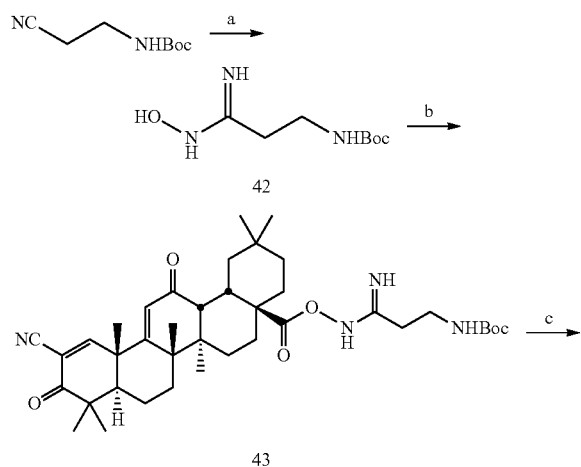
42
43
44
T16
Reagents and conditions:
a) NH$_2$OH·HCl, Et$_3$N, EtOH, 80° C.;
b) 35, Et$_3$N, CH$_2$Cl$_2$, rt;
c) Bu$_4$NOH, water, THF, rt, 45% from 34;
d) 12M aq. HCl, MeOH, rt, 83%.
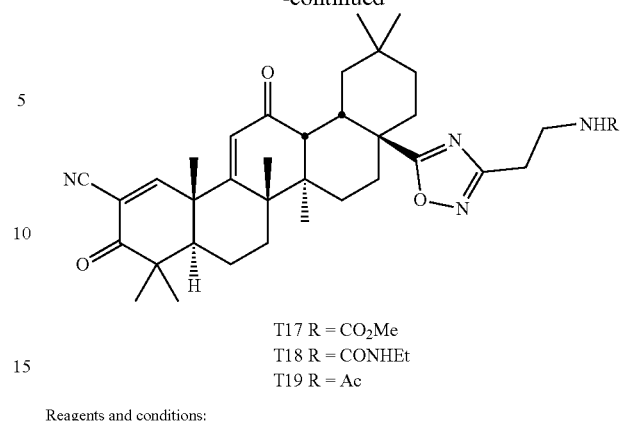
T17 R = CO$_2$Me
T18 R = CONHEt
T19 R = Ac
Reagents and conditions:
a) Methyl chloroformate, Et$_3$N, CH$_2$Cl$_2$, rt, 20% for T17;
b) Ethyl isocyanate, Et$_3$N, CH$_2$Cl$_2$, rt, 67% for T18;
c) acetyl chloride, Et$_3$N, CH$_2$Cl$_2$, rt, 33% for T19.
Scheme 16
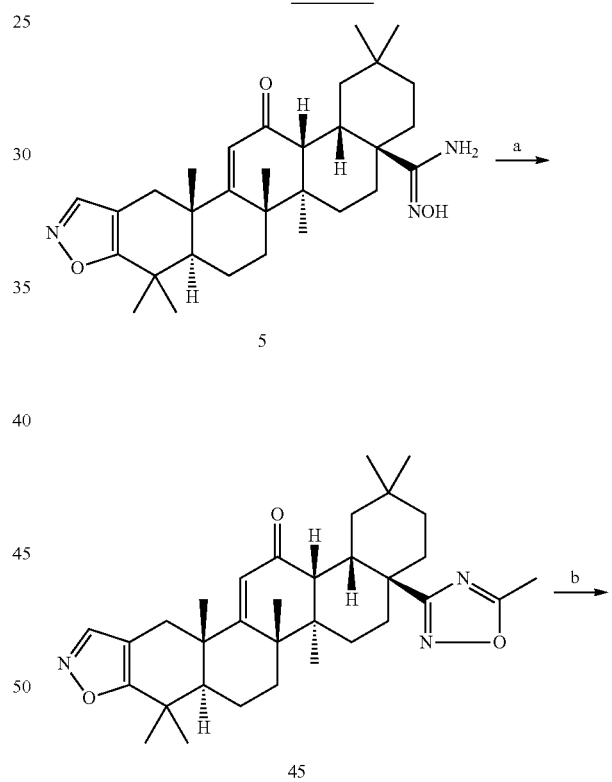
5
45
46
Scheme 15
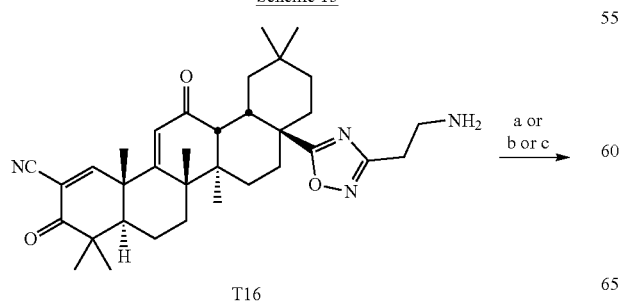
T16

85
-continued
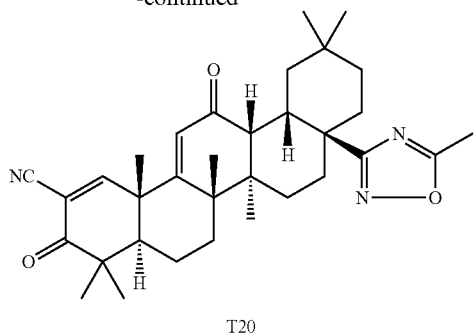
T20
Reagents and conditions:
a) Ac₂O, AcOH, rt-100° C., 95%;
b) K₂CO₃, MeOH, rt, 78%;
c) DBDMH, DMF, 0° C.; Py, 55° C., 78%.
Scheme 17
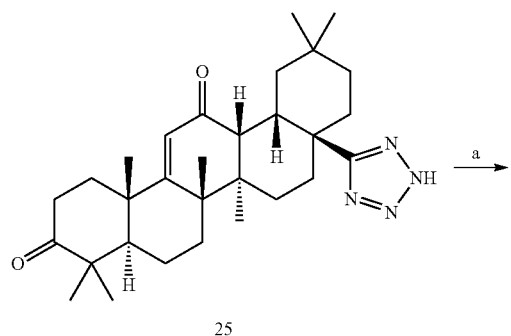
25
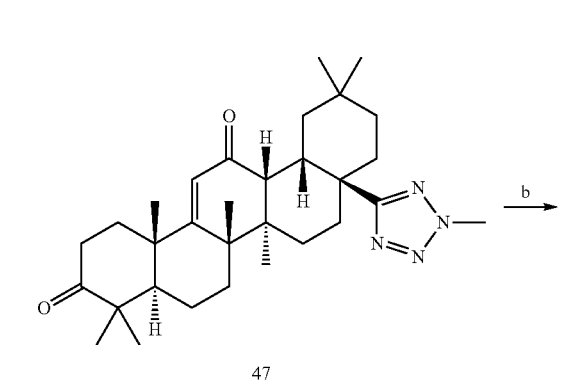
47
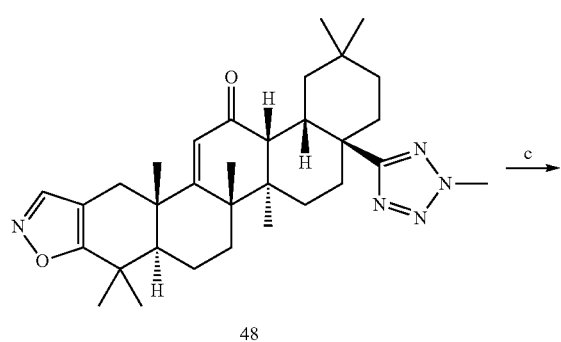
48
86
-continued
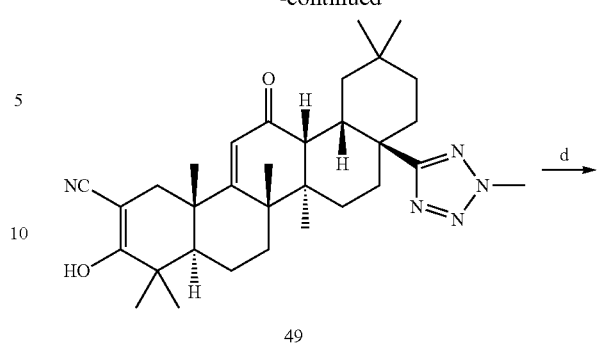
49
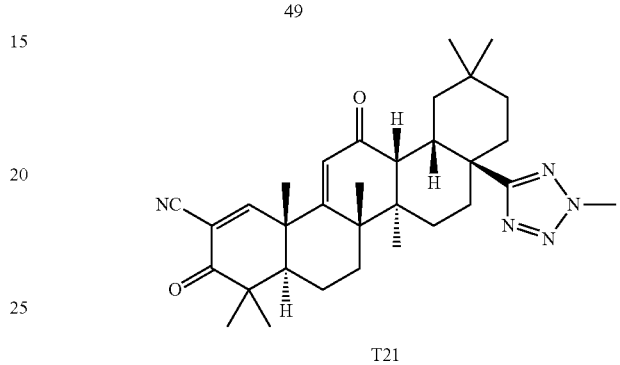
T21
Reagents and conditions:
a) (Trimethylsilyl)diazomethane, THF, MeOH, hexanes, 0° C., 90%;
b) HCO₂Et, NaOMe, MeOH, 0° C.; 6N aq. HCl, NH₂OH·HCl, EtOH, 60° C., 78%;
c) NaOMe, MeOH, 45° C., 77%;
d) DBDMH, DMF, 0° C.; pyridine, 55° C., 78%.
Scheme 18
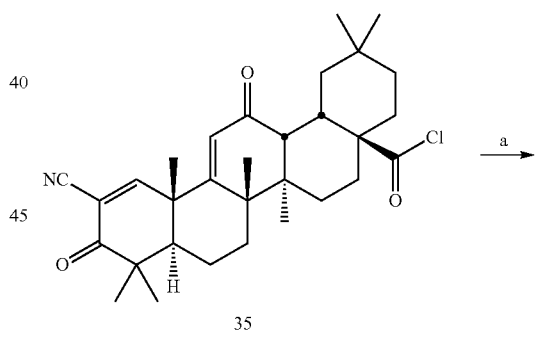
35
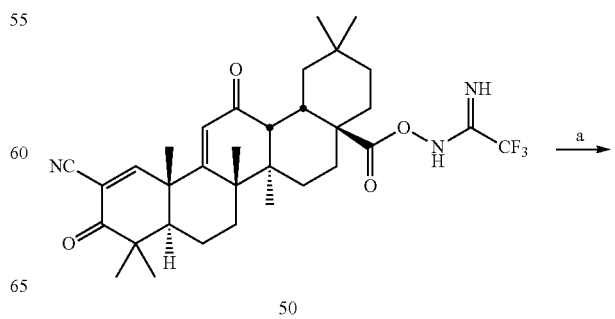
50

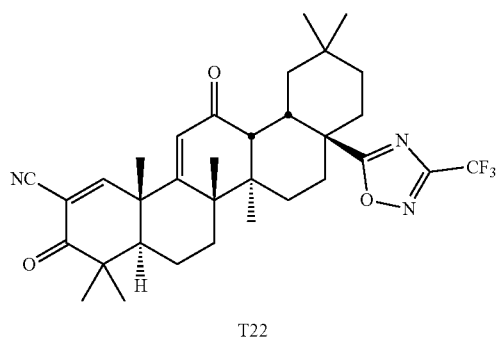
T22
Reagents and conditions: a) 2,2,2-Trifluoro-N'-hydroxy-ethanimidamide, Et₃N, CH₂Cl₂, rt; b) Bu₄NOH, water, THF, rt, 10% from 34.
Scheme 20
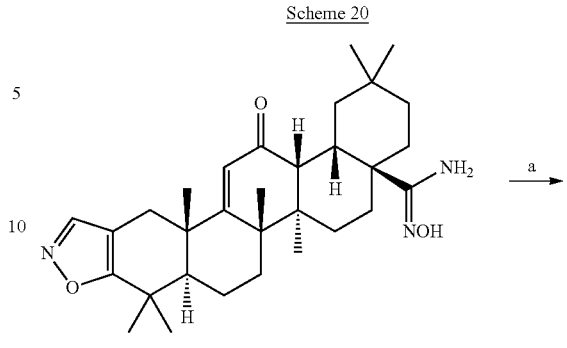
5
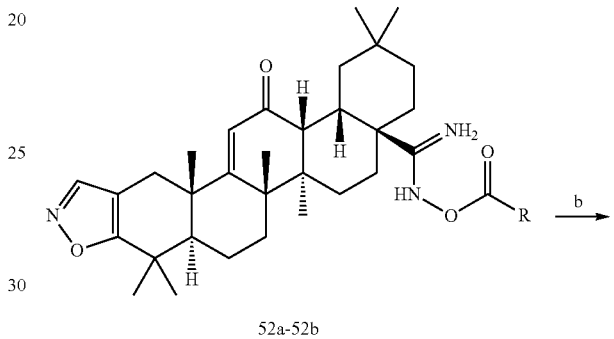
52a-52b
Scheme 19
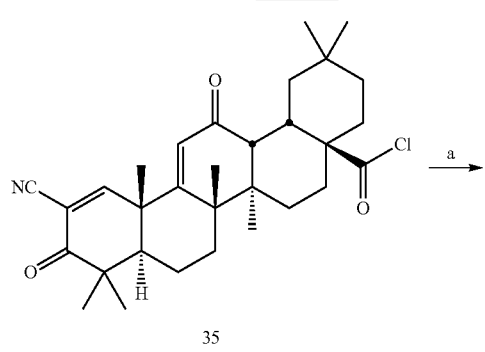
34
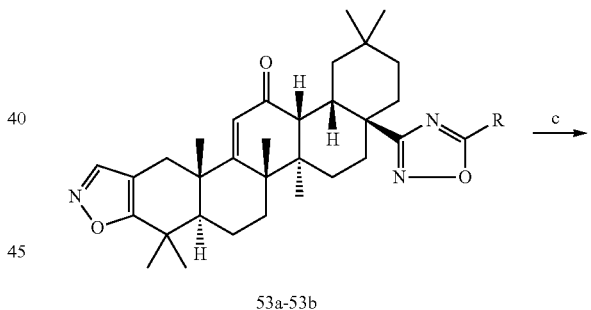
53a-53b
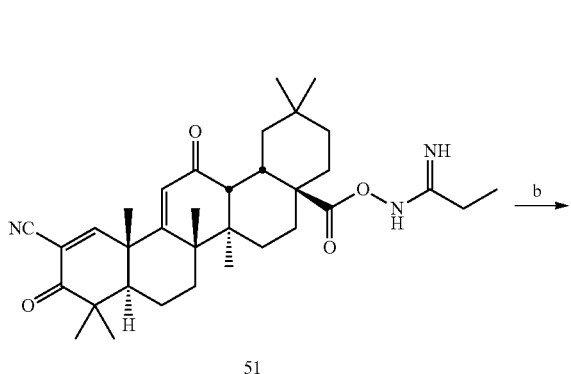
51
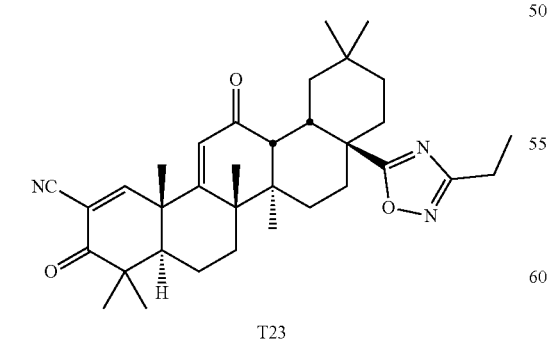
T23
Reagents and conditions:
a) propionamidoxime, Et₃N, CH₂Cl₂, rt;
b) Bu₄NOH, water, THF, rt, 36% from 34.
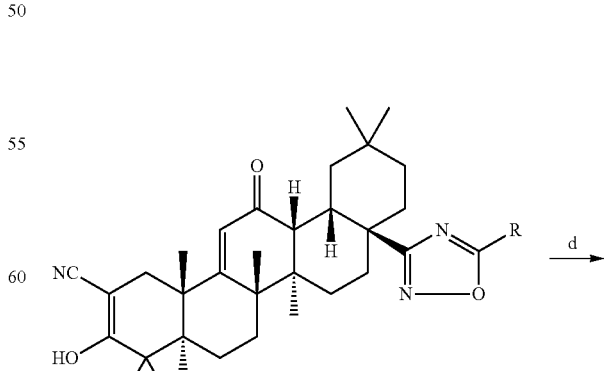
54a-54b 89
-continued
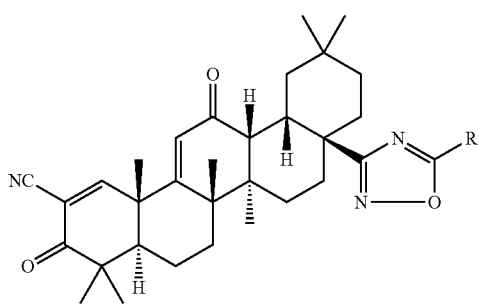
Reagents and conditions: a) propionyl chloride, Et$_3$N, CH$_2$Cl$_2$, 0° C., 89% for 52a; 82% for 52b: b) AcOH, 100° C., 77% for 53a; 72% for 53b; c) NaOMe, MeOH, 55° C., 97% for 54a; 89% for 54b, d) DBDMH, DMF, 0° C.; Py, 55-60° C., 76% for T24; 76% for T25.
Scheme 21
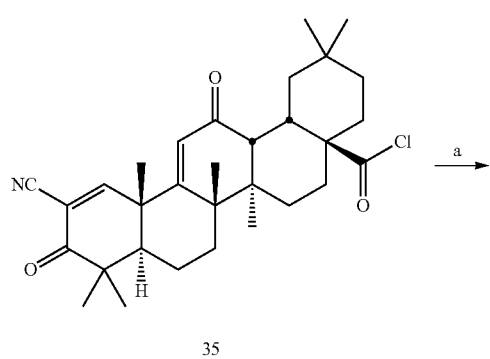
35
55a-55h
90
-continued
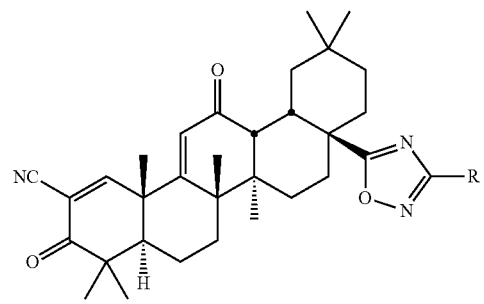
Reagents and conditions: a) RC(NH)NHOH, E$_3$N, CH$_2$Cl$_2$, rt; b) Bu$_4$NOH, water, THF, yield from 35: 47% for T26; 57% for T27; 52% for T28; 36% for T29; 52% for T30; 36% for T31; 16% for T32; 56% for T33.
Scheme 22
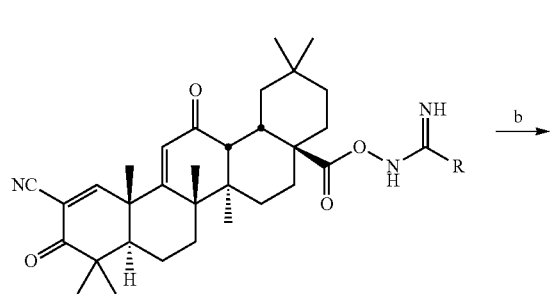
56
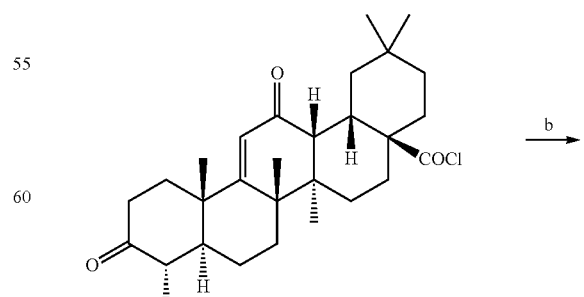
57

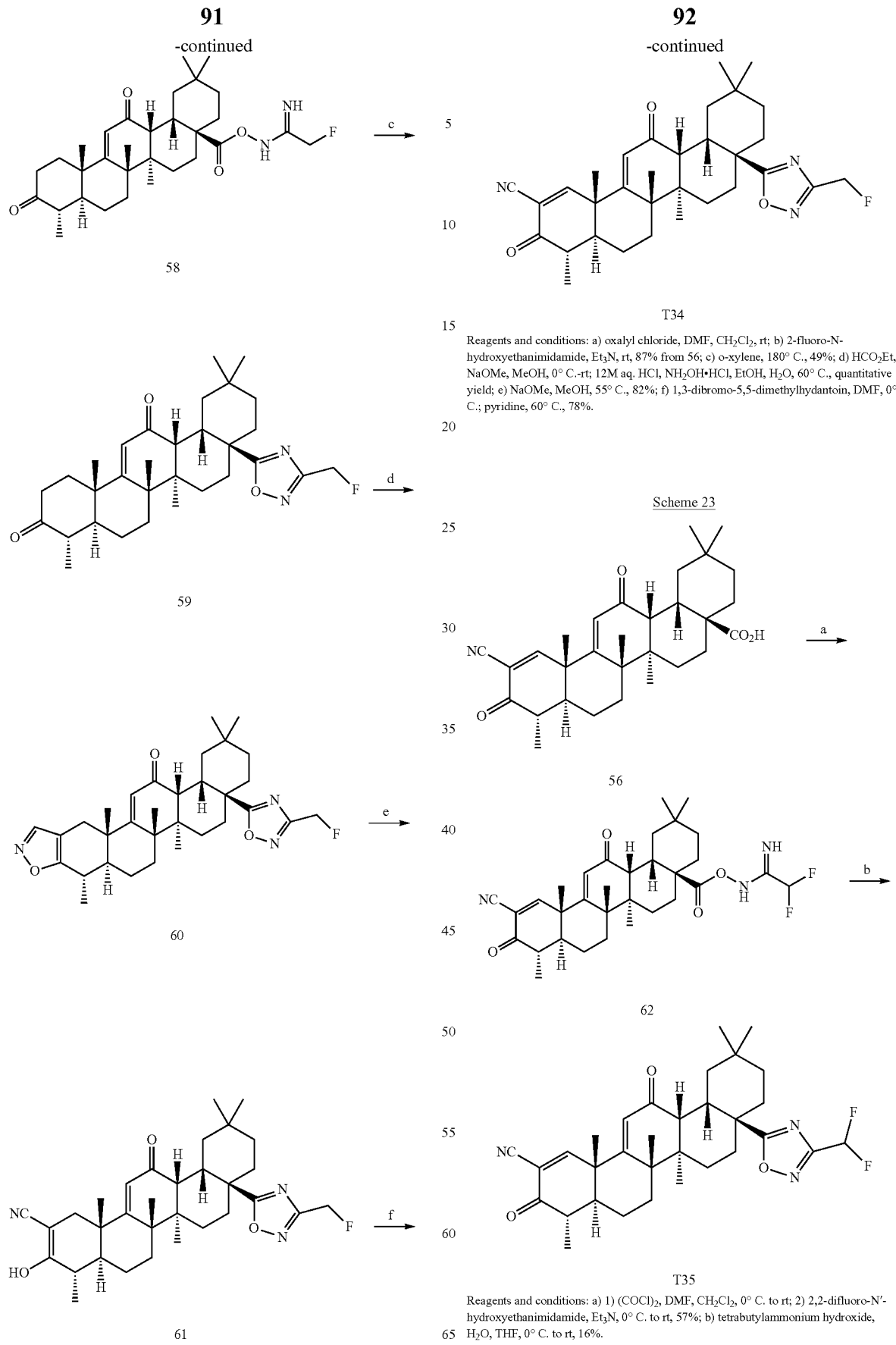

Reagents and conditions: a) oxalyl chloride, DMF, CH$_2$Cl$_2$, rt; b) 2-fluoro-N-hydroxyethanimidamide, Et$_3$N, rt, 87% from 56; c) o-xylene, 180° C., 49%; d) HCO$_2$Et, NaOMe, MeOH, 0° C.-rt; 12M aq. HCl, NH$_2$OH•HCl, EtOH, H$_2$O, 60° C., quantitative yield; e) NaOMe, MeOH, 55° C., 82%; f) 1,3-dibromo-5,5-dimethylhydantoin, DMF, 0° C.; pyridine, 60° C., 78%.

Scheme 23

Reagents and conditions: a) 1) (COCl)$_2$, DMF, CH$_2$Cl$_2$, 0° C. to rt; 2) 2,2-difluoro-N'-hydroxyethanimidamide, Et$_3$N, 0° C. to rt, 57%; b) tetrabutylammonium hydroxide, H$_2$O, THF, 0° C. to rt, 16%.

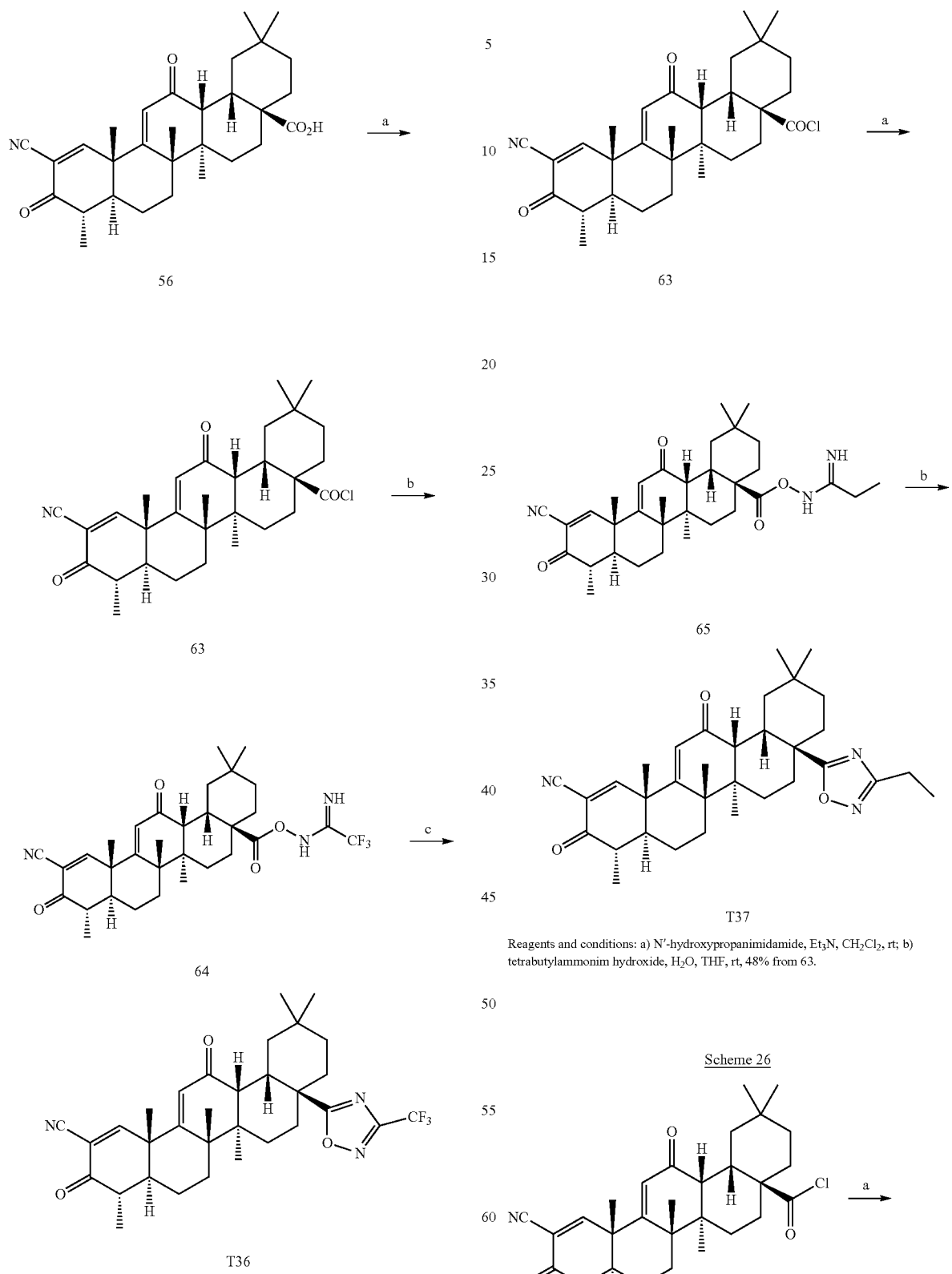

95
-continued
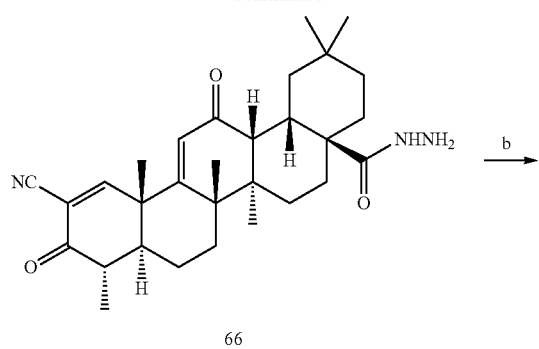
66
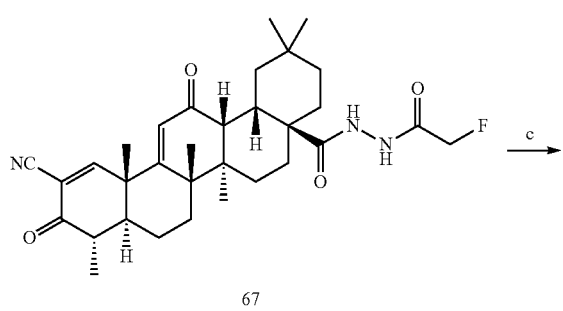
67
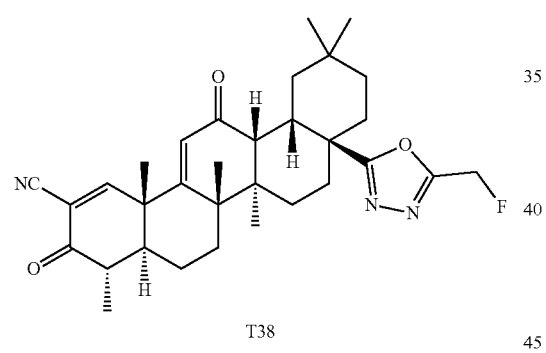
T38
Reagents and conditions: a) hydrazine hydrate, CH₂Cl₂, 0° C. to rt, 85%, b) 2-fluoroacetic acid, EDC•HCl, DMAP, CH₂Cl₂, rt, 29%; c) TsOH•H₂O, toluene, reflux, 48%.
Scheme 27
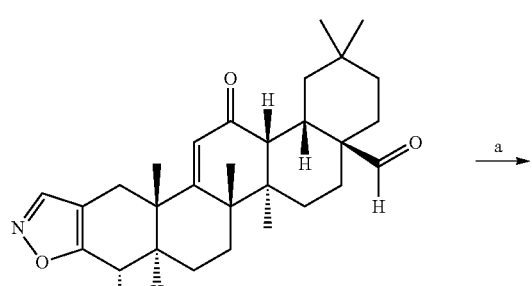
68
96
-continued
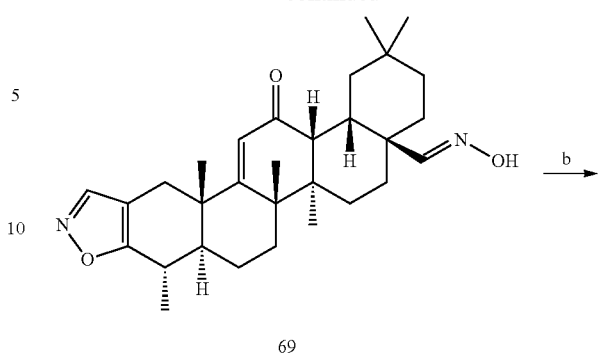
69
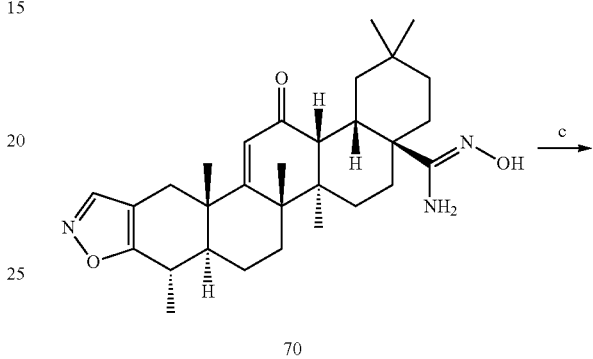
70
71
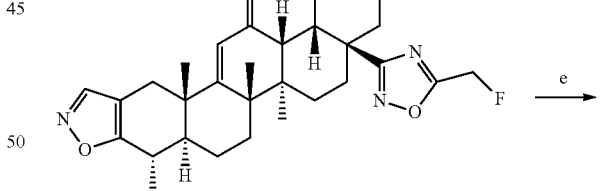
72
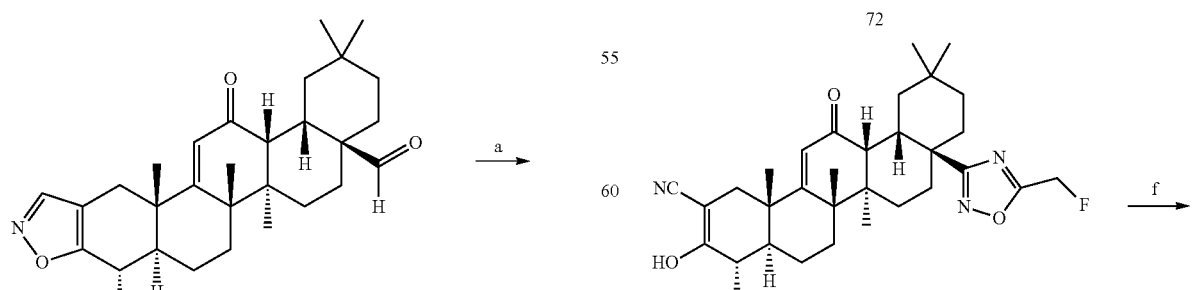
73

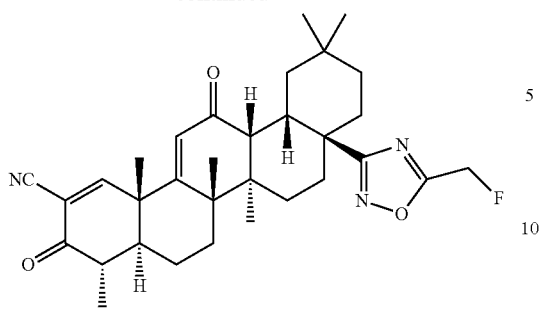
T39
Reagents and conditions: a) NH₂OH—HCl, NaOAc, EtOH, H₂O, rt, 93%; b) aq. HCl, NCS, MeCN, −10° C.; aq. NH₃, rt, 51%; c) 2-fluoroacetic acid, EDC·HCl, DMAP, CH₂Cl₂, rt, 38%; d) 1,4-dioxane, 100° C., 79%; e) NaOMe, MeOH, 55° C., 85%; f) DBDMH, DMF, 0° C.; Py, 60° C., 70%.
T40
Reagents and conditions: a) TFAA, Et₃N, 1,4-dioxane, 0° C. to rt, 56%; b) NaOMe, MeOH, 55° C., 68%; c) 1,3-dibromo-5,5-dimethylhydantoin, DMF, 0° C.; pyridine, 55° C., 85%.
Scheme 28
Scheme 29

-continued

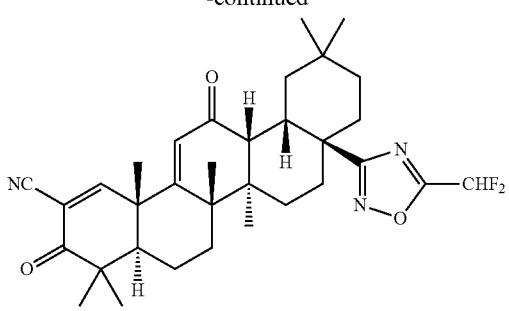

T41

Reagents and conditions: a) 2,2-difluoroacetic acid, EDC·HCl, DMAP, CH₂Cl₂, rt, 63%; b) NaOMe, MeOH, 55° C., 85%; c) 1,3-dibromo-5,5-dimethylhydantoin, DMF, 0° C.; pyridine, 55° C., 87%.

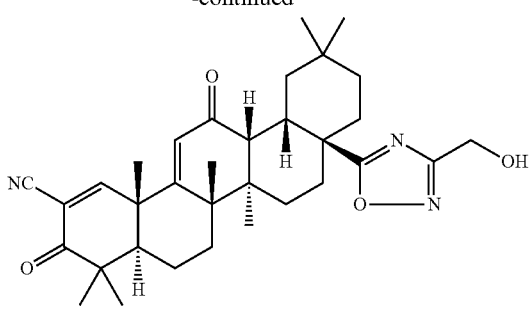

T42

Reagents and conditions: a) Et₃N, CH₂Cl₂, rt, 72%; b) tetrabutylammonium hydroxide, MeOH, rt, 61%; c) CF₃CO₂H, CH₂Cl₂, rt 76%.

Scheme 30

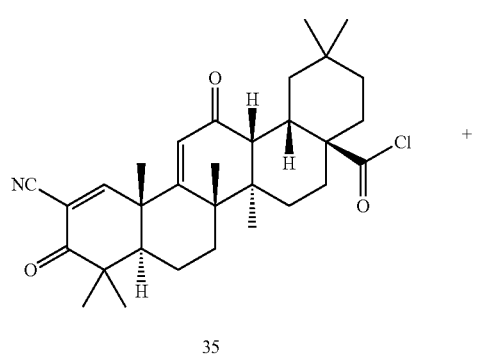

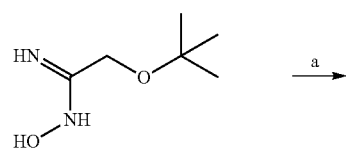

78

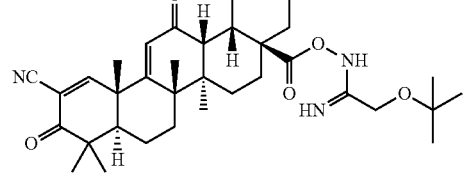

79

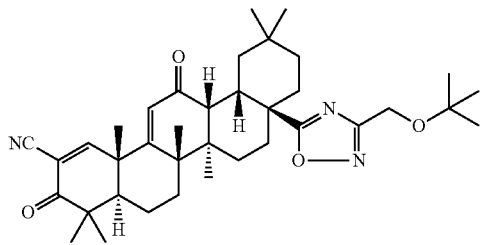

80

Scheme 31

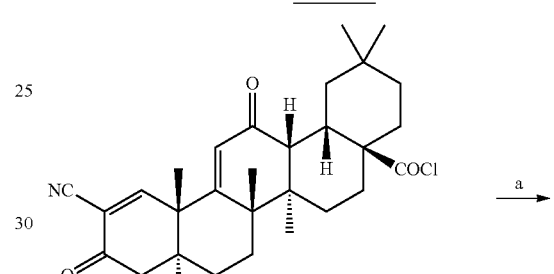

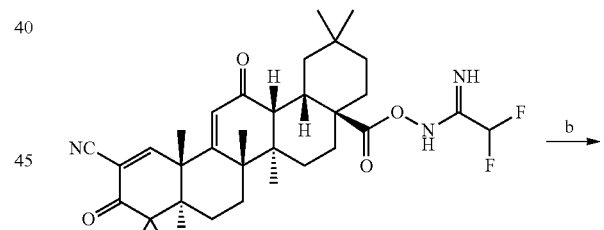

81

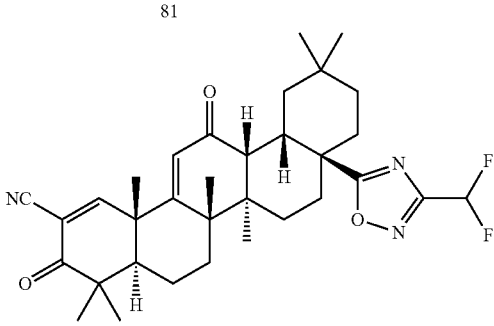

T43

Reagents and conditions: a) 2,2-difluoro-N-hydroxyethanimidamide, Et₃N, CH₂Cl₂, 0° C. to rt, 67%; b) TBAF, THF, reflux, 55%.

Scheme 32
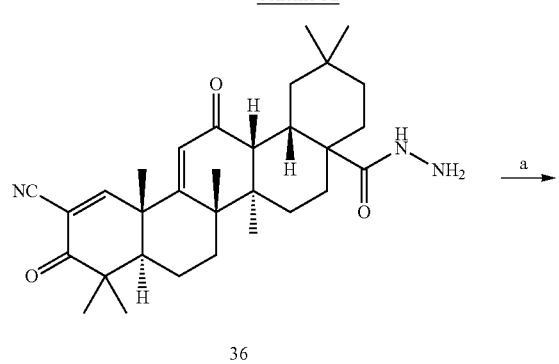
36
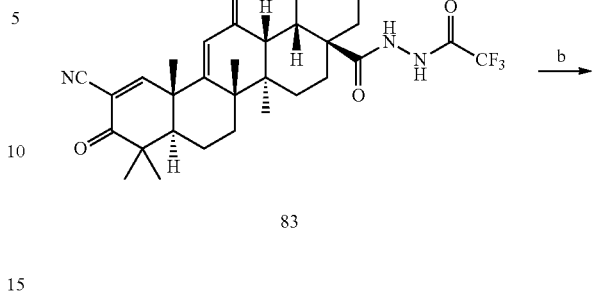
83
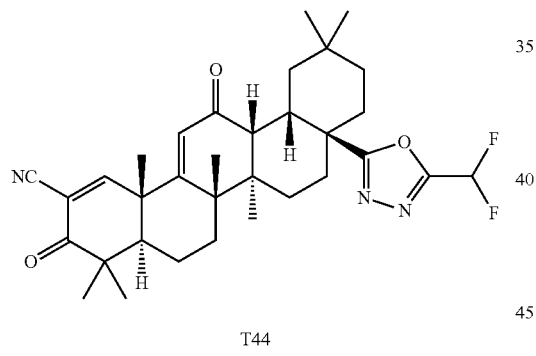
82
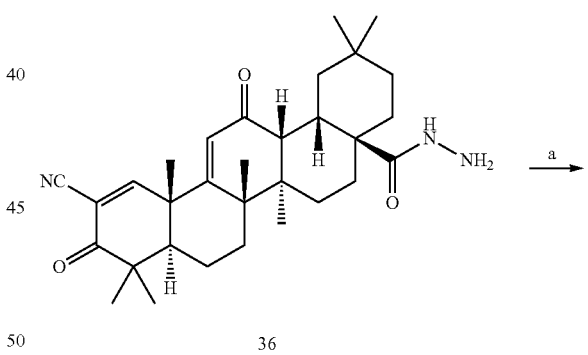
T45
Reagents and conditions: a) (CF₃CO)₂O, pyridine, CH₂Cl₂, 40° C., 84%; b) Burgess reagent, THF, reflux, 54%.
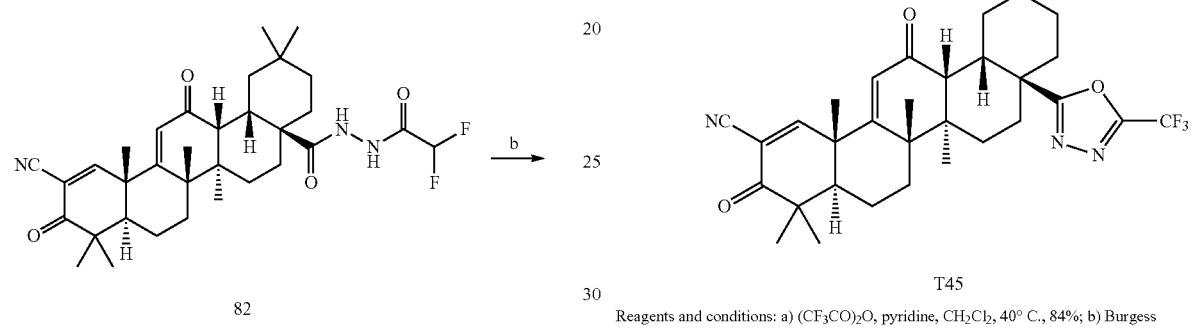
T44
Reagents and conditions: a) difluoroacetic anhydride, pyridine, CH₂Cl₂, 0° C. to rt, 79%; b) TsOH·H₂O, toluene, reflux, 31%.
Scheme 34
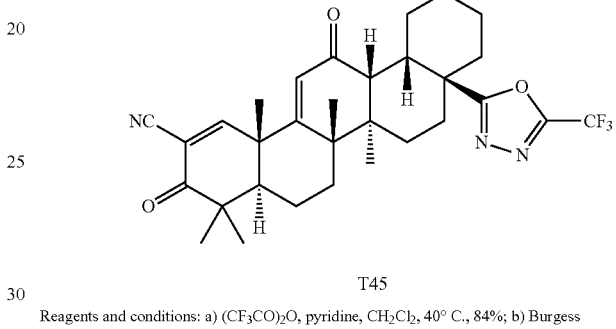
36
Scheme 33
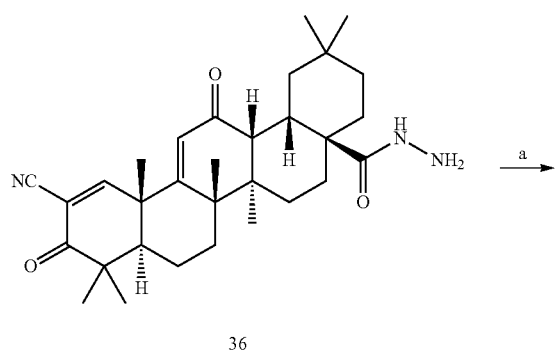
36
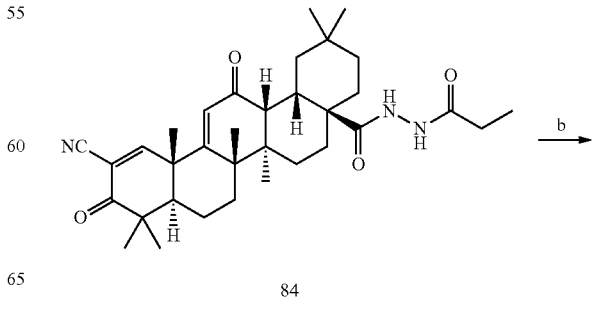
84

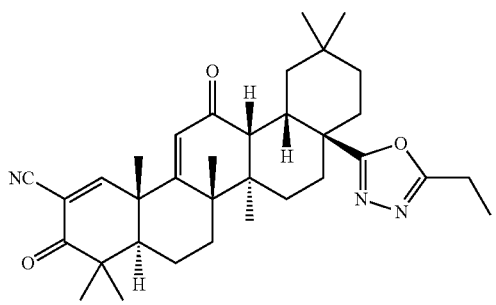

T46

Reagents and conditions: a) propionic anhydride, pyridine, CH₂Cl₂, 40° C., 76% b) Burgess reagent, THF, reflux, 74%.

Scheme 35 (alternative route to T12)

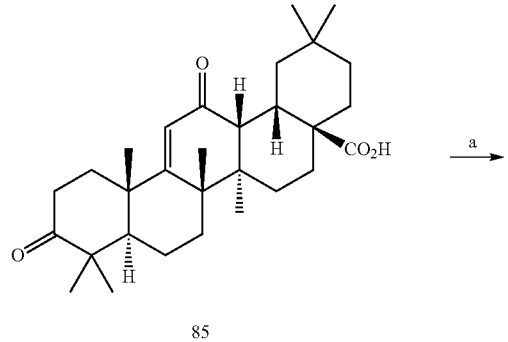

85

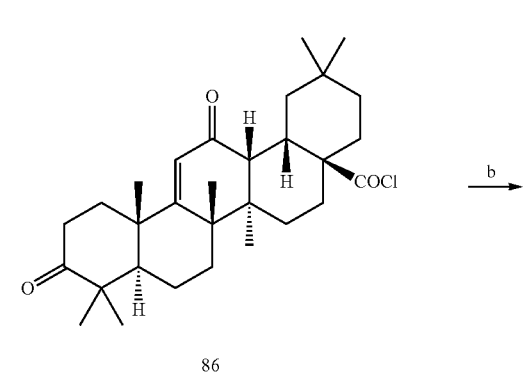

86

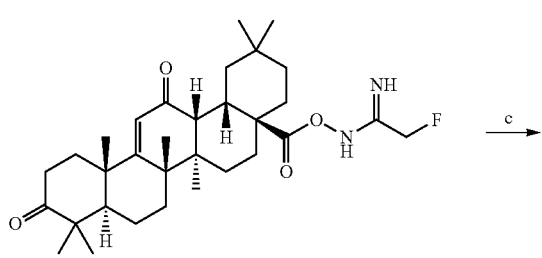

87

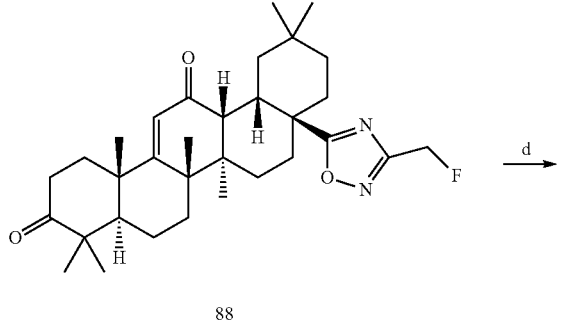

88

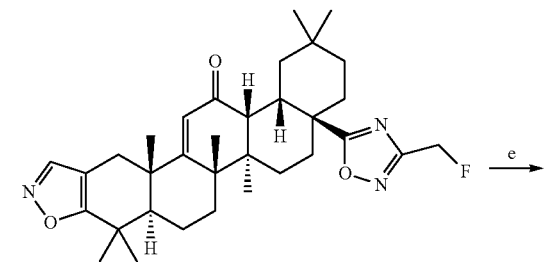

89

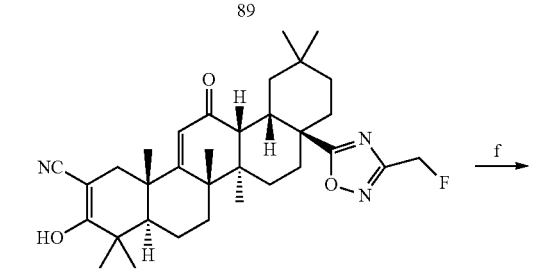

90

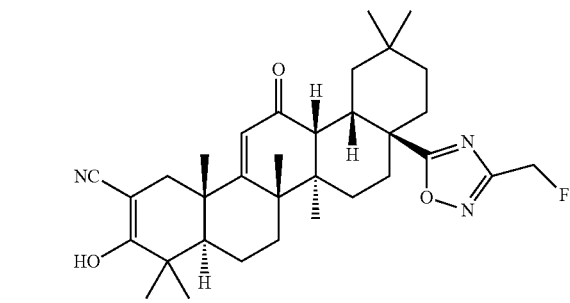

T12

Reagents and conditions: a) oxalyl chloride, DMF, CH₂Cl₂, 0° C.-rt; b) 2-fluoro-N-hydroxyethanimidamide, Et₃N, rt, 89% from 85; (c) T3P, Et₃N, o-xylene, 36%; d) HCO₂Et, NaOMe, MeOH, 0° C.-rt; 6M aq. HCl, NH₂OH·HCl, EtOH, 60° C., 92%; e) NaOMe, MeOH, 55° C., 92%; f) 1,3-dibromo-5,5-dimethylhydantoin, DMF, 0° C.; pyridine, 60° C., 96%.

C. Characterization Data

Compound 2: Compound 1 (10.00 g, 19.71 mmol) in THF (200 mL) was cooled to 0° C. under N₂. DIBAL-H (1.0 M in toluene, 100 mL, 100 mmol) was added. The mixture was stirred at 0° C. for 30 min, and then at room temperature for 2 h. The reaction was cooled to 0° C., and quenched with water (20 mL) carefully, followed by 1 N aq. HCl (300 mL). The mixture was extracted with EtOAc (4×150 mL). The combined organic extracts were washed with water (100 mL) and brine (100 mL); dried with Na₂SO₄; filtered and concentrated to give crude compound 2 (9.5 g, quantitative yield) as a white solid. m/z=482 (M+1).

Compound 3: Compound 2 (9.5 g, <19.71 mmol) was dissolved in $CH_2Cl_2$ (200 mL). 4 Å MS (20 g) and 4-methylmorpholine N-oxide (5.10 g, 43.53 mmol) were added. The mixture was stirred at room temperature for 10 min under $N_2$. TPAP (690 mg, 1.96 mmol) was added. The mixture was stirred at room temperature for 1.5 h, and then quenched with 10% $Na_2SO_3$ (50 mL). The mixture was stirred for 5 min at room temperature, and then filtered through a pad of celite. The celite was eluted with $CH_2Cl_2$ (50 mL). The organic phase from the filtrate was separated. The aqueous phase from the filtrate was extracted with $CH_2Cl_2$ (2×50 mL), and EtOAc (2×50 mL). The combined organic extracts were washed with water (100 mL); dried with $Na_2SO_4$; and filtered through a pad of silica gel, which was eluted with EtOAc (100 mL). The filtrate was concentrated. The residue was purified by column chromatography (silica gel, eluting with 0 to 35% EtOAc in hexanes) to give compound 3 (6.39 g, 68% yield) as a white solid. m/z=478 (M+1).

Compound 4: Compound 3 (2.72 g, 5.69 mmol), $NH_2OH \cdot HCl$ (514 mg, 7.40 mmol) and NaOAc (841 mg, 10.2 mmol) were weighed in a flask. EtOH (120 mL) and water (8 mL) were added. The mixture was stirred at room temperature for 14 h, and then concentrated. The residue was partitioned between EtOAc (50 mL) and water (30 mL). The aqueous phase was extracted with EtOAc (30 mL). The combined organic extracts were dried with $Na_2SO_4$, filtered and concentrated. The residue contains small amount of AcOH and water. EtOH (10 mL) and toluene (10 mL) were added, and then the mixture was concentrated. The residue was triturated with $CH_2Cl_2$ (30 mL) at reflux for 10 min. After cooled to room temperature, the mixture was kept at room temperature for 30 min. The precipitated solid was collected by filtration; washed with $CH_2Cl_2$ (2×5 mL); and dried under vacuum to give compound 4 (2.15 g, 77% yield) as a white solid. m/z=493 (M+1).

Compound 5: Under $N_2$, compound 4 (2.68 g, 5.44 mmol) was suspended in MeCN (11 mL) and cooled to −10° C. Aqueous HCl (12 N, 91 μL, 1.09 mmol) was added, followed by N-chlorosuccinimide (726 mg, 5.44 mmol) in MeCN (11 mL). The reaction was stirred at −10° C. for 30 min. LCMS indicated the starting material was almost all consumed. Aqueous ammonia (28%, 3.7 mL, 54.4 mmol) was added. The mixture was stirred at room temperature for 24 h. The reaction mixture was diluted with EtOAc (100 mL) and washed with water (2×40 mL). The combined aqueous wash was extracted with EtOAc (30 mL). The combined organic extracts were dried with $Na_2SO_4$, filtered and concentrated. The residue was purified by column chromatography (silica gel, eluting with 0 to 60% EtOAc in $CH_2Cl_2$) to give compound 5 (1.87 g, 68% yield) as a white solid. m/z=508 (M+1).

Compound 6: A solution of 2-fluoroacetic acid (23 mg, 0.30 mmol) in $CH_2Cl_2$ (1 mL) was added to N-(3-dimethylaminopropyl)-N'-ethylcarbodiimide hydrochloride (EDC·HCl, 57 mg, 0.30 mmol) at room temperature under $N_2$. Catalytic amount of DMAP (1.8 mg, 0.015 mmol) was added. The mixture was stirred at room temperature for 15 min. Compound 5 (50 mg, 0.098 mmol) in $CH_2Cl_2$ (2 mL) was added. The mixture was stirred at room temperature for 1 h. The mixture was diluted with $CH_2Cl_2$ (20 mL) and washed with water (2×10 mL). The combined aqueous wash was extracted with $CH_2Cl_2$ (20 mL). The combined organic extracts were dried with $Na_2SO_4$, filtered and concentrated. The residue was combined with the crude product obtained from compound 5 (11 mg, 0.022 mmol) using the same procedure, and purified by column chromatography (silica gel, eluting with 0 to 50% EtOAc in $CH_2Cl_2$) to give compound 6 (47 mg, 69% yield) as a white solid. m/z=568 (M+1).

Compound 7: Compound 6 (47 mg, 0.083 mmol) in AcOH (1 mL) was heated at 100° C. for 40 min under $N_2$. The mixture was cooled to room temperature; diluted with toluene (15 mL); and concentrated. The residue was diluted with toluene (15 mL) again, and concentrated. The residue was purified by column chromatography (silica gel, eluting with 0 to 30% EtOAc in hexanes) to give compound 7 (38 mg, 84% yield) as a white solid. m/z=550 (M+1).

Compound 8: To a mixture of compound 7 (52 mg, 0.095 mmol) in anhydrous MeOH (1 mL) was added NaOMe (4.37 M in MeOH, 43 μL, 0.19 mmol) under $N_2$. The mixture was heated at 55° C. for 1 h, and then cooled to 0° C. The mixture was diluted with 10% aq. $NaH_2PO_4$ (15 mL) and extracted with EtOAc (2×15 mL). The combined organic extracts were dried with $Na_2SO_4$, filtered and concentrated. The residue was purified by column chromatography (silica gel, eluting with 0 to 40% EtOAc in hexanes) to give compound 8 (46 mg, 88% yield) as a white solid. m/z=550 (M+1).

T1: Under $N_2$, compound 8 (46 mg, 0.084 mmol) was dissolved in anhydrous DMF (0.4 mL), and cooled to 0° C. 1,3-dibromo-5,5-dimethylhydantoin (DBDMH, 13 mg, 0.046 mmol) was added. The mixture was stirred at 0° C. for 1 h. Pyridine (30 μL, 0.38 mmol) was added. The mixture was heated at 55° C. for 6 h, and then cooled to room temperature. The mixture was diluted with EtOAc (25 mL); and washed with 1 N aqueous HCl (10 mL) and water (2×15 mL) sequentially. The organic extract was dried with $Na_2SO_4$, filtered and concentrated. The residue was purified by column chromatography (silica gel, eluting with 0 to 35% EtOAc in hexanes) to give compound T1 (36 mg, 79% yield) as a white solid. m/z=548 (M+1); $^1H$ NMR (400 MHz, $CDCl_3$) δ 8.02 (s, 1H), 5.95 (s, 1H), 5.54 (d, J=46.3 Hz, 2H), 3.21 (m, 1H), 2.96 (d, J=4.7 Hz, 1H), 2.19 (td, J=13.8, 4.2 Hz, 1H), 1.56-1.94 (m, 9H), 1.44 (s, 3H), 1.34-1.52 (m, 3H), 1.25 (s, 3H), 1.16-1.32 (m, 2H), 1.15 (s, 3H), 1.14 (s, 3H), 1.05 (s, 6H), 0.94 (s, 3H).

Compound 9: A mixture of Boc-glycine (207 mg, 1.18 mmol) and N-(3-dimethylaminopropyl)-N'-ethylcarbodiimide hydrochloride (227 mg, 1.18 mmol) in $CH_2Cl_2$ (4 mL) was treated with DMAP (4.8 mg, 0.039 mmol). The mixture was stirred at room temperature under $N_2$ for 15 min. Compound 5 (200 mg, 0.39 mmol) in $CH_2Cl_2$ (4 mL) was added. The mixture was stirred at room temperature for 1 h. Water (15 mL) was added. The mixture was extracted with $CH_2Cl_2$ (3×15 mL). The combined organic extracts were dried with $Na_2SO_4$, filtered and concentrated. The residue was purified by column chromatography (silica gel, eluting with 0 to 40% EtOAc in $CH_2Cl_2$) to give compound 9 (206 mg, 79% yield) as a white solid. m/z=665 (M+1).

Compound 10: A mixture of compound 9 (206 mg, 0.31 mmol) in 1,4-dioxane (4 mL) was heated at 160° C. in a pressure vessel for 100 min. After cooled to room temperature, the reaction mixture was concentration on a rotvap. The residue was dissolved in toluene (10 mL) and concentrated again. The residue was purified by column chromatography (silica gel, eluting with 0 to 60% EtOAc in hexanes) to give compound 10 (160 mg, 80% yield) as a white solid. m/z=647 (M+1).

Compound 11: Compound 10 (159 mg, 0.25 mmol) in MeOH (2.5 mL) was treated with $K_2CO_3$ (136 mg, 0.98 mmol) at room temperature under $N_2$. The mixture was stirred at room temperature for 14 h. LCMS indicated the reaction was complete. 10% aq. $NaH_2PO_4$ (15 mL) was added. The mixture was extracted with EtOAc (2×20 mL).

The combined organic extract was dried with $Na_2SO_4$, filtered and concentrated. The residue was purified by column chromatography (silica gel, eluting with 0 to 70% EtOAc in hexanes) to give compound 11 (141 mg, 89% yield) as a white solid. m/z=669 (M+Na).

Compound 12: Under $N_2$, compound 11 (140 mg, 0.22 mmol) was dissolved in anhydrous DMF (1.1 mL), and cooled to 0° C. 1,3-dibromo-5,5-dimethylhydantoin (34 mg, 0.12 mmol) was added. The mixture was stirred at 0° C. for 1 h. Pyridine (70 µL, 0.87 mmol) was added. The mixture was heated at 60° C. for 5 h, and then cooled to room temperature. The mixture was diluted with EtOAc (25 mL); and washed with 1 N aq. HCl (10 mL) and water (3×15 mL) sequentially. The organic extract was dried with $Na_2SO_4$, filtered and concentrated. The residue was purified by column chromatography (silica gel, eluting with 0 to 60% EtOAc in hexanes) to give compound 12 (126 mg, 90% yield) as a white solid. m/z=589 (M-$C_4H_7$).

T2: Compound 12 (113 mg, 0.18 mmol) in $CH_2Cl_2$ (1.8 mL) was treated with TFA (135 µL, 1.75 mmol) at room temperature under $N_2$. After stirring for 5 h at room temperature, sat. aq. $NaHCO_3$ (15 mL) was added. The mixture was extracted with $CH_2Cl_2$ (3×15 mL). The combined organic extracts were dried with $Na_2SO_4$, filtered and concentrated. The residue was purified by column chromatography (silica gel, eluting with 0 to 20% MeOH in $CH_2Cl_2$) to give compound T2 (47 mg, 49% yield) as a yellow foam. m/z=545 (M+1); $^1$H NMR (400 MHz, $CDCl_3$) δ 8.02 (s, 1H), 5.95 (s, 1H), 4.08 (s, 2H), 3.21 (m, 1H), 2.99 (d, J=4.7 Hz, 1H), 2.17 (td, J=13.6, 4.1 Hz, 1H), 1.44 (s, 3H), 1.25 (s, 3H), 1.15 (s, 6H), 1.12-1.96 (m, 16H), 1.05 (s, 6H), 0.94 (s, 3H).

Compound 13: To a mixture of Boc-β-Ala-OH (168 mg, 0.89 mmol) and EDC·HCl (170 mg, 0.89 mmol) in $CH_2Cl_2$ (3 mL) was added DMAP (5 mg, 0.04 mmol) at room temperature under $N_2$. The mixture was stirred at room temperature for 15 min. The solution of compound 5 (150 mg, 0.30 mmol) in $CH_2Cl_2$ (3 mL) was added. The mixture was stirred at room temperature for 1 h and was then treated with water (15 mL). The mixture was extracted with $CH_2Cl_2$ (3×15 mL). The combined organic extracts were dried with $Na_2SO_4$, filtered and concentrated. The residue was purified by column chromatography (silica gel, eluting with 0 to 70% EtOAc in hexanes) to give compound 13 (201 mg, quantitative yield) as a white solid. m/z=679 (M+1).

Compound 14: Compound 13 (200 mg, 0.30 mmol) in 1,4-dioxane (5 mL) was heated at 160° C. for 1 h. The mixture was cooled to room temperature, and concentrated. The residue was purified by column chromatography (silica gel, eluting with 0 to 55% EtOAc in hexanes) to give compound 14 (137 mg, 70% yield) as a white solid. m/z=661 (M+1).

Compound 15: A mixture of compound 14 (135 mg, 0.20 mmol) in MeOH (2 mL) was treated with $K_2CO_3$ (113 mg, 0.82 mmol) at room temperature. The mixture was stirred at room temperature for 14 h. 10% aq. $NaH_2PO_4$ (15 mL) was added. The mixture was extracted with EtOAc (30 mL). The organic extract was washed with water (10 mL); dried with $Na_2SO_4$, filtered and concentrated. The residue was purified by column chromatography (silica gel, eluting with 0 to 70% EtOAc in hexanes) to give compound 15 (114 mg, 84% yield) as a white solid. m/z=683 (M+Na).

Compound 16: A solution of compound 15 (114 mg, 0.17 mmol) and 1,3-dibromo-5,5-dimethylhydantoin (27 mg, 0.095 mmol) in anhydrous DMF (1.7 mL) was stirred at 0° C. for 1 h under $N_2$. The mixture was treated with pyridine (56 µL, 0.69 mmol), and then heated at 60° C. for 5 h. After cooled to room temperature, the mixture was diluted with EtOAc (25 mL); and washed with 1 N aq. HCl (10 mL) and water (3×15 mL). The organic extract was dried with $Na_2SO_4$, filtered and concentrated. The residue was purified by column chromatography (silica gel, eluting with 0 to 60% EtOAc in hexanes) to give compound 16 (93 mg, 82% yield) as a white solid. m/z=559 (M-$C_5H_7O_2$).

T3: Compound 16 (85 mg, 0.13 mmol) in $CH_2Cl_2$ (0.65 mL) was treated with TFA (99 µL, 1.32 mmol) at room temperature. The mixture was stirred at room temperature for 5 h, and then treated with sat. aq. $NaHCO_3$ (15 mL). The mixture was extracted with $CH_2Cl_2$ (3×15 mL). The combined organic extracts were dried with $Na_2SO_4$, filtered and concentrated. The residue was purified by column chromatography (silica gel, eluting with 0 to 20% MeOH in $CH_2Cl_2$) to give compound T3 (56 mg, 78% yield) as a yellow solid. m/z=559 (M+1); $^1$H NMR (400 MHz, $CDCl_3$) δ 8.02 (s, 1H), 5.94 (s, 1H), 3.21 (m, 1H), 3.16 (t, J=6.4 Hz, 2H), 3.01 (m, 3H), 2.16 (td, J=13.7, 4.2 Hz, 1H), 1.44 (s, 3H), 1.24 (s, 3H), 1.15 (s, 3H), 1.17-1.94 (m, 16H), 1.14 (s, 3H), 1.05 (s, 3H), 1.04 (s, 3H), 0.94 (s, 3H).

Compound 17: A solution of compound 5 (100 mg, 0.20 mmol) in $CH_2Cl_2$ (1 mL) was cooled to 0° C. $Et_3N$ (55 µL, 0.39 mmol) in $CH_2Cl_2$ (0.5 mL), and acetoxyacetyl chloride (40 mg, 0.30 mmol) in $CH_2Cl_2$ (0.5 mL) were added sequentially. The mixture was stirred at 0° C. for 1 h, and then treated with sat. aq. $NaHCO_3$ (5 mL). The mixture was stirred for 5 min, and then extracted with $CH_2Cl_2$ (3×10 mL). The combined organic extracts were dried with $Na_2SO_4$, filtered and concentrated. The residue was purified by column chromatography (silica gel, eluting with 0 to 60% EtOAc in hexanes) to give compound 17 (119 mg, quantitative yield) as a white solid. m/z=608 (M+1).

Compound 18: Compound 17 (119 mg, 0.20 mmol) in AcOH (1 mL) was heated at 100° C. for 1 h, and then cooled to room temperature. The mixture was diluted with toluene (15 mL), and then concentrated. The residue was diluted with toluene (10 mL) and concentrated again. The residue was purified by column chromatography (silica gel, eluting with 0 to 50% EtOAc in hexanes) to give compound 18 (100 mg, 86% yield) as a white solid. m/z=590 (M+1).

Compound 19: Compound 18 (99 mg, 0.17 mmol) in MeOH (1.7 mL) was treated with NaOMe (4.37 M in MeOH, 0.12 mL, 0.50 mmol) at room temperature. The mixture was heated at 55° C. for 1 h, and then cooled to room temperature. 10% aq. $NaH_2PO_4$ (10 mL) was added. The mixture was extracted with EtOAc (2×20 mL). The combined organic extracts were dried with $Na_2SO_4$, filtered and concentrated. The residue was purified by column chromatography (silica gel, eluting with 0 to 70% EtOAc in hexanes) to give compound 19 (83 mg, 90% yield) as a white solid. m/z=548 (M+1).

T4: A solution of compound 19 (82 mg, 0.15 mmol) and 1,3-dibromo-5,5-dimethylhydantoin (23.5 mg, 0.082 mmol) in anhydrous DMF (1.5 mL) was cooled to 0° C. under $N_2$. The mixture was stirred at 0° C. for 2 h, and then treated with pyridine (48 µL, 0.60 mmol). The mixture was heated at 60° C. for 6 h, and then cooled to room temperature. The mixture was diluted with EtOAc (25 mL) and washed with 1 N aq. HCl (10 mL) and water (2×15 mL). The organic extract was dried with $Na_2SO_4$, filtered and concentrated. The residue was purified by column chromatography (silica gel, eluting with 0 to 70% EtOAc in hexanes) to give compound T4 (67 mg, 82% yield) as a white solid. m/z=546 (M+1); $^1$H NMR (400 MHz, $CDCl_3$) δ 8.02 (s, 1H), 5.95 (s, 1H), 4.88 (d, J=6.5 Hz, 2H), 3.21 (dt, J=13.7, 4.2 Hz, 1H), 2.97 (d, J=4.7 Hz, 1H), 2.38 (m, 1H), 2.18 (td, J=13.7, 4.2 Hz, 1H), 1.44

(s, 3H), 1.25 (s, 3H), 1.15 (s, 3H), 1.15 (s, 3H), 1.12-1.95 (m, 14H), 1.05 (s, 6H), 0.94 (s, 3H).

Compound 20: 3-Acetoxypropanoic acid (78 mg, 0.59 mmol) in $CH_2Cl_2$ (2 mL) was added to EDC·HCl (113 mg, 0.59 mmol) at room temperature. DMAP (8 mg, 0.06 mmol) was added. The mixture was stirred at room temperature for 15 min. Compound 5 (100 mg, 0.20 mmol) in $CH_2Cl_2$ (2 mL) was added. The mixture was stirred at room temperature for 1 h. Sat. aq. $NaHCO_3$ (3 mL) and water (10 mL) were added. The mixture was diluted with $CH_2Cl_2$ (20 mL) and EtOAc (2×20 mL). The combined organic extracts were dried with $Na_2SO_4$, filtered and concentrated. The residue was purified by column chromatography (silica gel, eluting with 0 to 70% EtOAc in hexanes) to give compound 20 (80 mg, 66% yield) as a white solid. m/z=622 (M+1).

Compound 21: Compound 20 (77 mg, 0.12 mmol) was dissolved in AcOH (1 mL) and heated at 100° C. for 2 h. After cooled to room temperature, the mixture was diluted with toluene (10 mL), and concentrated. The residue was diluted with toluene (10 mL) and concentrated again. The residue was purified by column chromatography (silica gel, eluting with 0 to 50% EtOAc in hexanes) to give compound 21 (41 mg, 55% yield) as a white solid. m/z=604 (M+1).

Compound 22 and 23: Compound 21 (40 mg, 0.066 mmol) in MeOH (1.2 mL) was treated with NaOMe (4.37 M in MeOH, 45 µL, 0.20 mmol) at room temperature. The mixture was heated at 55° C. for 1 h, and then cooled to room temperature. 10% aq. $NaH_2PO_4$ (10 mL) was added. The mixture was extracted with EtOAc (2×20 mL). The combined organic extracts were dried with $Na_2SO_4$, filtered and concentrated. The residue was purified by column chromatography (silica gel, eluting with 0 to 70% EtOAc in hexanes) to give compound 22 (19 mg, 51% yield) and compound 23 (17 mg, 45% yield) as white solids. Compound 22: m/z=562 (M+1); Compound 23: m/z=576 (M+1).

T5: A solution of compound 22 (19 mg, 0.034 mmol) in anhydrous DMF (0.3 mL) was cooled to 0° C. 1,3-dibromo-5,5-dimethylhydantoin (5.3 mg, 0.019 mmol) in DMF (55 µL) was added. The mixture was stirred at 0° C. for 1 h, and then treated with pyridine (11 µL, 0.14 mmol). The mixture was heated at 60° C. for 5 h, and then cooled to room temperature. The mixture was diluted with EtOAc (25 mL) and washed with 1 N aq. HCl (10 mL) and water (2×15 mL) sequentially. The organic extract was dried with $Na_2SO_4$, filtered and concentrated. The residue was purified by column chromatography (silica gel, eluting with 0 to 70% EtOAc in hexanes) to give compound T5 (16 mg, 86% yield) as a white solid. m/z=560 (M+1); $^1$H NMR (400 MHz, $CDCl_3$) δ 8.02 (s, 1H), 5.95 (s, 1H), 4.05 (q, J=5.8 Hz, 2H), 3.19 (m, 1H), 3.11 (t, J=5.6 Hz, 2H), 3.01 (d, J=4.7 Hz, 1H), 2.58 (t, J=6.5 Hz, 1H), 2.17 (td, J=13.7, 4.1 Hz, 1H), 1.44 (s, 3H), 1.25 (s, 3H), 1.15 (s, 3H), 1.14 (s, 3H), 1.13-1.95 (m, 14H), 1.04 (s, 6H), 0.94 (s, 3H).

T6: A solution of compound 23 (17 mg, 0.030 mmol) in anhydrous DMF (0.3 mL) was cooled to 0° C. 1,3-dibromo-5,5-dimethylhydantoin (4.6 mg, 0.016 mmol) in DMF (46 µL) was added. The mixture was stirred at 0° C. for 1 h, and then treated with pyridine (9.5 µL, 0.12 mmol). The mixture was heated at 60° C. for 5 h, and then cooled to room temperature. The mixture was diluted with EtOAc (25 mL) and washed with 1 N aq. HCl (10 mL) and water (2×15 mL) sequentially. The organic extract was dried with $Na_2SO_4$, filtered and concentrated. The residue was purified by column chromatography (silica gel, eluting with 0 to 70% EtOAc in hexanes) to give compound T6 (14 mg, 83% yield) as a white solid. m/z=574 (M+1); $^1$H NMR (400 MHz, $CDCl_3$) δ 8.02 (s, 1H), 5.94 (s, 1H), 3.79 (t, J=6.5 Hz, 2H), 3.34 (s, 3H), 3.22 (m, 1H), 3.13 (t, J=6.5 Hz, 2H), 3.00 (d, J=4.7 Hz, 1H), 2.16 (td, J=13.6, 4.2 Hz, 1H), 1.44 (s, 3H), 1.24 (s, 3H), 1.15 (s, 3H), 1.14-1.94 (m, 14H), 1.13 (s, 3H), 1.05 (s, 3H), 1.04 (s, 3H), 0.94 (s, 3H).

Compound 25: To a mixture of compound 24 (1.366 g, 3.04 mmol) in o-xylene (5 mL) was added azidotributyltin (IV) (1.00 mL, 3.65 mmol). The mixture was heated at 150° C. for 48 h. The crude reaction mixture was purified by column chromatography (silica gel, eluting with 0 to 60% acetone in hexanes) to give partially purified compound 25, which was purified again by column chromatography (silica gel, eluting with 0 to 100% EtOAc in hexanes) to give compound 25 (710 mg, 47% yield) as a brown solid. m/z=493 (M+1).

Compound 26: A mixture of compound 25 (200 mg, 0.41 mmol) and $Cs_2CO_3$ (160 mg, 0.49 mmol) in MeCN (4 mL) was treated with 2-bromoethanol (40 µL, 0.56 mmol) at room temperature. The mixture was heated at 60° C. for 3 h, and then additional amount of 2-bromoethanol (40 µL, 0.56 mmol) was added. The mixture was heated at 60° C. for another 3 h and cooled to room temperature. The mixture was diluted with EtOAc (50 mL) and filtered. The filtrate was concentrated. The residue was combined with the crude product obtained from compound 25 (50 mg, 0.10 mmol), and was purified by column chromatography (silica gel, eluting with 0 to 50% acetone in hexanes) to give compound 26 (222 mg, 82% yield) as a white solid. m/z=537 (M+1).

Compound 27: A mixture compound 26 (220 mg, 0.41 mmol) in ethyl formate (1.00 mL, 12.29 mmol) was cooled to 0° C. under $N_2$ and treated dropwise with sodium methoxide solution (4.37 M in methanol, 1.40 mL, 6.12 mmol). The reaction mixture was stirred at room temperature for 1.5 h, and then cooled to 0° C. The mixture was treated with 6 N aq. HCl (1.1 mL, 6.6 mmol), followed by EtOH (8 mL) and hydroxylamine hydrochloride (43 mg, 0.62 mmol). The reaction mixture was heated at 55° C. for 5 h; cooled to room temperature; and concentrated. The residue was diluted with EtOAc and washed with water. The organic extract was dried with $Na_2SO_4$; filtered; and concentrated. The residue was purified by column chromatography (silica gel, eluting with 0 to 100% EtOAc in hexanes) to give compound 27 (166 mg, 72% yield) as a white solid. m/z=562 (M+1).

Compound 28: To a mixture of compound 27 (166 mg, 0.30 mmol) in anhydrous MeOH (3 mL) was added NaOMe (4.37 M in MeOH, 0.14 mL, 0.61 mmol) under $N_2$. The mixture was heated at 55° C. for 1 h, and then cooled to room temperature. The mixture was diluted with 10% aq. $NaH_2PO_4$ and extracted twice with EtOAc. The combined organic extracts were dried with $Na_2SO_4$, filtered and concentrated to give compound 28 (180 mg, quantitative yield) as a white solid. m/z=562 (M+1).

T7: Under $N_2$, compound 28 (180 mg, 0.30 mmol) was dissolved in anhydrous DMF (1 mL), and cooled to 0° C. 1,3-dibromo-5,5-dimethylhydantoin (42 mg, 0.15 mmol) was added. The mixture was stirred at 0° C. for 1 h. Pyridine (72 µL, 0.89 mmol) was added. The mixture was heated at 55° C. for 16 h, and then cooled to room temperature. The mixture was diluted with EtOAc and washed with 1 N aqueous HCl and water (3×) sequentially. The organic extract was dried with $Na_2SO_4$, filtered and concentrated. The residue was purified by column chromatography (silica gel, eluting with 0 to 70% EtOAc in hexanes) to give compound T7 (114 mg, 68% yield) as a white solid. m/z=560 (M+1); $^1$H NMR (400 MHz, $CDCl_3$) δ 8.01 (s, 1H), 5.94 (s, 1H), 4.72 (dd, J=5.9, 4.2 Hz, 2H), 4.16 (dd, J=6.1, 4.5 Hz, 2H), 3.32 (dt, J=13.7, 4.2 Hz, 1H), 2.97 (d, J=4.7 Hz, 1H), 2.24 (m, 1H), 2.21 (t, J=6.3 Hz, 1H), 2.03 (m, 1H), 1.83 (td, J=13.9, 4.5 Hz, 1H), 1.42 (s, 3H), 1.24 (s, 3H), 1.14 (s, 3H), 1.12-1.78 (m, 12H), 1.06 (s, 3H), 1.05 (s, 3H), 0.99 (s, 3H), 0.95 (s, 3H).

T8: The solution of compound T7 (30 mg, 0.054 mmol) in CH$_2$Cl$_2$ (0.5 mL) was cooled to 0° C. Pyridine (13 µL, 0.16 mmol), acetic anhydride (10 µL, 0.11 mmol) and catalytic amount of DMAP were added sequentially. The mixture was stirred at 0° C. for 2.5 h and was diluted with toluene (5 mL). The mixture was concentrated. The residue was purified by column chromatography (silica gel, eluting with 0 to 45% EtOAc in hexanes) to give compound T8 (23 mg, 71% yield) as a white solid. m/z=602 (M+1); $^1$H NMR (400 MHz, CDCl$_3$) δ 8.02 (s, 1H), 5.94 (s, 1H), 4.82 (m, 2H), 4.54 (m, 2H), 3.31 (m, 1H), 2.95 (d, J=4.7 Hz, 1H), 2.23 (td, J=13.7, 4.1 Hz, 1H), 2.03 (m, 1H), 2.00 (s, 3H), 1.81 (td, J=13.9, 4.5 Hz, 1H), 1.42 (s, 3H), 1.24 (s, 3H), 1.14 (s, 3H), 1.12-1.76 (m, 12H), 1.06 (s, 3H), 1.05 (s, 3H), 0.98 (s, 3H), 0.95 (s, 3H).

T9: A mixture of compound T7 (72 mg, 0.13 mmol), Proton sponge (82 mg, 0.38 mmol) and trimethyloxonium tetrafluoroborate (56 mg, 0.38 mmol) in CH$_2$Cl$_2$ (1.2 mL) was stirred at room temperature for 16 h. The reaction was quenched with sat. aq. NaHCO$_3$; stirred for 5 min; and extracted with EtOAc. The organic extract was washed with water, 1 N aq. HCl, and water sequentially; dried with Na$_2$SO$_4$; filtered and concentrated. The residue was purified by column chromatography (silica gel, eluting with 0 to 80% EtOAc in hexanes) to give compound T9 (32 mg, 43% yield) as a white solid. m/z=574 (M+1); $^1$H NMR (400 MHz, CDCl$_3$) δ 8.02 (s, 1H), 5.94 (s, 1H), 4.74 (m, 2H), 3.89 (t, J=5.4 Hz, 2H), 3.32 (m, 1H), 3.29 (s, 3H), 2.99 (d, J=4.7 Hz, 1H), 2.22 (td, J=13.6, 4.1 Hz, 1H), 2.05 (m, 1H), 1.82 (td, J=13.9, 4.5 Hz, 1H), 1.42 (s, 3H), 1.23 (s, 3H), 1.14 (s, 3H), 1.12-1.76 (m, 12H), 1.06 (s, 3H), 1.05 (s, 3H), 0.98 (s, 3H), 0.95 (s, 3H).

Compound 29: In a vial, a mixture of compound 25 (200 mg, 0.41 mmol) and Cs$_2$CO$_3$ (160 mg, 0.49 mmol) in MeCN (2 mL) was treated with 1-fluoro-2-iodoethane (100 mg, 0.58 mmol) in MeCN (2 mL). The vial was sealed and heated at 60° C. for 6 h. After cooled to room temperature, the mixture was diluted with EtOAc, and filtered through a pad of celite. The filter cake was washed with EtOAc. The combined filtrate and wash were concentrated. The residue was combined with the crude product obtained from compound 25 (50 mg, 0.10 mmol), and was purified by column chromatography (silica gel, eluting with 0 to 50% EtOAc in hexanes) to give compound 29 (142 mg, 52% yield) as a light yellow solid. m/z=539 (M+1).

Compound 30: A mixture compound 29 (142 mg, 0.26 mmol) in ethyl formate (0.64 mL, 7.86 mmol) was cooled to 0° C. under N$_2$ and treated dropwise with sodium methoxide solution (4.37 M in methanol, 0.90 mL, 3.93 mmol). The reaction mixture was stirred at room temperature for 1.5 h, and then cooled to 0° C. The mixture was treated with 6 N aq. HCl (0.66 mL, 3.96 mmol), followed by EtOH (5.2 mL) and hydroxylamine hydrochloride (28 mg, 0.40 mmol). The reaction mixture was heated at 55° C. for 5 h; cooled to room temperature; and concentrated. The residue was diluted with EtOAc and washed with water. The organic extract was dried with Na$_2$SO$_4$; filtered; and concentrated. The residue was purified by column chromatography (silica gel, eluting with 0 to 50% EtOAc in hexanes) to give compound 30 (102 mg, 71% yield) as a white solid. m/z=544 (M+1).

Compound 31: Compound 30 (102 mg, 0.19 mmol) was dissolved in MeOH (1 mL) and CH$_2$Cl$_2$ (1 mL), and cooled to −78° C. Ozone was bubbled through the reaction mixture until the starting material was completely consumed (~10 min). Oxygen was bubbled for 5 min. NaBH$_4$ (15 mg, 0.40 mmol) was added. The cold bath was removed. The mixture was stirred at room temperature for 3 h; diluted with EtOAc; and washed with 1 N aq. HCl and water. The aqueous washes were combined and extracted with EtOAc. The combined organic extracts were dried with Na$_2$SO$_4$; filtered; and concentrated to give compound 31 (96 mg, 99% yield) as a white solid. m/z=518 (M+1).

Compound 32: A mixture of compound 31 (96 mg, 0.19 mmol) and Cs$_2$CO$_3$ (73 mg, 0.22 mmol) was treated with 1-fluoro-2-iodoethane (45 mg, 0.26 mmol) in MeCN (1.8 mL). The mixture was heated at 60° C. under N$_2$ for 6 h. After cooled to room temperature, the mixture was diluted with EtOAc, and washed with 1 N aq. HCl, 10% aq. Na$_2$SO$_3$, and water sequentially. The organic extract was dried with Na$_2$SO$_4$; filtered; and concentrated. The residue was purified by column chromatography (silica gel, eluting with 0 to 50% EtOAc in hexanes) to give compound 32 (63 mg, 60% yield) as a white solid. m/z=564 (M+1).

Compound 33: A mixture of compound 32 (61 mg, 0.11 mmol) in MeOH (1 mL) was treated with K$_2$CO$_3$ (45 mg, 0.33 mmol) at room temperature. The mixture was stirred at room temperature for 16 h. 10% aq. NaH$_2$PO$_4$ (15 mL) was added. The mixture was extracted twice with EtOAc. The combined organic extracts were dried with Na$_2$SO$_4$, filtered and concentrated. The residue was purified by column chromatography (silica gel, eluting with 0 to 50% EtOAc in hexanes) to give compound 33 (48 mg, 79% yield) as a white solid. m/z=564 (M+1).

T10: A solution of compound 33 (48 mg, 0.085 mmol) in anhydrous DMF (0.42 mL) was cooled to 0° C. under N$_2$. 1,3-dibromo-5,5-dimethylhydantoin (12 mg, 0.042 mmol) was added. The mixture was stirred at 0° C. for 1 h, and then treated with pyridine (21 µL, 0.26 mmol). The mixture was heated at 55° C. for 16 h. After cooled to room temperature, the mixture was diluted with EtOAc; and washed with 1 N aq. HCl and water (3×) sequentially. The organic extract was dried with Na$_2$SO$_4$, filtered and concentrated. The residue was purified by column chromatography (silica gel, eluting with 0 to 50% EtOAc in hexanes) to give compound T10 (34 mg, 71% yield) as a white solid. m/z=562 (M+1); $^1$H NMR (400 MHz, CDCl$_3$) δ 8.01 (s, 1H), 5.94 (s, 1H), 4.78-5.01 (m, 4H), 3.32 (dt, J=13.6, 4.3 Hz, 1H), 2.99 (d, J=4.7 Hz, 1H), 2.24 (td, J=13.6, 4.1 Hz, 1H), 2.04 (m, 1H), 1.82 (td, J=13.9, 4.5 Hz, 1H), 1.42 (s, 3H), 1.23 (s, 3H), 1.13 (s, 3H), 1.12-1.77 (m, 12H), 1.06 (s, 3H), 1.05 (s, 3H), 0.96 (s, 3H), 0.95 (s, 3H).

Compound 35: Compound 34 (1.00 g, 2.03 mmol) was mixed with CH$_2$Cl$_2$ (20 mL) and cooled to 0° C. under N$_2$. Oxalyl chloride (0.54 mL, 6.17 mmol) and DMF (16 µL, 0.20 mmol) were added sequentially. The cold bath was removed. The mixture was stirred at room temperature for 2 h, and then concentrated. The residue was dissolved in toluene (3×10 mL) and concentrated to remove residual oxalyl chloride. Crude compound 35 (1 g) was obtained as a light yellow solid and used in the next step without further purification.

Compound 36: Compound 35 (200 mg, 0.39 mmol) in CH$_2$Cl$_2$ (4 mL) was cooled to 0° C. under N$_2$. Hydrazine hydrate (50 wt. %, 75 mg, 1.18 mmol) was added dropwise. The mixture was stirred at room temperature for 10 min; diluted with CH$_2$Cl$_2$ (10 mL); and washed with water (15 mL). The aqueous wash was extracted with CH$_2$Cl$_2$ (2×15 mL) and EtOAc (15 mL). The combined organic extracts were dried with Na$_2$SO$_4$, filtered and concentrated to give compound 36 (179 mg, 90% yield) as a glass.

Compound 37: A solution of 2-fluoroacetic acid (67 mg, 0.86 mmol) in $CH_2Cl_2$ (1 mL) was treated with EDC·HCl (164 mg, 0.85 mmol) and DMAP (3.5 mg, 0.028 mmol) at room temperature under $N_2$. The mixture was stirred at room temperature for 15 min. Compound 36 (144 mg, 0.29 mmol) in $CH_2Cl_2$ (2 mL) was then added. The mixture was stirred at room temperature for 14 h. The reaction mixture was washed with sat. aq. $NaHCO_3$ (10 mL) and water (10 mL). The aqueous phase was extracted with $CH_2Cl_2$ (2×10 mL). The combined organic extracts were dried with $Na_2SO_4$, filtered and concentrated. The residue was purified by column chromatography (silica gel, eluting with 0 to 60% EtOAc in $CH_2Cl_2$) to give compound 37 (96 mg, 60% yield) as a pink solid. m/z=566 (M+1).

T11: Compound 37 (115 mg, 0.20 mmol) and p-toluenesulfonic acid monohydrate (19 mg, 0.10 mmol) in toluene (10 mL) was heated at reflux while removing water by Dean-Stark apparatus for 3 h. The mixture was cooled to room temperature; diluted with EtOAc (10 mL); and washed with water (2×15 mL). The organic extract was dried with $Na_2SO_4$, filtered and concentrated. The residue was purified by column chromatography (silica gel, eluting with 0 to 40% acetone in hexanes) to give compound T11 (67 mg, 60% yield) as a white solid. m/z=548 (M+1); $^1H$ NMR (400 MHz, $CDCl_3$) δ 8.02 (s, 1H), 5.96 (s, 1H), 5.51 (dd, J=47.0 Hz, 2H), 3.18 (dt, J=13.5, 4.3 Hz, 1H), 2.99 (d, J=4.7 Hz, 1H), 2.23 (td, J=13.7, 4.2 Hz, 1H), 1.45 (s, 3H), 1.25 (s, 3H), 1.20-2.02 (m, 14H), 1.15 (s, 6H), 1.06 (s, 3H), 1.05 (s, 3H), 0.96 (s, 3H).

Compound 39: A solution of compound 35 [produced from compound 34 (1.52 g, 3.09 mmol)] in $CH_2Cl_2$ (25 mL) was cooled to 0° C. $Et_3N$ (1.70 mL, 12.4 mmol) and a solution of compound 38 (404 mg, 4.39 mmol) in $CH_2Cl_2$ (5 mL) were added sequentially. After stirring at room temperature for 4 h, the mixture was treated with water (30 mL). The organic phase was separated. The aqueous phase was extracted with $CH_2Cl_2$ (3×30 mL). The combined organic extracts were dried with $Na_2SO_4$, filtered and concentrated. The residue was purified by column chromatography (silica gel, eluting with 0 to 60% acetone in hexanes) to give compound 39 (1.46 g, 84% yield) as a white solid. m/z=566 (M+1).

T12: A mixture of compound 39 (148 mg, 0.26 mmol), T3P (50 wt. % in EtOAc, 0.40 g, 0.63 mmol) and $Et_3N$ (0.18 mL, 1.31 mmol) in EtOAc (1 mL) were heated at 125° C. in Biotage microwave synthesizer for 1 h. After cooled to room temperature, the mixture was diluted with EtOAc (20 mL) and washed with 1 N aq. HCl (15 mL), sat. aq. $NaHCO_3$ (15 mL) and water (15 mL) sequentially. The organic extract was dried with $Na_2SO_4$, filtered, and concentrated. The residue was purified by column chromatography (silica gel, eluting with 0 to 80% EtOAc in hexanes) to give compound T12 (9 mg, 6% yield) as a white solid. m/z=548 (M+1); $^1H$ NMR (400 MHz, $CDCl_3$) δ 8.02 (s, 1H), 5.97 (s, 1H), 5.44 (d, J=46.5 Hz, 2H), 3.26 (m, 1H), 3.03 (d, J=4.7 Hz, 1H), 2.24 (td, J=13.8, 4.1 Hz, 1H), 1.87-2.01 (m, 2H), 1.45 (s, 3H), 1.25 (s, 3H), 1.20-1.80 (m, 12H), 1.15 (s, 3H), 1.10 (s, 3H), 1.06 (s, 3H), 1.05 (s, 3H), 0.95 (s, 3H).

A stock solution of compound 35 (≤0.183 M) and trimethylamine (0.735 M) in $CH_2Cl_2$ was prepared by dissolving compound 35 (prepared from 11.11 mmol of compound 34) and triethylamine (6.20 mL, 44.5 mmol) in $CH_2Cl_2$ (52 mL). The total volume of the solution was 60.5 mL. The stock solution was used in the synthesis of compound 40 and 41.

Compound 40: The stock solution of compound 35 and $Et_3N$ in $CH_2Cl_2$ [12.5 mL, containing compound 35 (2.29 mmol) and trimethylamine (9.19 mmol)] was treated with 3-hydroxypropionamide oxime (347 mg, 3.33 mmol). The mixture was stirred overnight at room temperature. The resultant mixture was diluted with EtOAc; washed with water, sat. aq. $NaHCO_3$ and brine. The organic extract was dried with $Na_2SO_4$; filtered and concentrated. The residue was purified by column chromatography (silica gel, eluting with 0 to 10% MeOH in $CH_2Cl_2$) to give compound 40 (604.4 mg, 46% yield from compound 34) as a solid.

T13: A mixture of compound 40 (604.4 mmol, 1.046 mmol) and tetrabutylammonium hydroxide (40% w/w in water, 2.1 mL, 3.2 mmol) in THF (8.4 mL) was stirred at room temperature under $N_2$ overnight. The resultant mixture was diluted with EtOAc; washed with water, sat. aq. $NaHCO_3$ and brine. The organic extract was dried with $Na_2SO_4$; filtered and concentrated. The residue was purified by column chromatography (silica gel, eluting with 0 to 100% EtOAc in hexanes) to give compound T13 (265.5 mg, 45% yield) as a white solid. m/z=560.3 (M+1); $^1H$ NMR (400 MHz, $CDCl_3$) δ 8.02 (s, 1H), 5.96 (s, 1H), 3.98 (q, J=6.0 Hz, 2H), 3.24 (td, J=4.2, 13.9 Hz, 1H), 3.03 (d, J=4.7 Hz, 1H), 2.99 (t, J=5.6 Hz, 2H), 2.33 (t, J=6.3 Hz, 1H), 2.21 (dt, J=4.1, 13.8 Hz, 1H), 1.91 (m, 2H), 1.69 (m, 7H), 1.45 (s, 3H), 1.33 (m, 5H), 1.25 (s, 3H), 1.15 (s, 3H), 1.11 (s, 3H), 1.05 (s, 3H), 1.04 (s, 3H), 0.95 (s, 3H).

T14: A mixture of compound T13 (101.2 mg, 0.1808 mmol) and HCl (12 M aq, 0.5 mL, 6.0 mmol) in glacial acetic acid (10 mL) was stirred at 75° C. under $N_2$ for 20 h. The resultant mixture was azeotroped with toluene (60 mL, then 50 mL), and the residue was purified by column chromatography (silica gel, eluting with 0 to 100% EtOAc in hexanes) to give compound T14 (48.0 mg, 44% yield) as a white solid. m/z=602.3 (M+1); $^1H$ NMR (400 MHz, $CDCl_3$) δ 8.02 (s, 1H), 5.96 (s, 1H), 4.41 (m, 2H), 3.23 (td, J=3.9, 13.3 Hz, 1H), 3.05 (m, 3H), 2.20 (dt, J=4.1, 13.8 Hz, 1H), 2.02 (s, 3H), 1.90 (m, 2H), 1.70 (m, 7H), 1.45 (s, 3H), 1.35 (m, 5H), 1.24 (s, 3H), 1.15 (s, 3H), 1.10 (s, 3H), 1.04 (s, 3H), 1.04 (s, 3H), 0.94 (s, 3H).

Compound 41: The stock solution of compound 35 and $Et_3N$ in $CH_2Cl_2$ [12.5 mL, containing compound 35 (2.29 mmol) and trimethylamine (9.19 mmol)] was treated with 3-methoxypropionamidoxime hydrochloride (516 mg, 3.33 mmol) and additional triethylamine (0.46 mL, 3.3 mmol). The mixture stirred overnight at room temperature. The resultant mixture was diluted with EtOAc; washed with water, sat. aq. $NaHCO_3$ and brine. The organic extract was dried with $Na_2SO_4$; filtered and concentrated. The residue was purified by column chromatography (silica gel, eluting with 0 to 10% MeOH in $CH_2Cl_2$) to give a mixture of compound 41 and compound 34 (1.22 g, ~2.5:1-41:34) as a solid that was used without further purification.

T15: A mixture of compound 41 contaminated with compound 34 (1.22 g, ~2.5:1-41:34) and tetrabutylammonium hydroxide (40% w/w in water, 4.2 mL, 6.4 mmol) in THF (17 mL) was stirred at room temperature under $N_2$ overnight. The resultant mixture was diluted with EtOAc; washed with water, sat. aq. $NaHCO_3$ and brine. The organic extract was dried with $Na_2SO_4$; filtered and concentrated. The residue was purified by column chromatography (silica gel, eluting with 0 to 100% EtOAc in hexanes) to give compound T15 (494.7 mg, 37% yield from compound 34) as a white solid. m/z=574.4 (M+1); $^1H$ NMR (400 MHz, $CDCl_3$) δ 8.02 (s, 1H), 5.96 (s, 1H), 3.74 (t, J=6.6 Hz, 2H), 3.33 (s, 3H), 3.24 (td, J=4.1, 13.6 Hz, 1H), 3.09 (d, J=4.7 Hz, 1H), 2.99 (dt, J=2.6, 6.6 Hz, 2H), 2.20 (dt, J=4.1, 13.8 Hz, 1H), 1.90 (m, 2H), 1.71 (m, 7H), 1.45 (s, 3H), 1.35 (s, 5H), 1.25 (s, 3H), 1.15 (s, 3H), 1.11 (s, 3H), 1.05 (s, 3H), 1.04 (s, 3H), 0.95 (s, 3H).

Compound 42: A mixture of N-tert-butoxycarbonyl-3-aminopropionitrile (858 mg, 5.04 mmol), hydroxylamine hydrochloride (1.39 g, 20.0 mmol) and triethylamine (4.2 mL, 30 mmol) in ethanol (20 mL) was heated to 80° C. with stirring in a sealed tube for 2 d. The resultant solution was diluted with EtOAc (300 mL) and washed with water/sat. aq NaHCO$_3$ (1:1, 100 mL) and brine (25 mL). The organic extract was dried with Na$_2$SO$_4$, filtered and concentrated to give compound 42 contaminated with N-tert-butoxycarbonyl-3-aminopropionitrile (73:27, 773.4 mg) as a crystalline solid that was used without further purification.

Compound 43: A mixture of compound 35 [synthesized from compound 34 (1.08 g, 2.20 mmol)], impure compound 42 (73:27-Int4:N-tert-butoxycarbonyl-3-aminopropionitrile, 773.4 mg) and triethylamine (1.23 mL, 8.83 mmol) in CH$_2$Cl$_2$ (18 mL) was stirred at room temperature for 2 h. The resultant mixture was diluted with EtOAc (100 mL); washed with water (25 mL), sat. aq. NaHCO$_3$ (25 mL) and brine (25 mL). The organic extract was dried with Na$_2$SO$_4$; filtered and concentrated. The residue was purified by column chromatography (silica gel, eluting with 0 to 10% MeOH in CH$_2$Cl$_2$) to give a mixture of compound 43 and 34 (1.01 g, ~4:1-43:34) as a solid that was used without further purification.

Compound 44: A solution of impure compound 43 (~4:1-43:34, 904 mg, ~1.07 mmol) and tetrabutylammonium hydroxide (40% w/w in water, 3.6 mL, 5.5 mmol) in THF (14 mL) was stirred at room temperature under N$_2$ for 5 h. The resultant mixture was diluted with EtOAc (200 mL); washed with water (50 mL), sat. aq. NaHCO$_3$ (50 mL) and brine (50 mL). The organic extract was dried with Na$_2$SO$_4$, filtered and concentrated. The residue was purified by column chromatography (silica gel, eluting with 0 to 100% EtOAc in hexanes) to give compound 44 (578.2 mg, 45% yield from compound 34) as a solid. m/z=559.4 (M-Boc+2).

T16: A mixture of compound 44 (61 mg, 0.093 mmol) and HCl (12 M aq., 0.25 mL, 3.0 mmol) in MeOH (2.5 mL) was stirred at room temperature. Additional HCl (12 M aq., 0.75 mL, 9.0 mmol) was added after 3.5 h, and stirring continued at room temperature for a total of 24 h. The resultant mixture was diluted with EtOAc (50 mL) and washed with sat. aq. NaHCO$_3$ (25 mL). The organic extract was dried with Na$_2$SO$_4$, filtered and concentrated. The residue was purified by column chromatography (silica gel, eluting with 0 to 10% MeOH in CH$_2$Cl$_2$) to give compound T16 (43.1 mg, 83% yield) as an off-white solid. m/z=559.3 (M+1); $^1$H NMR (400 MHz, CDCl$_3$) δ 8.02 (s, 1H), 5.95 (s, 1H), 3.23 (td, J=4.1, 13.9 Hz, 1H), 3.06 (m, 3H), 2.84 (t, J=6.5 Hz, 2H), 2.19 (dt, J=4.1, 13.8 Hz, 1H), 1.76 (m, 11H), 1.43 (s, 3H), 1.23 (s, 3H), 1.20 (m, 5H), 1.13 (s, 3H), 1.10 (s, 3H), 1.03 (s, 6H), 0.93 (s, 3H).

T17: Methyl chloroformate (12 µL, 0.16 mmol) was added to a solution of compound T16 (51.7 mg, 0.0926 mmol) and triethylamine (42 µL, 0.301 mmol) in CH$_2$Cl$_2$ (1 mL), and was stirred at room temperature for 2 h. Additional methyl chloroformate (30 µL, 0.39 mmol) was added, and stirring continued overnight. The mixture was diluted with CH$_2$Cl$_2$ (35 mL), and washed with HCl (1M aq., 15 mL) and brine (15 mL). The organic extract was dried with Na$_2$SO$_4$, filtered and concentrated. The residue was purified by column chromatography (silica gel, eluting with 0 to 100% EtOAc in hexanes) to give compound T17 (11.6 mg, 20% yield) as a white solid. m/z=617.4 (M+1); $^1$H NMR (400 MHz, CDCl$_3$) δ 8.02 (s, 1H), 5.96 (s, 1H), 5.10 (br s, 1H), 3.64 (s, 3H), 3.57 (q, J=6.2 Hz, 2H), 3.23 (td, J=3.5, 13.4 Hz, 1H), 3.01 (d, J=4.7 Hz, 1H), 2.93 (t, J=6.4 Hz, 2H), 2.20 (dt, J=4.1, 13.8 Hz, 1H), 1.90 (m, 2H), 1.69 (m, 7H), 1.44 (s, 3H), 1.30 (m, 5H), 1.24 (s, 3H), 1.15 (s, 3H), 1.09 (s, 3H), 1.04 (s, 3H), 1.04 (s, 3H), 0.94 (s, 3H).

T18: Ethyl isocyanate (8 µL, 0.101 mmol) was added to a solution of compound T16 (55.8 mg, 0.0999 mmol) and triethylamine (0.14 mL, 1.0 mmol) in CH$_2$Cl$_2$ (1 mL), and was stirred at room temperature for 1 h. The resultant mixture was diluted with CH$_2$Cl$_2$ (35 mL), and washed with HCl (1M aq., 15 mL) and brine (15 mL). The organic extract was dried with Na$_2$SO$_4$, filtered and concentrated. The residue was purified by column chromatography (silica gel, eluting with 0 to 100% EtOAc in hexanes) to give compound T18 (42.1 mg, 67% yield) as a white solid. m/z=630.4 (M+1); $^1$H NMR (400 MHz, CDCl$_3$) δ 8.02 (s, 1H), 5.96 (s, 1H), 4.90 (t, J=5.8 Hz, 1H), 4.23 (t, J=5.5 Hz, 1H), 3.56 (m, 2H), 3.24 (td, J=4.2, 14.4 Hz, 1H), 3.16 (ddq, J=1.9, 5.5, 7.2 Hz, 2H), 3.02 (d, J=4.7 Hz, 1H), 2.92 (m, 2H), 2.20 (dt, J=4.1, 13.8 Hz, 1H), 1.90 (m, 2H), 1.70 (m, 7H), 1.44 (s, 3H), 1.33 (m, 5H), 1.24 (s, 3H), 1.15 (s, 3H), 1.13 (t, J=7.2 Hz, 3H), 1.09 (s, 3H), 1.04 (s, 6H), 0.94 (s, 3H).

T19: Acetyl chloride (0.15 mL, 2.1 mmol) was added to a solution of compound T16 (45.7 mg, 0.0818 mmol) and triethylamine (0.11 mL, 0.79 mmol) in CH$_2$Cl$_2$ (1 mL), and the mixture was stirred at room temperature for 15 min. The resultant heterogeneous mixture was diluted with HCl (1M aq., 15 mL) and extracted with EtOAc (50 mL). The organic fraction was washed with brine (10 mL), dried with Na$_2$SO$_4$, filtered and concentrated. The residue was purified by column chromatography (silica gel, eluting with 0 to 15% MeOH in CH$_2$Cl$_2$) to give compound T19 (16.3 mg, 33% yield) as a white solid. m/z=601.4 (M+1); $^1$H NMR (400 MHz, CDCl$_3$) δ 8.02 (s, 1H), 6.01 (br s, 1H), 5.97 (s, 1H), 3.62 (m, 2H), 3.24 (td, J=4.2, 13.6 Hz, 1H), 3.01 (d, J=4.7 Hz, 1H), 2.93 (t, J=6.3 Hz, 2H), 2.21 (m, 1H), 1.95 (s, 3H), 1.77 (m, 9H), 1.45 (s, 3H), 1.24 (s, 3H), 1.22 (m, 5H), 1.15 (s, 3H), 1.10 (s, 3H), 1.05 (s, 3H), 1.04 (s, 3H), 0.95 (s, 3H).

Compound 45: Compound 5 (40 mg, 0.079 mmol) in AcOH (1 mL) was treated with acetic anhydride (11 µL, 0.12 mmol) at room temperature. The mixture was stirred at room temperature for 30 min, and then heated at 100° C. for 2 h. The mixture was cooled to room temperature, diluted with toluene (10 mL), and concentrated. The residue was purified by column chromatography (silica gel, eluting with 0-40% EtOAc in hexanes) to give compound 45 (40 mg, 95% yield) as a white foam. m/z=532 (M+1).

Compound 46: Compound 45 (40 mg, 0.075 mmol) was mixed with K$_2$CO$_3$ (44 mg, 0.32 mmol) and MeOH (2 mL). The mixture was stirred at room temperature under N$_2$ for 14 h; treated with 10% NaH$_2$PO$_4$ (20 mL); and extracted with EtOAc (2×20 mL). The combined organic extracts were dried with Na$_2$SO$_4$, filtered, and concentrated. The residue was combined with crude product obtained from compound 46 (16 mg, 0.030 mmol), and purified by column chromatography (silica gel, eluting with 0-40% EtOAc in hexanes) to give compound 46 (43.5 mg, 78% yield) as a white solid. m/z=532 (M+1).

T20: Compound 46 (43.5 mg, 0.082 mmol) and 1,3-dibromo-5,5-dimethylhydantoin (13 mg, 0.045 mmol) were mixed with anhydrous DMF (0.8 mL) at 0° C. under N$_2$. The mixture was stirred at 0° C. for 1 h, and treated with pyridine (20 µL, 0.25 mmol). The mixture was heated at 55° C. for 6 h; cooled to room temperature; diluted with EtOAc (25 mL); and washed with 1 N aq. HCl (10 mL) and water (2×15 mL). The organic extract was dried with Na$_2$SO$_4$, filtered and concentrated. The residue was purified by column chromatography (silica gel, eluting with 0-35% EtOAc in hexanes) to give compound T20 (34 mg, 78% yield) as a white solid. m/z=530 (M+1); $^1$H NMR (400 MHz, CDCl$_3$)

δ 8.02 (s, 1H), 5.95 (s, 1H), 3.20 (m, 1H), 3.01 (d, J=4.7 Hz, 1H), 2.57 (s, 3H), 2.16 (td, J=13.5, 4.2 Hz, 1H), 1.44 (s, 3H), 1.24 (s, 3H), 1.15 (s, 6H), 1.12-1.93 (m, 14H), 1.05 (s, 3H), 1.04 (s, 3H), 0.94 (s, 3H).

Compound 47: A solution of compound 25 (150 mg, 0.30 mmol) in THF (2.4 mL) and MeOH (0.6 mL) was cooled to 0° C. (Trimethylsilyl)diazomethane (2 M in hexanes solution, 183 µL, 0.366 mmol) was added. The mixture was stirred at 0° C. for 20 min; quenched with acetic acid; diluted with toluene; and concentrated. The residue was combined with the crude product obtained from compound 25 (50 mg, 0.10 mmol), and purified by column chromatography (silica gel, eluting with 0 to 35% acetone in hexanes) to give compound 47 (139 mg, 90% yield) as a white solid. m/z=507 (M+1).

Compound 48: A mixture compound 47 (137 mg, 0.27 mmol) in ethyl formate (0.65 mL, 8.08 mmol) was cooled to 0° C. under $N_2$ and treated dropwise with sodium methoxide solution (4.37 M in methanol, 0.62 mL, 2.71 mmol). The reaction mixture was stirred at 0° C. for 1 h, and then treated with 6 N aq. HCl (0.45 mL, 2.7 mmol), followed by EtOH (2.7 mL) and hydroxylamine hydrochloride (28 mg, 0.40 mmol). The reaction mixture was heated at 60° C. for 6 h; cooled to room temperature; diluted with EtOAc; and washed with water. The organic extract was dried with $Na_2SO_4$; filtered; and concentrated. The residue was purified by column chromatography (silica gel, eluting with 0 to 50% EtOAc in hexanes) to give compound 48 (112 mg, 78% yield) as a white solid. m/z=532 (M+1).

Compound 49: To a mixture of compound 48 (110 mg, 0.21 mmol) in anhydrous MeOH (2 mL) was added NaOMe (4.37 M in MeOH, 95 µL, 0.42 mmol) under $N_2$. The mixture was heated at 45° C. for 1 to 2 h, and then cooled to room temperature. The mixture was diluted with 10% aq. $NaH_2PO_4$ and extracted twice with EtOAc. The combined organic extracts were dried with $Na_2SO_4$, filtered and concentrated. The residue was purified by column chromatography (silica gel, eluting with 0 to 50% EtOAc in hexanes) to give compound 49 (86 mg, 77% yield) as a white solid. m/z=532 (M+1).

T21: Under $N_2$, compound 49 (84 mg, 0.16 mmol) was dissolved in anhydrous DMF (0.4 mL), and cooled to 0° C. A solution of 1,3-dibromo-5,5-dimethylhydantoin (23 mg, 0.080 mmol) in DMF (0.4 mL) was added. The mixture was stirred at 0° C. for 2 h. Pyridine (40 µL, 0.50 mmol) was added.

The mixture was heated at 55° C. for 6 h, and then cooled to room temperature. The mixture was diluted with EtOAc and washed with 1 N aqueous HCl and water (3×) sequentially. The organic extract was dried with $Na_2SO_4$, filtered and concentrated. The residue was purified by column chromatography (silica gel, eluting with 0 to 50% EtOAc in hexanes) to give compound T21 (65 mg, 78% yield) as a white solid. m/z=530 (M+1); $^1$H NMR (400 MHz, CDCl$_3$) δ 8.02 (s, 1H), 5.94 (s, 1H), 4.31 (s, 3H), 3.30 (m, 1H), 2.97 (d, J=4.7 Hz, 1H), 2.23 (td, J=13.6, 4.2 Hz, 1H), 2.02 (m, 1H), 1.83 (td, J=13.9, 4.5 Hz, 1H), 1.59-1.77 (m, 7H), 1.42 (s, 3H), 1.38-1.49 (m, 3H), 1.24 (s, 3H), 1.14-1.30 (m, 2H), 1.14 (s, 3H), 1.06 (s, 3H), 1.05 (s, 3H), 1.00 (s, 3H), 0.95 (s, 3H).

A stock solution of compound 35 (<0.113 M) and trimethylamine (0.453 M) in $CH_2Cl_2$ was prepared by dissolving compound 35 (prepared from 28.92 mmol of compound 34) and triethylamine (16.1 mL, 116 mmol) in $CH_2Cl_2$ (230 mL). The total volume of the solution was 256 mL. The stock solution is used for the synthesis of compound 50 and 52.

Compound 50: 2,2,2-Trifluoro-N'-hydroxy-ethanimidamide (229.2 mg, 1.79 mmol) was added to the stock solution of compound 35 and $Et_3N$ in $CH_2Cl_2$ [26.1 mL, containing compound 35 (2.95 mmol) and $Et_3N$ (11.8 mmol)], and the mixture stirred overnight at room temperature. The resultant mixture was diluted with EtOAc; washed with water, sat. aq. NaHCO$_3$, and brine. The organic extract was dried with $Na_2SO_4$; filtered and concentrated. The residue was purified by column chromatography (silica gel, eluting with 0 to 10% MeOH in $CH_2Cl_2$) to give impure compound 50 (965.7 mg) as a solid that was used without further purification. m/z=602.3 (M+1).

T22: A mixture of impure compound 50 (353 mg) and tetrabutylammonium hydroxide (40% w/w in water, 1.25 mL, 1.9 mmol) in THF (5 mL) was stirred at room temperature under $N_2$ overnight. The resultant mixture was diluted with EtOAc; washed with water, sat. aq. NaHCO$_3$ and brine. The organic extract was dried with $Na_2SO_4$, filtered and concentrated. The residue was purified by column chromatography (silica gel, eluting with 0 to 100% EtOAc in hexanes) to give compound T22 (63.3 mg, 10% yield from compound 34) as a white solid. m/z=584.3 (M+1); $^1$H NMR (400 MHz, CDCl$_3$) δ 8.02 (s, 1H), 5.98 (s, 1H), 3.26 (td, J=4.1, 14.1 Hz, 1H), 2.99 (d, J=4.7 Hz, 1H), 2.27 (dt, J=4.2, 13.9 Hz, 1H), 1.96 (m, 2H), 1.74 (m, 6H), 1.61 (dt, J=4.4, 13.9 Hz, 1H), 1.46 (s, 3H), 1.36 (s, 5H), 1.25 (s, 3H), 1.16 (s, 3H), 1.11 (s, 3H), 1.06 (s, 3H), 1.06 (s, 3H), 0.96 (s, 3H).

Compound 51: Propionamidoxime (250 mg, 2.84 mmol) was added to the stock solution of compound 35 and $Et_3N$ in $CH_2Cl_2$ [30 mL, containing compound 35 (3.38 mmol) and $Et_3N$ (13.5 mmol)], and the mixture stirred overnight at room temperature. The resultant mixture was diluted with EtOAc; washed with water, sat. aq. NaHCO$_3$, and brine. The organic extract was dried with $Na_2SO_4$; filtered and concentrated. The residue was purified by column chromatography (silica gel, eluting with 0 to 10% MeOH in $CH_2Cl_2$) to give impure compound 51 (1.0959 g) that was used without further purification. m/z=562.3 (M+1).

T23: A mixture of impure compound 51 (346.2 mg) and tetrabutylammonium hydroxide (40% w/w in water, 1.25 mL, 1.9 mmol) in THF (5 mL) was stirred at room temperature under $N_2$ overnight. The resultant mixture was diluted with EtOAc; washed with water, sat. aq. NaHCO$_3$ and brine. The organic extract was dried with $Na_2SO_4$, filtered and concentrated. The residue was purified by column chromatography (silica gel, eluting with 0 to 100% EtOAc in hexanes) to give compound T23 (209.9 mg, 36% yield from compound 34) as a white solid. m/z=544.3 (M+1); $^1$H NMR (400 MHz, CDCl$_3$) δ 8.02 (s, 1H), 5.96 (s, 1H), 3.24 (dt, J=13.1, 4.3 Hz, 1H), 3.11 (d, J=4.7 Hz, 1H), 2.73 (qd, J=7.6, 1.5 Hz, 2H), 2.20 (td, J=13.8, 4.1 Hz, 1H), 1.45 (s, 3H), 1.29 (t, J=7.6 Hz, 3H), 1.24 (s, 3H), 1.18-1.97 (m, 14H), 1.15 (s, 3H), 1.11 (s, 3H), 1.05 (s, 3H), 1.04 (s, 3H), 0.94 (s, 3H).

Compound 52a: Compound 5 (84 mg, 0.17 mmol) in $CH_2Cl_2$ (6 mL) was cooled to 0° C. $Et_3N$ (46 µL, 0.33 mmol) and propionyl chloride (23 mg, 0.25 mmol) in $CH_2Cl_2$ (1 mL) were added sequentially. After stirring at 0° C. for 1 h, the mixture was treated with sat. aq. NaHCO$_3$ (5 mL); stirred for 5 min; and extracted with $CH_2Cl_2$ (3×10 mL). The combined organic extracts were dried with $Na_2SO_4$, filtered and concentrated. The residue was purified by column chromatography (silica gel, eluting with 0-60% EtOAc in hexanes) to give compound 52a (83 mg, 89% yield) as a white solid. m/z=564.3 (M+1)

Compound 53a: Compound 52a (83 mg, 0.15 mmol) in AcOH (1 mL) was heated at 100° C. for 1 h. The mixture was cooled to room temperature; diluted with toluene (15 mL); and concentrated. The residue was diluted with toluene (10 mL) and concentrated again. The residue was purified by column chromatography (silica gel, eluting with 0-40% EtOAc in hexanes) to give compound 53a (67 mg, 77% yield) as a white solid. m/z=546.3 (M+1).

Compound 54a: Compound 53a (67 mg, 0.12 mmol) in MeOH (1.2 mL) was treated with sodium methoxide (25 wt. % in MeOH, 66 mg, 0.31 mmol) at room temperature. The mixture was stirred at 55° C. for 1 h. After cooled to room temperature, the mixture was treated with 10% $NaH_2PO_4$ (5 mL); and extracted with EtOAc (2×15 mL). The combined organic extracts were dried with $Na_2SO_4$, filtered, and concentrated. The residue was purified by column chromatography (silica gel, eluting with 0-45% EtOAc in hexanes) to give compound 54a (65 mg, 97% yield) as a white solid. m/z=546.3 (M+1).

T24: Compound 54a (65 mg, 0.12 mmol) and 1,3-dibromo-5,5-dimethylhydantoin (18.7 mg, 0.066 mmol) were mixed with anhydrous DMF (0.6 mL) at 0° C. under $N_2$. The mixture was stirred at 0° C. for 1 h, and treated with pyridine (38 μL, 0.48 mmol). The mixture was heated at 55° C. for 2 h, and at 60° C. for 4 h; cooled to room temperature; diluted with EtOAc (25 mL); and washed with 1 N aq. HCl (10 mL) and water (2×15 mL). The organic extract was dried with $Na_2SO_4$, filtered and concentrated. The residue was purified by column chromatography (silica gel, eluting with 0-45% EtOAc in hexanes) to give compound T24 (49 mg, 76% yield) as a white solid. m/z=544.3 (M+1); $^1$H NMR (400 MHz, $CDCl_3$) δ 8.03 (s, 1H), 5.95 (s, 1H), 3.21 (dt, J=13.7, 4.3 Hz, 1H), 3.03 (d, J=4.7 Hz, 1H), 2.89 (q, J=7.6 Hz, 2H), 2.16 (td, J=13.7, 4.2 Hz, 1H), 1.44 (s, 3H), 1.36 (t, J=7.6 Hz, 3H), 1.24 (s, 3H), 1.15 (s, 3H), 1.14 (s, 3H), 1.10-1.95 (m, 14H), 1.05 (s, 3H), 1.04 (s, 3H), 0.94 (s, 3H).

Compound 52b: Using the same procedure as described for the synthesis of compound 52a, compound 52b (white solid, 96 mg, 82% yield) was synthesized from compound 5 (103 mg, 0.20 mmol). m/z=576 (M+1).

Compound 53b: Using the same procedure as described for the synthesis of compound 53a, compound 53b (solid, 67 mg, 72% yield) was synthesized from compound 52b (96 mg, 0.17 mmol). m/z=558 (M+1).

Compound 54b: Using the same procedure as described for the synthesis of compound 54a, compound 54b (white solid, 58 mg, 89% yield) was synthesized from compound 53b (65 mg, 0.12 mmol). m/z=558 (M+1).

T25: Using the same procedure as described for the synthesis of compound T24, compound T25 (white solid, 44 mg, 76% yield) was synthesized from compound 54b (58 mg, 0.10 mmol). m/z=556 (M+1); $^1$H NMR (400 MHz, $CDCl_3$) δ 8.03 (s, 1H), 5.94 (s, 1H), 3.17 (dt, J=13.7, 4.2 Hz, 1H), 3.02 (d, J=4.7 Hz, 1H), 2.15 (m, 2H), 1.44 (s, 3H), 1.24 (s, 3H), 1.15 (s, 6H), 1.11-1.92 (m, 18H), 1.03 (s, 6H), 0.93 (s, 3H).

Compound 55a: Using the same procedure as described for the synthesis of compound 51, impure compound 55a (1.3624 g) was synthesized from compound 35 (3.67 mmol), n-butyramidoxime (234.6 mg, 2.30 mmol) and trimethylamine (14.6 mmol). m/z=576 (M+1).

T26: Using the same procedure as described for the synthesis of compound T23, compound T26 (white solid, 159.3 mg, 47% yield from 35) was synthesized from compound 55a (361.1 mg) and tetrabutylammonium hydroxide (40% w/w in water, 1.25 mL, 1.9 mmol). m/z=558 (M+1); $^1$H NMR (400 MHz, $CDCl_3$) δ 8.02 (s, 1H), 5.96 (s, 1H), 3.25 (m, 1H), 3.08 (d, J=4.7 Hz, 1H), 2.68 (t, J=7.5 Hz, 2H), 2.20 (td, J=13.8, 4.1 Hz, 1H), 1.90 (m, 2H), 1.45 (s, 3H), 1.24 (s, 3H), 1.17-1.81 (m, 14H), 1.15 (s, 3H), 1.10 (s, 3H), 1.05 (s, 3H), 1.04 (s, 3H), 0.95 (t, J=7.4 Hz, 3H), 0.94 (s, 3H).

Compound 55b: Using the same procedure as described for the synthesis of compound 51, impure compound 55b (1.1737 g) was synthesized from compound 35 (3.67 mmol), isobutyramidoxime (255.1 mg, 2.50 mmol) and trimethylamine (14.6 mmol). m/z=576 (M+1).

T27: Using the same procedure as described for the synthesis of compound T23, compound T27 (white solid, 240.3 mg, 57% yield from 35) was synthesized from compound 55b (354.1 mg) and tetrabutylammonium hydroxide (40% w/w in water, 1.25 mL, 1.9 mmol). m/z=558 (M+1); $^1$H NMR (400 MHz, $CDCl_3$) δ 8.02 (s, 1H), 5.96 (s, 1H), 3.22 (m, 1H), 3.18 (d, J=4.8 Hz, 1H), 3.07 (hept, J=6.9 Hz, 1H), 2.19 (td, J=13.8, 4.1 Hz, 1H), 1.90 (td, J=13.7, 5.4 Hz, 2H), 1.45 (s, 3H), 1.30 (d, J=6.9 Hz, 3H), 1.30 (d, J=6.9 Hz, 3H), 1.24 (s, 3H), 1.16-1.79 (m, 12H), 1.15 (s, 3H), 1.11 (s, 3H), 1.05 (s, 3H), 1.04 (s, 3H), 0.94 (s, 3H).

Compound 55c: Using the same procedure as described for the synthesis of compound 51, impure compound 55c (1.4948 g) was synthesized from compound 35 (3.13 mmol), V-hydroxy-2,2-dimethylpropanimidamide (258.2 mg, 2.22 mmol) and trimethylamine (12.5 mmol). m/z=590 (M+1).

T28: Using the same procedure as described for the synthesis of compound T23, compound T28 (white solid, 157.2 mg, 52% yield from 35) was synthesized from compound 55c (357.7 mg) and tetrabutylammonium hydroxide (40% w/w in water, 1.25 mL, 1.9 mmol). m/z=572 (M+1); $^1$H NMR (400 MHz, $CDCl_3$) δ 8.02 (s, 1H), 5.96 (s, 1H), 3.23 (m, 2H), 2.19 (td, J=13.7, 4.0 Hz, 1H), 1.90 (m, 2H), 1.47 (m, 12H), 1.45 (s, 3H), 1.33 (s, 9H), 1.24 (s, 3H), 1.15 (s, 3H), 1.11 (s, 3H), 1.04 (s, 3H), 1.03 (s, 3H), 0.94 (s, 3H).

Compound 55d: Using the same procedure as described for the synthesis of compound 51, impure compound 55d (279.1 mg) was synthesized from compound 35 (0.64 mmol), N' hydroxycyclopropanecarboximidamide (84.3 mg, 0.842 mmol) and trimethylamine (2.6 mmol). m/z=574 (M+1).

T29: Using the same procedure as described for the synthesis of compound T23, compound T29 (white solid, 129.3 mg, 36% yield from 35) was synthesized from compound 55d (279.1 mg) and tetrabutylammonium hydroxide (40% w/w in water, 1 mL, 1.5 mmol). m/z=556 (M+1); $^1$H NMR (400 MHz, $CDCl_3$) δ 8.02 (s, 1H), 5.96 (s, 1H), 3.17 (m, 1H), 3.12 (d, J=4.8 Hz, 1H), 2.17 (td, J=13.8, 4.1 Hz, 1H), 2.06 (m, 1H), 1.87 (m, 2H), 1.46 (s, 3H), 1.24 (s, 3H), 1.15 (s, 3H), 1.12 (s, 3H), 1.02 (s, 6H), 0.93 (s, 3H). 0.88-1.80 (m, 16H).

Compound 55e: Using the same procedure as described for the synthesis of compound 51, impure compound 55e (514.3 mg) was synthesized from compound 35 (1.33 mmol), 2-cyclopropyl-N'-hydroxyethanimidamide (101.3 mg, 0.887 mmol) and trimethylamine (5.31 mmol). m/z=588 (M+1).

T30: Using the same procedure as described for the synthesis of compound T23, compound T30 (white solid, 176.0 mg, 52% yield from 35) was synthesized from compound 55e (344.0 mg) and tetrabutylammonium hydroxide (40% w/w in water, 1.25 mL, 1.9 mmol). m/z=570 (M+1); $^1$H NMR (400 MHz, $CDCl_3$) δ 8.02 (s, 1H), 5.96 (s, 1H), 3.24 (m, 1H), 3.12 (d, J=4.7 Hz, 1H), 2.61 (m, 2H), 2.20 (td, J=13.8, 4.1 Hz, 1H), 1.91 (m, 2H), 1.45 (s, 3H), 1.24 (s, 3H), 1.15 (s, 3H), 1.12 (s, 3H), 1.07-1.79 (m, 13H), 1.05 (s, 3H), 1.04 (s, 3H), 0.95 (s, 3H), 0.50 (m, 2H), 0.24 (m, 2H).

Compound 55f: Using the same procedure as described for the synthesis of compound 51, impure compound 55f (239.0 mg) was synthesized from compound 35 (0.64 mmol), N'-hydroxycyclobutanecarboximidamide (89.8 mg, 0.787 mmol) and trimethylamine (2.6 mmol). m/z=588 (M+1).

T31: Using the same procedure as described for the synthesis of compound T23, compound T31 (white solid, 129.9 mg, 36% yield from 35) was synthesized from compound 55f (239.0 mg) and tetrabutylammonium hydroxide (40% w/w in water, 0.9 mL, 1.35 mmol). m/z=570 (M+1); $^1$H NMR (400 MHz, CDCl$_3$) δ 8.03 (s, 1H), 5.97 (s, 1H), 3.63 (m, 1H), 3.21 (m, 2H), 2.33 (m, 4H), 2.20 (td, J=13.9, 4.1 Hz, 1H), 1.45 (s, 3H), 1.24 (s, 3H), 1.17-2.14 (m, 16H), 1.15 (s, 3H), 1.11 (s, 3H), 1.05 (s, 3H), 1.04 (s, 3H), 0.94 (s, 3H).

Compound 55g: Using the same procedure as described for the synthesis of compound 51, compound 55g (115.6 mg) was synthesized from compound 35 (0.64 mmol), N-hydroxycyclopentanecarboximidamide (97.7 mg, 0.762 mmol) and trimethylamine (2.6 mmol). m/z=602 (M+1).

T32: Using the same procedure as described for the synthesis of compound T23, compound T32 (white solid, 60.9 mg, 16% yield from 35) was synthesized from compound 55g (115.6 mg, 0.192 mmol) and tetrabutylammonium hydroxide (40% w/w in water, 0.4 mL, 0.6 mmol). m/z=584 (M+1); $^1$H NMR (400 MHz, CDCl$_3$) δ 8.02 (s, 1H), 5.96 (s, 1H), 3.19 (m, 3H), 2.19 (td, J=13.8, 4.1 Hz, 1H), 1.45 (s, 3H), 1.24 (s, 3H), 1.17-2.07 (m, 22H), 1.15 (s, 3H), 1.11 (s, 3H), 1.04 (s, 3H), 1.03 (s, 3H), 0.94 (s, 3H).

Compound 55h: Using the same procedure as described for the synthesis of compound 51, impure compound 55h (544.9 mg) was synthesized from compound 35 (1.06 mmol), N'-hydroxycyclohexanecarboximidamide (99.5 mg, 0.700 mmol) and trimethylamine (4.2 mmol). m/z=616 (M+1).

T33: Using the same procedure as described for the synthesis of compound T23, compound T33 (white solid, 149.8 mg, 56% yield from 35) was synthesized from compound 55h (346.1 mg) and tetrabutylammonium hydroxide (40% w/w in water, 1.25 mL, 1.9 mmol). m/z=598 (M+1); $^1$H NMR (400 MHz, CDCl$_3$) δ 8.02 (s, 1H), 5.96 (s, 1H), 3.22 (m, 1H), 3.14 (d, J=4.7 Hz, 1H), 2.77 (tt, J=11.4, 3.6 Hz, 1H), 2.19 (td, J=13.8, 4.1 Hz, 1H), 1.58 (m, 24H), 1.45 (s, 3H), 1.24 (s, 3H), 1.15 (s, 3H), 1.10 (s, 3H), 1.05 (s, 3H), 1.03 (s, 3H), 0.94 (s, 3H).

Compound 58: Compound 56 (0.86 g, 1.9 mmol) in CH$_2$Cl$_2$ (19 mL) was treated with oxalyl chloride (0.5 mL, 5.7 mmol) and DMF (15 µL, 0.19 mmol) at 0° C. sequentially. The reaction was stirred at room temperature for 2 h, and then concentrated. The residue was dissolved in toluene (3×20 mL) and concentrated to give the compound 57 as a yellow solid. Compound 57 was dissolved in CH$_2$Cl$_2$ (25 mL) and cooled to 0° C. Et$_3$N (1.1 mL, 7.6 mmol) was added, followed by the addition of 2-fluoro-N-hydroxyethanimidamide (0.26 g, 2.8 mmol). The reaction was stirred at room temperature for 2 h. The reaction mixture was then concentrated and partitioned between EtOAc (30 mL) and water (20 mL). The layers were separated; and the organic layer was washed with water (2×20 mL). The aqueous washes were extracted with EtOAc (20 mL). The combined organic extracts were washed with brine (20 mL), dried with Na$_2$SO$_4$, filtered, and concentrated. The residue was purified by column chromatography (silica gel, eluting with 0-100% EtOAc in CH$_2$Cl$_2$) to give compound 58 (0.87 g, 87% yield) as a white solid. m/z=529 (M+1).

Compound 59: Compound 58 (20 mg, 0.038 mmol) was dissolved in o-xylene (0.5 mL) and the reaction was heated at 180° C. for 14 h in a sealed-tube. The reaction mixture was concentrated, and the residue was purified by column chromatography (silica gel, eluting with 0-100% EtOAc in hexane) to give compound 59 (9 mg, 49% yield) as a white solid. m/z=511 (M+1).

Compound 60: Compound 59 (233 mg, 0.46 mmol) was dissolved in ethyl formate (3.3 mL, 41 mmol) and cooled to 0° C. Sodium methoxide solution (25 wt. % in MeOH, 1 mL, 4.56 mmol) was added under N$_2$. After stirring at room temperature for 1.5 h, the reaction mixture was cooled to 0° C. HCl (12 N aqueous solution, 0.8 mL, 4.56 mmol) was added, followed by the addition of EtOH (5 mL) and hydroxylamine hydrochloride (47.6 mg, 0.68 mmol). The reaction was heated at 60° C. for 4 h, and then cooled to room temperature. The reaction mixture was diluted with EtOAc (30 mL); washed with water (2×20 mL) and sat. aq. NaHCO$_3$ (20 mL). The aqueous washes were extracted with EtOAc (20 mL). The combined organic extracts were washed with brine (20 mL), dried with Na$_2$SO$_4$, filtered, and concentrated. The residue was purified by column chromatography (silica gel, eluting with 0-100% EtOAc in hexane) to give compound 60 (265 mg, quantitative yield) as an off-white solid. m/z=536 (M+1).

Compound 61: Compound 60 (265 mg, 0.49 mmol) in MeOH (5 mL) was treated with sodium methoxide (25 wt. % in MeOH, 226 µL, 0.99 mmol) at room temperature. The reaction was heated at 55° C. for 1.5 h, and then cooled to 0° C. 10% aq. NaH$_2$PO$_4$ (10 mL) was added and the mixture was extracted with EtOAc (2×20 mL). The combined organic extracts were washed with brine, dried with Na$_2$SO$_4$, filtered and concentrated. The residue was purified by column chromatography (silica gel, eluting with 0-100% EtOAc in hexane) to give compound 61 (217 mg, 82% yield) as a white solid. m/z=536 (M+1).

T34: Compound 61 (217 mg, 0.41 mmol) was dissolved in DMF (1 mL) and cooled to 0° C. under N$_2$. 1,3-Dibromo-5,5-dimethylhydantoin (58 mg, 0.20 mmol) in DMF (1 mL) was added dropwise. The mixture was stirred at 0° C. for 2 h. Pyridine (98 µL, 1.21 mmol) was then added. The reaction was heated at 60° C. for 4 h. After cooled to room temperature, the mixture was diluted with EtOAc (20 mL) and washed with 1 N aq. HCl (10 mL), water (2×15 mL) and brine (10 mL). The organic extract was dried with Na$_2$SO$_4$, filtered, and concentrated. The residue was purified by column chromatography (silica gel, eluting with 0-100% EtOAc in hexane) to give compound T34 (168 mg, 78% yield) as a white solid. m/z=534 (M+1); $^1$H NMR (400 MHz, CDCl$_3$) δ 8.00 (s, 1H), 6.02 (s, 1H), 5.44 (d, J=46.5 Hz, 2H), 3.27 (dt, J=13.9, 4.6 Hz, 1H), 3.05 (d, J=4.7 Hz, 1H), 2.45 (dq, J=6.7, 13.4 Hz, 1H), 2.23 (td, J=13.8, 4.1 Hz, 1H), 1.57 (s, 3H), 1.41 (s, 3H), 1.24 (d, J=6.7 Hz, 3H), 1.21-2.00 (m, 11H), 1.11 (s, 3H), 1.06 (s, 3H), 1.05 (s, 3H), 0.95 (s, 3H).

Compound 62: Compound 56 (500 mg, 1.02 mmol) in CH$_2$Cl$_2$ (14 mL) was treated with oxalyl chloride (275 µL, 3.14 mmol) and N,N-dimethylformamide (8 µL, 0.1 mmol) sequentially at 0° C. The reaction was stirred at room temperature for 2 h and then concentrated. The residue was dissolved in toluene (3×20 mL) and concentrated to give the acid chloride as a yellow solid. The acid chloride was dissolved in CH$_2$Cl$_2$ (14 mL) and cooled to 0° C. Triethylamine (0.58 mL, 4.16 mmol) and 2,2-difluoro-N'-hydroxyethanimidamide (173 mg, 1.57 mmol) were added. The reaction was stirred at room temperature for overnight. LC-MS indicates that the reaction was complete. The reaction was concentrated, and the residue was partitioned between ethyl acetate (20 mL) and sat. aq. NaHCO$_3$ (10 mL). The organic layer was separated and washed with sat. aq. NaHCO$_3$ (10 mL). The combined aqueous washes were extracted with ethyl acetate (20 mL). The combined organic extracts were washed with brine, dried with Na$_2$SO$_4$, filtered and concentrated. The residue was purified by column chromatography (silica gel, eluting with 0-100% EtOAc in hexanes) to give compound 62 (337 mg, 57% yield). m/z=570 (M+1).

T35: To a solution of compound 62 (100 mg, 0.176 mmol) THF (4 mL) at 0° C., was added tetrabutylammonium hydroxide (40 wt. % in water, 0.36 mL, 0.55 mmol) dropwise. The reaction was stirred at room temperature for overnight. LC-MS indicates that the reaction was complete. The mixture was partitioned between ethyl acetate (20 mL) and water (20 mL). The organic layer was separated and washed with water (2×10 mL). The combined aqueous washes were extracted with ethyl acetate (20 mL). The combined organic extracts were washed with brine (20 mL), dried with Na$_2$SO$_4$, filtered and concentrated. The residue was purified by column chromatography (silica gel, eluting with 0-100% EtOAc in hexanes) to give compound T35 (15.7 mg, 16% yield). m/z=552 (M+1); $^1$H NMR (400 MHz, CDCl$_3$) δ 8.00 (s, 1H), 6.75 (t, J=52.5 Hz, 1H), 6.02 (s, 1H), 3.26 (dd, J=13.5, 3.5 Hz, 1H), 3.02 (d, J=4.7 Hz, 1H), 2.45 (dt, J=13.3, 6.7 Hz, 1H), 2.25 (td, J=13.9, 4.2 Hz, 1H), 2.01-1.20 (m, 14H), 1.41 (s, 3H), 1.24 (d, J=6.8 Hz, 3H), 1.11 (s, 3H), 1.06 (s, 3H), 1.05 (s, 3H), 0.96 (s, 3H).

Compound 63: To a solution of compound 56 (1.21 g, 2.46 mmol) in CH$_2$Cl$_2$ (50 mL) at 0° C. were added oxalyl chloride (0.65 mL, 7.43 mmol) and N,N-dimethylformamide (20 µL, 0.26 mmol) sequentially. The mixture was stirred at 0° C. for 20 h, and then concentrated in vacuo to give compound 63 (1.48 g, quantitative yield) as a yellow foamy solid, which was used in next step without further purification.

Compound 64: Triethylamine (0.79 mL, 5.67 mmol) was added slowly to a solution of compound 63 (82 wt. %, 860 mg, 1.42 mmol) in CH$_2$Cl$_2$ (15 mL) at room temperature under N$_2$. A solution of 2,2,2-Trifluoro-N'-hydroxy-ethanimidamide (181 mg, 1.42 mmol) in CH$_2$Cl$_2$ (6 mL) was then added dropwise. The reaction mixture was stirred at room temperature for 16 h, and then concentrated. The residue was diluted with EtOAc (100 mL). The mixture was washed with sat. aq. NaHCO$_3$ (30 mL) and brine (30 mL). The organic extract was dried with Na$_2$SO$_4$, filtered and concentrated. The residue was purified by column chromatography (silica gel, eluting with 0-10% MeOH in CH$_2$Cl$_2$) to give partially purified compound 64 (615 mg) as an orange foamy solid, which was used in next step without further purification. m/z=588.2 (M+1).

T36: A mixture of compound 64 (615 mg, <1.04 mmol) and tetrabutylammonium hydroxide (40 wt. % in water, 2.16 mL, 3.31 mmol) in THF (20 mL) was stirred at room temperature for 20 h under N$_2$. The reaction mixture was concentrated. The residue was diluted with EtOAc (40 mL). The mixture was washed with water (20 mL). The aqueous phase was separated and extracted with EtOAc (2×20 mL). The combined organic extracts were washed with brine (20 mL), dried with Na$_2$SO$_4$, filtered and concentrated. The residue was purified by column chromatography (silica gel, eluting with 0-50% EtOAc in hexanes) to give compound T36 (72.3 mg, 9% yield from compound 63) as white solid. m/z=570.2 (M+1); $^1$H NMR (400 MHz, CDCl$_3$) δ 8.00 (s, 1H), 6.03 (s, 1H), 3.30-3.22 (m, 1H), 3.01 (d, J=4.7 Hz, 1H), 2.46 (dt, J=13.3, 6.7 Hz, 1H), 2.27 (td, J=13.9, 4.2 Hz, 1H), 2.02-1.20 (m, 14H), 1.42 (s, 3H), 1.24 (d, J=6.8 Hz, 3H), 1.11 (s, 3H), 1.07 (s, 3H), 1.06 (s, 3H), 0.96 (s, 3H).

Compound 65: Triethylamine (0.579 mL, 4.15 mmol) was added slowly to a solution of compound 63 (83 wt. %, 620 mg, 1.04 mmol) in CH$_2$Cl$_2$ (10 mL) at room temperature under N$_2$. Then a solution of N'-hydroxypropanimidamide (92 mg, 1.04 mmol) in CH$_2$Cl$_2$ (6 mL) was added dropwise. The mixture was stirred at room temperature for 16 h, and then concentrated. The residue was diluted with EtOAc (100 mL). The resultant mixture was washed with sat. aq. NaHCO$_3$ (30 mL) and brine (30 mL). The organic extract was dried with Na$_2$SO$_4$, filtered and concentrated. The residue was purified by column chromatography (silica gel, eluting with 0-10% MeOH in CH$_2$Cl$_2$) to give partially purified compound 65 (520 mg) as a yellow solid, which was used in next step without further purification. m/z=548.3 (M+1).

T37: A mixture of compound 65 (520 mg, 0.95 mmol) and tetrabutylammonium hydroxide (40% w/w in water, 1.98 mL, 3.04 mmol) in THF (15 mL) was stirred at room temperature for 15 h under N$_2$. The reaction mixture was concentrated. The residue was diluted with EtOAc (30 mL) and washed with water (20 mL). The aqueous phase was separated and extracted with EtOAc (2×20 mL). The combined organic extracts were washed with brine (20 mL), dried with Na$_2$SO$_4$, filtered and concentrated. The residue was purified by column chromatography (silica gel, eluting with 0-50% EtOAc in hexanes) to give compound T37 (267 mg, 48% yield from compound 63) as white solid. m/z=530.3 (M+1); $^1$H NMR (400 MHz, CDCl$_3$) δ 8.01 (s, 1H), 6.02 (s, 1H), 3.28-3.20 (m, 1H), 3.13 (d, J=4.7 Hz, 1H), 2.73 (qd, J=7.6, 1.6 Hz, 2H), 2.45 (dt, J=13.3, 6.7 Hz, 1H), 2.20 (td, J=13.8, 4.2 Hz, 1H), 2.02-1.18 (m, 14H), 1.41 (s, 3H), 1.29 (t, J=7.6 Hz, 3H), 1.24 (d, J=6.7 Hz, 3H), 1.11 (s, 3H), 1.05 (s, 3H), 1.04 (s, 3H), 0.94 (s, 3H).

Compound 66: Compound 65 (260 mg, 0.524 mmol) in CH$_2$Cl$_2$ (5 mL) was cooled to 0° C. under N$_2$. Hydrazine hydrate (50 wt. %, 98 µL, 1.57 mmol) was added dropwise. The mixture was stirred at room temperature for 10 min; diluted with CH$_2$Cl$_2$ (10 mL); and washed with water (15 mL). The aqueous wash was extracted with CH$_2$Cl$_2$ (3×15 mL) and EtOAc (15 mL). The combined organic extracts were dried with MgSO$_4$, filtered and concentrated to give compound 66 (220 mg, 85% yield). m/z=492 (M+1)

Compound 67: A solution of 2-fluoroacetic acid (38 µL, 0.67 mmol) in CH$_2$Cl$_2$ (2 mL) was treated with N-(3-dimethylaminopropyl)-N'-ethylcarbodiimide hydrochloride (129 mg, 0.67 mmol) and DMAP (5 mg, 0.045 mmol) at room temperature under N$_2$. The mixture was stirred at room temperature for 15 min. Compound 66 (220 mg, 0.45 mmol) was then added and the mixture was stirred at room temperature for 24 h. The reaction mixture was concentrated, and the residue was purified by column chromatography (silica gel, eluting with 0 to 60% EtOAc in CH$_2$Cl$_2$) to give compound 67 (72 mg, 29% yield). m/z=552 (M+1).

T38: Compound 67 (70 mg, 0.13 mmol) and p-toluenesulfonic acid monohydrate (12 mg, 0.063 mmol) in toluene (7 mL) was heated at reflux while removing water by Dean-Stark apparatus for 5 h. The mixture was cooled to room temperature; diluted with EtOAc (10 mL); and washed with water (2×15 mL). The organic extract was dried with MgSO$_4$, filtered and concentrated. The residue was purified by column chromatography (silica gel, eluting with acetone in hexanes) to give compound T38 (33 mg, 49% yield) as a white solid. m/z=534 (M+1); $^1$H NMR (400 MHz, CDCl$_3$) δ 8.00 (s, 1H), 6.02 (s, 1H), 5.51 (d, J=47.1, 2H), 3.19 (dt, J=13.4, 4.0 Hz, 1H), 3.02 (d, J=4.7 Hz, 1H), 2.46 (dq, J=13.3, 6.7 Hz, 1H), 2.23 (td, J=13.7, 4.2 Hz, 1H), 2.01-1.20 (m, 14H), 1.41 (s, 3H), 1.24 (d, J=6.8 Hz, 3H), 1.16 (s, 3H), 1.06 (s, 6H), 0.95 (s, 3H).

Compound 69: A mixture of compound 68 (898 mg, 1.94 mmol), NaOAc (286 mg, 3.49 mmol) and hydroxylamine hydrochloride (175 mg, 2.52 mmol) in EtOH (30 mL) and $H_2O$ (2 mL) were stirred at room temperature for 16 h. The mixture was concentrated. The residue was partitioned between ethyl acetate (20 mL) and water (10 mL). The organic layer was separated, and the aqueous layer was extracted with ethyl acetate (2×20 mL). The combined organic extracts were washed with brine (20 mL), dried with $Na_2SO_4$, filtered, and concentrated to give compound 69 (863 mg, 93% yield) as a white solid, which was carried to the next step without further purification. m/z=479 (M+1).

Compound 70: Compound 69 (863 mg, 1.80 mmol) in MeCN (9 mL) was cooled to −10° C. 12 N aq. HCl (30 µL, 0.36 mmol), and a solution of N-chlorosuccinimide (241 mg, 1.80 mmol) in MeCN (9 mL) were added sequentially. The reaction was run at −10° C. for 30 min, and then ammonium hydroxide (28 wt. % aqueous, 3 mL, 21.5 mmol) was added. The reaction was stirred at room temperature for overnight. Ethyl acetate (30 mL) and water (20 mL) were added. The layers were separated. The aqueous layer was extracted with ethyl acetate (4×20 mL). The combined organic extracts were washed with brine (20 mL), dried with $Na_2SO_4$, filtered, and concentrated. The residue was purified by column chromatography (silica gel, 0-100% EtOAc in $CH_2Cl_2$) to give compound 70 (457 mg, 51% yield). m/z=494 (M+1).

Compound 71: A solution of 2-fluoroacetic acid (169 mg, 2.17 mmol) in $CH_2Cl_2$ (15 mL) was added to N-(3-dimethylaminopropyl)-N'-ethylcarbodiimide hydrochloride (EDC·HCl, 416 mg, 2.17 mmol) at room temperature under $N_2$. Catalytic amount of DMAP (8 mg, 0.072 mmol) was added. The mixture was stirred at room temperature for 15 min. Compound 70 (357 mg, 0.72 mmol) was then added. The mixture was stirred at room temperature for 2 h, and then concentrated. The residue was diluted with ethyl acetate (30 mL) and washed with water (2×20 mL). The combined aqueous washes were extracted with ethyl acetate (20 mL). The combined organic extracts were washed with brine (20 mL), dried with $Na_2SO_4$, filtered and concentrated. The residue was purified by column chromatography (silica gel, eluting with 0-100% EtOAc in hexanes) to give compound 71 (150 mg, 38% yield). m/z=554 (M+1).

Compound 72: Compound 71 (207 mg, 0.374 mmol) in 1,4-dioxane (3 mL) was heated at 100° C. for 5 h under $N_2$. The mixture was cooled to room temperature and concentrated. The residue was purified by column chromatography (silica gel, eluting with 0-30% EtOAc in hexanes) to give compound 72 (158 mg, 79% yield). m/z=536 (M+1).

Compound 73: Compound 72 (158 mg, 0.295 mmol) in MeOH (4 mL) was treated with NaOMe (25 wt. % in MeOH, 135 µL, 0.59 mmol) at room temperature. The reaction was heated at 55° C. for 2.5 h, and then was cooled to room temperature. 10% aq. $NaH_2PO_4$ (20 mL) was added. The mixture was extracted with ethyl acetate (2×30 mL). The combined organic extracts were washed with brine (20 mL), dried with $Na_2SO_4$, filtered and concentrated. The residue was purified by column chromatography (silica gel, eluting with 0-40% EtOAc in hexanes) to give compound 73 (134 mg, 85% yield). m/z=536 (M+1).

T39: Compound 73 (134 mg, 0.25 mmol) was dissolved in DMF (3 mL) and cooled to 0° C. under $N_2$. A solution of 1,3-Dibromo-5,5-dimethylhydantoin (38 mg, 0.13 mmol) in DMF (1 mL) was added dropwise. The mixture was stirred at 0° C. for 2 h. Pyridine (61 µL, 0.75 mmol) was then added and the reaction was heated at 60° C. for 4 h. After cooled to room temperature, the mixture was diluted with EtOAc (20 mL) and washed with 1 N aq. HCl (10 mL), water (2×10 mL) and brine (10 mL). The organic extract was dried with $MgSO_4$, filtered, and concentrated. The residue was purified by column chromatography (silica gel, eluting with 0-50% EtOAc in hexanes) to give compound T39 (96 mg, 70% yield) as a white foam. m/z=534 (M+1); $^1H$ NMR (400 MHz, $CDCl_3$) δ 8.01 (s, 1H), 6.01 (s, 1H), 5.54 (d, J=46.3, 2H), 3.22 (dt, J=13.2, 3.9 Hz, 1H), 2.98 (d, J=4.7 Hz, 1H), 2.45 (dq, J=13.3, 6.7 Hz, 1H), 2.19 (td, J=13.8, 4.2 Hz, 1H), 2.01-1.20 (m, 14H), 1.41 (s, 3H), 1.24 (d, J=6.7 Hz, 3H), 1.14 (s, 3H), 1.06 (s, 3H), 1.05 (s, 3H), 0.94 (s, 3H).

Compound 74: Compound 5 (150 mg, 0.295 mmol) in 1,4-dioxane (3 mL) was cooled to 0° C. Triethylamine (124 µL, 0.886 mmol) and trifluoroacetic anhydride (45 µL, 0.325 mmol) were added sequentially. The reaction was stirred at room temperature for 19 h. The reaction mixture was combined with another same reaction starting with compound 5. The mixture was diluted with EtOAc (40 mL), and washed with sat. aq. $NaHCO_3$ (2×20 mL) and brine (10 mL). The organic extract was dried with $MgSO_4$, filtered and concentrated. The residue was purified by column chromatography (silica gel, eluting with 0-100% EtOAc in hexanes) to give compound 74 (130 mg, 56% yield) as a white solid. m/z=586 (M+1).

Compound 75: Compound 74 (125 mg, 0.213 mmol) in MeOH (2 mL) was treated with sodium methoxide (25 wt. % in MeOH, 100 µL, 0.44 mmol) at room temperature. The reaction was heated at 55° C. for 2 h, and then was cooled to room temperature. 10% aq. $NaH_2PO_4$ (20 mL) was added and the mixture was extracted with EtOAc (2×30 mL). The combined organic extracts were washed with brine (20 mL), dried with $MgSO_4$, filtered and concentrated. The residue was purified by column chromatography (silica gel, eluting with 0-40% EtOAc in hexanes) to give compound 75 (85 mg, 68% yield) as a white solid. m/z=586 (M+1).

T40: Compound 75 (82 mg, 0.14 mmol) was dissolved in DMF (0.7 mL) and cooled to 0° C. under $N_2$. A solution of 1,3-Dibromo-5,5-dimethylhydantoin (20 mg, 0.070 mmol) in DMF (0.2 mL) was added dropwise. The mixture was stirred at 0° C. for 1 h. DMF (0.5 mL) was added to dissolve the white solid precipitated during the reaction. The reaction was stirred at room temperature for 10 min. Pyridine (45 µL, 0.56 mmol) was then added and the reaction was heated at 55° C. for 5 h. The mixture was cooled to room temperature; diluted with EtOAc (20 mL); and washed with 1 N aq. HCl (10 mL), water (2×10 mL) and brine (10 mL). The organic extract was dried with $MgSO_4$, filtered, and concentrated. The residue was purified by column chromatography (silica gel, eluting with 0-40% acetone in hexanes) to give compound T40 (70 mg, 85% yield) as a white solid. m/z=584 (M+1); $^1H$ NMR (400 MHz, $CDCl_3$) δ 8.02 (s, 1H), 5.97 (s, 1H), 3.26-3.19 (m, 1H), 2.95 (d, J=4.7 Hz, 1H), 2.22 (td, J=13.8, 4.2 Hz, 1H), 1.96-1.83 (m, 2H), 1.80-1.20 (m, 12H), 1.45 (s, 3H), 1.25 (s, 3H), 1.16 (s, 3H), 1.14 (s, 3H), 1.06 (s, 3H), 1.05 (s, 3H), 0.95 (s, 3H).

Compound 76: To a solution of N-(3-dimethylaminopropyl)-N'-ethylcarbodiimide hydrochloride (170 mg, 0.886 mmol) in $CH_2Cl_2$ (3 mL) was added 2,2-difluoroacetic acid (85 mg, 0.886 mmol) in $CH_2Cl_2$ (3 mL) and DMAP (3.6 mg, 0.030 mmol) sequentially at room temperature. After stirring the reaction mixture for 15 min, a solution of compound 5 (150 mg, 0.295 mmol) in $CH_2Cl_2$ (4 mL) was added. The reaction was stirred at room temperature for another 19 h. The mixture was then diluted with $CH_2Cl_2$ (20 mL) and washed with water (15 mL). The aqueous wash was extracted with EtOAc (2×15 mL). The combined organic extracts were dried with $Na_2SO_4$, filtered and concentrated. The residue was purified by column chromatography (silica gel, eluting with 0-40% EtOAc in hexanes) to give compound 76 (106 mg, 63% yield) as a white solid. m/z=568 (M+1).

Compound 77: Compound 76 (106 mg, 0.187 mmol) in MeOH (1.8 mL) was treated with sodium methoxide (25 wt. % in MeOH, 85.5 µL, 0.373 mmol) at room temperature. The reaction was heated at 55° C. for 2 h, and then was cooled to room temperature. 10% aq. $NaH_2PO_4$ (20 mL) was added. The mixture was extracted with EtOAc (2×20 mL). The combined organic extracts were dried with $MgSO_4$, filtered and concentrated. The residue was purified by column chromatography (silica gel, eluting with 0-40% EtOAc in hexanes) to give compound 77 (90 mg, 85% yield) as a white solid. m/z=568 (M+1).

T41: Compound 77 (66 mg, 0.12 mmol) and 1,3-dibromo-5,5-dimethylhydantoin (17 mg, 0.058 mmol) were weighed in a round-bottom flask, and cooled to 0° C. DMF (1.2 mL) was added under $N_2$. The mixture was stirred at 0° C. for 1 h. Pyridine (38 µL, 0.47 mmol) was then added and the reaction was heated at 55° C. for 5 h. After cooled to room temperature, the mixture was diluted with EtOAc (20 mL) and washed with 1 N aq. HCl (10 mL), water (2×10 mL) and brine (10 mL). The organic extract was dried with $MgSO_4$, filtered, and concentrated. The residue was purified by column chromatography (silica gel, eluting with 0-40% EtOAc in hexanes) to give compound T41 (57 mg, 87% yield) as a white solid. m/z=566 (M+1); $^1$H NMR (400 MHz, $CDCl_3$) δ 8.02 (s, 1H), 6.79 (t, J=52.2 Hz, 1H), 5.96 (s, 1H), 3.22 (dt, J=13.4, 4.4 Hz, 1H), 2.92 (d, J=4.7 Hz, 1H), 2.21 (td, J=13.8, 4.2 Hz, 1H), 1.96-1.83 (m, 2H), 1.80-1.20 (m, 12H), 1.45 (s, 3H), 1.25 (s, 3H), 1.15 (s, 3H), 1.13 (s, 3H), 1.05 (s, 6H), 0.95 (s, 3H).

Compound 79: Compound 35 (500 mg, 0.980 mmol) in $CH_2Cl_2$ (10 mL) was cooled to 0° C., and treated with triethylamine (0.55 mL, 3.95 mmol) and compound 78 (215 mg, 1.47 mmol). The reaction mixture was stirred at ambient temperature for 2 h, and then washed with water. The aqueous layer was separated and extracted with $CH_2Cl_2$. The combined organic extracts were dried with $Na_2SO_4$, filtered and concentrated. The residue was purified by column chromatography (silica gel, eluting with 60% EtOAc in hexanes) to give compound 79 (437 mg, 72% yield) as a white solid. m/z=620 (M+1).

Compound 80: A solution of compound 79 (437 mg, 0.705 mmol) in THF (15 mL) was treated with tetrabutylammonium hydroxide (1.0 M solution in methanol, 1.41 mL, 1.41 mmol) at room temperature. The reaction was stirred at room temperature for 11 h, and then was diluted with ethyl acetate. The mixture was washed with water and brine. The organic extract was dried with $Na_2SO_4$, filtered and concentrated. The residue was purified by column chromatography (silica gel, eluting with 30% EtOAc in hexanes) to give compound 80 (258 mg, 61% yield) as an off-white solid. m/z=602 (M+1).

T42: A solution of compound 80 (258 mg, 0.428 mmol) in $CH_2Cl_2$ (10 mL) was treated with trifluoroacetic acid (1 mL, 12.98 mmol) at room temperature. The reaction was stirred for 22 h, and then was concentrated. The residue was dissolved in toluene and concentrated. The residue was purified by column chromatography (silica gel, eluting with 30-100% EtOAc in hexanes) give compound T42 (178 mg, 76% yield) as a white solid. m/z=546 (M+1); $^1$H NMR (400 MHz, $CDCl_3$) δ 8.02 (s, 1H), 5.97 (s, 1H), 4.77 (d, J=6.7 Hz, 2H), 3.33-3.20 (m, 1H), 3.04 (d, J=4.7 Hz, 1H), 2.27-2.16 (m, 2H), 2.00-1.20 (m, 14H), 1.45 (s, 3H), 1.25 (s, 3H), 1.15 (s, 3H), 1.11 (s, 3H), 1.05 (s, 6H), 1.00 (s, 3H).

Compound 81: A solution of triethylamine (0.266 mL, 1.90 mmol) and 2,2-difluoro-N-hydroxyethanimidamide (78.6 mg, 0.71 mmol) in $CH_2Cl_2$ (3.0 mL) was added dropwise to a solution of compound 35 (243 mg, 0.476 mmol) in $CH_2Cl_2$ (4.0 mL) at 0° C. under $N_2$. The mixture was stirred at room temperature for 18 h, and then partitioned between $CH_2Cl_2$ (40 mL) and water (40 mL). The aqueous phase was separated and extracted with $CH_2Cl_2$ (2×30 mL). The combined organic extracts were washed with brine, dried with $Na_2SO_4$, filtered and concentrated. The residue was purified by column chromatography (silica gel, eluting with 0-100% EtOAc in hexane) to give compound 81 (186 mg, 67% yield) as a solid. m/z=584.3 (M+1).

T43: To a solution of compound 81 (136.0 mg, 0.23 mmol) in anhydrous THF (10 mL) was added of tetrabutylammonium fluoride (1.0 M in THF, 0.70 mL, 0.70 mmol) at room temperature under $N_2$. The mixture was stirred at reflux for 5.5 h, and then was concentrated. The residue was partitioned between EtOAc (40 mL) and water (40 mL). The aqueous layer was separated and extracted with EtOAc (3×30 mL). The combined organic extracts were washed with brine, dried $Na_2SO_4$, filtered and concentrated. The residue was purified by column chromatography (silica gel, eluting with 0-50% acetone in $CH_2Cl_2$) to give T43 (73 mg, 55% yield) as a solid. m/z=566.4 (M+1); $^1$H NMR (400 MHz, $CDCl_3$) δ 8.02 (s, 1H), 6.75 (t, J=52.5 Hz, 1H), 5.97 (s, 1H), 3.29-3.23 (m, 1H), 3.00 (d, J=4.7 Hz, 1H), 2.25 (td, J=13.9, 4.2 Hz, 1H), 2.01-1.88 (m, 2H), 1.51-1.20 (m, 12H), 1.45 (s, 3H), 1.25 (s, 3H), 1.15 (s, 3H), 1.10 (s, 3H), 1.06 (s, 3H), 1.05 (s, 3H), 0.96 (s, 3H).

Compound 82: Difluoroacetic anhydride (52 µL, 0.45 mmol) was added to a solution of compound 36 (0.19 g, 0.38 mmol) and pyridine (46 µL, 0.56 mmol) in $CH_2Cl_2$ (4 mL) at 0° C. under $N_2$. The reaction was stirred at 0° C. for 30 min, and then at room temperature for 75 min. The reaction mixture was diluted with EtOAc (25 mL) and washed with 1 N aq. HCl (20 mL), water (20 mL) and brine (10 mL). The organic extract was dried with $Na_2SO_4$, filtered and concentrated. The residue was purified by column chromatography (silica gel, eluting with 0-40% EtOAc in $CH_2Cl_2$) to give compound 82 (95 mg, 43% yield) and a mixture of compound 82 and T44 (4/1, 80 mg, 36% yield). Compound 82: m/z=584.3 (M+1).

T44: p-Toluenesulfonic acid monohydrate (13 mg, 0.068 mmol) was added to a mixture of compound 82 (80.0 mg, 0.14 mmol) in toluene (8 mL) at room temperature. The reaction was heated at reflux while removing water by Dean-Stark apparatus for 3 h. After cooled to room temperature, the mixture was partitioned between EtOAc (30 mL) and water (10 mL). The organic extract was washed with water (2×10 mL) and brine (10 mL); dried with $Na_2SO_4$; filtered and concentrated. The residue was purified by column chromatography (silica gel, eluting with EtOAc in hexanes) to give compound T44 (24 mg, 31% yield) as a white solid. m/z=566.4 (M+1); $^1$H NMR (400 MHz, $CDCl_3$) δ 8.02 (s, 1H), 6.83 (t, J=51.8 Hz, 1H), 5.97 (s, 1H), 3.25-3.17 (m, 1H), 3.05 (d, J=4.7 Hz, 1H), 2.25 (td, J=13.9, 4.2 Hz, 1H), 2.01-1.88 (m, 2H), 1.51-1.20 (m, 12H), 1.45 (s, 3H), 1.25 (s, 3H), 1.15 (s, 6H), 1.06 (s, 6H), 0.96 (s, 3H).

Compound 83: Trifluoroacetic anhydride (74 µL, 0.52 mmol) was added to a solution of compound 36 (0.22 g, 0.44 mmol) and pyridine (53 µL, 0.65 mmol) in $CH_2Cl_2$ (5 mL) at room temperature. The mixture was stirred at 40° C. for 75 min. Additional amount of trifluoroacetic anhydride (20

µL, 0.14 mmol) was added and the resultant mixture was stirred for additional 1 h. Compound 83 was completely consumed. The reaction mixture was then cooled to room temperature; diluted with EtOAc (25 mL); and washed with 1 N aq. HCl (20 mL), water (2×20 mL) and brine (10 mL). The organic extract was dried with $Na_2SO_4$, filtered and concentrated. The residue was purified by column chromatography (silica gel, eluting with 0-75% EtOAc in hexanes) to give compound 83 (0.22 g, 84% yield) as a white solid.

T45: Burgess reagent (0.42 g, 1.76 mmol) was added to a solution of compound 83 (0.21 g, 0.35 mmol) in THF (4 mL) at room temperature. The reaction was stirred at 70° C. for 7 h. Additional amount of Burgess reagent (210 mg, 0.88 mmol) was added and the resultant mixture was stirred at 70° C. for overnight. Compound 83 was completely consumed. The reaction mixture was cooled to room temperature, and then partitioned between EtOAc (25 mL) and water (10 mL). The aqueous phase was separated and extracted with EtOAc (20 mL). The combined organic extracts were washed with water (2×10 mL) and brine (10 mL); dried with $Na_2SO_4$; filtered and concentrated. The residue was purified by column chromatography (silica gel, eluting with 0-40% EtOAc in hexanes) to give compound T45 (0.11 g, 54% yield) as a white solid. m/z=584.3 (M+1); $^1$H NMR (400 MHz, $CDCl_3$) δ 8.02 (s, 1H), 5.98 (s, 1H), 3.24-3.16 (m, 1H), 3.05 (d, J=4.7 Hz, 1H), 2.26 (td, J=14.0, 4.2 Hz, 1H), 2.01-1.88 (m, 2H), 1.80-1.20 (m, 12H), 1.46 (s, 3H), 1.25 (s, 3H), 1.16 (s, 6H), 1.06 (s, 3H), 1.05 (s, 3H), 0.96 (s, 3H).

Compound 84: Propionic anhydride (0.076 mL, 0.59 mmol) was added to a solution of compound 36 (0.25 g, 0.49 mmol) and pyridine (60 µL, 0.74 mmol) in $CH_2Cl_2$ (5 mL). The reaction was stirred at 40° C. for 2 h. The mixture was diluted with EtOAc (25 mL) and washed with 1 N aq. (1 N, 20 mL), water (2×20 mL) and brine (10 mL). The organic extract was dried with $Na_2SO_4$, filtered and concentrated. The residue was purified by column chromatography (silica gel, eluting with 0-100% EtOAc in hexanes) to give compound 84 (0.21 g, 76% yield) as a white solid. m/z=562.3 (M+1).

T46: Burgess reagent (0.21 g, 0.88 mmol) was added to a mixture of compound 84 (99 mg, 0.18 mmol) in THF (2 mL) at room temperature. The reaction was stirred at 70° C. for overnight, and then cooled to room temperature. The mixture was partitioned between EtOAc (25 mL) and water (10 mL). The aqueous phase was separated and extracted with EtOAc (20 mL). The combined organic extracts were washed with water (2×10 mL) and brine (10 mL), dried with $Na_2SO_4$, filtered and concentrated. The residue was purified by column chromatography (silica gel, eluting with 0-80% EtOAc in hexanes) to give compound T46 (71 mg, 74% yield) as a white solid. m/z 544.3 (M+1); $^1$H NMR (400 MHz, $CDCl_3$) δ 8.02 (s, 1H), 5.95 (s, 1H), 3.13 (dt, J=13.4, 4.1 Hz, 1H), 2.96 (d, J=4.7 Hz, 1H), 2.85 (q, J=7.6 Hz, 2H), 2.21-2.13 (m, 1H), 2.01-1.20 (m, 14H), 1.44 (s, 3H), 1.35 (t, J=7.5 Hz, 3H), 1.24 (s, 3H), 1.17 (s, 3H), 1.15 (s, 3H), 1.05 (s, 3H), 1.04 (s, 3H), 0.94 (s, 3H).

Compound 87: To a solution of compound 85 (6.58 g, 14.0 mmol) in $CH_2Cl_2$ (66 mL) was added oxalyl chloride (3.69 mL, 42.1 mmol) and DMF (0.11 mL, 1.40 mmol) sequentially at 0° C. under $N_2$. The mixture was stirred at room temperature for 2 h, and then concentrated. The residue was dissolved in toluene (3×60 mL) and concentrated to remove residual oxalyl chloride. Compound 86 was obtained as a yellow solid, which was used in the next step without further purification.

Compound 86 was dissolved in $CH_2Cl_2$ (100 mL) and cooled to 0° C. Triethylamine (7.83 mL, 56.2 mmol) and 2-fluoro-N-hydroxyacetimidamide (1.94 g, 21.1 mmol) were added sequentially. The mixture was stirred at room temperature for 4 h, and then washed with water (20 mL). The aqueous phase was separated, and extracted with $CH_2Cl_2$ (20 mL). The combined organic extracts were dried with $Na_2SO_4$, filtered and concentrated. The residue was purified by column chromatography (silica gel, eluting with 0-100% EtOAc in hexanes) to give compound 87 (6.81 g, 89% yield) as a yellow solid. m/z=543.3 (M+1).

Compound 88: Compound 87 (4.782 g, 8.811 mmol) was dissolved in anhydrous o-xylene (48 mL). Triethylamine (6.75 mL, 48.5 mmol) and propylphosphonic anhydride (50 wt. % solution in EtOAc, 17.3 mL, 29.1 mmol) were added sequentially. The mixture was heated at reflux for 7 h, and then was cooled to 0° C. Sat. aq. $NaHCO_3$ (100 mL) was added slowly. After the addition was complete, the mixture was extracted with $CH_2Cl_2$ (100 mL). The organic extract was washed with sat. aq. $NaHCO_3$ (100 mL) and water (100 mL). The combined aqueous washes were extracted with EtOAc (2×150 mL). The organic extracts were dried with $Na_2SO_4$; filtered through a pad of silica gel (25 g); and eluted with EtOAc (100 mL). The filtrate was concentrated. The residue was purified by column chromatography (silica gel, eluting with 0-100% EtOAc in hexanes) to give compound (1.65 g, 36% yield) as an off-white solid. m/z=525.3 (M+1).

Compound 89: A mixture of compound 88 (2.865 g, 5.460 mmol) in ethyl formate (13.2 mL, 164 mmol) was cooled to 0° C. under $N_2$. Sodium methoxide (25 wt. % in MeOH, 12.3 mL, 53.8 mmol) was added. The mixture was stirred at room temperature for 1.5 h, and then cooled to 0° C. HCl (6 M aqueous, 9.10 mL, 54.6 mmol), EtOH (55 mL) and hydroxylamine hydrochloride (569 mg, 8.19 mmol) were added sequentially. The mixture was heated at 60° C. for 3 h; cooled to room temperature; and concentrated. The residue was dissolved in EtOAc (60 mL) and washed with water (2×30 mL). The combined aqueous washes were extracted with EtOAc (2×20 mL). The combined organic extracts were dried with $MgSO_4$, filtered and concentrated. The residue was purified by column chromatography (silica gel, eluting with 0-50% EtOAc in hexanes) to give compound 89 (2.754 g, 92% yield) as a white solid. m/z=550.3 (M+1).

Compound 90: Compound 89 (2.754 g, 5.010 mmol) in MeOH (50 mL) was treated with sodium methoxide (25 wt. % in MeOH, 2.29 mL, 10.0 mmol) at room temperature under $N_2$. The mixture was heated at 55° C. for 1.5 h; cooled to 0° C.; and treated with 10% aq. $NaH_2PO_4$ (30 mL). The mixture was partitioned between EtOAc (50 mL) and brine (30 mL). The aqueous phase was separated and extracted with EtOAc (50 mL). The combined organic extracts were dried with $MgSO_4$, filtered and concentrated. The residue was purified by column chromatography (silica gel, eluting with 0-30% acetone in hexanes) to give compound 90 (2.52 g, 92% yield) as a white solid. m/z=550.3 (M+1).

T12: Compound 90 (2.570 g, 4.675 mmol) was dissolved in DMF (12 mL) and cooled to 0° C. under $N_2$. 1,3-Dibromo-5,5-dimethylhydantoin (735 mg, 2.57 mmol) was added, followed by additional amount of DMF (11 mL). The mixture was stirred at 0° C. for 2 h. Pyridine (1.51 mL, 18.7 mmol) was added. The mixture was heated at 60° C. for 4 h, and then was cooled to room temperature. The mixture was diluted with EtOAc (50 mL), and washed sequentially with 1 N aq. HCl (30 mL), water (2×30 mL), and brine (20 mL). The aqueous washes were combined and extracted with EtOAc (2×30 mL). The combined organic extracts were washed with water (2×30 mL) and brine (20 mL); dried with $Na_2SO_4$, filtered and concentrated. The residue was purified by column chromatography (silica gel, eluting with 0-30% acetone in hexanes) to give compound T12 (2.456 g, 96% yield) as a light yellow solid. m/z=548.3 (M+1); $^1$H NMR (400 MHz, CDCl$_3$) δ 8.02 (s, 1H), 5.97 (s, 1H), 5.44 (d, J=46.5 Hz, 2H), 3.26 (m, 1H), 3.03 (d, J=4.7 Hz, 1H), 2.24 (td, J=13.8, 4.1 Hz, 1H), 1.87-2.01 (m, 2H), 1.45 (s, 3H), 1.25 (s, 3H), 1.20-1.80 (m, 12H), 1.15 (s, 3H), 1.10 (s, 3H), 1.06 (s, 3H), 1.05 (s, 3H), 0.95 (s, 3H).

Example 2: Nitric Oxide Suppression Data

Tissue Culture. RAW 264.7, a mouse macrophage cell line, was obtained from American Type Culture Collection (Manassas VA) and maintained in the log phase of growth in Roswell Park Memorial Institute Medium 1640 (RPMI 1640) supplemented with 10% heat inactivated fetal bovine serum (FBS) and 1% penicillin-streptomycin. Cells were cultured and maintained in a humidified incubator at 37° C. under 5% CO$_2$. Cells were sub-cultured every 3 days. Alpha Mouse Liver (AML-12) cells were purchased from ATCC and cultured in DMEM/F12 medium supplemented with 10% FBS, 1% penicillin/streptomycin. All cell culture supplies were obtained from Life Technologies (Grand Island, NY) and VWR (Radnor, PA).

Nitric Oxide Suppression Assay. RAW 264.7 cells were plated 1 day in advance of experimental treatments at a concentration of 30,000 cells per well onto Falcon-96 well clear bottom plates (Corning, NY) in a total volume of 200 µL per well using RPMI 1640 supplemented with 0.5% fetal bovine serum and 1% penicillin-streptomycin. The next day, cells were pretreated with compounds serially diluted from 1000× stocks. All compounds were dissolved in dimethyl sulfoxide (DMSO) at 10 mM stock solutions. Compounds were subsequently diluted in DMSO and RPMI 1640. Each well received a final concentration of 0.1% DMSO. Cells were pretreated for 2 hours and incubation at 37° C., followed by treatment with 20 ng/mL of interferon gamma (R&D Systems, Minneapolis, MN) per well for 24 hours. The next day, a nitrite standard was serially diluted from 100 µM to 1.6 µM in RPMI 1640. Afterwards, 50 µL of cell culture supernatant was transferred from each well into a new Falcon-96 well clear bottom plate. Nitrite was measured as surrogate for nitric oxide using Promega's Griess Detection Kit #G2930 (Madison, WI) which involves the addition of 50 µL of the provided sulfanilamide solution to each well of the transferred cell culture supernatant and standards, followed by a 10-minute incubation at room temperature. Next, 50 µL of the provided N-1-napthylethylenediamine dihydrochloride (NED) solution was added to the sulfanilamide reaction and incubated for 10 minutes at room temperature in the dark. Afterwards, air bubbles were removed using ethanol vapor and absorbance was measured using a Spectramax M2e plate reader with a wavelength set to 525 nm. Viability was assessed using WST-1 cell proliferation reagent from Roche (Basel, Switzerland). After media was removed for the Nitric Oxide suppression assay, 15 µL of WST-1 reagent was added to each well of cells. Plates were briefly mixed on an orbital shaker and the cells were incubated at 37° C. for 30 minutes. Absorbance was measured using a Spectramax M2e plate reader with wavelengths set to 440 nm and 700 nm.

For the ability of compounds to suppress the increase in nitric oxide release caused by interferon gamma, the absolute amount of nitrite that was produced in each well was extrapolated from the nitrite standards using a linear regression fit. All values were then normalized to the DMSO-interferon gamma treated wells and plotted as percent nitric oxide. IC$_{50}$ values were calculated with a dependence on WST1 viability using Excel and/or GraphPad Prism (San Diego, CA). The data is shown in Table 2.

TABLE 2

Nitric Oxide Inhibition (NO IC$_{50}$) and NO IC$_{50}$ Relative to RTA 402.

| ID # | Structure | NO IC$_{50}$ (nM) (Mean ± SD) | NO IC$_{50}$ Relative to RTA 402 (fold)[a] (Mean ± SD) | # of Repeats |
|---|---|---|---|---|
| CC2 | 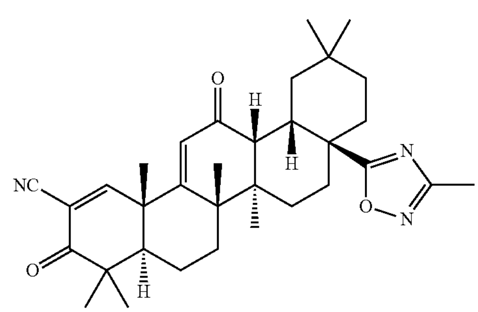 | 1.98 ± 0.56 | 0.70 ± 0.18 | 13 |

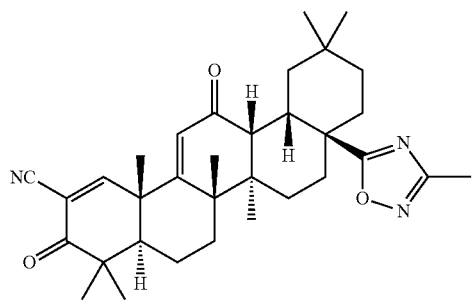

TABLE 2-continued

Nitric Oxide Inhibition (NO IC$_{50}$) and NO IC$_{50}$ Relative to RTA 402.

| ID # | Structure | NO IC$_{50}$ (nM) (Mean ± SD) | NO IC$_{50}$ Relative to RTA 402 (fold)$^a$ (Mean ± SD) | # of Repeats |
|---|---|---|---|---|
| T1 | 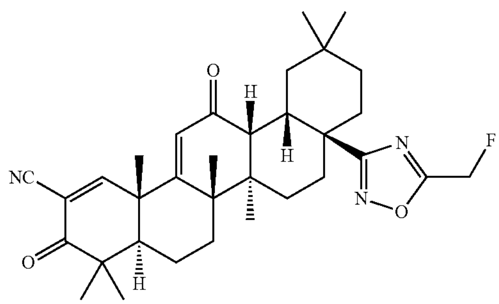 | 1.24 ± 0.38 | 0.52 ± 0.12 | 8 |
| T41 | 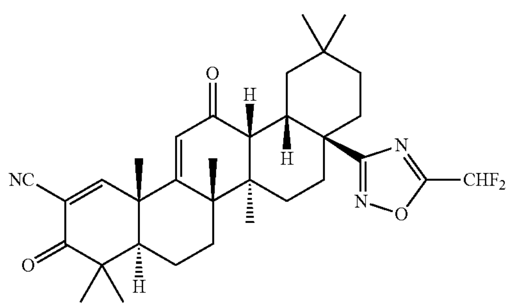 | 9.84 ± 3.52 | 2.79 ± 0.64 | 4 |
| T40 | 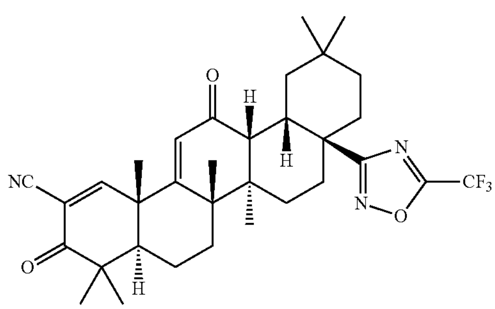 | 24.25 ± 7.64 | 7.76 ± 2.19 | 5 |
| T24 | 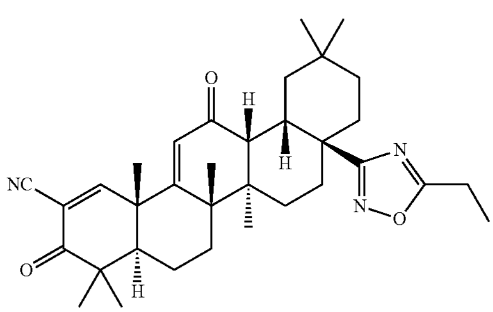 | 9.21 ± 2.66 | 2.56 ± 0.62 | 6 |

TABLE 2-continued

Nitric Oxide Inhibition (NO IC$_{50}$) and NO IC$_{50}$ Relative to RTA 402.

| ID # | Structure | NO IC$_{50}$ (nM) (Mean ± SD) | NO IC$_{50}$ Relative to RTA 402 (fold)$^a$ (Mean ± SD) | # of Repeats |
|---|---|---|---|---|
| T2 | 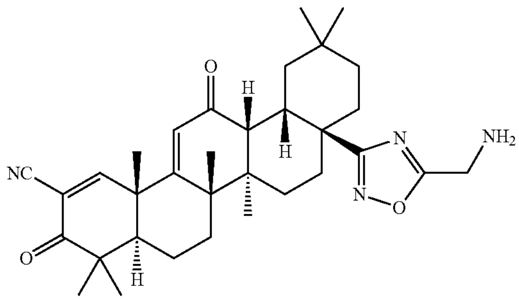 | 1.15 ± 0.44 | 0.38 ± 0.09 | 10 |
| T12 | 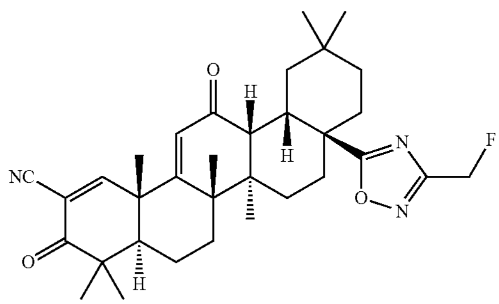 | 1.27 ± 0.34 | 0.52 ± 0.12 | 8 |
| T43 | 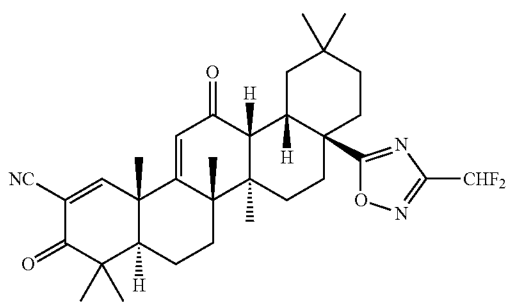 | 6.45 ± 1.29 | 1.90 ± 0.49 | 4 |
| T22 | 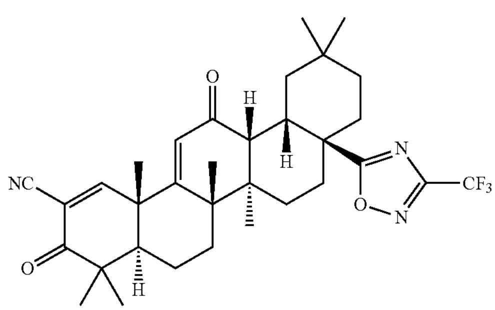 | 23.95 ± 10.04 | 7.71 ± 2.33 | 5 |

TABLE 2-continued

Nitric Oxide Inhibition (NO IC$_{50}$) and NO IC$_{50}$ Relative to RTA 402.

| ID # | Structure | NO IC$_{50}$ (nM) (Mean ± SD) | NO IC$_{50}$ Relative to RTA 402 (fold)$^a$ (Mean ± SD) | # of Repeats |
|---|---|---|---|---|
| T23 | 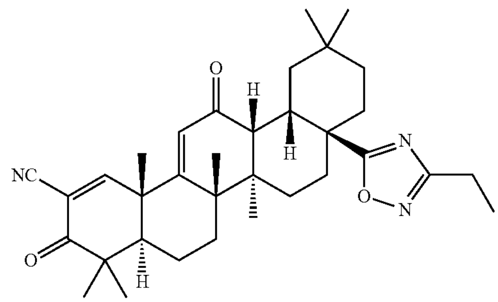 | 4.85 ± 2.61 | 1.93 ± 0.54 | 7 |
| CC1 | 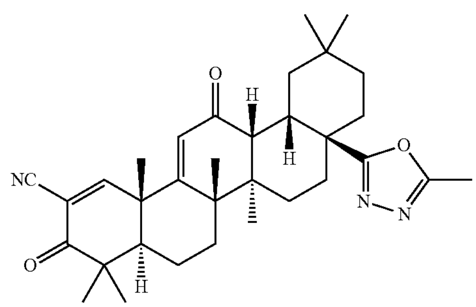 | 2.05 ± 1.36 | 0.78 ± 0.10 | 10 |
| T11 | 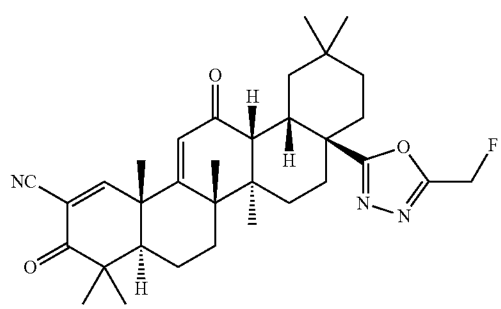 | 0.98 ± 0.54 | 0.37 ± 0.07 | 10 |
| T44 | 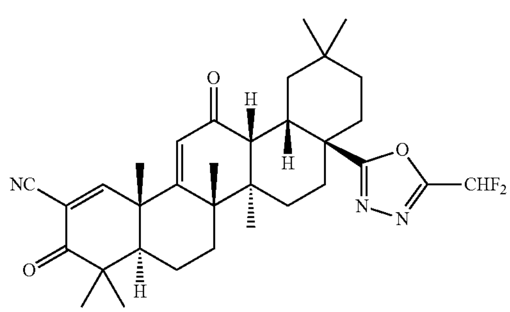 | 4.24 ± 2.23 | 1.24 ± 0.04 | 4 |

TABLE 2-continued

Nitric Oxide Inhibition (NO IC$_{50}$) and NO IC$_{50}$ Relative to RTA 402.

| ID # | Structure | NO IC$_{50}$ (nM) (Mean ± SD) | NO IC$_{50}$ Relative to RTA 402 (fold)$^a$ (Mean ± SD) | # of Repeats |
|---|---|---|---|---|
| T45 | 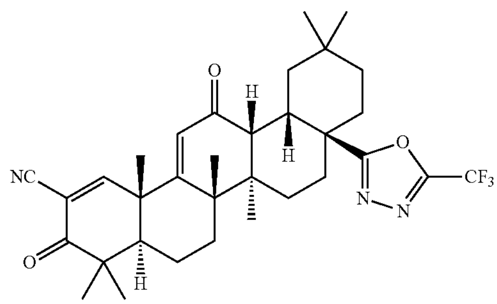 | 12.90 ± 6.38 | 3.81 ± 0.34 | 4 |
| T46 | 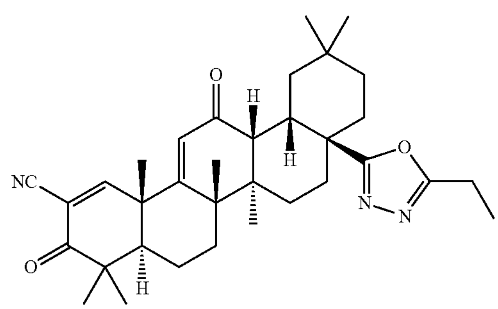 | 5.44 ± 2.81 | 1.60 ± 0.29 | 4 |
| CC3 | 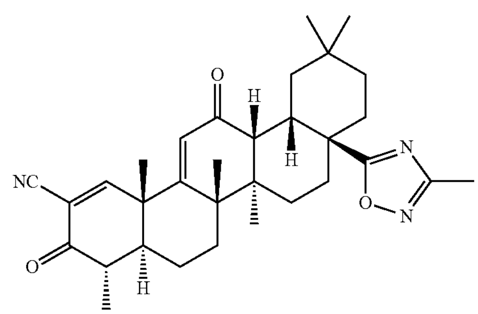 | 1.34 ± 0.52 | 0.40 ± 0.06 | 11 |
| T34 | 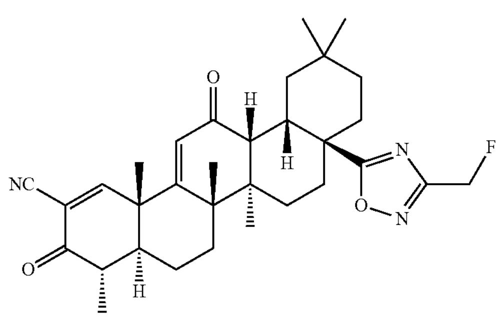 | 0.93 ± 0.52 | 0.28 ± 0.06 | 9 |

TABLE 2-continued

Nitric Oxide Inhibition (NO IC$_{50}$) and NO IC$_{50}$ Relative to RTA 402.

| ID # | Structure | NO IC$_{50}$ (nM) (Mean ± SD) | NO IC$_{50}$ Relative to RTA 402 (fold)[a] (Mean ± SD) | # of Repeats |
|---|---|---|---|---|
| T35 | 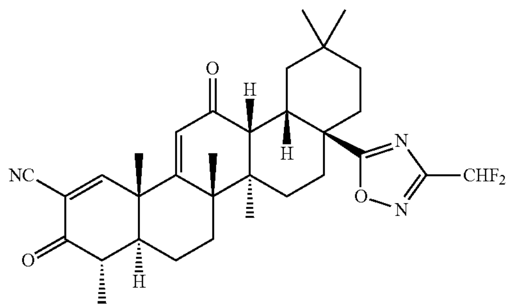 | 5.48 ± 3.04 | 1.21 ± 0.21 | 4 |
| T36 | 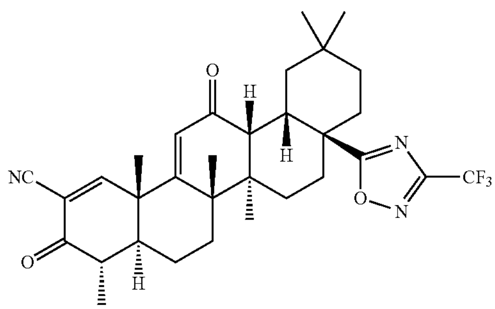 | 17.79 ± 9.89 | 3.95 ± 0.84 | 4 |
| T37 | 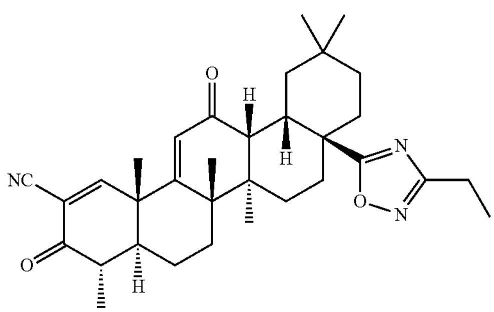 | 3.45 ± 1.87 | 0.76 ± 0.12 | 4 |
| CC4 | 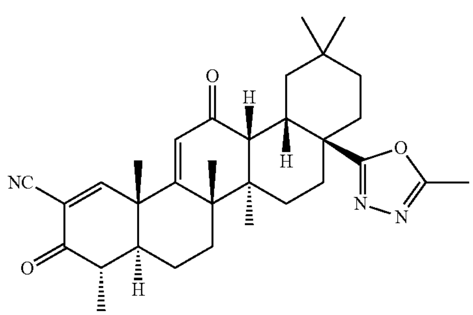 | 0.66 ± 0.06 | 0.51 ± 0.02 | 3 |

TABLE 2-continued

Nitric Oxide Inhibition (NO IC$_{50}$) and NO IC$_{50}$ Relative to RTA 402.

| ID # | Structure | NO IC$_{50}$ (nM) (Mean ± SD) | NO IC$_{50}$ Relative to RTA 402 (fold)$^a$ (Mean ± SD) | # of Repeats |
|---|---|---|---|---|
| T38 | 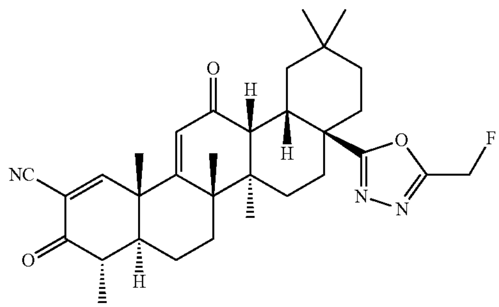 | 0.46 ± 0.02 | 0.20 ± 0.02 | 2 |
| T3 | 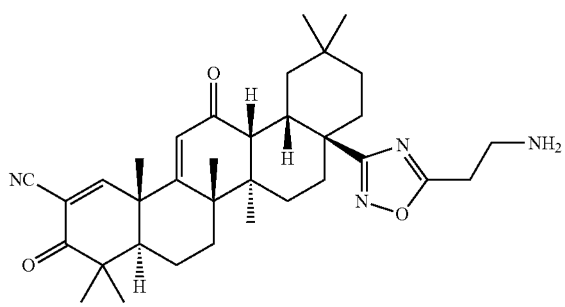 | 2.60 ± 0.03 | 0.69 ± 0.22 | 2 |
| T4 | 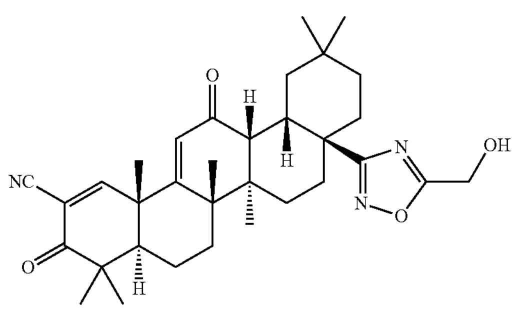 | 1.82 ± 0.13 | 0.48 ± 0.13 | 2 |
| T5 | 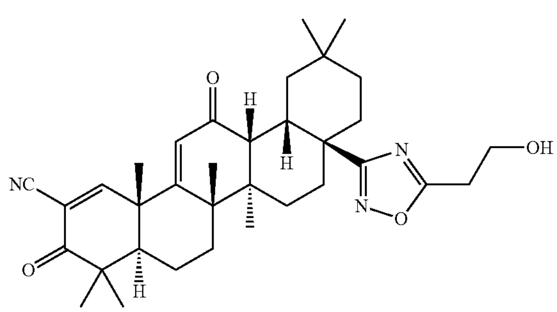 | 1.57 ± 0.05 | 0.42 ± 0.15 | 2 |

TABLE 2-continued

Nitric Oxide Inhibition (NO IC$_{50}$) and NO IC$_{50}$ Relative to RTA 402.

| ID # | Structure | NO IC$_{50}$ (nM) (Mean ± SD) | NO IC$_{50}$ Relative to RTA 402 (fold)$^a$ (Mean ± SD) | # of Repeats |
|---|---|---|---|---|
| T6 | 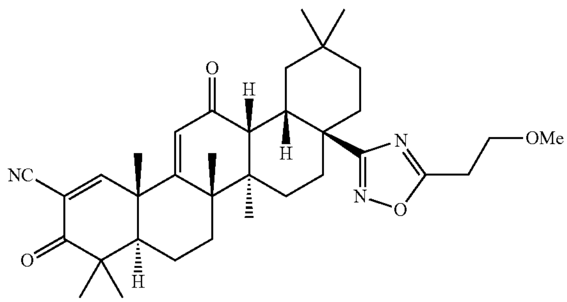 | 2.95 ± 0.11 | 0.79 ± 0.29 | 2 |
| T7 | 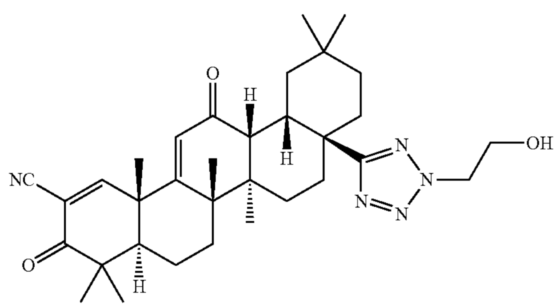 | 1.13 ± 0.18 | 0.43 ± 0.13 | 7 |
| T8 | 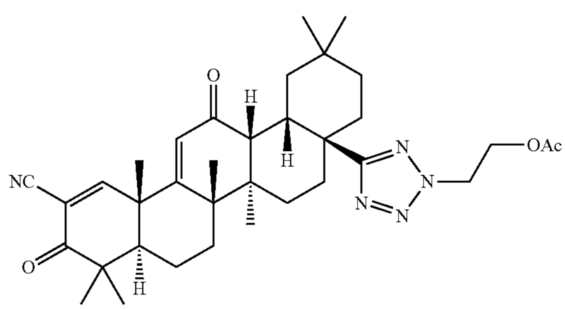 | 0.64 | 0.41 | 1 |
| T9 | 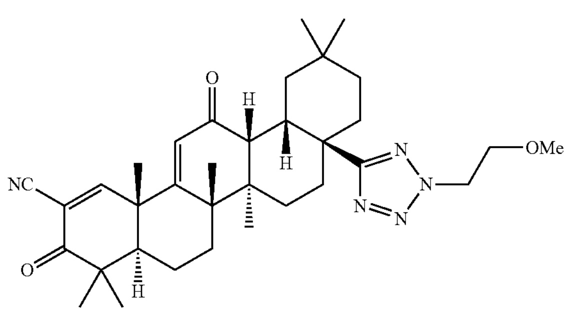 | 1.27 | 0.82 | 1 |

TABLE 2-continued

Nitric Oxide Inhibition (NO IC$_{50}$) and NO IC$_{50}$ Relative to RTA 402.

| ID # | Structure | NO IC$_{50}$ (nM) (Mean ± SD) | NO IC$_{50}$ Relative to RTA 402 (fold)$^a$ (Mean ± SD) | # of Repeats |
|---|---|---|---|---|
| T10 | 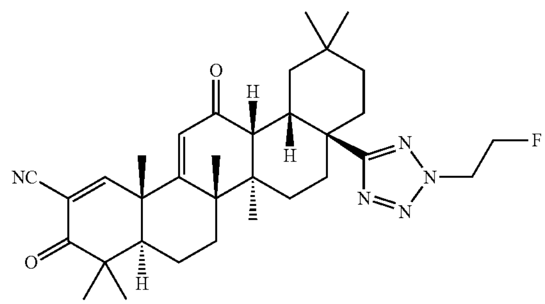 | 2.20 ± 0.20 | 1.62 ± 0.16 | 3 |
| T13 | 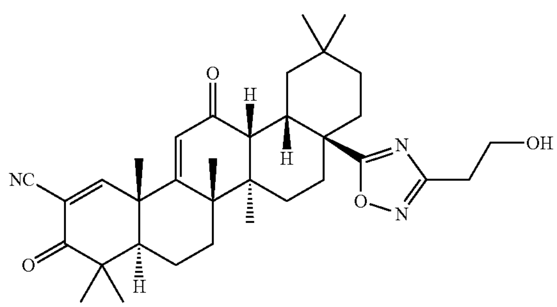 | 0.56 ± 0.26 | 0.22 ± 0.07 | 5 |
| T14 | 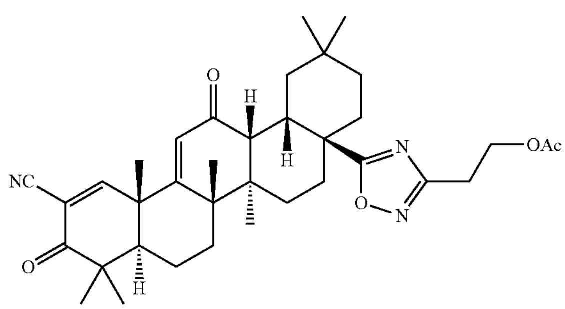 | 0.48 | 0.31 | 1 |
| T15 | 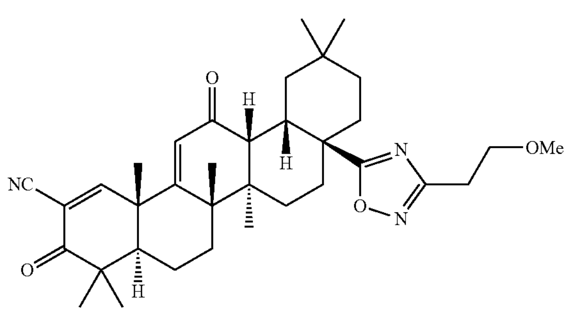 | 0.60 ± 0.05 | 0.38 ± 0.04 | 2 |

TABLE 2-continued

Nitric Oxide Inhibition (NO IC$_{50}$) and NO IC$_{50}$ Relative to RTA 402.

| ID # | Structure | NO IC$_{50}$ (nM) (Mean ± SD) | NO IC$_{50}$ Relative to RTA 402 (fold)$^a$ (Mean ± SD) | # of Repeats |
|---|---|---|---|---|
| T16 | 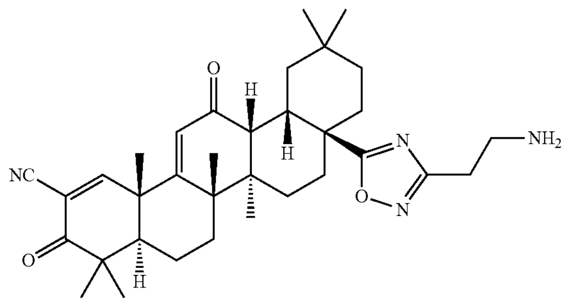 | 1.26 ± 0.12 | 0.94 ± 0.19 | 3 |
| T17 | 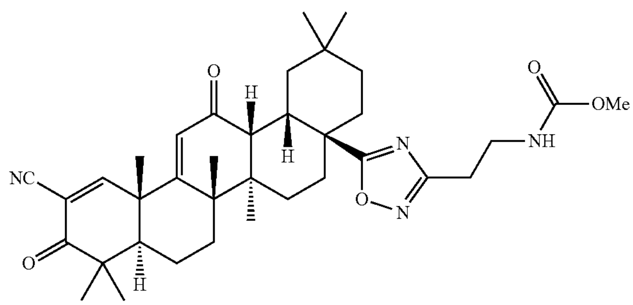 | 0.75 | 0.48 | 1 |
| T18 | 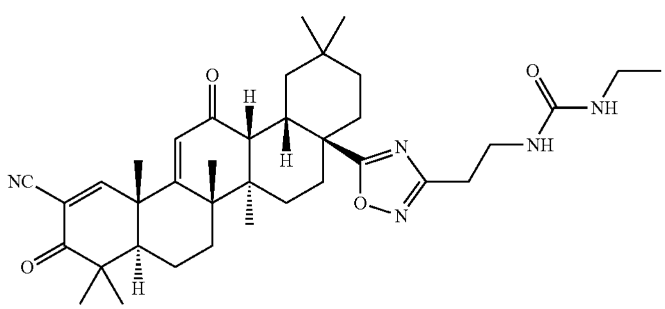 | 1.33 | 0.86 | 1 |
| T19 | 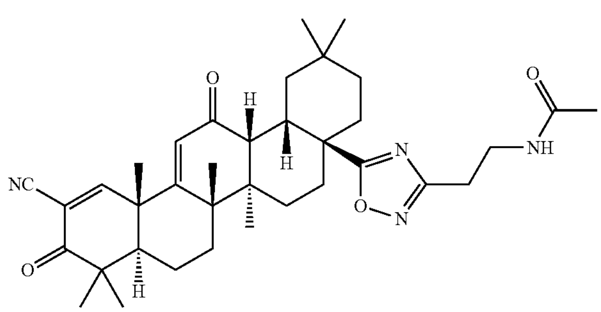 | 0.94 | 0.60 | 1 |

TABLE 2-continued

Nitric Oxide Inhibition (NO IC$_{50}$) and NO IC$_{50}$ Relative to RTA 402.

| ID # | Structure | NO IC$_{50}$ (nM) (Mean ± SD) | NO IC$_{50}$ Relative to RTA 402 (fold)$^a$ (Mean ± SD) | # of Repeats |
|---|---|---|---|---|
| T20 | 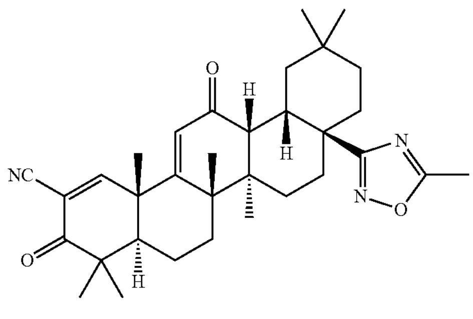 | 3.79 ± 1.58 | 1.30 ± 0.26 | 6 |
| T21 | 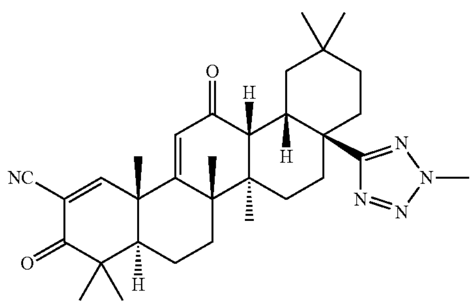 | 1.89 ± 0.67 | 0.76 ± 0.36 | 8 |
| T25 | 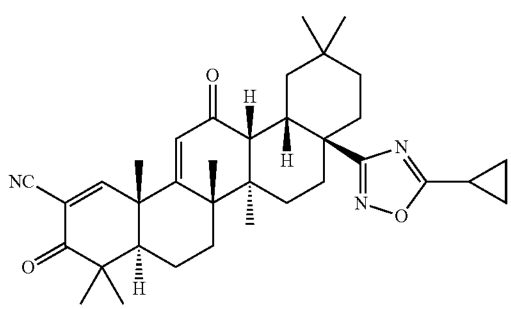 | 11.22 ± 2.09 | 3.08 ± 1.54 | 2 |
| T26 | 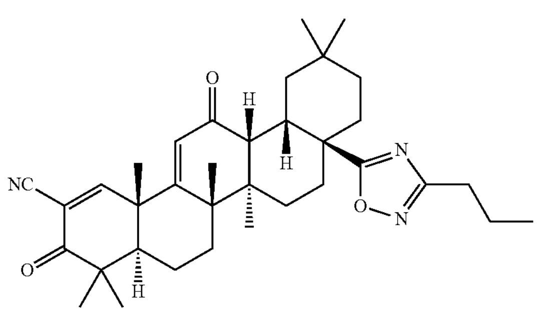 | 7.82 | 4.83 | 1 |

TABLE 2-continued

Nitric Oxide Inhibition (NO IC$_{50}$) and NO IC$_{50}$ Relative to RTA 402.

| ID # | Structure | NO IC$_{50}$ (nM) (Mean ± SD) | NO IC$_{50}$ Relative to RTA 402 (fold)$^a$ (Mean ± SD) | # of Repeats |
|---|---|---|---|---|
| T27 | 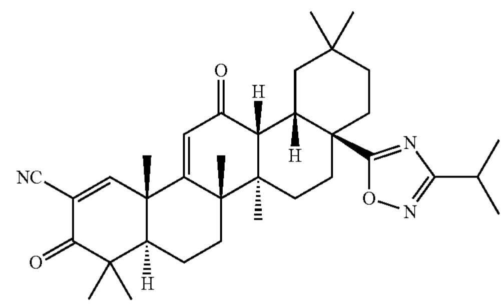 | 6.03 | 3.72 | 1 |
| T28 | 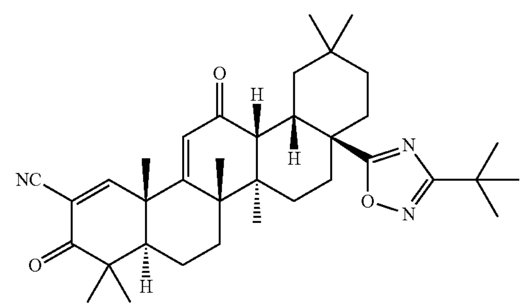 | 22.27 | 13.75 | 1 |
| T29 | 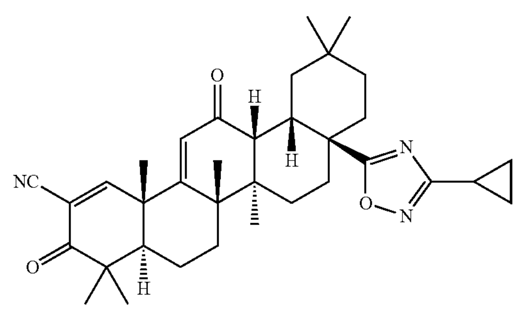 | 4.03 | 2.49 | 1 |
| T30 | 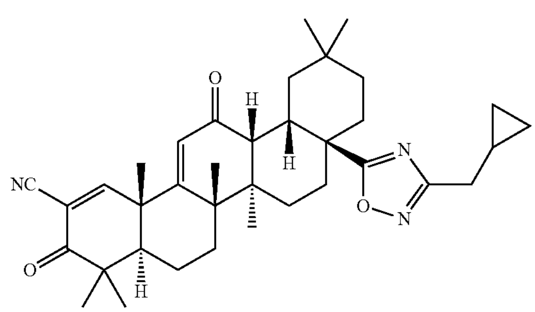 | 4.82 | 2.97 | 1 |

TABLE 2-continued

Nitric Oxide Inhibition (NO IC$_{50}$) and NO IC$_{50}$ Relative to RTA 402.

| ID # | Structure | NO IC$_{50}$ (nM) (Mean ± SD) | NO IC$_{50}$ Relative to RTA 402 (fold)$^a$ (Mean ± SD) | # of Repeats |
|---|---|---|---|---|
| T31 | 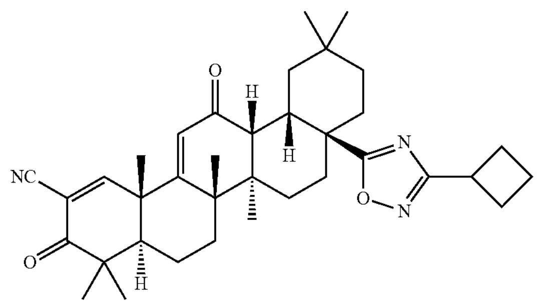 | 9.34 | 5.76 | 1 |
| T32 | 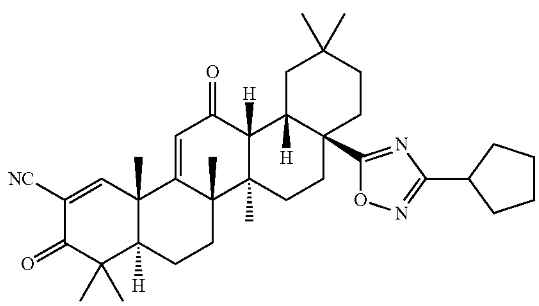 | 20.80 | 12.84 | 1 |
| T33 | 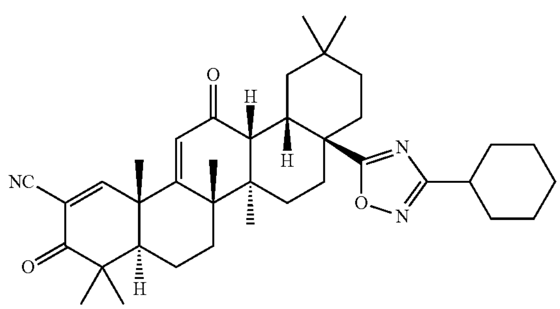 | 25.62 | 15.81 | 1 |
| T39 | 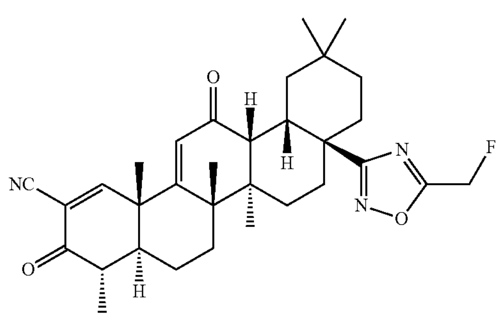 | 1.98 | 0.42 | 1 |

TABLE 2-continued

Nitric Oxide Inhibition (NO IC$_{50}$) and NO IC$_{50}$ Relative to RTA 402.

| ID # | Structure | NO IC$_{50}$ (nM) (Mean ± SD) | NO IC$_{50}$ Relative to RTA 402 (fold)[a] (Mean ± SD) | # of Repeats |
|---|---|---|---|---|
| T42 | 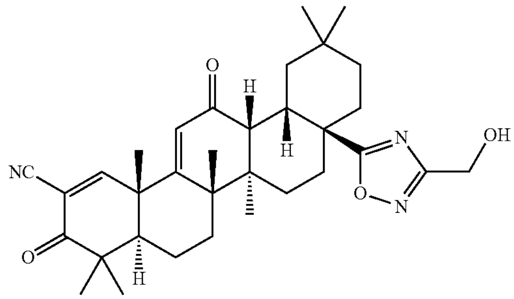 | 0.44 | 0.32 | 1 |

[a]Average of ratios from replicate experiments.

TABLE 3

NO IC$_{50}$ Relative to Comparison Compounds.

| ID # | Structure | Comparison Compound | NO IC$_{50}$ Relative to Comparison Compound in Same Experiment[b] | # of Repeats |
|---|---|---|---|---|
| CC2 | 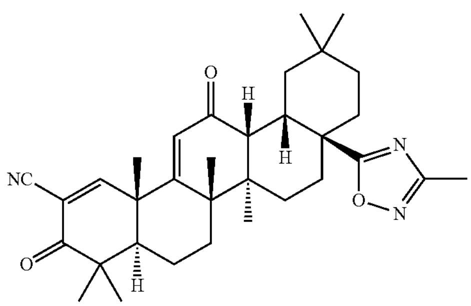 | CC2 | 1.00 | N/A |
| T1 | 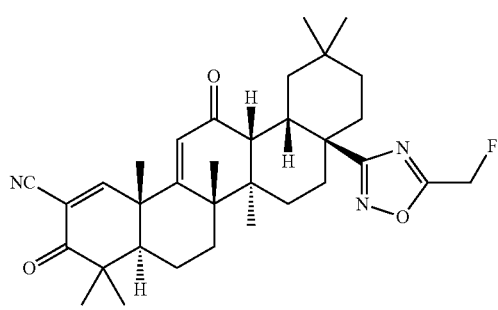 | CC2 | 0.67 ± 0.10 | 5 |

TABLE 3-continued

NO IC$_{50}$ Relative to Comparison Compounds.

| ID # | Structure | Comparison Compound | NO IC$_{50}$ Relative to Comparison Compound in Same Experiment[b] | # of Repeats |
|---|---|---|---|---|
| T2 | 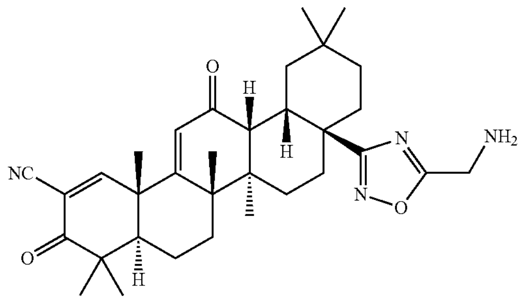 | CC2 | 0.69 ± 0.04 | 4 |
| T12 | 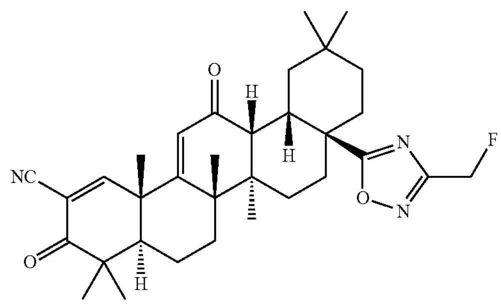 | CC2 | 0.65 ± 0.04 | 5 |
| T13 | 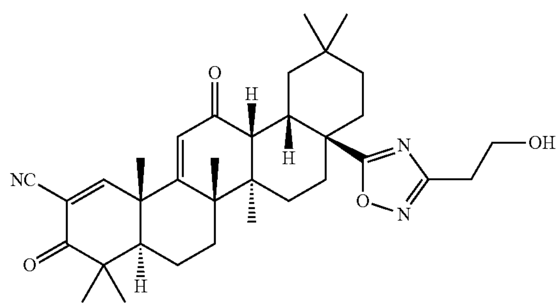 | CC2 | 0.30 ± 0.07 | 4 |
| T20 | 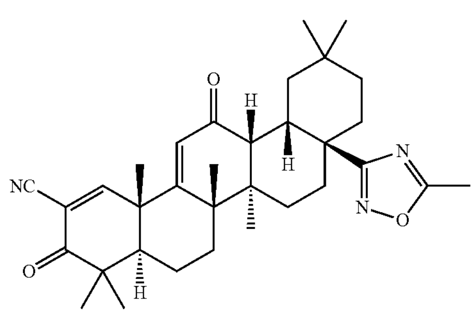 | CC2 | 1.85 ± 0.49 | 6 |

TABLE 3-continued

NO IC$_{50}$ Relative to Comparison Compounds.

| ID # | Structure | Comparison Compound | NO IC$_{50}$ Relative to Comparison Compound in Same Experiment[b] | # of Repeats |
|---|---|---|---|---|
| CC1 | 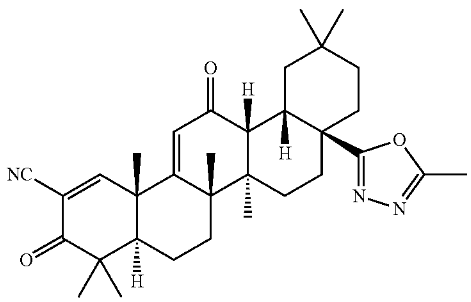 | CC1 | 1.00 | N/A |
| T11 | 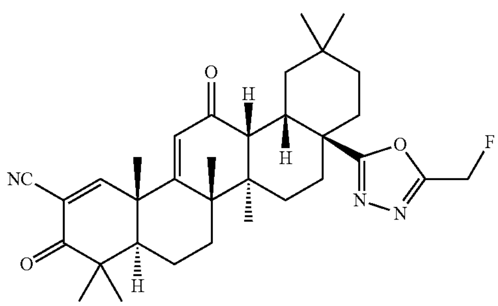 | CC1 | 0.40 ± 0.09 | 4 |
| T44 | 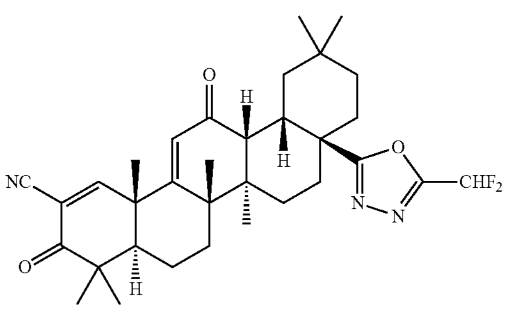 | CC1 | 1.55 ± 0.16 | 4 |
| CC3 | 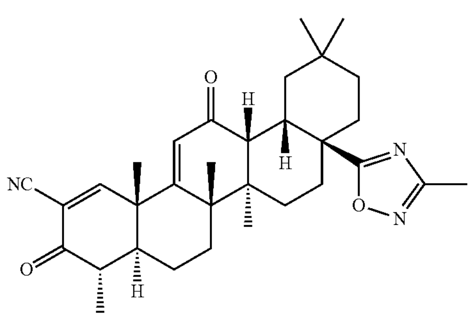 | CC3 | 1.00 | N/A |

TABLE 3-continued

NO IC$_{50}$ Relative to Comparison Compounds.

| ID # | Structure | Comparison Compound | NO IC$_{50}$ Relative to Comparison Compound in Same Experiment[b] | # of Repeats |
|---|---|---|---|---|
| T34 | 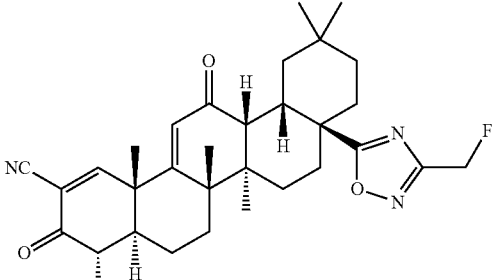 | CC3 | 0.70 ± 0.11 | 4 |

[b]Average of ratios from experiments with direct comparisons.

Example 3: CYP3A4 Inhibition

Methods. Several compounds were evaluated for CYP3A4 (midazolam) inhibition in human liver microsomes at 1 µM. CYP3A4 inhibition was tested using an in vitro assay as generally described in Dierks et al. (Drug Metabolism Deposition, 29:23-29, 2001, which is incorporated by reference herein). Each sample, containing 0.1 mg/mL human liver microsomes, 5 µM midazolam as substrate, and 1 µM of test compound, was incubated at 37° C. for 10 min. Following incubation, the metabolite 1-hydroxymidazolam was measured using HPLC-MS/MS. Peak areas corresponding to the metabolite of the substrate were recorded. The percent of control activity was then calculated by comparing the peak area obtained in the presence of the test compound to that obtained in the absence of the test compound. Subsequently, the percent inhibition was calculated by subtracting the percent control activity from 100 for each compound. The results of the CYP3A4 assays are show below in Tables 4-7.

TABLE 4

CYP3A4 (Midazolam) Inhibition.

| Compound ID | Structure | % Inhibition |
|---|---|---|
| RTA 402 | 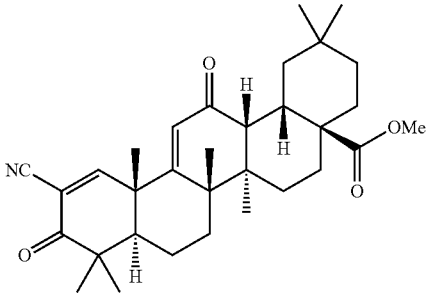 | 48.4 |
| RTA 408 | 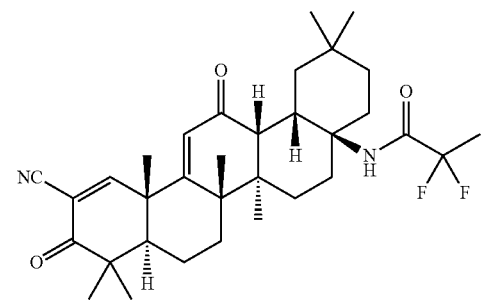 | 56.6 |

TABLE 4-continued
CYP3A4 (Midazolam) Inhibition.
| Compound ID | Structure | % Inhibition |
|---|---|---|
| T1 | 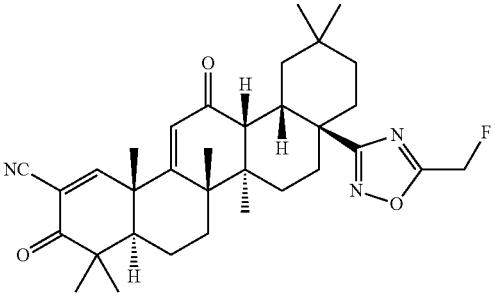 | 29.1 |
| T2 | 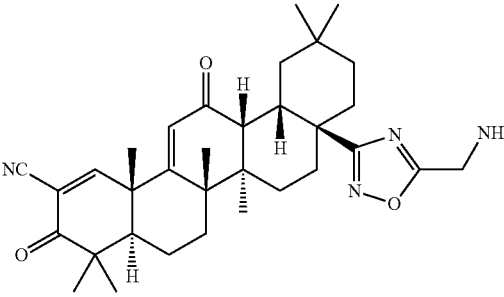 | 21.4 |
| T11 | 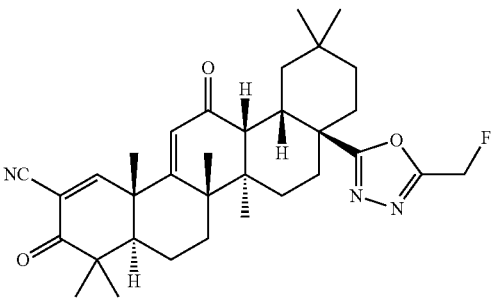 | 17.7 |
| T12 | 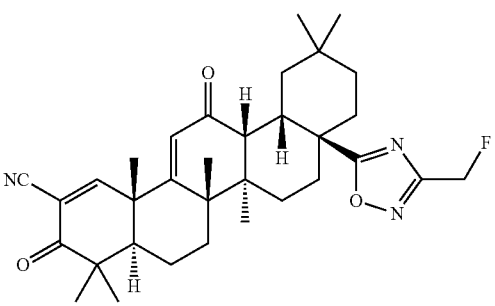 | 29.7 |
| T34 | 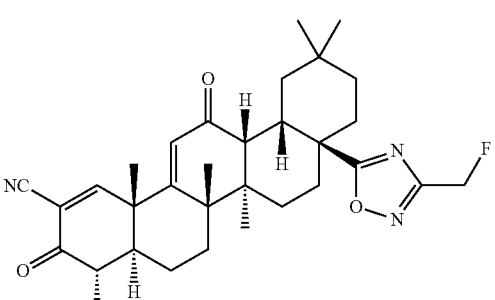 | 29.4 |

Comparison compound CC1 and T11, both comprising a 1,3,4-oxadiazole-2,5-diyl moiety, were also tested for CYP3A4 inhibition. The results of the CYP3A4 assay are shown below in Table 5.

TABLE 5

CYP3A4 (Midazolam) Inhibition of T11 Compared with CC1.

| Compound ID | Structure | % Inhibition |
|---|---|---|
| CC1 | 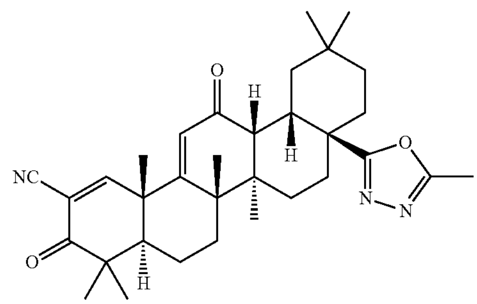 | 20.7 |
| T11 | 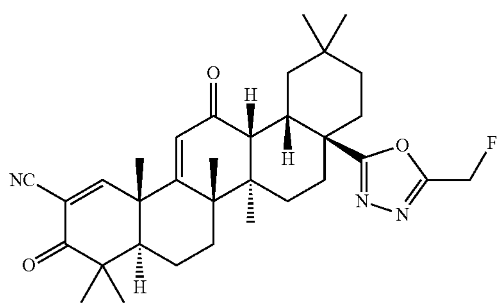 | 17.7 |

Comparison compound CC2 and T12, both comprising a 1,2,4-oxadiazole-3,5-diyl moiety, were also tested for CYP3A4 inhibition. The results of the CYP3A4 assay are shown below in Table 6.

TABLE 6

CYP3A4 (Midazolam) Inhibition of T12 Compared with CC2.

| Compound ID | Structure | % Inhibition |
|---|---|---|
| CC2 | 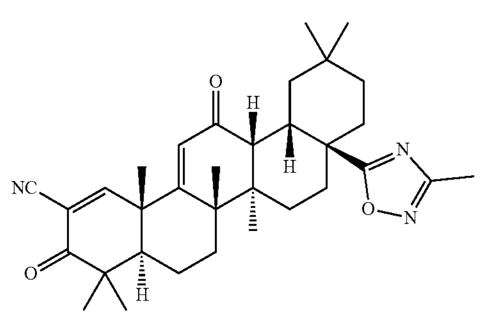 | 45.8 |

TABLE 6-continued

CYP3A4 (Midazolam) Inhibition of T12 Compared with CC2.

| Compound ID | Structure | % Inhibition |
|---|---|---|
| T12 | [structure] | 29.7 |

Comparison compound CC3 and T34, both comprising a 1,2,4-oxadiazole-3,5-diyl moiety and monomethyl substitution at C4, were also tested for CYP3A4 inhibition. The results are shown below in Table 7.

TABLE 7

CYP3A4 (Midazolam) Inhibition of T34 Compared with CC3.

| Compound ID | Structure | % Inhibition |
|---|---|---|
| CC3 | [structure] | 37.7 |
| T34 | [structure] | 29.4 |

Example 4: Glutathione Assay

The effect of compound treatment on total glutathione levels was evaluated in the mouse AML-12 hepatocyte cell line. Glutathione—a tripeptide consisting of cysteine, glutamate, and glycine—is the major thiol-containing protein within the cell and regulates cellular redox balance. Glutathione also plays important roles in detoxification, protein glutathionylation, and iron-sulfur cluster biogenesis (Bachhawat and Yadav, 2018). Nrf2 regulates the expression of many genes involved in glutathione synthesis and metabolism, including both subunits of glutamate cysteine ligase (GCL), the enzyme that catalyzes the rate limiting step of glutathione biosynthesis (Thimmulappa et al., 2002).

AML-12 cells were plated in white, clear-bottom 96-well plates at a density of 8,000 cells/well in 200 μL of DMEM/F12 medium supplemented with 10% FBS and 1% penicillin/streptomycin. The next day, cells were treated with vehicle (DMSO) or test compound (0.03 nM to 1000 nM). Each well received a final concentration of 0.1% DMSO. Cells were incubated at 37° C., 5% $CO_2$ for 24 hours. Total glutathione concentrations were measured using the GSH-Glo Glutathione Assay kit (Promega) according to the manufacturer's instructions. Briefly, a standard curve was prepared by serially diluting the provided glutathione solution. Final concentrations of total glutathione standards were 5, 2.5, 1.25, 0.625, 0.313, 0.156, 0.078, 0.039, and 0.0195

μM. Following media removal from sample wells, 100 μL of glutathione reaction mix consisting of GSH-Glo reaction buffer, Glutathione S-Transferase, Luciferin-NT, and TCEP was added to each sample well and to all standard curve wells. After a 30-minute incubation at room temperature, 100 μL of Luciferin detection reagent was added to all sample and standard wells and incubated for 15 minutes. Luminescence was measured using a PHERAstar plate reader. The $EC_{50}$ value was determined using Excel and GraphPad Prism software. The basal concentration of glutathione was set to 0% and the highest concentration of glutathione produced following treatment with a test compound was set to 100% and a dose-response curve was generated. The dose-response curve was fit using nonlinear regression analysis and used to extrapolate the $EC_{50}$ value. The $EC_{50}$ value is defined as the concentration of test compound required to increase glutathione concentrations to 50% of the maximal concentration. The data are shown in Table 8 and Table 9.

TABLE 8

Glutathione (GSH) EC50 and EC50 Relative to RTA 402.

| ID # | Structure | GSH $EC_{50}$ (nM) (Mean ± SD) | GSH $EC_{50}$ Relative to RTA 402 (fold)$^c$ (Mean ± SD) | # of Repeats |
|---|---|---|---|---|
| CC2 | 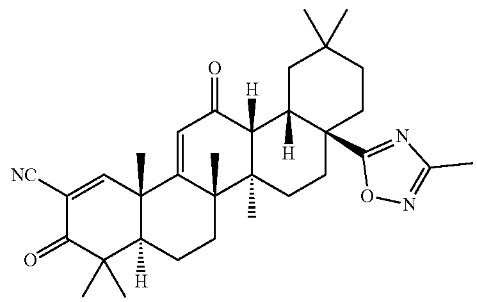 | 2.00 ± 1.24 | 0.80 ± 0.16 | 8 |
| T1 | 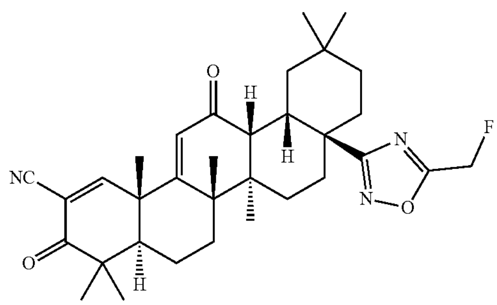 | 0.57 ± 0.22 | 0.35 ± 0.12 | 4 |
| T41 | 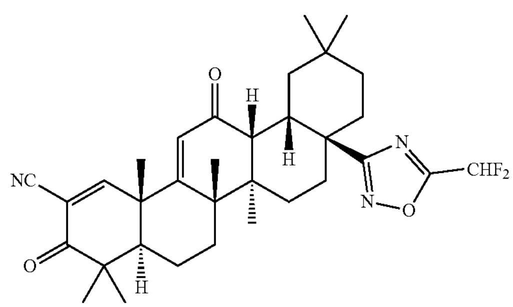 | 4.85 ± 0.36 | 2.38 ± 0.29 | 2 |
| T40 | 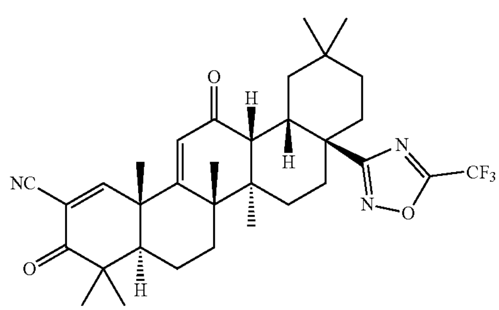 | 18.33 ± 2.19 | 8.96 ± 0.68 | 2 |

TABLE 8-continued

Glutathione (GSH) EC50 and EC50 Relative to RTA 402.

| ID # | Structure | GSH EC$_{50}$ (nM) (Mean ± SD) | GSH EC$_{50}$ Relative to RTA 402 (fold)$^c$ (Mean ± SD) | # of Repeats |
|---|---|---|---|---|
| T24 | 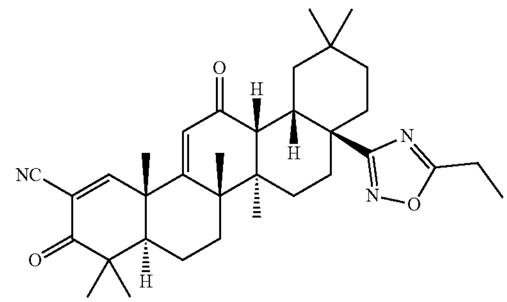 | 6.11 ± 2.23 | 2.53 ± 0.52 | 4 |
| T2 | 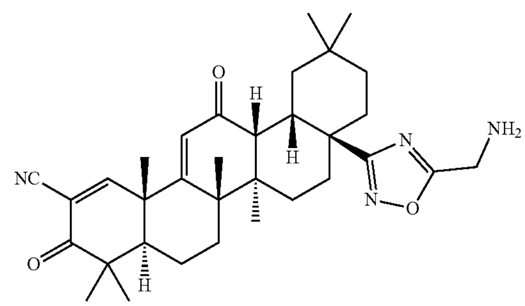 | 1.21 ± 1.15 | 0.47 ± 0.38 | 4 |
| T12 | 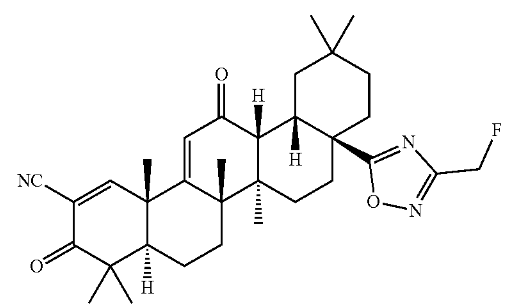 | 0.82 ± 0.40 | 0.50 ± 0.19 | 4 |
| T43 | 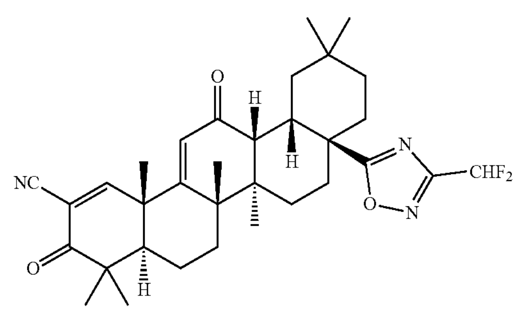 | 3.29 ± 0.55 | 1.60 ± 0.05 | 2 |

TABLE 8-continued

Glutathione (GSH) EC50 and EC50 Relative to RTA 402.

| ID # | Structure | GSH EC$_{50}$ (nM) (Mean ± SD) | GSH EC$_{50}$ Relative to RTA 402 (fold)$^c$ (Mean ± SD) | # of Repeats |
|---|---|---|---|---|
| T22 | 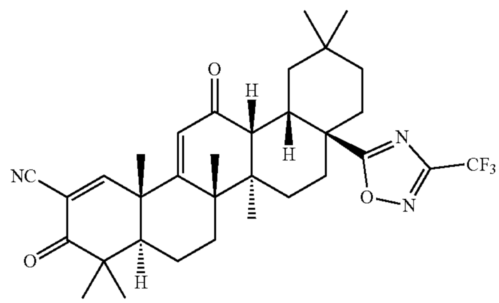 | 17.59 ± 0.59 | 8.72 ± 1.98 | 2 |
| T23 | 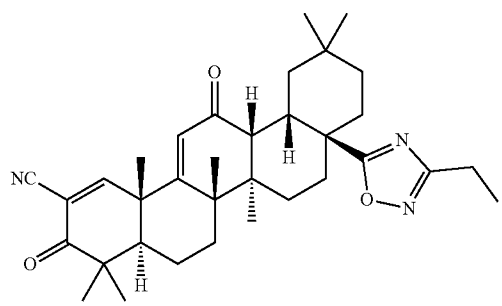 | 3.26 ± 0.51 | 2.05 ± 0.44 | 4 |
| CC1 | 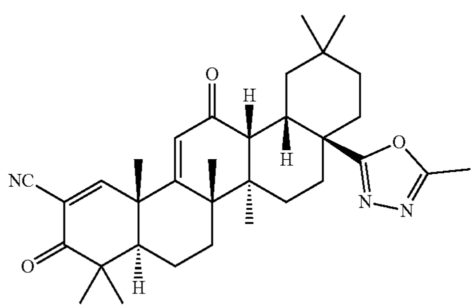 | 1.09 ± 0.13 | 0.70 ± 0.12 | 4 |
| T11 | 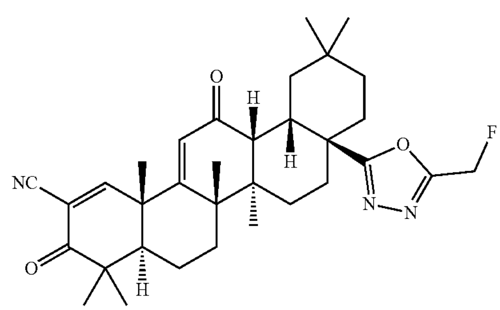 | 0.54 ± 0.29 | 0.32 ± 0.13 | 4 |

TABLE 8-continued

Glutathione (GSH) EC50 and EC50 Relative to RTA 402.

| ID # | Structure | GSH EC$_{50}$ (nM) (Mean ± SD) | GSH EC$_{50}$ Relative to RTA 402 (fold)$^c$ (Mean ± SD) | # of Repeats |
|---|---|---|---|---|
| T44 | 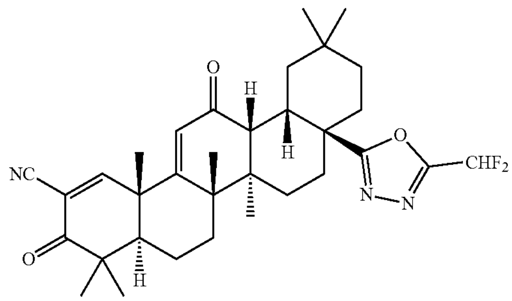 | 2.05 ± 0.64 | 1.04 ± 0.06 | 2 |
| T45 | 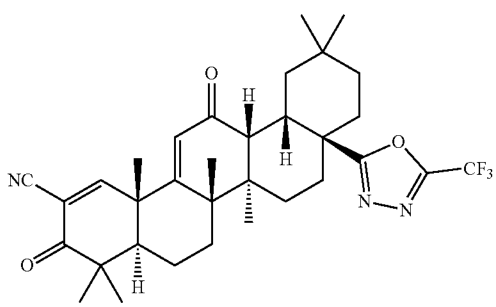 | 8.00 ± 1.37 | 4.14 ± 0.35 | 2 |
| T46 | 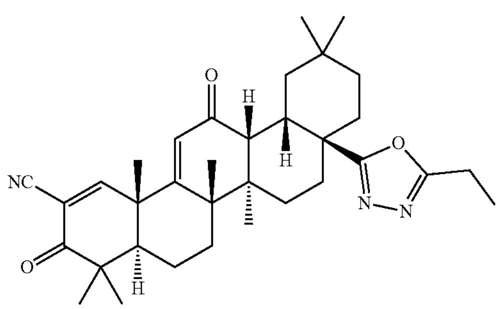 | 2.39 ± 0.29 | 1.24 ± 0.17 | 2 |
| CC3 | 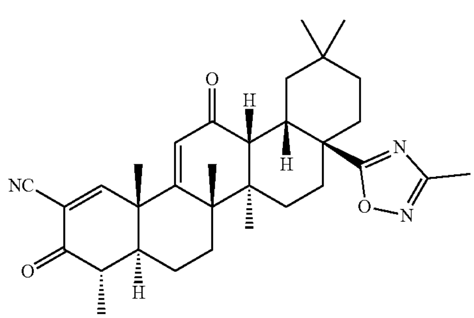 | 1.16 ± 0.53 | 0.43 ± 0.14 | 6 |

TABLE 8-continued
Glutathione (GSH) EC50 and EC50 Relative to RTA 402.
| ID # | Structure | GSH EC$_{50}$ (nM) (Mean ± SD) | GSH EC$_{50}$ Relative to RTA 402 (fold)$^c$ (Mean ± SD) | # of Repeats |
|---|---|---|---|---|
| T34 | 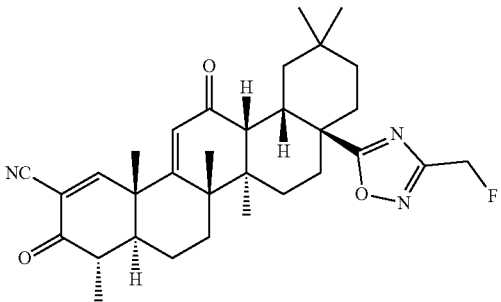 | 0.35 ± 0.06 | 0.18 ± 0.02 | 2 |
| T35 | 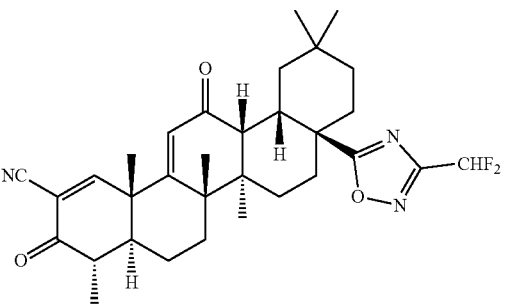 | 1.99 ± 0.42 | 1.02 ± 0.04 | 2 |
| T36 | 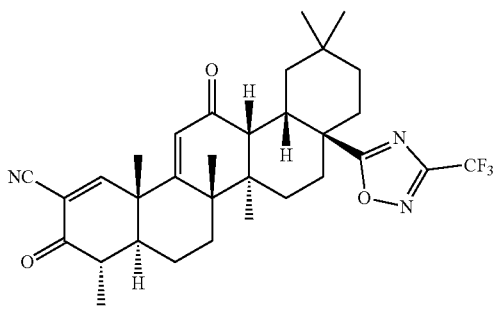 | 10.43 ± 1.62 | 5.40 ± 0.54 | 2 |
| T37 | 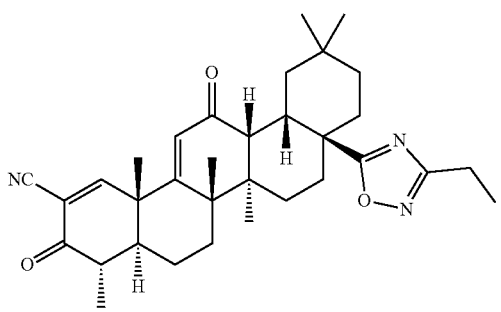 | 1.69 ± 0.19 | 0.88 ± 0.13 | 2 |

TABLE 8-continued

Glutathione (GSH) EC50 and EC50 Relative to RTA 402.

| ID # | Structure | GSH EC$_{50}$ (nM) (Mean ± SD) | GSH EC$_{50}$ Relative to RTA 402 (fold)$^c$ (Mean ± SD) | # of Repeats |
|---|---|---|---|---|
| T3 | 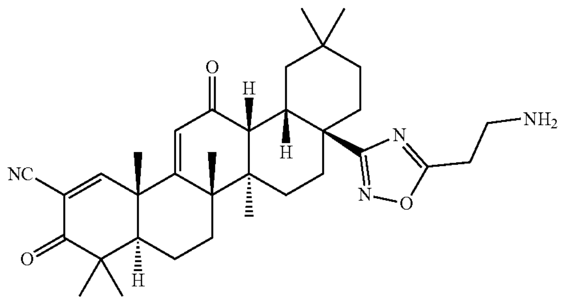 | 1.45 ± 0.28 | 0.54 ± 0.06 | 2 |
| T4 | 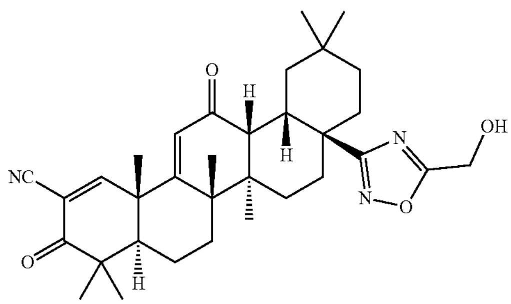 | 2.46 ± 1.80 | 0.89 ± 0.61 | 2 |
| T5 | 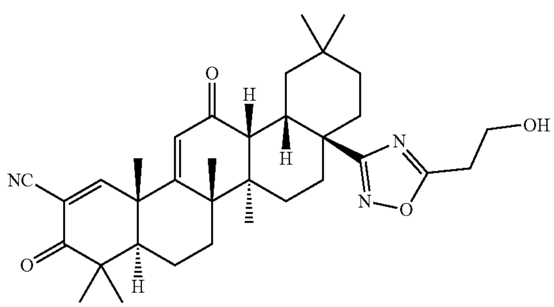 | 1.77 ± 0.98 | 0.65 ± 0.32 | 2 |
| T6 | 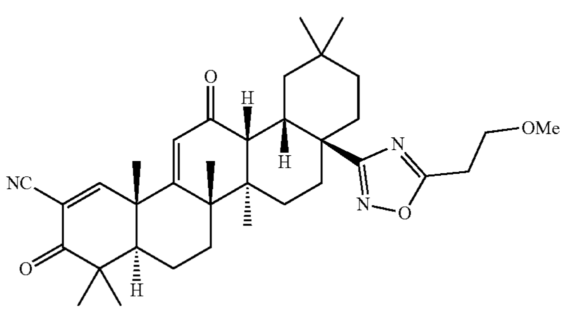 | 2.90 ± 0.96 | 1.07 ± 0.28 | 2 |

TABLE 8-continued

Glutathione (GSH) EC50 and EC50 Relative to RTA 402.

| ID # | Structure | GSH EC$_{50}$ (nM) (Mean ± SD) | GSH EC$_{50}$ Relative to RTA 402 (fold)$^c$ (Mean ± SD) | # of Repeats |
|---|---|---|---|---|
| T7 | 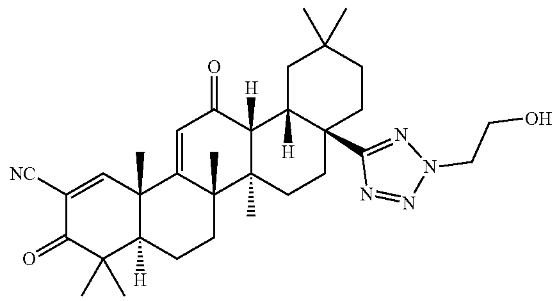 | 2.87 ± 3.17 | 0.80 ± 0.59 | 4 |
| T10 | 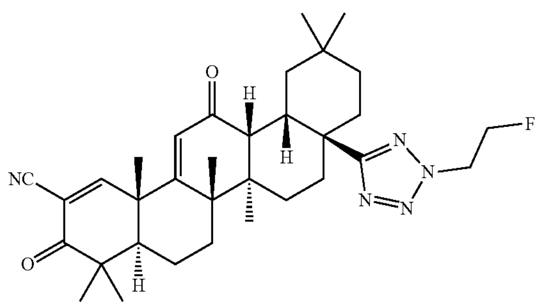 | 1.45 ± 0.17 | 1.14 ± 0.03 | 2 |
| T13 | 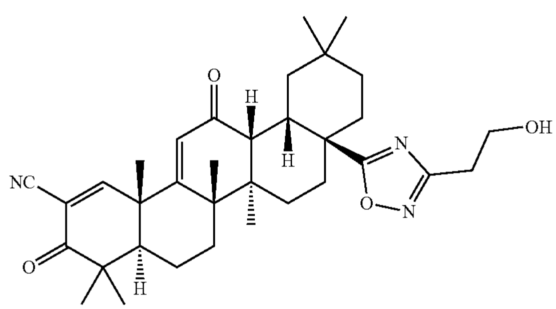 | 2.04 ± 1.94 | 0.55 ± 0.33 | 4 |
| T16 | 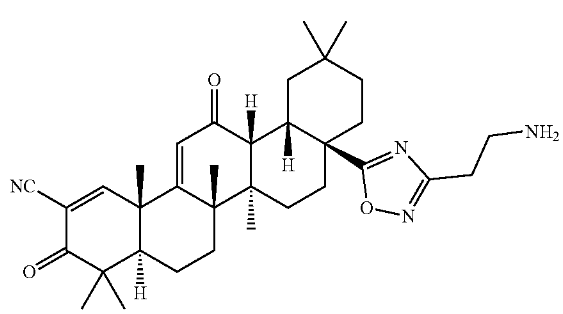 | 0.58 ± 0.04 | 0.46 ± 0.09 | 2 |

TABLE 8-continued

Glutathione (GSH) EC50 and EC50 Relative to RTA 402.

| ID # | Structure | GSH EC$_{50}$ (nM) (Mean ± SD) | GSH EC$_{50}$ Relative to RTA 402 (fold)$^c$ (Mean ± SD) | # of Repeats |
|---|---|---|---|---|
| T20 | 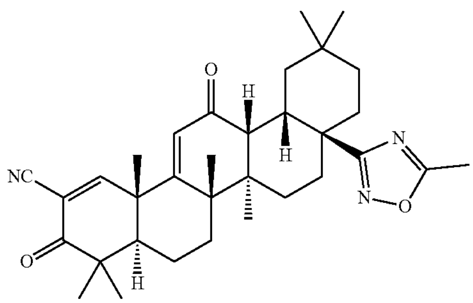 | 1.66 ± 0.66 | 0.96 ± 0.15 | 4 |
| T21 | 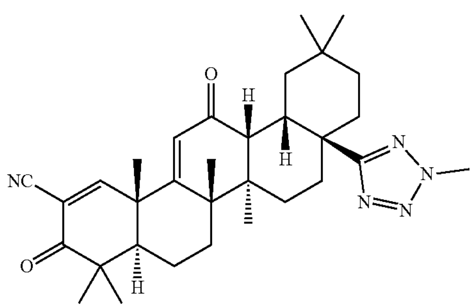 | 3.18 ± 2.22 | 0.95 ± 0.34 | 4 |
| T25 | 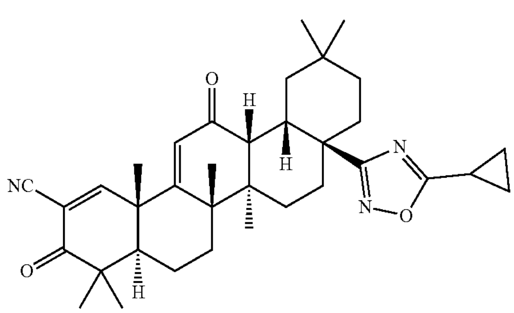 | 9.07 ± 1.55 | 3.36 ± 0.34 | 2 |

TABLE 9
Glutathione (GSH) EC50 Relative to Comparison Compounds.
| ID # | Structure | Comparison Compound (CC) | GSH EC$_{50}$ Relative to CC in Same Experiment$^d$ (Mean ± SD) | # of Repeats |
|---|---|---|---|---|
| CC2 | 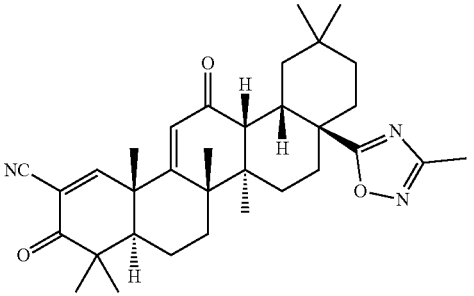 | CC2 | 1.00 | N/A |
| T1 | 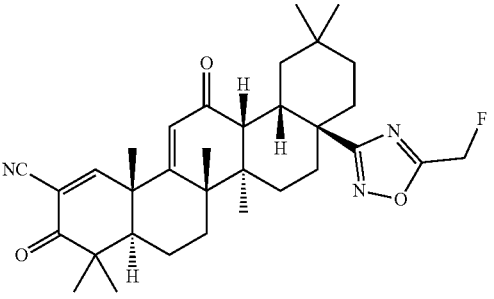 | CC2 | 0.50 ± 0.09 | 4 |
| T2 | 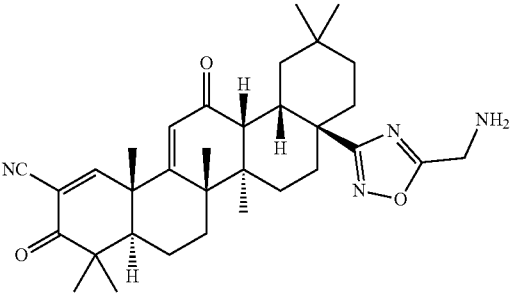 | CC2 | 0.41 ± 0.09 | 2 |
| T12 | 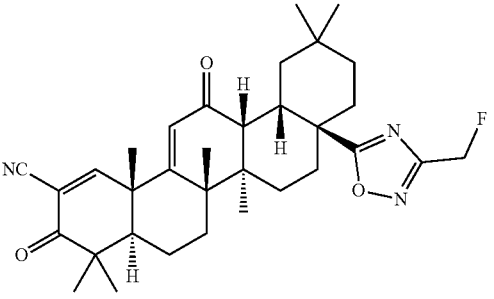 | CC2 | 0.69 ± 0.20 | 4 |

TABLE 9-continued

Glutathione (GSH) EC50 Relative to Comparison Compounds.

| ID # | Structure | Comparison Compound (CC) | GSH EC$_{50}$ Relative to CC in Same Experiment[d] (Mean ± SD) | # of Repeats |
|---|---|---|---|---|
| CC1 | 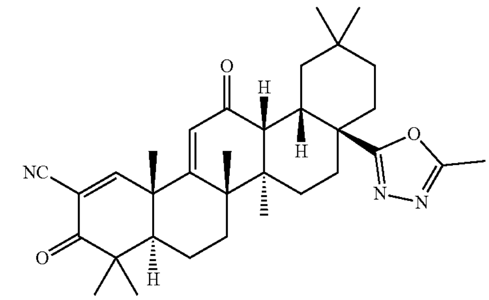 | CC1 | 1.00 | N/A |
| T11 | 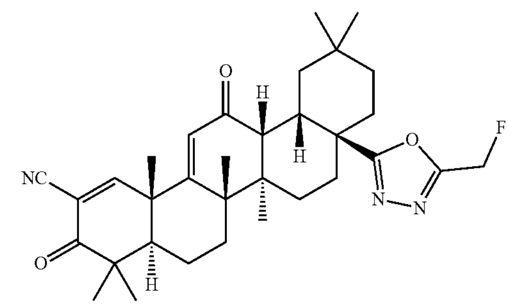 | CC1 | 0.42 ± 0.02 | 2 |
| T44 | 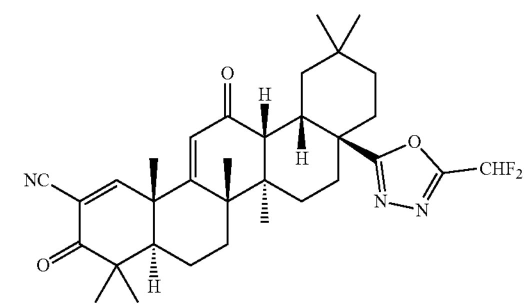 | CC1 | 1.72 ± 0.32 | 2 |
| CC3 | 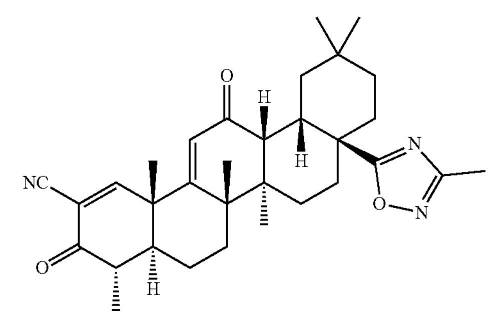 | CC3 | 1.00 | N/A |

TABLE 9-continued

Glutathione (GSH) EC50 Relative to Comparison Compounds.

| ID # | Structure | Comparison Compound (CC) | GSH EC$_{50}$ Relative to CC in Same Experiment[d] (Mean ± SD) | # of Repeats |
|---|---|---|---|---|
| T34 | 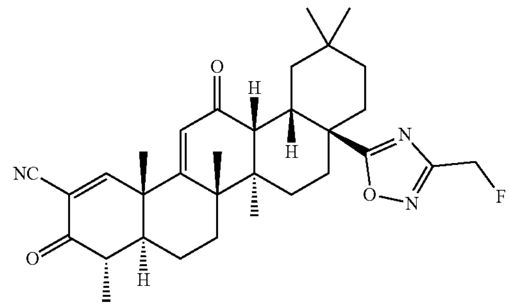 | CC3 | 0.58 ± 0.02 | 2 |
| T13 | 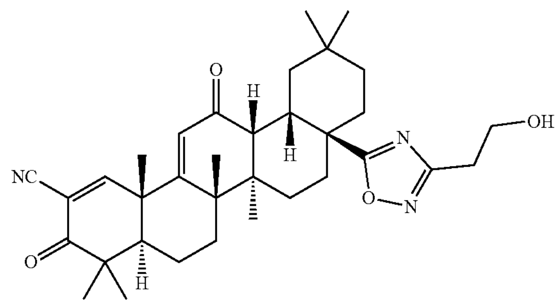 | CC2 | 0.62 ± 0.36 | 4 |
| T20 | 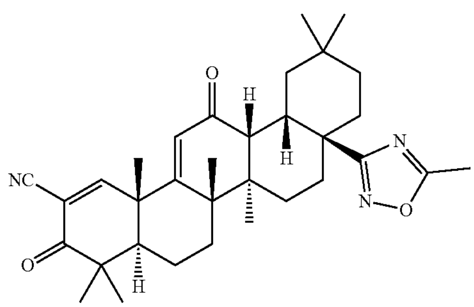 | CC2 | 1.41 ± 0.33 | 4 |

[d]Average of ratios from experiments with direct comparisons.

Example 5: Effect on Luciferase Reporter Activation

AREc32 reporter cell line (derived from human breast carcinoma MCF7 cells) was obtained was from CXR Bioscience Limited (Dundee, UK) and cultured in DMEM (low glucose) supplemented with 10% FBS, 1% penicillin/streptomycin, and 0.8 mg/ml Geneticin (G418). This cell line is stably transfected with a luciferase reporter gene under the transcriptional control of eight copies of the rat GSTA2 ARE sequence.

The effect of several compounds disclosed herein on luciferase reporter activation was assessed in the AREc32 reporter cell line (see Table 10 and Table 11). This cell line is derived from human breast carcinoma MCF-7 cells and is stably transfected with a luciferase reporter gene under the transcriptional control of eight copies of the antioxidant response element from the rat Gsta2 gene, an Nrf2 target gene (Frilling et al., 1990). AREc32 cells were plated in black 96-well plates in 200 μL media at 20,000 cells per well. Twenty-four hours after plating, cells were treated with vehicle (DMSO) or test compounds at concentrations ranging from 0.03 to 1000 nM for nineteen hours. Media was removed and 100 μL of 1:1 mixture of the One-Glo Luciferase assay reagent and culture medium was added to each well. After incubation for 5 min at room temperature, the luminescence signal was measured on a PHERAstar plate reader. The $EC_{2X}$ value was determined using Excel and GraphPad Prism software. The fold increase in luminescence signal for cells treated with each concentration of compound relative to cells treated with vehicle was determined and a dose-response curve was generated. The dose-response curve was fit using nonlinear regression analysis and used to extrapolate the $EC_{2X}$ value. The $EC_{2X}$ value is defined as the concentration of test compound required to increase the luminescence signal 2-fold above levels in vehicle-treated samples.

TABLE 10
ARTc32 EC2X and EC2X Relative to RTA 402.
| ID # | Structure | AREc32 EC$_{2X}$ (nM) (Mean ± SD) | AREc32 EC$_{2X}$ Relative to RTA 402 (fold)$^e$ (Mean ± SD) | # of Repeats |
|---|---|---|---|---|
| CC2 | 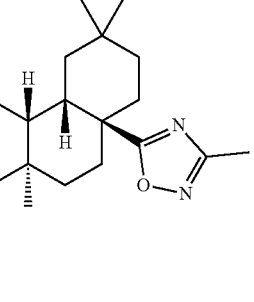 | 8.59 ± 1.88 | 0.74 ± 0.16 | 11 |
| T1 | 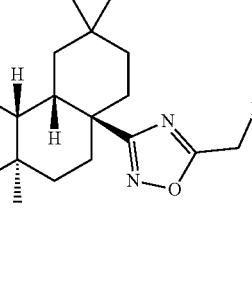 | 6.20 ± 1.37 | 0.46 ± 0.13 | 7 |
| T41 | 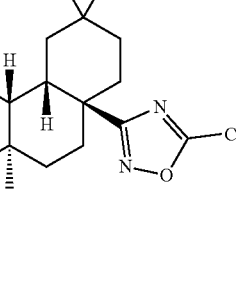 | 24.18 ± 3.36 | 1.52 ± 0.19 | 3 |
| T40 | 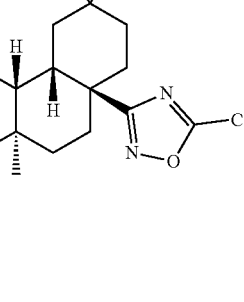 | 64.93 ± 12.64 | 4.76 ± 0.93 | 4 |

TABLE 10-continued

AREc32 EC2X and EC2X Relative to RTA 402.

| ID # | Structure | AREc32 EC$_{2X}$ (nM) (Mean ± SD) | AREc32 EC$_{2X}$ Relative to RTA 402 (fold)[e] (Mean ± SD) | # of Repeats |
|---|---|---|---|---|
| T24 | 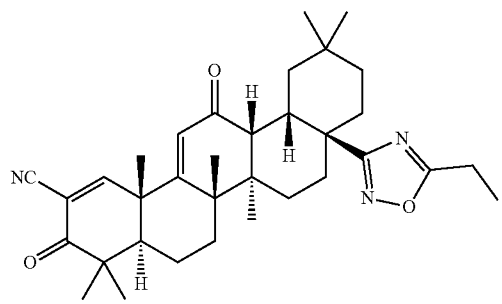 | 32.20 ± 2.59 | 2.50 ± 0.66 | 5 |
| T2 | 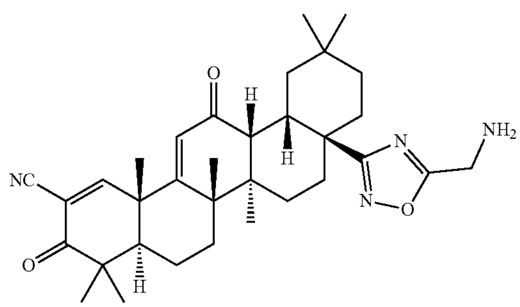 | 3.67 ± 0.28 | 0.28 ± 0.04 | 7 |
| T12 | 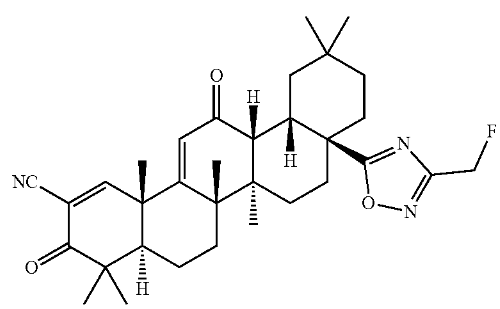 | 6.87 ± 1.57 | 0.53 ± 0.12 | 8 |
| T43 | 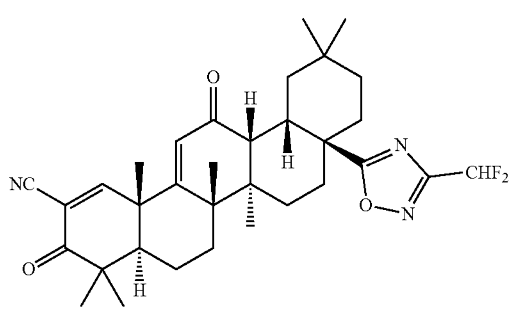 | 9.92 ± 2.32 | 0.62 ± 0.09 | 3 |

TABLE 10-continued

AREc32 EC2X and EC2X Relative to RTA 402.

| ID # | Structure | AREc32 EC$_{2X}$ (nM) (Mean ± SD) | AREc32 EC$_{2X}$ Relative to RTA 402 (fold)[e] (Mean ± SD) | # of Repeats |
|---|---|---|---|---|
| T22 | 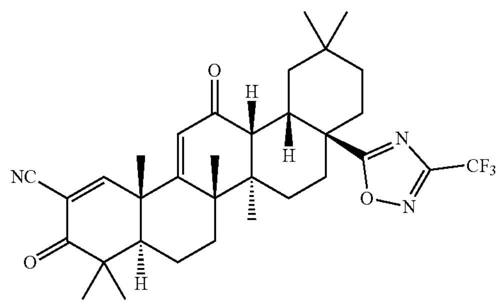 | 54.63 ± 8.83 | 3.45 ± 0.69 | 3 |
| T23 | 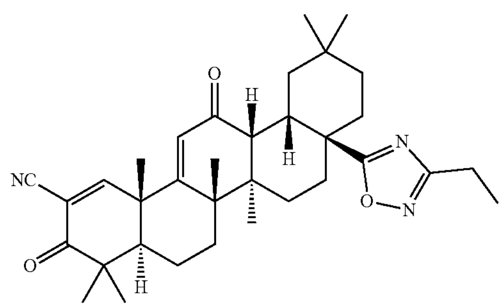 | 20.25 ± 2.51 | 1.43 ± 0.26 | 5 |
| CC1 | 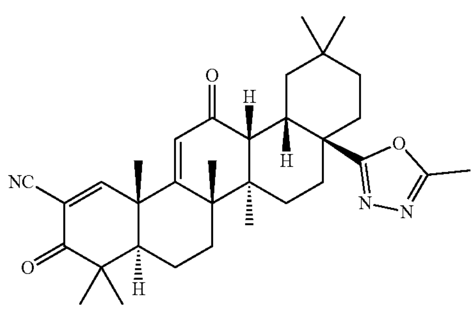 | 10.63 ± 2.73 | 0.79 ± 0.24 | 5 |
| T11 | 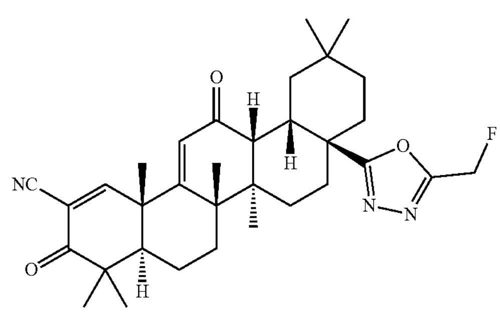 | 3.23 ± 0.77 | 0.25 ± 0.08 | 8 |

TABLE 10-continued

AREc32 EC2X and EC2X Relative to RTA 402.

| ID # | Structure | AREc32 EC$_{2X}$ (nM) (Mean ± SD) | AREc32 EC$_{2X}$ Relative to RTA 402 (fold)$^e$ (Mean ± SD) | # of Repeats |
|---|---|---|---|---|
| T44 | 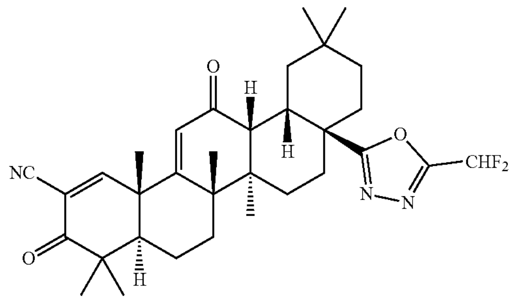 | 8.62 ± 0.45 | 0.57 ± 0.12 | 3 |
| T45 | 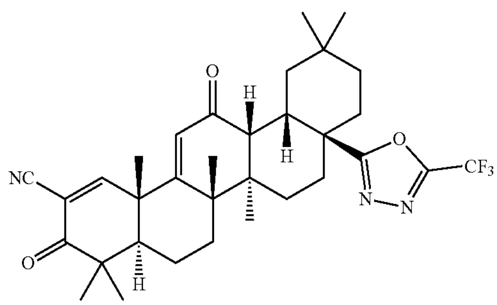 | 29.09 ± 2.09 | 1.95 ± 0.57 | 3 |
| T46 | 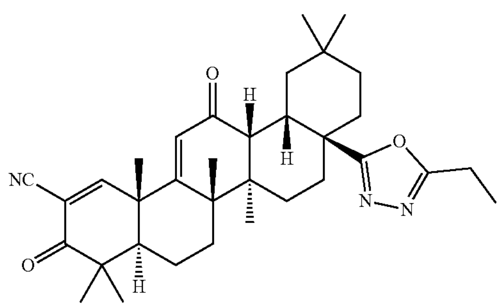 | 24.02 ± 1.50 | 1.60 ± 0.44 | 3 |
| CC3 | 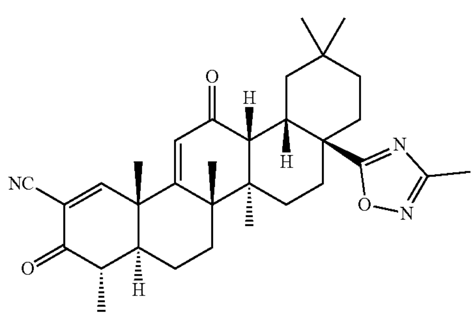 | 7.11 ± 1.15 | 0.66 ± 0.21 | 9 |

TABLE 10-continued
AREc32 EC2X and EC2X Relative to RTA 402.
| ID # | Structure | AREc32 EC$_{2X}$ (nM) (Mean ± SD) | AREc32 EC$_{2X}$ Relative to RTA 402 (fold)[e] (Mean ± SD) | # of Repeats |
|---|---|---|---|---|
| T34 | 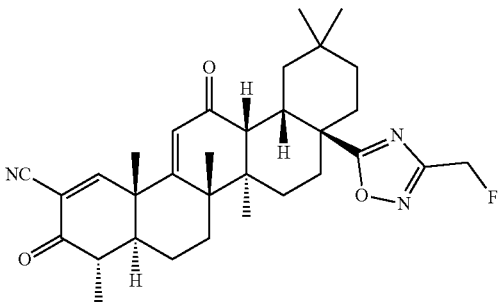 | 4.50 ± 0.66 | 0.36 ± 0.05 | 8 |
| T35 | 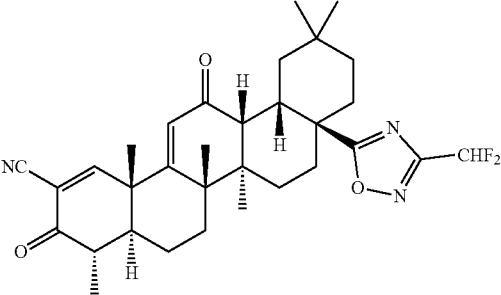 | 10.74 ± 1.02 | 0.73 ± 0.14 | 3 |
| T36 | 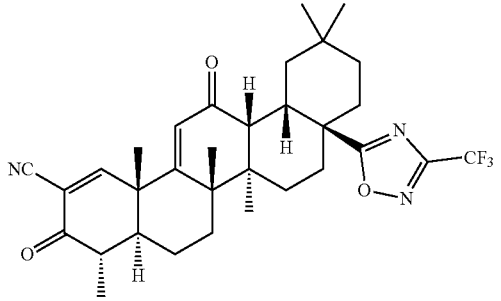 | 33.72 ± 6.99 | 2.25 ± 0.31 | 3 |
| T37 | 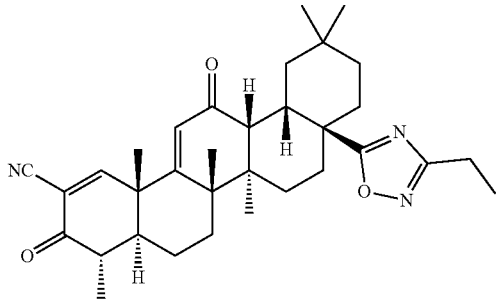 | 10.33 ± 1.35 | 0.69 ± 0.06 | 3 |

TABLE 10-continued

AREc32 EC2X and EC2X Relative to RTA 402.

| ID # | Structure | AREc32 EC$_{2X}$ (nM) (Mean ± SD) | AREc32 EC$_{2X}$ Relative to RTA 402 (fold)$^e$ (Mean ± SD) | # of Repeats |
| --- | --- | --- | --- | --- |
| CC4 | 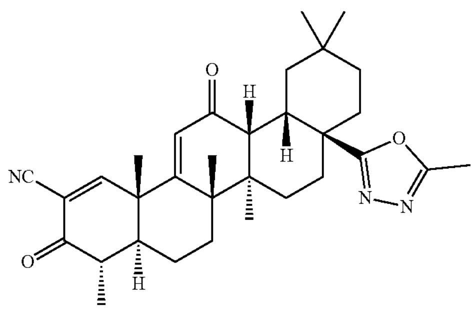 | 8.12 ± 3.53 | N/A | 3$^f$ |
| T38 | 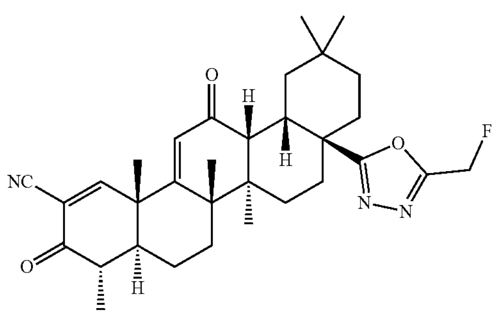 | 3.95 ± 1.12 | 0.43 ± 0.14 | 2 |
| T3 | 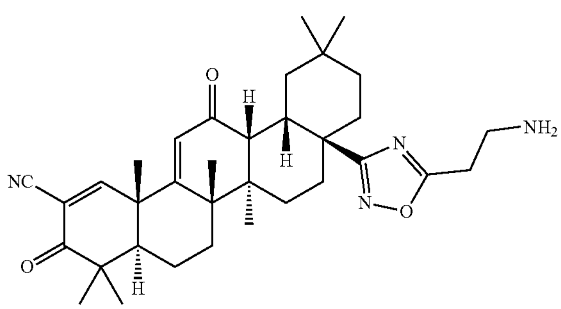 | 9.21 ± 3.66 | 0.91 ± 0.29 | 2 |
| T4 | 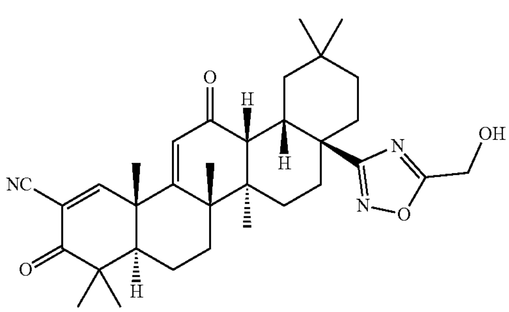 | 10.48 ± 1.03 | 1.04 ± 0.02 | 2 |

TABLE 10-continued

AREc32 EC2X and EC2X Relative to RTA 402.

| ID # | Structure | AREc32 EC$_{2X}$ (nM) (Mean ± SD) | AREc32 EC$_{2X}$ Relative to RTA 402 (fold)$^e$ (Mean ± SD) | # of Repeats |
|---|---|---|---|---|
| T5 | 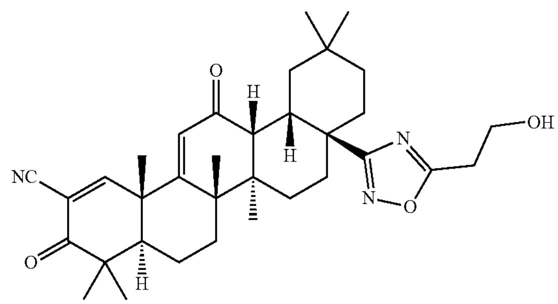 | 11.68 ± 2.80 | 1.16 ± 0.19 | 2 |
| T6 | 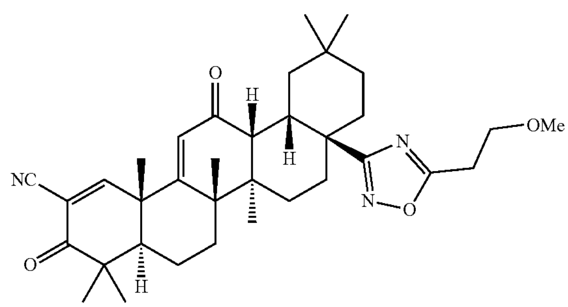 | 17.66 ± 0.10 | 1.77 ± 0.15 | 2 |
| T7 | 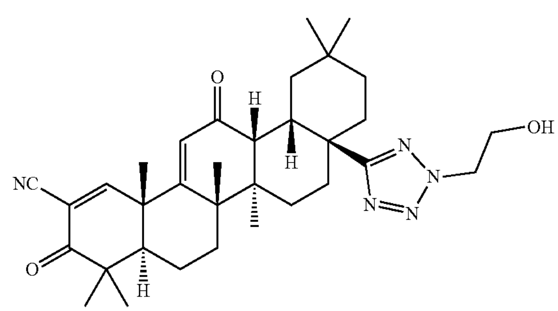 | 10.46 ± 3.66 | 1.10 ± 0.33 | 5 |
| T10 | 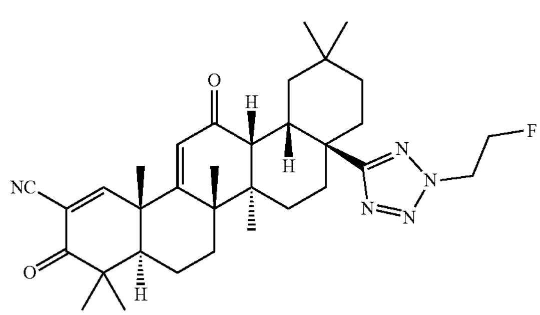 | 28.41 ± 9.42 | 2.41 ± 0.98 | 2 |

TABLE 10-continued
AREc32 EC2X and EC2X Relative to RTA 402.
| ID # | Structure | AREc32 EC$_{2X}$ (nM) (Mean ± SD) | AREc32 EC$_{2X}$ Relative to RTA 402 (fold)$^e$ (Mean ± SD) | # of Repeats |
|---|---|---|---|---|
| T13 | 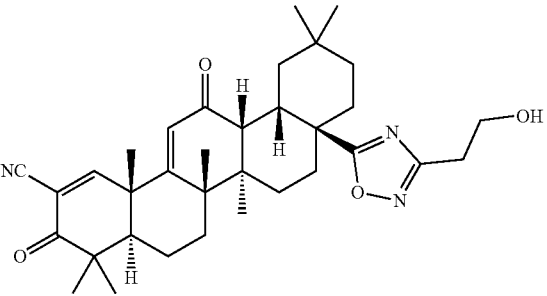 | 3.53 ± 0.98 | 0.37 ± 0.04 | 5 |
| T16 | 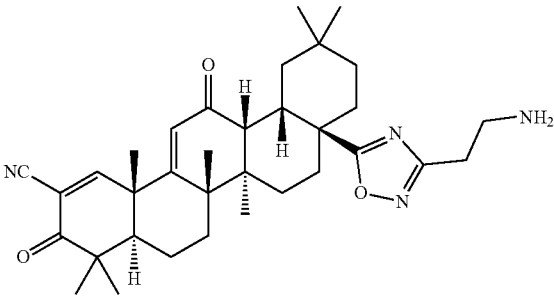 | 3.56 ± 0.31 | 0.30 ± 0.00 | 2 |
| T20 | 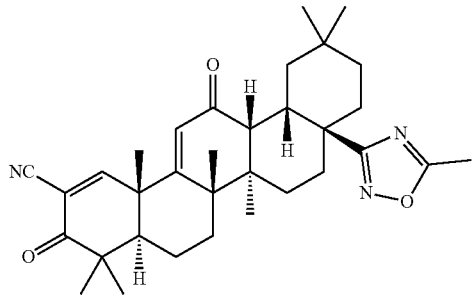 | 21.50 ± 2.85 | 1.50 ± 0.18 | 5 |
| T21 | 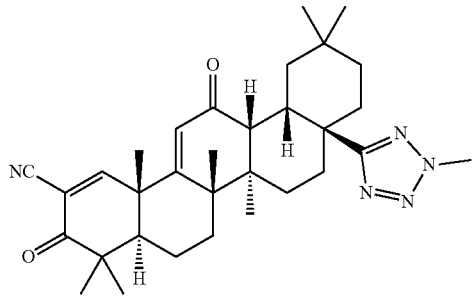 | 16.17 ± 4.20 | 1.67 ± 0.15 | 5 |

TABLE 10-continued

AREc32 EC2X and EC2X Relative to RTA 402.

| ID # | Structure | AREc32 EC$_{2X}$ (nM) (Mean ± SD) | AREc32 EC$_{2X}$ Relative to RTA 402 (fold)$^e$ (Mean ± SD) | # of Repeats |
|---|---|---|---|---|
| T25 | 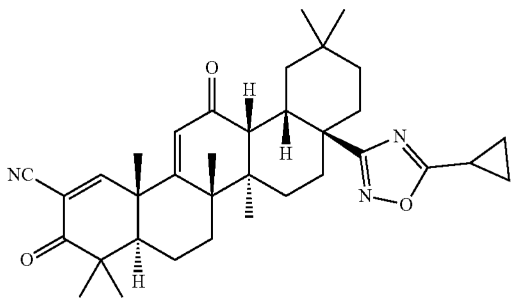 | 43.96 ± 1.20 | 4.39 ± 0.23 | 2 |
| T29 | 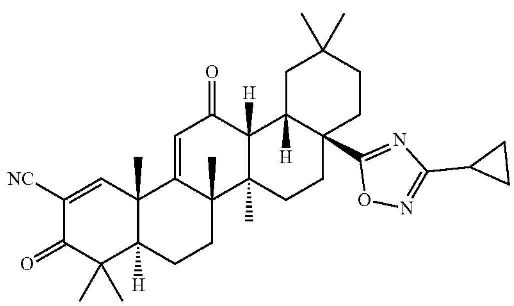 | 43.70 | 2.84 | 1 |
| T30 | 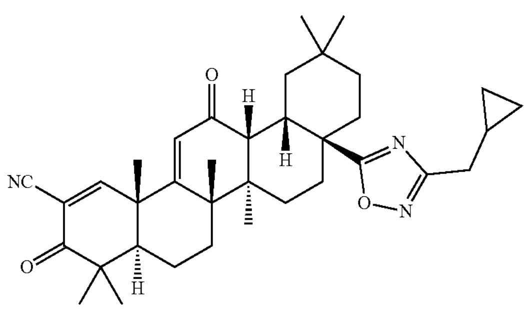 | 64.54 | 4.19 | 1 |
| T39 | 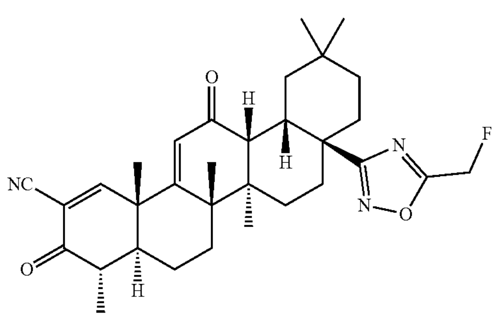 | 1.88 | 0.20 | 1 |

TABLE 10-continued

AREc32 EC2X and EC2X Relative to RTA 402.

| ID # | Structure | AREc32 EC$_{2X}$ (nM) (Mean ± SD) | AREc32 EC$_{2X}$ Relative to RTA 402 (fold)[e] (Mean ± SD) | # of Repeats |
|---|---|---|---|---|
| T42 | 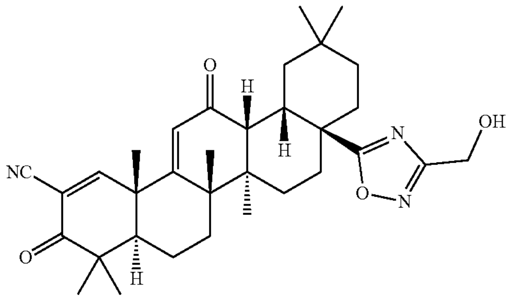 | 2.58 | 0.26 | 1[f] |

[e] Average of ratios from replicate experiments.
[f] # of repeats in this case refers only to AREc32 EC$_{2x}$ measurement. This compound was not run side by side by side against RTA 402 in the same experiment.

TABLE 11

AREc32 EX$_{2X}$ Relative to Comparison Compounds.

| ID # | Structure | Comparison Compound (CC) | AREc32 Relative to CC in Same Experiment[g] (Mean ± SD) | # of Repeats |
|---|---|---|---|---|
| CC2 | 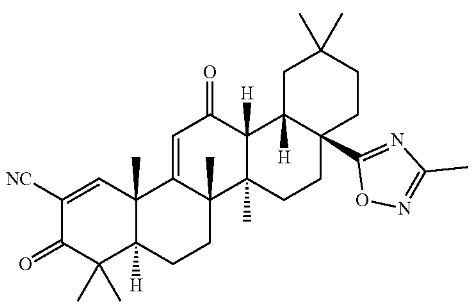 | CC2 | 1.00 | N/A |
| T1 | 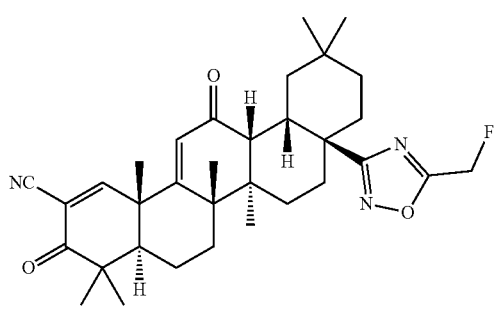 | CC2 | 0.62 ± 0.07 | 5 |

TABLE 11-continued

AREc32 EX$_{2X}$ Relative to Comparison Compounds.

| ID # | Structure | Comparison Compound (CC) | AREc32 Relative to CC in Same Experiment[g] (Mean ± SD) | # of Repeats |
|------|-----------|--------------------------|---------------------------------------------------------|--------------|
| T2   | 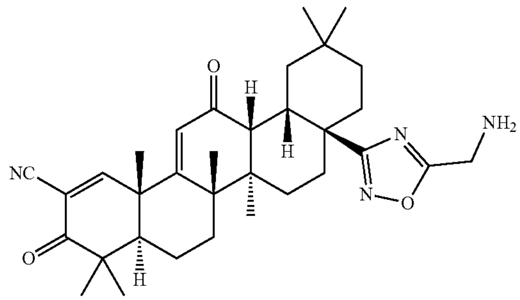          | CC2                      | 0.43 ± 0.00                                             | 3            |
| T12  | 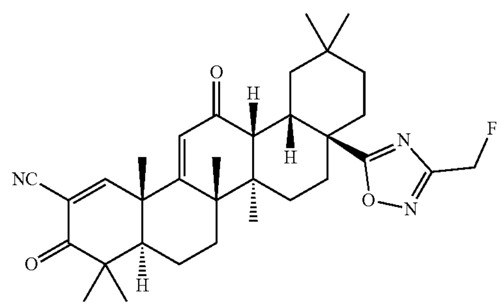          | CC2                      | 0.75 ± 0.05                                             | 5            |
| T43  | 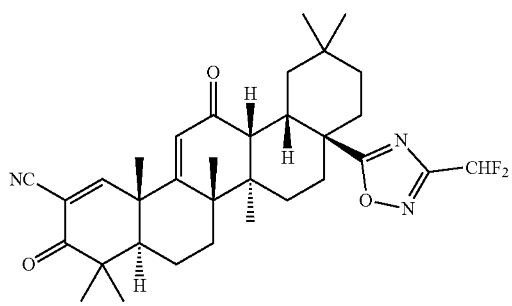          | CC2                      | 1.09 ± 0.09                                             | 3            |
| T23  | 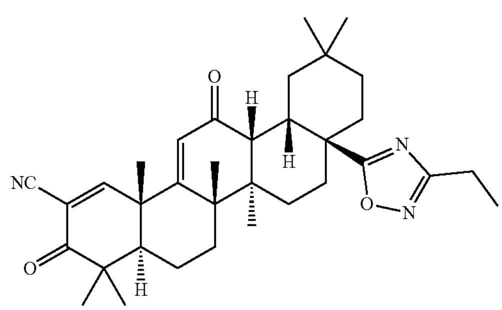          | CC2                      | 2.41 ± 0.42                                             | 3            |

TABLE 11-continued

AREc32 EX$_{2X}$ Relative to Comparison Compounds.

| ID # | Structure | Comparison Compound (CC) | AREc32 Relative to CC in Same Experiment[g] (Mean ± SD) | # of Repeats |
|---|---|---|---|---|
| CC1 | 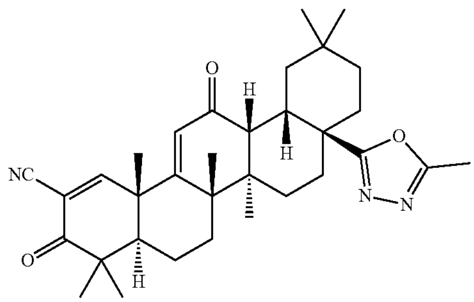 | CC1 | 1.00 | N/A |
| T11 | 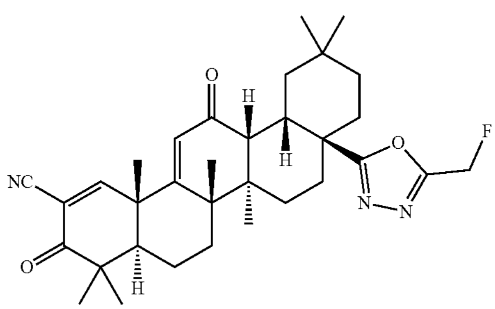 | CC1 | 0.27 ± 0.03 | 3 |
| T44 | 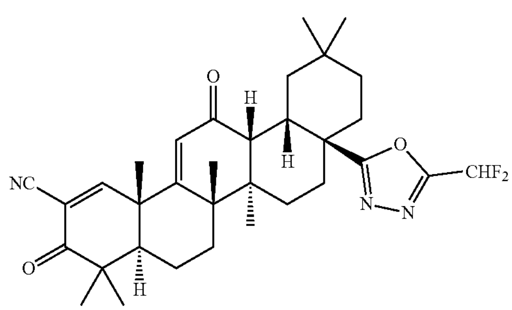 | CC1 | 0.91 ± 0.21 | 3 |
| CC3 | 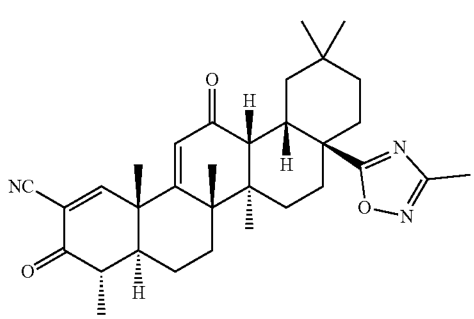 | CC3 | 1.00 | N/A |

TABLE 11-continued

AREc32 EX$_{2X}$ Relative to Comparison Compounds.

| ID # | Structure | Comparison Compound (CC) | AREc32 Relative to CC in Same Experiment[g] (Mean ± SD) | # of Repeats |
|---|---|---|---|---|
| T34 | 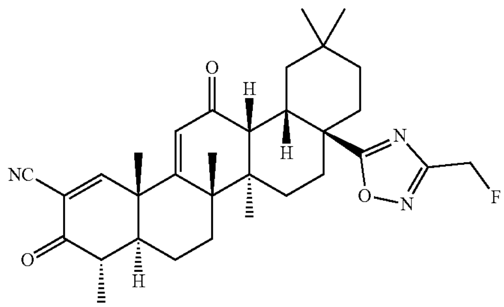 | CC3 | 0.76 ± 0.14 | 3 |
| T35 | 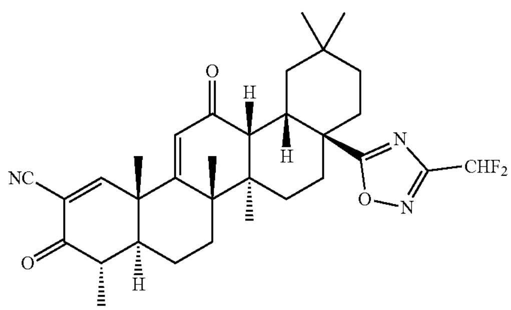 | CC3 | 1.66 ± 0.31 | 3 |
| T37 | 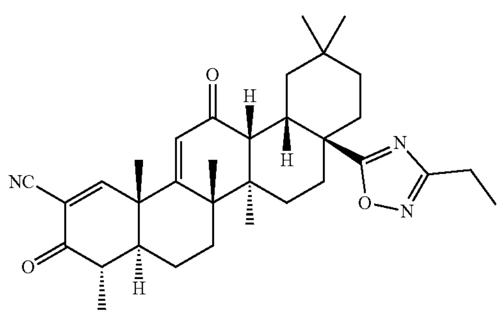 | CC3 | 1.58 ± 0.16 | 3 |
| T13 | 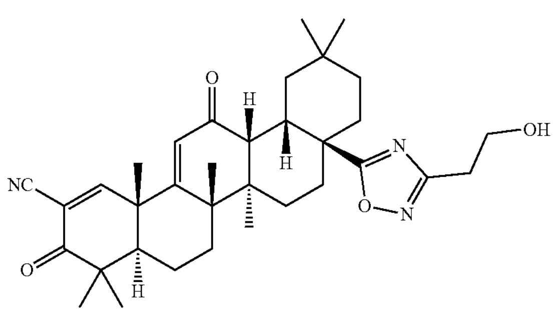 | CC2 | 0.44 ± 0.07 | 5 |

[g]Average of ratios from experiments with direct comparisons.

All the compounds, formulations, and methods disclosed and claimed herein can be made and executed without undue experimentation in light of the present disclosure. While the compounds, formulations, and methods of the present disclosure have been described in terms of preferred embodiments, it will be apparent to those of skill in the art that variations may be applied to the compounds, formulations, and methods, as well as in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

U.S. Pat. No. 6,326,507
U.S. Pat. No. 6,974,801
U.S. Pat. No. 7,435,755
U.S. Pat. No. 7,795,305
U.S. Pat. No. 7,863,327
U.S. Pat. No. 7,915,402
U.S. Pat. No. 7,943,778
U.S. Pat. No. 8,034,955
U.S. Pat. No. 8,071,632
U.S. Pat. No. 8,124,656
U.S. Pat. No. 8,124,799
U.S. Pat. No. 8,129,429
U.S. Pat. No. 8,338,618
U.S. Pat. No. 8,394,967
U.S. Pat. No. 8,440,820
U.S. Pat. No. 8,440,854
U.S. Pat. No. 8,455,544
U.S. Pat. No. 8,586,775
U.S. Pat. No. 8,993,640
U.S. Pat. No. 9,090,574
U.S. Pat. No. 9,102,681
U.S. Pat. No. 9,249,089
U.S. Pat. No. 9,278,912
U.S. Pat. No. 9,278,913
U.S. Pat. No. 9,290,536
U.S. Pat. No. 9,512,094
U.S. Pat. No. 9,556,222
U.S. Pat. No. 9,593,074
U.S. Pat. No. 9,670,147
U.S. Pat. No. 9,701,709
U.S. Pat. No. 9,757,359
U.S. Pat. No. 9,856,286
U.S. Pat. No. 9,889,143
U.S. Pat. No. 10,093,614
U.S. Pat. No. 10,105,372
U.S. Pat. No. 10,398,711
U.S. Pat. No. 10,501,489
U.S. Pat. No. 10,556,858
WO 2012/125488
WO 2014/040056
WO 2017/053868
WO 2018/089539

Abraham and Kappas, *Free Radical Biol. Med.,* 39:1-25, 2005.
Ahmad et al., *Cancer Res.,* 68:2920-2926, 2008.
Ahmad et al., *J. Biol. Chem.,* 281:35764-35769, 2006.
Anderson, *Practical Process Research & Development—A Guide for Organic Chemists,* $2^{nd}$ ed., Academic Press, New York, 2012.
Araujo et al., *J. Immunol.,* 171(3):1572-1580, 2003.
Bach, *Hum. Immunol.,* 67(6):430-432, 2006.
Bachhawat and Yadav, *IUBMB Life,* 70(7):585-592, 2018.
Chauhan and Chauhan, *Pathophysiology,* 13(3):171-181 2006.
Dickerson et al., *Prog Neuropsychopharmacol Biol. Psychiatry,* Mar. 6, 2007.
Dinkova-Kostova et al., *Proc. Natl. Acad. Sci. USA,* 102 (12):4584-4589, 2005.
Dudhgaonkar et al., *Eur. J. Pain,* 10(7):573-579, 2006.
Favaloro, et al., *J. Med. Chem.,* 45:4801-4805, 2002.
Florczyk et al., *Pharmacol. Rep.,* 60(1):38-48, 2008.
Forstermann, *Biol. Chem.,* 387:1521, 2006.
Frilling et al., *Proc Natl Acad Sci USA,* 87(16):6258-6262, 1990.
*Handbook of Pharmaceutical Salts: Properties, and Use,* Stahl and Wermuth Eds., Verlag Helvetica Chimica Acta, 2002.
Hanson et al., *BMC Medical Genetics,* 6(7), 2005.
Honda et al. *Bioorg. Med. Chem. Lett.,* 12:1027-1030, 2002.
Honda et al., *Bioorg. Med. Chem. Lett.,* 16(24):6306-6309, 2006.
Honda et al., *Bioorg. Med. Chem. Lett.,* 7:1623-1628, 1997.
Honda et al., *Bioorg. Med. Chem. Lett.,* 8(19):2711-2714, 1998.
Honda et al., *Bioorg. Med. Chem. Lett.,* 9(24):3429-3434, 1999.
Honda et al., *J. Med. Chem.,* 43:4233-4246, 2000a.
Honda et al., *Org. Biomol. Chem.,* 1:4384-4391, 2003.
Honda et al., *J. Med. Chem.,* 43:1866-1877, 2000b.
Honda et al., *Bioorg. Med. Chem. Lett.,* 12(7):1027-1030, 2002.
Honda et al., *J. Med. Chem.,* 54(6):1762-1778, 2011.
Hong et al., *Clin. Cancer Res.,* 18(12):3396-3406, 2012.
Ishikawa et al., *Circulation,* 104(15):1831-1836, 2001.
Kawakami et al., *Brain Dev* 28(4):243-246, 2006.
Kendall-Tackett, *Trauma Violence Abuse,* 8(2):117-126, 2007.
Kruger et al., *J. Pharmacol. Exp. Ther.,* 319(3):1144-1152, 2006.
Lee et al., *Glia.,* 55(7):712-22, 2007.
Lencz et al., *Mol. Psychiatry,* 12(6):572-80, 2007.
Liby et al., *Cancer Res.,* 65(11):4789-4798, 2005.
Liby et al., *Mol. Cancer Ther.,* 6(7):2113-9, 2007b.
Liby et al., *Nat. Rev. Cancer,* 7(5):357-356, 2007a.
Liu et al., *FASEB J.,* 20(2):207-216, 2006.
Lu et al., *J. Clin. Invest.,* 121(10):4015-29, 2011.
McIver et al., *Pain,* 120 (1-2):161-9, 2005.
Morris et al., *J. Mol. Med.,* 80(2):96-104, 2002.
Morse and Choi, *Am. J. Respir. Crit. Care Med.,* 172(6): 660-670, 2005.
Morse and Choi, *Am. J. Respir. Crit. Care Med.,* 27(1):8-16, 2002.
Motterlini and Foresti, *Am. J. Physiol. Cell Physiol.,* 312: C302-C313, 2017.
Pall, *Med. Hypoth.,* 69:821-825, 2007.
Pergola et al., *N. Engl. J. Med.,* 365:327-336, 2011.
Place et al., *Clin. Cancer Res.,* 9(7):2798-806, 2003.
Rajakariar et al., *Proc. Natl. Acad. Sci. USA,* 104(52):20979-84, 2007.

Reagan-Shaw et al., *FASEB J.*, 22(3):659-661, 2008
Reisman et al., *Arch. Dermatol. Res.,* 306(5):447-454, 2014.
Ross et al., *Am. J. Clin. Pathol.,* 120 (Suppl):S53-71, 2003.
Ross et al., *Expert Rev. Mol. Diagn.,* 3(5):573-585, 2003.
Ruster et al., *Scand. J. Rheumatol.,* 34(6):460-3, 2005.
Sacerdoti et al., *Curr Neurovasc Res.* 2(2):103-111, 2005.
Salvemini et al., *J. Clin. Invest.,* 93(5):1940-1947, 1994.
Sarchielli et al., *Cephalalgia,* 26(9):1071-1079, 2006.
Satoh et al., *Proc. Natl. Acad. Sci. USA,* 103(3):768-773, 2006.
Schulz et al., *Antioxid. Redox. Sig.,* 10:115, 2008.
Smith, *March's Advanced Organic Chemistry: Reactions, Mechanisms, and Structure,* 7th Ed., Wiley, 2013.
Sporn et al *J. Exp. Med.,* 184(4):1425-1433, 1996.
Suh et al., *Cancer Res.,* 58:717-723, 1998.
Suh et al., *Cancer Res.,* 59(2):336-341, 1999.
Szabo et al., *Nature Rev. Drug Disc.,* 6:662-680, 2007.
Takahashi et al., *Cancer Res.,* 57:1233-1237, 1997.
Tamir and Tannebaum, *Chem. Res. Toxicol.,* 9(5):821-827, 1996.
Thimmulappa et al., *Cancer Res.,* 62(18):5196-5203, 2002.
Tamir and Tannebaum, *Biochim. Biophys. Acta,* 1288:F31-F36, 1996.
Xie et al., *J Biol Chem.* 270(12):6894-6900, 1995.
Zhou et al., *Am. J Pathol.,* 166(1):27-37, 2005.

What is claimed is:

1. A compound of the formula:

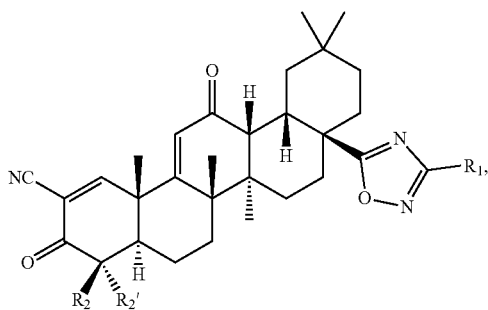

wherein:
$R_1$ is a monopolar-substituted alkyl$_{(C \leq 3)}$ wherein the monopolar substituent is —F;
$R_2$ is hydrogen or methyl; and
$R_2'$ is methyl;
or a pharmaceutically acceptable salt thereof.

2. The compound of claim 1, wherein the compound is further defined:

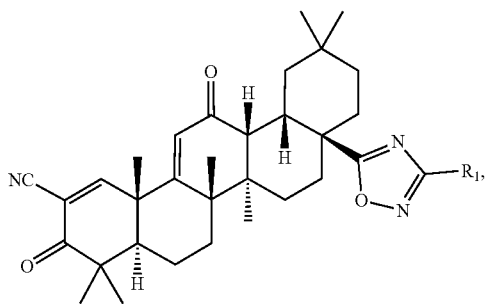

wherein:
$R_1$ is a monopolar-substituted alkyl$_{(C \leq 3)}$ wherein the monopolar substituent is —F;
or a pharmaceutically acceptable salt thereof.

3. The compound of claim 1, wherein the compound is further defined:

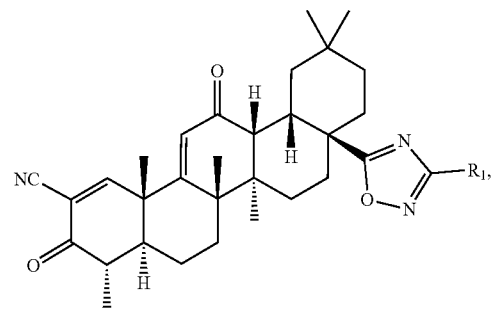

wherein:
$R_1$ is a monopolar-substituted alkyl$_{(C \leq 3)}$ wherein the monopolar substituent is —F;
or a pharmaceutically acceptable salt thereof.

4. The compound of claim 1, wherein $R_1$ is fluoromethyl.

5. The compound of claim 1, further defined as:

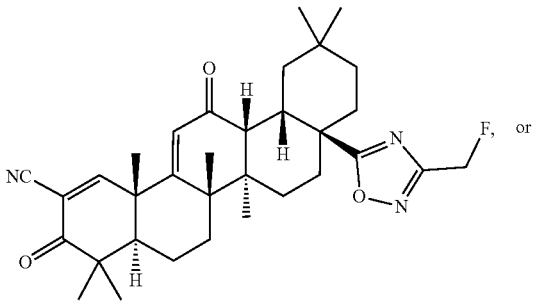

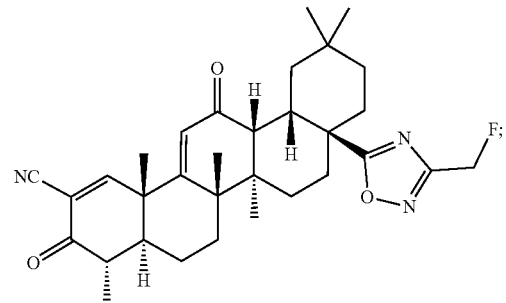

or a pharmaceutically acceptable salt of either of these formulas.

6. The compound of claim 1, further defined as:

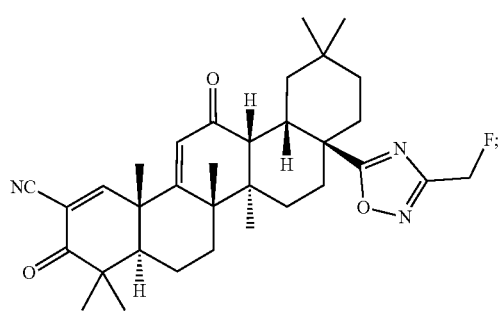

or a pharmaceutically acceptable salt thereof.

7. The compound of claim 1, further defined as:

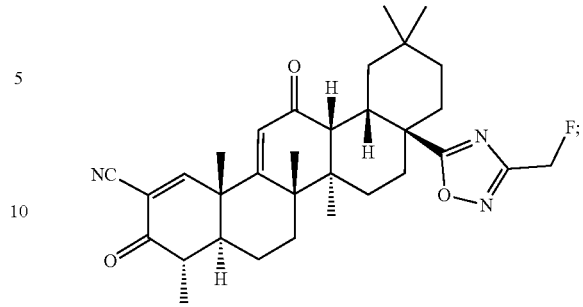

or a pharmaceutically acceptable salt thereof.

8. A pharmaceutical composition comprising:
   (A) a compound of claim 1; and
   (B) an excipient.

9. The pharmaceutical composition of claim 8, wherein the pharmaceutical composition is formulated for administration orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion.

* * * * *